United States Patent
Ashby et al.

(10) Patent No.: US 10,306,891 B2
(45) Date of Patent: Jun. 4, 2019

(54) PLANT GROWTH-PROMOTING MICROBES, COMPOSITIONS, AND USES

(71) Applicant: TAXON BIOSCIENCES INC, Belvedere Tiburon, CA (US)

(72) Inventors: Matthew N. Ashby, Mill Valley, CA (US); Christopher P. Belnap, El Cerrito, CA (US); Matthew Cornyn Kuchta, San Francisco, CA (US); Victor Kunin, San Rafael, CA (US); Caroline Kostecki, San Rafael, CA (US); Ulrika Lidstrom, San Francisco, CA (US); Natalia Shestakova, San Rafael, CA (US); Ladonna Wood, Mill Valley, CA (US)

(73) Assignee: TAXON BIOSCIENCES IN (PIONEER PAT)

( * ) Notice: Subject to any disclaimer, the term of this patent is extended or adjusted under 35 U.S.C. 154(b) by 0 days.

(21) Appl. No.: 15/511,533

(22) PCT Filed: Sep. 11, 2015

(86) PCT No.: PCT/US2015/049636
§ 371 (c)(1),
(2) Date: Mar. 15, 2017

(87) PCT Pub. No.: WO2016/044085
PCT Pub. Date: Mar. 24, 2016

(65) Prior Publication Data
US 2017/0245503 A1    Aug. 31, 2017

Related U.S. Application Data

(60) Provisional application No. 62/113,107, filed on Feb. 6, 2015, provisional application No. 62/080,143, filed on Nov. 14, 2014, provisional application No. 62/052,765, filed on Sep. 19, 2014.

(51) Int. Cl.
| | | |
|---|---|---|
| *A01H 11/00* | (2006.01) | |
| *C12N 1/20* | (2006.01) | |
| *A01N 63/00* | (2006.01) | |
| *C12R 1/01* | (2006.01) | |
| *C12R 1/41* | (2006.01) | |

(52) U.S. Cl.
CPC ............ *A01N 63/00* (2013.01); *C12N 1/20* (2013.01); *C12R 1/01* (2013.01); *C12R 1/41* (2013.01)

(58) Field of Classification Search
CPC .............................. C12Q 1/6809; C12N 1/20
USPC ...................................................... 435/252.3
See application file for complete search history.

(56) References Cited

U.S. PATENT DOCUMENTS

| | | |
|---|---|---|
| 8,476,016 B2 | 7/2013 | Ashby |
| 9,206,680 B2 | 12/2015 | Ashby et al. |
| 9,593,382 B2 | 4/2017 | Kunin et al. |
| 2006/0258534 A1 | 11/2006 | Hill et al. |
| 2007/0142226 A1 | 6/2007 | Franco |
| 2017/0245503 A1* | 8/2017 | Ashby .................... A01N 63/00 |

OTHER PUBLICATIONS

Jin et al. 2014, Systematic and Applied Microbiology 37:376-385.*
International Search Report for International Application No. PCT/US15/49636 dated Jan. 3, 2016.
International Written Opinion for International Application No. PCT/US15/49636 dated Jan. 3, 2016.
Hui Jin et al, "Characterization of rhizosphere and endophytic bacterial communities from leaves, stems and roots of medicinal Stellera chamaejasme L.", Systematic and Applied Microbiology, vol. 37, No. 5: 376-385 (2014).
Shoenborn et al, "Liquid Serial Dilution Is Inferior to Solid Media for Isolation of Cultures Representative of Phylum-Level Diversity of Soil Bacteria", Applied and Enviromental Microbiology, vol. 70, No. 7: 4363-4366 (2004).
Tringe et al, "Comparative Metagenomics of Microbial Communities", Science, vol. 308, No. 5721: 554-557 (2005).
Figueiredo et al, "Plant Growth Promoting Rhizobacteria: Fundamentals and Applications", Springer-Verlag, vol. 18: 21-43 (2010).

* cited by examiner

*Primary Examiner* — Tekchand Saidha

(57) ABSTRACT

The present application relates to plant growth promoting microbes (PGPMs), compositions comprising these PGPMs and methods of using these PGPMs and/or compositions for enhancing plant health, plant growth and/or plant yield, and/or for preventing, inhibiting, or treating the development of plant pathogens or the development of phytopathogenic diseases. This application also provides non-naturally occurring plant varieties that are artificially infected with a PGPM descried herein, as well as seed, reproductive tissue, vegetative tissue, regenerative tissues, plant parts, or progeny thereof.

9 Claims, 23 Drawing Sheets
Specification includes a Sequence Listing.

PLANT GROWTH-PROMOTING MICROBES, COMPOSITIONS, AND USES

FIELD

This application relates to microbial strains, compositions and methods useful for enhancing plant growth or yield and/or for suppressing the development of plant pathogens and phytopathogenic diseases.

REFERENCE TO A SEQUENCE LISTING SUBMITTED AS A TEXT FILE VIA EFS-WEB

The Sequence Listing created on Aug. 18, 2015 as a text file named "6824_Seq_List.txt," and having a size of 110542 bytes is hereby incorporated by reference pursuant to 37 C.F.R. § 1.52(e)(5).

BACKGROUND

Plant growth promoting microbes (PGPMs), such as plant growth-promoting rhizobacteria (PGPR), have gained worldwide importance and acceptance for agricultural benefits. PGPMs can affect plant growth by different direct and indirect mechanisms. Some examples of these mechanisms, which can be active simultaneously or sequentially at the same or different stages of plant growth, include (1) increased mineral nutrient solubilization and nitrogen fixation (i.e., making nutrients more available for the plant); (2) repression of soilborne pathogens (e.g., by the production of hydrogen cyanide, siderophores, antibiotics, and/or competition for nutrients); (3) improving plant stress tolerance to drought, flooding, salinity, and metal toxicity; and (4) production of phytohormones such as indole-3-acetic acid (IAA). Moreover, some PGPMs produce the enzyme 1-aminocyclopropane-1-carboxylate (ACC) deaminase, which hydrolyses 1-aminocyclopropane-1-carboxylate (ACC), the immediate precursor of ethylene in plants. By lowering ethylene concentration in seedlings and thus its inhibitory effect, these PGPMs stimulate the root length of seedlings. Some exemplary groups of PGPMs can be found among the phyla: Cyanobacteria, Actinobacteria, Bacteroidetes, Firmicutes, and Proteobacteria. There is a considerable amount of ongoing scientific research directed to understanding PGPMs, including the aspects of their adaptation, effects on plant physiology and growth, induced systemic resistance, biocontrol of plant pathogens, biofertilization, viability of co-inoculation, interactions with plant microorganisms, and mechanisms of root colonization.

By virtue of their rapid rhizosphere colonization and stimulation of plant growth and/or yield, there is currently considerable interest in exploiting PGPMs to improve crop production. In fact, the inoculation of cultivated plants with PGPMs is currently considered a promising agricultural approach. As environmental concerns increase, e.g., concerns about groundwater quality with excess fertilizer and pesticide exposure in foods, biological alternatives are promising and becoming necessary. Thus, developing biological treatments compatible with fertilizers and pesticides and/or even reducing the amount of these chemical compounds used could be a significant advancement in the agricultural industry.

However, there is a lack of efficient screening and selection procedures for obtaining microbial strains that have plant health/growth/yield promoting abilities. There is also a lack of efficient selection methods for obtaining combinations of microbial stains (or microbial consortia) that interact synergistically in the context of promoting plant health, growth and/or yield. The lack of such screening and/or selection procedures, unfortunately, slows down the study of plant-bacterial symbioses, and the deployment of new PGPMs in agriculture. Therefore, there is a continuing and pressing need for the identification of new PGPMs, PGPM synthetic consortia, and/or testing of their compatibility with existing commercially available crop management products.

SUMMARY

The embodiments of this application address the aforementioned need by providing new microbial strains (PGPMs), isolates, cultures, compositions, synthetic consortia, and methods useful for enhancing the health, growth and/or yield of a plant. Other aspects of the present embodiments provide methods for identifying microbial consortia comprising two or more PGPMs useful for promoting plant health, growth and/or yield. Also provided are methods for the treatment of plant seeds by using the microbial strains (PGPMs), isolates, cultures or compositions disclosed herein. Further provided are methods for preventing, inhibiting, or treating the development of plant pathogens or the development of phytopathogenic diseases. This application also provides non-naturally occurring plant varieties that are artificially infected with at least one microbial endophyte disclosed herein. Other embodiments provide seed, reproductive tissue, vegetative tissue, regenerative tissues, plant parts, or progeny of the non-naturally occurring plant varieties. Other embodiments further provide a method for preparing agricultural compositions.

Other embodiments provide isolated microbial strains (PGPMs), isolated cultures thereof, biologically pure cultures thereof, and enriched cultures thereof. In some embodiments, the microbial strain comprises a 16S rRNA gene comprising a nucleotide sequence selected from SEQ ID Nos.: 1-164. In some embodiments, the microbial strain comprises a 16S rRNA gene comprising a nucleotide sequence selected from SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, 158, and 159. In some embodiments, the microbial strain comprises a 16S rRNA gene comprising a nucleotide sequence selected from SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158. In some embodiments, the microbial strain comprises a 16S rRNA gene comprising a nucleotide sequence selected from SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, and 159. In some embodiments, the microbial strain comprises a 16S rRNA gene comprising a nucleotide sequence selected from SEQ ID Nos.: 113, 123, 126, 131, and 149. In some embodiments, the microbial strain comprises a 16S rRNA gene comprising a nucleotide sequence selected from SEQ ID Nos.: 133, 134 and 138. In some embodiments, a 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, at least 99.5%, or at least 99.9% sequence identity to any one of the nucleotide sequences as set forth in any one of the SEQ ID Nos.:1-164. Some embodiments provide a genus of microorganisms comprising any of the DNA sequences described above and which enhances the health, growth and/or yield of a plant, as described herein. In some embodiments, the microbial strain is P0032_C7, P0048_B9, P0050_F5 (also referred to as S2199,), P0035_B2 (also referred to as S2145, NRRL Deposit No. B-67091), P0020_B1, P0047_A1 (also referred to as S2284, NRRL Deposit No. B-67102), P0033_E1 (also referred to as S2177), P0032_A8 (also referred to as S2181, NRRL Deposit No. B-67099), P0049_E7, P0042_A8 (also referred to as S2167), P0042_D5 (also referred to as S2165), P0042_B2 (also referred to as S2168, NRRL Deposit No. B-67096), P0042_B12 (also referred to as S2189), P0042_C2 (also referred to as S2173, NRRL Deposit No. B-67098), P0042_D10 (also referred to as S2172, NRRL Deposit No. B-67097), P0044_A3 (also referred to as S2476), P0018_A11, P0044_A5, P0047_E2, P0047_C1, P0038_D2 or S2166, P0042_E1, P0047_E8, P0018_A1, S2159_P0058_B9 (NRRL Deposit No. B-67092), S2161_P0054_E8 (NRRL Deposit No. B-67094), S2164_P0054_F4, P0057_A3 (also referred to as S2160, NRRL Deposit No. B-67093), S2142_P0061_E11, S2163_P0019_A12 (NRRL Deposit No. B-67095), P0147_D10 (also referred to as S2291, NRRL Deposit No. B-67104), P0147_G10 (also referred to as S2292, NRRL Deposit No. B-67105), P0160_F7 (also referred to as S2351), P0140_C10 (also referred to as S2300, NRRL Deposit No. B-67107), S2387, P0157_G5 (also referred to as S2303, NRRL Deposit No. B-67108), P0160_E1 (also referred to as S2374), P0134_G7 (also referred to as S2280), S2384 (NRRL Deposit No. B-67112), S2275 (NRRL Deposit No. B-67101), S2278, S2373 (NRRL Deposit No. B-67109), S2370, S2293 (NRRL Deposit No. B-67106) S2382 (NRRL Deposit No. B-67111), P0132_A12, P0132_C12, P0140_D9, P0173_H3 (also referred to as S2404), S2385 (NRRL Deposit No. B-67113), S2197 (NRRL Deposit No. 67100), S2285 (NRRL Deposit No. B-67103), S2477, S2376, S2420, S2424, S2445, S2333, S2329, S2327, S2330, S2423 (NRRL Deposit No. B-67115), S2435, S2158, S2437, S2332, S2521, S2228, S2473, P0156_G2, P0154_G3, S2487, S2488, S2421 (NRRL Deposit No. B-67114), P0105_C5, P0154_H3, P0156_G1, S1112 (NRRL Deposit No. B-67090), S2375 (NRRL Deposit No. B-67110), and S2669 (NRRL Deposit No. B-67117), S2651, S2652, S2653, S2654, S2655, S2656, S2668, S2644 (NRRL Deposit No. B-67116), S2328, S2646, or a strain derived from any one of these strains.

Another embodiment provides a microbial composition that comprises a microbial strain (PGPM), such as a microbial strain selected from those described herein, or a culture thereof. In some embodiments, the microbial composition comprises a microbial strain, wherein the 16S rRNA gene of said strain comprises a sequence selected from the group consisting of SEQ ID Nos.: 1-164. In some embodiments, the microbial composition comprises a microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, and 159, or a culture thereof. In some embodiments, the microbial composition comprises a microbial strain, wherein the 16S rRNA gene of said strain comprises a sequence selected from the group consisting of SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155 and 158, or a culture thereof. In some embodiments, the microbial composition comprises a microbial strain, wherein the 16S rRNA gene of said strain comprises a sequence selected from the group consisting of SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 159, 160, 161, 162, 163 and 164, or a culture thereof. In some embodiments, the microbial composition comprises a microbial strain, wherein the 16S rRNA gene of said strain comprises a sequence selected from the group consisting of SEQ ID Nos.: 113, 123, 126, 131, and 149, or a culture thereof. In some embodiments, the microbial composition comprises a microbial strain, wherein the 16S rRNA gene of said strain comprises a sequence selected from the group consisting of SEQ ID Nos.: 133, 134 and 138, or a culture thereof. Any of the above microbial compositions may optionally further comprise a second microbial strain whose 16S rRNA gene sequence comprises a sequence selected from the group consisting of SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163 and 164, or a culture thereof. In some embodiments, the microbial composition comprises at least two microbial strains, wherein the 16S rRNA gene of each of said at least two microbial strains comprises a sequence independently selected from the group consisting of SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163 and 164, or cultures thereof.

In some embodiments, the microbial composition comprises one or more microbial strains, wherein the 16S rRNA gene of each of said strains comprises a sequence independently selected from SEQ ID Nos.: 1, 2, 4, 5, 6, 10, 12, 50, 55, 56, and 57, or a culture thereof.

In some embodiments, the microbial composition comprises one or more microbial strains, wherein the 16S rRNA gene of each of said strains comprises a sequence independently selected from SEQ ID Nos.: 34, 35, 46, 47, 48, 65, 66, 67, 68, 69, 70, 71, 72, 73, and 74, or a culture thereof.

In some embodiments, the microbial composition comprises one or more microbial strains, wherein the 16S rRNA gene of each of said strains comprises a sequence independently selected from SEQ ID Nos.: 20, 21, 22, 23, 24, 25, 26, 30, 31, 32, 33, 41, 42, 62, 63, and 64, or a culture thereof.

In some embodiments, the microbial composition comprises one or more microbial strains, wherein the 16S rRNA gene of each of said strains comprises a sequence independently selected from SEQ ID Nos.: 18, 19, 36, 37, 75, and 76, or a culture thereof.

In some embodiments, the microbial composition comprises one or more microbial strains, wherein the 16S rRNA gene of each of said strains comprises a sequence independently selected from SEQ ID Nos.: 11, 13, 58, 59, 60, and 61, or a culture thereof.

In some embodiments, the microbial composition comprises one or more microbial strains, wherein the 16S rRNA gene of each of said strains comprises a sequence independently selected from SEQ ID Nos.: 27, 38, 39, 40, 43, 44, 45, and 77, or a culture thereof.

In some embodiments, the microbial composition comprises one or more microbial strains, wherein the 16S rRNA gene of each of said strains comprises a sequence independently selected from SEQ ID Nos.: 1, 3, 4, 7, 8, 51, 52, 53, 134, and 135, or a culture thereof.

In some embodiments, the microbial composition comprises one or more microbial strains, wherein the 16S rRNA gene of each of said strains comprises a sequence independently selected from SEQ ID Nos.: 14, 16, 78, 79, and 80, or a culture thereof.

In some embodiments, the microbial composition comprises one or more microbial strains, wherein the 16S rRNA gene of each of said strains comprises a sequence independently selected from SEQ ID Nos.: 43, 44, 45, 81, 82, 83, 84, 145 and 146, or a culture thereof.

In some embodiments, the microbial composition comprises one or more microbial strains, wherein the 16S rRNA gene of each of said strains comprises a sequence independently selected from SEQ ID Nos.: 24, 86, 87, and 88, or a culture thereof.

In some embodiments, the microbial composition comprises one or more microbial strains, wherein the 16S rRNA gene of each of said strains comprises a sequence independently selected from SEQ ID Nos.: 51, 52, 53, 81, 82 and 83, or a culture thereof.

In some embodiments, the microbial composition comprises one or more microbial strains, wherein the 16S rRNA gene of each of said strains comprises a sequence independently selected from SEQ ID Nos.: 51, 52, 53, 75, 76, 81, 82, 83, 84, 145, 146, or a culture thereof.

In some embodiments, the microbial composition comprises one or more microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328 and S2646 or a strain derived therefrom, or a culture thereof.

Other embodiments provide a composition comprising a synthetic microbial consortium. In some embodiments, a synthetic consortium comprises a) a first set of microbes comprising one or more microbes that promote plant health, growth, and/or yield; and b) a second set of microbes comprising one or more microbes that increase the competitive fitness of the first set of microbes in a); wherein the first and the second sets of microbes are combined into a single mixture as a synthetic consortium. In some embodiments, the synthetic consortium or a composition promotes or enhances plant health, growth and/or yield. In some embodiments, the synthetic consortium or a composition thereof according to the present application is applied to a plant (or a part thereof), a seed, or a seedling.

In some embodiments, a microbial composition as described herein, such as any of the microbial compositions described above and below, further comprises an agriculturally effective amount of a compound or composition selected from, but not limited to, a nutrient, a fertilizer, an acaricide, a bactericide, a fungicide, an insecticide, a microbicide, a nematicide, and a pesticide and combinations thereof. In some embodiments of the microbial compositions described herein, the microbial composition further comprises a carrier, such as (but not limited to) an organic or an inorganic carrier and combinations thereof. In some embodiments, the carriers suitable for the microbial compositions include, but are not limited to, silt, peat, turf, talc, lignite, kaolinite, pyrophyllite, zeolite, montmorillonite, alginate, press mud, sawdust and vermiculite and combinations thereof. In some embodiments, the carrier is a plant seed. In some embodiments, the microbial composition is prepared as a formulation selected from, but not limited to, an emulsion, a colloid, a dust, a granule, a pellet, a powder, a spray, and a solution. In some embodiments, the microbial composition described herein is a seed coating formulation.

Other embodiments provide a plant seed treatment having a coating comprising a microbial strain (PGPM) or a culture thereof as described herein. Also provided is a plant having a coating comprising a microbial composition as described herein.

Other embodiments provide a method of preparing a synthetic microbial consortium, comprising a) selecting a first set of microbes comprising one or more microbes that promote plant health, growth, and/or yield; b) selecting a second set of microbes comprising one or more microbes that increase the competitive fitness of the first set of microbes in step a); and c) combining these microbes into a single mixture and designating the combination as a synthetic consortium. In some embodiments, the method comprises a further step of applying the synthetic consortium as described herein to a plant (or a part thereof), a seed, or a seedling. The present embodiments also provide a synthetic microbial consortium prepared as described herein. The present embodiments further provide a method of promoting plant health, plant growth and/or plant yield, comprising applying a synthetic microbial consortium prepared as described herein to a plant, a plant part, or the plant's surroundings.

Other embodiments provide a method for treating plant seeds or seed priming. In some embodiments, the method includes exposing or contacting the plant seed with a microbial strain (PGPM) according to the present embodiments or a culture thereof. In some embodiments, the method includes exposing or contacting the plant seed with a microbial composition according to the present embodiments.

Other embodiments provide a method for enhancing the health, growth and/or yield of a plant. In some embodiments, such method involves applying an effective amount of a microbial strain (PGPM), or a culture thereof to the plant, a plant part, or to the plant's surroundings. In some embodiments, such method involves applying an effective amount of a microbial composition to the plant or the plant's surroundings. In some embodiments, the method involves growing one or more microbial strains in a growth medium or soil of a host plant or plant part prior to or concurrent with the host plant's growth in said growth medium or soil. In some embodiments of the above method, a microbial strain (PGPM) is applied to the plant, plant part, or to the plant's surroundings (e.g., immediate soil layer or rhizosphere) in a culture or a composition according to the present embodiments at a concentration that is at least 2×, 5×, 10×, 100×, 500×, or 1000× the concentration of the same microbial strain found or detected in an untreated control plant, plant part, or the control plant's surroundings, respectively. In some embodiments, upon or after application, the concentration of the microbial strain (PGPM) in the treated plant, plant part, or the plant's surroundings (e.g., immediate soil layer or rhizosphere) is at least 2×, 5×, 10×, 100×, 500×, or 1000× the concentration of the same microbial strain found or detected in an untreated control plant, plant part, or the control plant's surroundings. In some embodiments of the above method, a microbial strain (PGPM) is applied to the plant, plant part, or to the plant's surroundings (e.g., immediate soil layer or rhizosphere) in a culture or a composition at a concentration that is higher than $1 \times 10^2$ CFU/mL. In some embodiments, concentration ranges are from about $1 \times 10^2$ to about $1 \times 10^{10}$ CFU/mL, such as the concentrations ranging from $1 \times 10^5$ to $1 \times 10^9$ CFU/mL. In some embodiments, application of a microbial strain (PGPM) as described herein to a plant, plant part, or to the plant's surroundings (e.g., immediate soil layer or rhizosphere) in a culture or a composition at a concentration that is at least $1 \times 10^6$ CFU/mL leads to a concentration of the microbial strain in the treated plant, plant part or the plant's surroundings that is at least 2× the amount of the strain found in an untreated plant or its surroundings.

In some embodiments, one or more microbial strains are established as endophytes on the plant, after being applied to the plant, plant part, or to the plant's surroundings. In some embodiments, one or more microbial strains are established as endophytes on the plant in the reproductive tissue, vegetative tissue, regenerative tissues, plant parts, and/or progeny thereof. In some embodiments, one or more microbial strains are established as endophytes in the seed offspring of the plant that is exposed to or treated with a microbial strain, isolate, culture, or composition as described herein. Some embodiments relate to a plant, plant part, or a seed that is infected with at least one microbial strain as described herein.

Other embodiments provide a method for preventing, inhibiting or treating the development of a pathogenic disease of a plant or the development of a plant pest, insect, or pathogen. In some embodiments, such method involves applying an effective amount of a microbial strain (PGPM), or a culture thereof to the plant, plant part, or to the plant's surroundings. In some embodiments, such method involves applying an effective amount of a microbial composition to the plant, plant part, or the plant's surroundings. In some embodiments, the method involves growing one or more microbial strains in a growth medium or soil of a host plant prior to or concurrent with the host plant growth in said growth medium or soil. In some embodiments of the above method, a microbial strain (PGPM) is applied to the plant (or a part thereof) or to the plant's surroundings (e.g., immediate soil layer or rhizosphere) in a culture or a composition at a concentration that is at least 2×, 5×, 10×, 100×, 500×, or 1000× the concentration of the same microbial strain found or detected in an untreated control plant, plant part, or the control plant's surroundings, respectively. In some embodiments, upon or after application, the concentration of the microbial strain (PGPM) in the treated plant (or a part thereof) or the plant's surroundings (e.g., immediate soil layer or rhizosphere) is at least 2×, 5×, 10×, 100×, 500×, or 1000× the concentration of the same microbial strain found or detected in an untreated control plant, plant part, or the control plant's surroundings. In some embodiments of the above method, a microbial strain (PGPM) is applied to the plant, plant part, or to the plant's surroundings (e.g., immediate soil layer or rhizosphere) in a culture or a composition at a concentration that is higher than $1 \times 10^2$ CFU/mL. In some embodiments, the concentration ranges from about $1 \times 10^2$ to about $1 \times 10^{10}$ CFU/mL, such as concentrations ranging from $1 \times 10^5$ to $1 \times 10^9$ CFU/mL. In some embodiments, application of a microbial strain (PGPM) to a plant, plant part, or to the plant's surroundings (e.g., immediate soil layer or rhizosphere) in a culture or a composition at a concentration that is at least $1 \times 10^6$ CFU/mL leads to a concentration of the microbial strain in the treated plant, plant part or the plant's surroundings that is at least 2× the amount of the strain found in an untreated plant or its surroundings.

In some embodiments a method comprising one or more microbial strains are established as endophytes on the plant, after being applied to the plant, plant part or to the plant's surroundings. In some embodiments, one or more microbial strains are established as endophytes on the plant in the reproductive tissue, vegetative tissue, regenerative tissues, plant parts, and/or progeny thereof. In some embodiments, one or more microbial strains are established as endophytes in the pollen of the plant. In some embodiments, one or more microbial strains are established as endophytes in the seed offspring of the plant that is exposed to or treated with a microbial strain, isolate, culture, or composition as described herein. In some embodiments, the development of a pathogenic disease of a plant, or plant part, that may be prevented, inhibited, or treated by a microbial strain, isolate, culture, or composition according to the present embodiments, is caused by a plant pathogen selected from, but not limited to, *Colletotrichum, Fusarium, Gibberella, Monographella, Penicillium, Pythium, Xanthomonas, Ralstonia* and *Stagnospora* organisms. In some embodiments, the pathogen whose development may be prevented, inhibited or treated by a microbial strain or a culture thereof, or a microbial composition, according to the present embodiments, is selected from, but not limited to, *Colletotrichum, Fusarium, Gibberella, Monographella, Penicillium, Pythium, Xanthomonas, Ralstonia*, and *Stagnospora* organisms.

Other embodiments provide a non-naturally occurring plant. In some embodiments, the non-naturally occurring plant is artificially infected with one or more microbial strains (PGPMs) according to the present embodiments. Further provided in some embodiments of this aspect is a plant seed, reproductive tissue, vegetative tissue, regenerative tissue, plant part or progeny of the non-naturally occurring plant.

Other embodiments provide a method for preparing an agricultural composition. Such methods involve inoculating the microbial strain, an isolate or a culture thereof, or a microbial composition, according to the present embodiments, into or onto a substratum and allowing it to grow.

Certain Embodiments Include:

1. An isolated microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, 158, and 159.

2. An enriched culture of a microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, 158, and 159.

3. An isolated culture of a microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, 158 and 159.

4. A biologically pure culture of a microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, 158 and 159.

5. The culture according to any one of embodiments 1-4, wherein the 16S rRNA gene of said strain comprises a sequence selected from the group consisting of SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158.

6. The culture according to any one of embodiments 1-4, wherein the 16S rRNA gene of said strain comprises a sequence selected from the group consisting of SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159.

7. An isolated microbial strain selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646 or a strain derived therefrom.

8. An isolated culture of a microbial strain selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646 or a strain derived therefrom.

9. An enriched culture of a microbial strain selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646 or a strain derived therefrom.

10. A biologically pure culture of a microbial strain selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646 or a strain derived therefrom.

11. A composition comprising a microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, 158, and 159.

12. The composition according to embodiment 11, wherein the 16S rRNA gene of said strain comprises a sequence selected from the group consisting of SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158.

13. The composition according to embodiment 11, wherein the 16S rRNA gene of said strain comprises a sequence selected from the group consisting of SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159.

14. The composition according to any one of embodiments 11-13, further comprising a second microbial strain whose 16S rRNA gene sequence comprises a sequence selected from the group consisting of SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163 and 164.

15. A composition comprising at least two microbial strains, wherein the 16S rRNA gene of each of said microbial strains comprises a sequence independently selected from the group consisting of SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163 and 164.

16. A composition comprising a microbial strain, wherein the 16S rRNA gene of said strain comprises a sequence selected from the group consisting of SEQ ID Nos.: 1, 2, 4, 5, 6, 10, 12, 50, 55, 56, and 57.

17. The composition according to embodiment 16, wherein said composition comprises one or more microbial strains, wherein the 16S rRNA gene of each of said strains comprises a sequence independently selected from SEQ ID Nos.: 6 and 57.

18. The composition according to embodiment 16 or 17, wherein said composition comprises at least two microbial strains, wherein the 16S rRNA genes of said at least two strains comprise sequences of SEQ ID Nos.: 6 and 57, respectively.

19. The composition according to embodiment 16, wherein the composition comprises one or more microbial strains, wherein the 16S rRNA gene of each of said strains comprises a sequence independently selected from SEQ ID Nos.: 2, 5, 10, 12, 50, 55, and 56.

20. The composition according to embodiment 16 or 19, wherein the composition comprises two or more microbial strains, wherein the 16S rRNA gene of each of said strains comprises a sequence independently selected from SEQ ID Nos.: 2, 5, 10, 12, 50, 55, and 56.

21. The composition according to any one of embodiments 16, 19 and 20, wherein the microbial composition comprises one or more microbial strains, wherein the 16S rRNA gene of each of said strains comprises a sequence independently selected from SEQ ID Nos.: 5 and 56, and optionally further comprises one or more additional microbial strains, wherein the 16S rRNA gene of each of said additional strains comprises a sequence independently selected from the group consisting of SEQ ID Nos.: 2, 10, 12, 50, and 55.

22. The composition according to any one of embodiments 16 and 19-21, wherein the composition comprises at least seven (7) microbial strains, wherein the 16S rRNA genes of said at least seven strains comprise sequences of SEQ ID Nos.: 2, 5, 10, 12, 50, 55, and 56, respectively.

23. The composition of embodiment 16, wherein the composition comprises one or more microbial strains, wherein the 16S rRNA gene of each of said strains comprises a sequence independently selected from SEQ ID Nos.: 1, 4, 9, 11, 49, and 54.

24. The composition of embodiment 16 or 23, wherein the composition comprises two or more microbial strains, wherein the 16S rRNA gene of each of said strains comprises a sequence independently selected from SEQ ID Nos.: 1, 4, 9, 11, 49, and 54.

25. A composition comprising a microbial strain, wherein the 16S rRNA gene of said strain comprises a sequence selected from the group consisting of SEQ ID Nos.: 34, 35, 46, 47, 48, 65, 66, 67, 68, 69, 70, 71, 72, 73, and 74.

26. The composition according to embodiment 25, wherein the composition comprises one or more microbial strains, wherein the 16S rRNA gene of each of said strains comprises a sequence independently selected from SEQ ID Nos.: 48, 69, and 72.

27. The composition according to embodiment 25 or 26, wherein the composition comprises two or more microbial strains, wherein the 16S rRNA gene of each of said strains comprises a sequence independently selected from SEQ ID Nos.: 48, 69, and 72.

28. The composition according to any one of embodiments 25-27, wherein said composition comprises at least three (3) microbial strains, wherein the 16S rRNA genes of said at least three strains comprise sequences of SEQ ID Nos.: 48, 69 and 72.

29. The composition according to embodiment 25, wherein the composition comprises one or more microbial strains, wherein the 16S rRNA gene of each of said strains comprises a sequence independently selected from SEQ ID Nos.: 35, 47, 66, 68, 71, 73, and 74.

30. The composition according to embodiment 25 or 29, wherein the composition comprises two or more microbial strains, wherein the 16S rRNA gene of each of said strains comprises a sequence independently selected from SEQ ID Nos.: 35, 47, 66, 68, 71, 73, and 74.

31. The composition according to any one of embodiments 25, 29 and 30, wherein the composition comprises one or more microbial strains, wherein the 16S rRNA gene of each of said strains comprises a sequence independently selected from SEQ ID Nos.: 47, 68 and 71, and wherein said composition optionally further comprises one or more additional microbial strains, wherein the 16S rRNA gene of each of said additional strains comprises a sequence independently selected from the group consisting of SEQ ID Nos.: 35, 66, 73 and 74.

32. The composition according to any one of embodiments 25 and 29-31, wherein the composition comprises at least seven (7) microbial strains, wherein the 16S rRNA genes of said at least seven strains comprise sequences of SEQ ID Nos.: 35, 47, 66, 68, 71, 73, and 74, respectively.

33. The composition according to embodiment 25, wherein the composition comprises one or more microbial strains, wherein the 16S rRNA gene of each of said strains comprises a sequence independently selected from SEQ ID Nos.: 34, 46, 65, 67, and 70.

34. The composition according to embodiment 25 or 33, wherein the composition comprises two or more microbial strains, wherein the 16S rRNA gene of each of said strains comprises a sequence independently selected from SEQ ID Nos.: 34, 46, 65, 67, and 70.

35. The composition according to any one of embodiments 25, 33 and 34, wherein the composition comprises at least five (5) microbial strains, wherein the 16S rRNA genes of said at least five strains comprise sequences of SEQ ID Nos.: 34, 46, 65, 67, and 70.

36. A composition comprising a microbial strain, wherein the 16S rRNA gene of said strain comprises a sequence selected from the group consisting of SEQ ID Nos.: 20, 21, 22, 23, 24, 25, 26, 30, 31, 32, 33, 41, 42, 62, 63, and 64.

37. The composition according to embodiment 36, wherein the composition comprises one or more microbial strains, wherein the 16S rRNA gene of each of said strains comprises a sequence independently selected from SEQ ID Nos.: 26 and 64.

38. The composition according to embodiment 36 or 37, wherein the composition comprises at least two (2) microbial strains, wherein the 16S rRNA genes of said at least two strains comprise sequences of SEQ ID Nos.: 26 and 64, respectively.

39. The composition according to embodiment 36, wherein the composition comprises one or more microbial strains, wherein the 16S rRNA gene of each of said strains comprises a sequence independently selected from SEQ ID Nos.: 21, 22, 23, 25, 31, 33, 42, and 63.

40. The composition according to embodiment 36 or 39, wherein the composition comprises two or more microbial strains, wherein the 16S rRNA gene of each of said strains comprises a sequence independently selected from SEQ ID Nos.: 21, 22, 23, 25, 31, 33, 42, and 63.

41. The composition according to any one of embodiments 36, 39 or 40, wherein the composition comprises one or more microbial strains, wherein the 16S rRNA gene of each of said strains comprises a sequence independently selected from SEQ ID Nos.: 25 and 63, and wherein said composition optionally further comprises one or more additional microbial strains, wherein the 16S rRNA gene of each of said additional strains comprises a sequence independently selected from the group consisting of SEQ ID Nos.: 21, 22, 23, 31, 33, and 42.

42. The composition according to any one of embodiments 36 and 39-41, wherein the composition comprises at least eight (8) microbial strains, wherein the 16S rRNA genes of said at least eight strains comprise sequences of SEQ ID Nos.: 21, 22, 23, 25, 31, 33, 42, and 63, respectively.

43. The composition according to embodiment 36, wherein the composition comprises one or more microbial strains, wherein the 16S rRNA gene of each of said strains comprises a sequence independently selected from SEQ ID Nos.: 20, 24, 30, 32, 41, and 62.

44. The composition according to embodiment 36 or 43, wherein the composition comprises two or more microbial strains, wherein the 16S rRNA gene of each of said strains comprises a sequence independently selected from SEQ ID Nos.: 20, 24, 30, 32, 41, and 62.

45. The composition according to any one of the embodiments 36, 43 and 44, wherein the composition comprises at least six (6) microbial strains, wherein the 16S rRNA genes of said at least six strains comprise sequences of SEQ ID Nos.: 20, 24, 30, 32, 41, and 62, respectively.

46. A composition comprising a microbial strain, wherein the 16S rRNA gene of said strain comprises a sequence selected from the group consisting of SEQ ID Nos.: 18, 19, 36, 37, 75, and 76.

47. The composition according to embodiment 46, wherein the composition comprises one or more microbial strains, wherein the 16S rRNA gene of each of said strains comprises a sequence independently selected from SEQ ID Nos.: 19, 37, and 76.

48. The composition according to embodiment 46 or 47, wherein the composition comprises two or more microbial strains, wherein the 16S rRNA gene of each of said strains comprises a sequence independently selected from SEQ ID Nos.: 19, 37, and 76.

49. The composition according to anyone of embodiments 46-48, wherein the composition comprises at least three (3) microbial strains, wherein the 16S rRNA genes of said at least three strains comprise sequences of SEQ ID Nos.: 19, 37, and 76, respectively.

50. The composition according to embodiment 46, wherein the composition comprises one or more microbial strains, wherein the 16S rRNA gene of each of said strains comprises a sequence independently selected from SEQ ID Nos.: 18, 36, and 75.

51. The composition according to embodiment 46 or 50, wherein the composition comprises two or more microbial strains, wherein the 16S rRNA gene of each of said strains comprises a sequence independently selected from SEQ ID Nos.: 18, 36, and 75.

52. The composition according to any one of embodiments 46, 50 and 51, wherein the composition comprises at least three (3) microbial strains, wherein the 16S rRNA genes of said at least three strains comprise sequences of SEQ ID Nos.: 18, 36, and 75, respectively.

53. A composition comprising a microbial strain, wherein the 16S rRNA gene of each of said strain comprises a sequence independently selected from SEQ ID Nos.: 11, 13, 58, 59, 60, and 61.

54. The composition according to embodiment 53, wherein the microbial composition comprises one or more microbial strains, wherein the 16S rRNA gene of each of said strains comprises a sequence independently selected from SEQ ID Nos.: 13, 59, and 61, or a culture thereof.

55. The composition according to embodiment 53, wherein the microbial composition comprises two or more microbial strains, wherein the 16S rRNA gene of each of said strains comprises a sequence independently selected from SEQ ID Nos.: 13, 59, and 61, or cultures thereof.

56. The composition according to embodiment 53, wherein the microbial composition comprises at least three (3) microbial strains, wherein the 16S rRNA genes of said at least three strains comprise sequences of SEQ ID Nos.: 13, 59, and 61, respectively, or cultures thereof.

57. The composition according to embodiment 53, wherein the microbial composition comprises one or more microbial strains, wherein the 16S rRNA gene of each of said strains comprises a sequence independently selected from SEQ ID Nos.: 11, 58, and 60, or a culture thereof.

58. The composition according to embodiment 53, wherein the microbial composition comprises two or more microbial strains, wherein the 16S rRNA gene of each of said strains comprises a sequence independently selected from SEQ ID Nos.: 11, 58, and 60, or cultures thereof.

59. The composition according to embodiment 53, wherein the microbial composition comprises at least three (3) microbial strains, wherein the 16S rRNA genes of said at least three strains comprise sequences of SEQ ID Nos.: 11, 58, and 60, respectively, or cultures thereof.

60. A composition comprising a microbial strain, wherein the 16S rRNA gene of each of said strain comprises a sequence independently selected from SEQ ID Nos.: 27, 38, 39, 40, 43, 44, 45, and 77.

61. The composition according to embodiment 60, wherein the microbial composition comprises one or more microbial strains, wherein the 16S rRNA gene of each of said strains comprises a sequence independently selected from SEQ ID Nos.: 40 and 45, or a culture thereof.

62. The composition according to embodiment 60, wherein the microbial composition comprises at least two (2) microbial strains, wherein the 16S rRNA genes of said at least two strains comprise sequences of SEQ ID Nos.: 40 and 45, respectively, or cultures thereof.

63. The composition according to embodiment 60, wherein the microbial composition comprises one or more microbial strains, wherein the 16S rRNA gene of each of said strains comprises a sequence independently selected from SEQ ID Nos.: 39, 44, and 77, or a culture thereof.

64. The composition according to embodiment 60, wherein the microbial composition comprises two or more microbial strains, wherein the 16S rRNA gene of each of said strains comprises a sequence independently selected from SEQ ID Nos.: 39, 44, and 77, or cultures thereof.

65. The composition according to embodiment 60, wherein the microbial composition comprises one or more microbial strains, wherein the 16S rRNA gene of each of said strains comprises a sequence independently selected from SEQ ID Nos.: 39 and 44, and wherein said composition optionally further comprises one additional microbial strains, wherein the 16S rRNA gene of said additional strain comprises a sequence independently selected from the group consisting of SEQ ID No.: 77, or cultures thereof.

66. The composition according to embodiment 60, wherein the microbial composition comprises at least three microbial strains, wherein the 16S rRNA genes of said at least three strains comprise sequences of SEQ ID Nos.: 39, 44, and 77, respectively, or cultures thereof.

67. The composition according to embodiment 60, wherein the microbial composition comprises one or more microbial strains, wherein the 16S rRNA gene of each of said strains comprises a sequence independently selected from SEQ ID Nos.: 27, 38, and 43, or a culture thereof.

68. The composition according to embodiment 60, wherein the microbial composition comprises two or more microbial strains, wherein the 16S rRNA gene of each of said strains comprises a sequence independently selected from SEQ ID Nos.: 27, 38, and 43, or cultures thereof.

69. The composition according to embodiment 60, wherein the microbial composition comprises at least three microbial strains, wherein the 16S rRNA genes of said at least three strains comprise sequences of SEQ ID Nos.: 27, 38, and 43, respectively, or cultures thereof.

70. A composition comprising a microbial strain, wherein the 16S rRNA gene of each of said strain comprises a sequence independently selected from SEQ ID Nos.: 1, 3, 4, 7, 8, 51, 52, 53, 134, and 135.

71. The composition according to embodiment 70, wherein the microbial composition comprises one or more microbial strains, wherein the 16S rRNA gene of each of said strains comprises a sequence independently selected from SEQ ID Nos.: 8, 53, and 135, or a culture thereof.

72. The composition according to embodiment 70, wherein the microbial composition comprises two or more microbial strains, wherein the 16S rRNA gene of each of said strains comprises a sequence independently selected from SEQ ID Nos.: 8, 53, and 135, or a culture thereof.

73. The composition according to embodiment 70, wherein the microbial composition comprises at least three microbial strains, wherein the 16S rRNA genes of said at least three strains comprise sequences of SEQ ID Nos.: 8, 53, and 135, respectively, or cultures thereof.

74. The composition according to embodiment 70, wherein the microbial composition comprises one or more microbial strains, wherein the 16S rRNA gene of each of said strains comprises a sequence independently selected from SEQ ID Nos.: 3, 7, 52, and 134, or a culture thereof.

75. The composition according to embodiment 70, wherein the microbial composition comprises two or more microbial strains, wherein the 16S rRNA gene of each of said strains comprises a sequence independently selected from SEQ ID Nos.: 3, 7, 52, and 134, or cultures thereof.

76. The composition according to embodiment 70, wherein the microbial composition comprises one or more microbial strains, wherein the 16S rRNA gene of each of said strains comprises a sequence independently selected from SEQ ID Nos.: 7, 52, and 134, and wherein said composition optionally further comprises an additional microbial strains, wherein the 16S rRNA gene of said additional strain comprises a sequence independently selected from the group consisting of SEQ ID No.: 3, or cultures thereof.

77. The composition according to embodiment 70, wherein the microbial composition comprises at least four microbial strains, wherein the 16S rRNA genes of said at least four strains comprise sequences of SEQ ID Nos.: 3, 7, 52, and 134, respectively, or cultures thereof 78. The composition according to embodiment 70, wherein the microbial composition comprises one or more microbial strains, wherein the 16S rRNA gene of each of said strains comprises a sequence independently selected from SEQ ID Nos.: 1, 4, and 51, or a culture thereof.

79. The composition according to embodiment 70, wherein the microbial composition comprises two or more microbial strains, wherein the 16S rRNA gene of each of said strains comprises a sequence independently selected from SEQ ID Nos.: 1, 4, and 51, or cultures thereof.

80. The composition according to embodiment 70, wherein the microbial composition comprises at least three microbial strains, wherein the 16S rRNA genes of said at least three strains comprise sequences of SEQ ID Nos.: 1, 4, and 51, respectively, or cultures thereof.

81. A composition comprising a microbial strain, wherein the 16S rRNA gene of each of said strain comprises a sequence independently selected from SEQ ID Nos.: 14, 16, 78, 79, and 80.

82. The composition according to embodiment 81, wherein the microbial composition comprises a microbial strain, wherein the 16S rRNA gene of said strain comprises a sequence that is SEQ ID No.: 79, or a culture thereof.

83. The composition according to embodiment 81, the microbial composition comprises one or more microbial strains, wherein the 16S rRNA gene of each of said strains comprises a sequence independently selected from SEQ ID Nos.: 78 and 80, or a culture thereof.

84 The composition according to embodiment 81, the microbial composition comprises at least two microbial strains, wherein the 16S rRNA genes of said at least two strains comprise sequences of SEQ ID Nos.: 78 and 80, respectively, or cultures thereof.

85. The composition according to embodiment 81, the microbial composition comprises one or more microbial strains, wherein the 16S rRNA gene of each of said strains comprises a sequence independently selected from SEQ ID Nos.: 14 and 16, or a culture thereof.

86. The composition according to embodiment 81, the microbial composition comprises at least two microbial strains, wherein the 16S rRNA genes of said at least two strains comprise sequences of SEQ ID Nos.: 14 and 16, respectively, or cultures thereof.

87. A composition comprising a microbial strain, wherein the 16S rRNA gene of each of said strain comprises a sequence independently selected from SEQ ID Nos.: 43, 44, 45, 81, 82, 83, 84, 145 and 146.

88. The composition according to embodiment 87, wherein the microbial composition comprises one or more microbial strains, wherein the 16S rRNA gene of each of said strains comprises a sequence independently selected from SEQ ID Nos.: 45, 83 and 146, or a culture thereof.

89. The composition according to embodiment 87, wherein the microbial composition comprises at least two (2) microbial strains, wherein the 16S rRNA genes of said at least two strains comprise sequences of SEQ ID Nos.: 45, 83 and 146, respectively, or cultures thereof.

90. The composition according to embodiment 87, wherein the microbial composition comprises one or more microbial strains, wherein the 16S rRNA gene of each of said strains comprises a sequence independently selected from SEQ ID Nos.: 44, 82 and 145, or a culture thereof.

91. The composition according to embodiment 87, wherein the microbial composition comprises two or more microbial strains, wherein the 16S rRNA gene of each of said strains comprises a sequence independently selected from SEQ ID Nos.: 44, 82, and 145, or cultures thereof.

92. The composition according to embodiment 87, wherein the microbial composition comprises one or more microbial strains, wherein the 16S rRNA gene of each of said strains comprises a sequence independently selected from SEQ ID Nos.: 44 and 82, and wherein said composition optionally further comprises one additional microbial strains, wherein the 16S rRNA gene of said additional strain comprises a sequence independently selected from the group consisting of SEQ ID No.: 145, or cultures thereof.

93. The composition according to embodiment 87, wherein the microbial composition comprises at least three microbial strains, wherein the 16S rRNA genes of said at least three strains comprise sequences of SEQ ID Nos.: 44, 82 and 145, respectively, or cultures thereof.

94. The composition according to embodiment 87, wherein the microbial composition comprises one or more microbial strains, wherein the 16S rRNA gene of each of said strains comprises a sequence independently selected from SEQ ID Nos.: 43, 81 and 84, or a culture thereof.

95. The composition according to embodiment 87, wherein the microbial composition comprises two or more microbial strains, wherein the 16S rRNA gene of each of said strains comprises a sequence independently selected from SEQ ID Nos.: 43, 81, and 84, or cultures thereof.

96. The composition according to embodiment 87, wherein the microbial composition comprises at least three microbial strains, wherein the 16S rRNA genes of said at least three strains comprise sequences of SEQ ID Nos.: 43, 81 and 84, respectively, or cultures thereof.

97. A composition comprising a microbial strain, wherein the 16S rRNA gene of each of said strain comprises a sequence independently selected from SEQ ID Nos.: 24, 86, 87, and 88.

98. The composition according to embodiment 97, wherein the microbial composition comprises one or more microbial strains, wherein the 16S rRNA gene of each of said strains comprises a sequence independently selected from SEQ ID Nos.: 87 and 88, or a culture thereof.

99. The composition according to embodiment 97, wherein the microbial composition comprises at least two microbial strains, wherein the 16S rRNA genes of said at least two strains comprise sequences of SEQ ID Nos.: 87 and 88, respectively, or cultures thereof.

100. The composition according to embodiment 97, wherein the microbial composition comprises one or more microbial strains, wherein the 16S rRNA gene of each of said strains comprises a sequence independently selected from SEQ ID Nos.: 24 and 86, or a culture thereof.

101. The composition according to embodiment 97, wherein the microbial composition comprises at least two microbial strains, wherein the 16S rRNA genes of said at least two strains comprise sequences of SEQ ID Nos.: 24 and 86, respectively, or cultures thereof.

102 A composition comprising a microbial strain, wherein the 16S rRNA gene of each of said strain comprises a sequence independently selected from SEQ ID Nos.: 51, 52, 53, 81, 82, and 83.

103. The composition according to embodiment 102, wherein the microbial composition comprises one or more microbial strains, wherein the 16S rRNA gene of each of said strains comprises a sequence independently selected from SEQ ID Nos.: 53 and 83, or a culture thereof.

104. The composition according to embodiment 102, wherein the microbial composition comprises at least two (2) microbial strains, wherein the 16S rRNA genes of said at least two strains comprise sequences of SEQ ID Nos.: 53 and 83, respectively, or cultures thereof.

105. The composition according to embodiment 102 wherein the microbial composition comprises one or more microbial strains, wherein the 16S rRNA gene of each of said strains comprises a sequence independently selected from SEQ ID Nos.: 52 and 82, or a culture thereof.

106. The composition according to embodiment 102, wherein the microbial composition comprises at least two microbial strains, wherein the 16S rRNA genes of said at least two strains comprise sequences of SEQ ID Nos.: 52 and 82, respectively, or cultures thereof.

107. The composition according to embodiment 102, wherein the microbial composition comprises one or more microbial strains, wherein the 16S rRNA gene of each of said strains comprises a sequence independently selected from SEQ ID Nos.: 51 and 81, or a culture thereof.

108. The composition according to embodiment 102, wherein the microbial composition comprises at least two microbial strains, wherein the 16S rRNA genes of said at least two strains comprise sequences of SEQ ID Nos.: 51 and 81, respectively, or cultures thereof.

109. A composition comprising a microbial strain, wherein the 16S rRNA gene of each of said strain comprises a sequence independently selected from SEQ ID Nos.: 51, 52, 53, 75, 76, 81, 82, 83, 84, 145, and 146.

110. The composition according to embodiment 109, wherein the microbial composition comprises one or more microbial strains, wherein the 16S rRNA gene of each of said strains comprises a sequence independently selected from SEQ ID Nos.: 53, 83, and 146, or a culture thereof.

111. The composition according to embodiment 109, wherein the microbial composition comprises two or more microbial strains, wherein the 16S rRNA gene of each of said strains comprises a sequence independently selected from SEQ ID Nos.: 53, 83 and 146, or cultures thereof.

112. The composition according to embodiment 109, wherein the microbial composition comprises at least three microbial strains, wherein the 16S rRNA gene of each of said strains comprises a sequence independently selected from SEQ ID Nos.: 53, 83 and 146, or cultures thereof.

113. The composition according to embodiment 109 wherein the microbial composition comprises one or more microbial strains, wherein the 16S rRNA gene of each of said strains comprises a sequence independently selected from SEQ ID Nos.: 52, 76, 82 and 145, or a culture thereof.

114. The composition according to embodiment 109, wherein the microbial composition comprises two or more microbial strains, wherein the 16S rRNA gene of each of said strains comprises a sequence independently selected from SEQ ID Nos.: 52, 76, 82 and 145, or cultures thereof.

115. The composition according to embodiment 109, wherein the microbial composition comprises one or more microbial strains, wherein the 16S rRNA gene of each of said strains comprises a sequence independently selected from SEQ ID Nos.: 52, 82, and 145, and wherein said composition optionally further comprises an additional microbial strains, wherein the 16S rRNA gene of said additional strain comprises a sequence independently selected from the group consisting of SEQ ID No.: 76, or cultures thereof.

116. The composition according to embodiment 109, wherein the microbial composition comprises at least four microbial strains, wherein the 16S rRNA genes of said at least four strains comprise sequences of SEQ ID Nos.: 52, 76, 82, and 145, respectively, or cultures thereof.

117. The composition according to embodiment 109, wherein the microbial composition comprises one or more microbial strains, wherein the 16S rRNA gene of each of said strains comprises a sequence independently selected from SEQ ID Nos.: 51, 75, 81 and 84, or a culture thereof.

118. The composition according to embodiment 109, wherein the microbial composition comprises two or more microbial strains, wherein the 16S rRNA gene of each of said strains comprises a sequence independently selected from SEQ ID Nos.: 51, 75, 81 and 84, or cultures thereof.

119. The composition according to embodiment 109, wherein the microbial composition comprises three or more microbial strains, wherein the 16S rRNA gene of each of said strains comprises a sequence independently selected from SEQ ID Nos.: 51, 75, 81 and 84, or cultures thereof.

120. The composition according to embodiment 109, wherein the microbial composition comprises at least four microbial strains, wherein the 16S rRNA gene of each of said strains comprises a sequence independently selected from SEQ ID Nos.: 51, 75, 81 and 84, or cultures thereof.

121. A composition comprising a microbial strain, wherein the 16S rRNA gene of said strain comprises a sequence independently selected from SEQ ID Nos.: 51, 52, 53, 75, 76, 81, 82, 83, 84, 145, 146, 86, 87, 160, 161.

122. The composition according to embodiment 121, wherein the microbial composition comprises one or more microbial strains, wherein the 16S rRNA gene of each of said strains comprises a sequence independently selected from SEQ ID Nos.: 53, 83, and 146, or a culture thereof.

123. The composition according to embodiment 121, wherein the microbial composition comprises two or more microbial strains, wherein the 16S rRNA gene of each of said strains comprises a sequence independently selected from SEQ ID Nos.: 53, 83 and 146, or cultures thereof.

124. The composition according to embodiment 121, wherein the microbial composition comprises at least three microbial strains, wherein the 16S rRNA gene of each of said strains comprises a sequence independently selected from SEQ ID Nos.: 53, 83 and 146, or cultures thereof.

125. The composition according to embodiment 121 wherein the microbial composition comprises one or more microbial strains, wherein the 16S rRNA gene of each of said strains comprises a sequence independently selected from SEQ ID Nos.: 52, 76, 82, 145, 87, and 161, or a culture thereof.

126. The composition according to embodiment 121, wherein the microbial composition comprises two or more microbial strains, wherein the 16S rRNA gene of each of said strains comprises a sequence independently selected from SEQ ID Nos.: 52, 76, 82, 145, 87, and 161, or cultures thereof.

127. The composition according to embodiment 121, wherein the microbial composition comprises one or more microbial strains, wherein the 16S rRNA gene of each of said strains comprises a sequence independently selected from SEQ ID Nos.: 52, 82, and 145, and wherein said composition optionally further comprises an additional microbial strains, wherein the 16S rRNA gene of said additional strain comprises a sequence independently selected from the group consisting of SEQ ID No.: 76, 87 and 161, or cultures thereof.

128. The composition according to embodiment 121, wherein the microbial composition comprises at least six microbial strains, wherein the 16S rRNA genes of said at least six strains comprise sequences of SEQ ID Nos.: 52, 76, 82, 145, 87, and 161, respectively, or cultures thereof.

129. The composition according to embodiment 121, wherein the microbial composition comprises one or more microbial strains, wherein the 16S rRNA gene of each of said strains comprises a sequence independently selected from SEQ ID Nos.: 51, 75, 81, 84, 86, and 160, or a culture thereof.

130. The composition according to embodiment 121, wherein the microbial composition comprises two or more microbial strains, wherein the 16S rRNA gene of each of said strains comprises a sequence independently selected from SEQ ID Nos.: 51, 75, 81, 84, 86, and 160, or cultures thereof.

131. The composition according to embodiment 121, wherein the microbial composition comprises three or more microbial strains, wherein the 16S rRNA gene of each of said strains comprises a sequence independently selected from SEQ ID Nos.: 51, 75, 81, 84, 86, and 160, or cultures thereof.

131. The composition according to embodiment 121, wherein the microbial composition comprises at least four microbial strains, wherein the 16S rRNA gene of each of said strains comprises a sequence independently selected from SEQ ID Nos.: 51, 75, 81, 84, 86, and 160, or cultures thereof.

132. The composition according to embodiment 121, wherein the microbial composition comprises at least five microbial strains, wherein the 16S rRNA gene of each of said strains comprises a sequence independently selected from SEQ ID Nos.: 51, 75, 81, 84, 86, and 160, or cultures thereof.

133. The composition according to embodiment 121, wherein the microbial composition comprises at least six microbial strains, wherein the 16S rRNA gene of each of said strains comprises a sequence independently selected from SEQ ID Nos.: 51, 75, 81, 84, 86, and 160, or cultures thereof.

134. A composition comprising one or more microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646, and strains derived therefrom, or cultures thereof.

135. The composition according to embodiment 134, wherein the one or more microbial strains are selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, and strains derived therefrom, or cultures thereof.

136. The composition according to embodiment 134, wherein the one or more microbial strains are selected from P0042_A8 or S2167, P0042_D5 or S2165, P0042_B2 or S2168, P0042_B12 or S2189, P0042_C2 or S2173, P0042_D10 or S2172, P0044_A3 or S2476, and strains derived therefrom, or cultures thereof.

137. The composition according to embodiment 134, wherein the one or more microbial strains are selected from P0018_A11, P0044_A5, P0047_E2, P0047_C1, P0038_D2 or S2166, P0042_E1, 106_E8, P0018_A1, and strains derived therefrom, or cultures thereof.

138. The composition according to embodiment 134, wherein the one or more microbial strains are selected from S2159_P0058_B9, S2161_P0054_E8, S2164_P0054_F4, P0057_A3 or S2160, S2142_P0061_E11, S2163_P0019_A12, and strains derived therefrom, or cultures thereof.

139. The composition according to embodiment 134, wherein the one or more microbial strains are selected from P0147_D10 or S2291; P0147_G10 or S2292; PS160_F7 or S2351, and strains derived therefrom, or cultures thereof.

140. The composition according to embodiment 134, wherein the one or more microbial strains are selected from P0140_C10 or S2300; S2387; P0157_G5 or S2303, and strains derived therefrom, or cultures thereof.

141. The composition according to embodiment 134, wherein the one or more microbial strains are selected from P0160_E1 or S2374; P0134_G7 or S2280; S2384, and strains derived therefrom, or cultures thereof.

142. The composition according to embodiment 134, wherein the one or more microbial strains are selected from S2275; S2278, and strains derived therefrom, or cultures thereof.

143. The composition according to embodiment 134, wherein the one or more microbial strains are selected from P0157_G5 or S2303; S2373; S2375, and strains derived therefrom, or cultures thereof.

144. The composition according to embodiment 134, wherein the one or more microbial strains are selected from S2293; S2382, and strains derived therefrom, or cultures thereof.

145. The composition according to embodiment 134, wherein the one or more microbial strains are selected from S2385 and S2373, and strains derived therefrom, or cultures thereof.

146. The composition according to embodiment 134, wherein the one or more microbial strains are selected from S2385, S2669, S2373 and S2375, and strains derived therefrom, or cultures thereof.

147. The composition according to embodiment 134, wherein the one or more microbial strains are selected from S2385, S2669, S2373, S2375, S2293, and S2644, and strains derived therefrom, or cultures thereof.

148. A synthetic microbial consortium, comprising:
a) a first set of microbes comprising one or more microbes that promote plant health, growth, and/or yield; and
b) a second set of microbes comprising one or more microbes that increase the competitive fitness of the first set of microbes in a);
wherein the first and the second sets of microbes are combined into a single mixture as a synthetic consortium.

149. The synthetic microbial consortium according to embodiment 148, wherein one or more microbes of the first set of microbes enhance nutrient availability and/or nutrient uptake of a plant, modulate plant hormone levels, or inhibit or suppress a plant pathogen (e.g., as a biological pesticide).

150. The synthetic microbial consortium according to embodiment 148, wherein one or more microbes in the first set of microbes demonstrate one or more of the activities selected from nitrogen fixation, IAA production, ACC deaminase activity, phosphate solubilization, and/or iron solubilization.

151. The synthetic microbial consortium according to embodiment 148, wherein one or more microbes in the second set of microbes produce a metabolite that enhances the competitive fitness of one or more microbes in the first set of microbes.

152. The synthetic microbial consortium according to embodiment 148, wherein one or more microbes in the second set of microbes produce a siderophore that enhances iron acquisition of one or more of the microbes in the first set of microbes.

153. The synthetic microbial consortium according to embodiment 148, wherein one or more microbes in the second set of microbes produce a metabolite that is bactericidal, bacteriostatic or otherwise modulates growth of a microorganism that is distinct from the microbes of the first and the second sets of microbes, and that is detrimental to the fitness of one or more microbes in the first set of microbes.

154. The synthetic consortia according to embodiment 148, wherein one or more microbes in the second set of microbes produce a siderophore that inhibits the growth or fitness of a microorganism that is potentially detrimental to one or more microbes in the first set.

155. A composition comprising a synthetic consortium according to any one of embodiments 148-154.

156. A method of preparing a synthetic microbial consortium to benefit plant health and growth performance comprising,
a) selecting a first set of microbes comprising one or more microbes that promote plant health, growth, and/or yield;
b) selecting a second set of microbes comprising one or more microbes that increase the competitive fitness of the first set of microbes; and
c) combining these microbes into a single mixture and designating the combination as a synthetic consortium.

157. The method according to embodiment 156, wherein one or more microbes of the first set of microbes enhance nutrient availability and/or nutrient uptake of a plant, modulate plant hormone levels, or inhibit or suppress a plant pathogen (e.g., as a biological pesticide).

158. The method according to embodiment 156 wherein one or more microbes in the first set of microbes demonstrate one or more of the activities selected from nitrogen fixation, IAA production, ACC deaminase activity, phosphate solubilization, and/or iron solubilization.

159. The method according to embodiment 156, wherein one or more microbes in the second set of microbes produce a metabolite that enhances the competitive fitness of one or more microbes in the first set of microbes.

160. The method according to embodiment 159, wherein one or more microbes in the second set of microbes produce a siderophore that enhances iron acquisition of one or more of the microbes in the first set of microbes.

161. The method according to embodiment 156, wherein one or more microbes in the second set of microbes produce a metabolite that is bactericidal, bacteriostatic or otherwise modulates growth of a microorganism that is distinct from the microbes of the first and the second sets of microbes, and potentially detrimental to the fitness of one or more microbes in the first set of microbes.

162. The method according to embodiment 161, wherein one or more microbes in the second set of microbes produce a siderophore that inhibits the growth or fitness of a microorganism that is potentially detrimental to one or more microbes in the first set.

163. The method of any one of embodiments 156-161, wherein the microbes in step (b) are supplemented with an inert formulary component.

164. A synthetic microbial consortia prepared by a method according to any one of embodiments 156-163.

165. A composition comprising a synthetic microbial consortia prepared by a method according to any one of embodiments 156-163.

166. The composition according to any one of embodiments 11-133, 155 and 165, further comprising an agriculturally effective amount of a compound or composition selected from the group consisting of a nutrient, a fertilizer, an acaricide, a bactericide, a fungicide, an insecticide, a microbicide, a nematicide, and a pesticide.

167. A composition comprising a microbial strain, wherein the 16S rRNA gene of said strain comprises a sequence selected from the group consisting of SEQ ID Nos.: 1-164, and further comprising an agriculturally effective amount of a compound or composition selected from the group consisting of a nutrient, a fertilizer, an acaricide, a bactericide, a fungicide, an insecticide, a microbicide, a nematicide, and a pesticide.

168. The composition according to any one of embodiments 11-133, 155, and 165-167, further comprising a carrier.

169. The composition according to embodiment 168, wherein said carrier is selected from peat, turf, talc, lignite, kaolinite, pyrophyllite, zeolite, montmorillonite, alginate, press mud, sawdust and vermiculite.

170. The composition according any one of embodiments 11-133, 155, and 165-169, wherein the composition is prepared as a formulation selected from the group consisting of an emulsion, a colloid, a dust, a granule, a pellet, a powder, a spray, and a solution.

171. The composition according to embodiment 168, wherein said carrier is a plant seed.

172. A plant seed having a coating comprising a microbial strain or a culture according to any one of embodiments 1-10.

173. A plant seed having a coating comprising the composition according to any one of embodiments 11-133, 155, and 165-170.

174. A method for treating a plant seed or seed priming, said method comprising a step of exposing or contacting said plant seed with a microbial strain or culture according to any one of embodiments 1-10.

175. A method for treating a plant seed or seed priming, said method comprising a step of exposing or contacting said plant seed with a composition according to any one of embodiments 11-133, 155, and 165-170.

176. A method for enhancing the health, growth or yield of a plant, said method comprising applying an effective amount of a microbial strain or culture according to any one of embodiments 1-10 to the plant or to the plant's surroundings.

177. A method for enhancing the growth or yield of a plant, said method comprising applying an effective amount of a composition according to any one of embodiments 11-133, 155, and 165-170 to the plant or to the plant's surroundings.

178. The method according to embodiment 176 or 177, further comprising a step of sterilizing soil before planting a plant, a plant seed or a plant seedling in said soil.

179. The method according to any one of embodiments 176-178, wherein said microbial strain is grown in a growth medium or soil of a host plant prior to or concurrent with the host plant growth in said growth medium or soil.

180. The method according to any one of embodiments 176-179, wherein said microbial strain is established as an endophyte on said plant.

181. A method for preventing, inhibiting or treating the development of a pathogenic disease of a plant, said method comprising applying an effective amount of a microbial strain or culture according to any one of embodiments 1-10 to the plant or to the plant's surroundings.

182. A method for preventing, inhibiting or treating the development of a pathogenic disease of a plant, said method comprising applying an effective amount of a composition according to any one of embodiments 11-133, 155, and 165-170 to the plant or to the plant's surroundings.

183. The method according to embodiment 181 or 182, wherein the microbial strain is grown in a growth medium or soil of a host plant prior to or concurrent with the host plant growth in said growth medium or soil.

184. The method according to any one of embodiments 181-183, wherein the pathogenic disease is caused by a plant pathogen selected from the group consisting of *Colletotrichum*, *Fusarium*, *Gibberella*, *Monographella*, *Penicillium*, *Pythium*, and *Stagnospora* organisms.

185. The method according to any one of embodiments 176-184, wherein the microbial strain is applied to soil, a seed, a root, a flower, a leaf, a fruit, a portion of the plant or the whole plant.

186. The method according to any one of embodiments 176-185, wherein said plant is a corn plant, a soy bean plant or a tomato plant.

187. A plant that is artificially infected with a microbial strain or culture according to any one of embodiments 1-10.

188. A plant that is artificially infected with a composition according to any one of embodiments 11-133, 155, and 165-170.

189. A plant seed, reproductive tissue, vegetative tissue, regenerative tissue, plant part or progeny of the plant according to embodiment 188.

190. A method for assembling a microbial consortium comprising two or more microbial strains associated with plant health, growth and/or yield, said method comprising the steps of:

(1) providing a plurality of plant rhizosphere samples;
(2) isolating a plurality of genomic DNAs from each of the samples provided in step (1);
(3) determining the sequences of a plurality of 16S rRNA gene segments from each plurality of genomic DNAs isolated in step (2);
(4) determining the abundance (absolute or relative) of each of said 16S rRNA gene segments in each plurality of 16S rRNA gene segments whose sequences were determined in step (3);
(5) determining the plant biomass or the abundance of a parameter associated therewith (e.g., plant weight, plant height, root size/length, etc.) or the plant yield for each of the plants from which the rhizosphere samples of step (1) were collected;
(6) correlating the abundance of each 16S rRNA gene segment determined in step (4) with the plant biomass or the abundance of a parameter associated therewith (e.g., plant weight, plant height, root size/length, etc.) or the plant yield determined in step (5);
(7) selecting at least one 16S rRNA gene segment whose abundance correlates to the plant biomass or the abundance of a parameter associated therewith (e.g., plant weight, plant height, root size/length, etc.) or the plant yield, as determined in step (6);
(8) correlating the abundance of the at least one 16S rRNA gene segment selected in step (7) with the abundances of the other of the plurality of 16S rRNA gene segments whose sequences were determined in step (3) across said plurality of samples;
(9) identifying one or more 16S rRNA gene segments whose abundances correlate with the abundance of the at least one 16S rRNA gene segment selected in step (7) across said plurality of samples;
(10) identifying two or more microbial strains, which comprises the 16S rRNA gene segments identified in steps (7) and (9), respectively; and
(11) assembling said two or more microbial strains identified in step (10) into a microbial consortium by combining said strains into a single mixture.

191. A microbial consortium assembled by the method according to embodiment 190.

192. A method of enhancing the health, growth or yield of a plant, said method comprising applying an effective amount of a microbial consortium according to embodiment 191 to the plant or to the plant's surroundings.

193. A composition comprising one or more microbial strains wherein the 16S sequence of the one or more microbial strains comprises any one of SEQ ID Nos: 1-164.

194. The composition of embodiment 193, comprising at least two microbial strains wherein the 16S sequence of the at least two microbial strains comprises any one of SEQ ID Nos: 1-164.

195. The composition of embodiment 193, comprising at least three microbial strains wherein the 16S sequence of at least three microbial strains comprises any one of SEQ ID Nos: 1-164.

196. The composition of embodiment 193, comprising at least four microbial strains wherein the 16S sequence of at least four microbial strains comprises any one of SEQ ID Nos: 1-164.

197. A composition comprising a microbial consortium selected from the group comprising:
a) Consortium A: P0035_B2 or S2145, P0032_C7, P0020_B1, P0047_A1 or S2284, P0032_A8 or S2181, P0049_E7, P0033_E1 or S2177;
b) Consortium B: P0042_A8 or S2167, P0042_C2 or S2173, P0042_D10 or S2172, P0044_A3 or S2476, P0042_B12 or S2189, P0042_B2 or S2168, P0042_D5 or S2165;
c) Consortium C: P0038_D2 or S2166, P0018_A11, P0047_E2, P0018_A1, P0047_C1, P0042_E1, P0047_E8;
d) Consortium D: S2142_P0061_E11, S2161_P0054_E8, S2164_P0054_F4, P0057_A3 or S2160, S2159_P0058_B9, S2163_P0019_A12;
e) Consortium E: P0147_D10 or S2291, P0160_F7 or S2351, P0147_G10 or S2292;
f) Consortium F: P0140_C10 or S2300, S2387, P0157_G5 or S2303;
g) Consortium G: S2384, P0160_E1 or S2374, P0134_G7 or S2280;
h) Consortium H: S2275, S2278;
i) Consortium I: S2373, S2375, P0157_G5 or S2303;
j) Consortium J: S2293, S2382;
k) Consortium K: S2385 and S2373;
l) Consortium N: S2327 (or SEQ ID Nos.: 99 or 100), S2329 (or SEQ ID Nos.: 97 or 98), S2330 (or SEQ ID Nos.: 101 or 102), S2332 (or SEQ ID Nos.: 113, 114 or 115), S2333 (or SEQ ID Nos.: 95 or 96) and S2328 (or SEQ ID Nos.: 162 or 163);
m) Consortium P: S2373 (or SEQ ID Nos.: 81, 82, or 83) and P0042_B2 or S2168 (or SEQ ID Nos.: 65 or 66);
n) Consortium R: S2385 (or SEQ ID Nos.: 51, 52 or 53) and P0042_B2 or S2168 (or SEQ ID Nos.: 65 or 66);
o) Consortium S: S2385 (or SEQ ID Nos.: 51, 52 or 53) and S2421 (or SEQ ID Nos.: 136 or 137);
p) Consortium T: S2385 (or SEQ ID Nos.: 51, 52 or 53) and S2330 (or SEQ ID Nos.: 101 or 102);
q) Consortium AB: S2159_P0058_B9 (or SEQ ID Nos.: 18 or 19), S2161_P0054_E8 (or SEQ ID Nos.: 36 or 37) and S2163_P0019_A12 (or SEQ ID Nos. 75 or 76);
r) Consortium AC: S2373 (or SEQ ID Nos.: 81, 82, or 83), S2385 (or SEQ ID Nos.: 51, 52 or 53), P0147_D10 or S2291 (or SEQ ID Nos.: 11 or 13), S2293 (or SEQ ID Nos.: 86 or 87), S2382 (or SEQ ID Nos.: 24 or 88), S2487 (or SEQ ID Nos.: 20 or 129), S2644 (or SEQ ID Nos.: 160 or 161), P0042_A8 or S2167 (or SEQ ID Nos.: 34 or 35), P0038_D2 or S2166 (or SEQ ID Nos.: 30 or 31), P0042_D10 or S2172 (or SEQ ID Nos.: 70, 73 or 74), S2159_P0058_B9 (or SEQ ID Nos.: 18 or 19), S2161_P0054_E8 (or SEQ ID Nos.: 36 or 37), and S2163_P0019_A12 (or SEQ ID Nos. 75 or 76); or
s) Consortium AF: S2373 (or SEQ ID Nos.: 81, 82, or 83), S2385 (or SEQ ID Nos.: 51, 52 or 53) and S2646 (or SEQ ID Nos.: 16 or 164).

198. The composition of claim 134, comprising at least two microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646, and strains derived therefrom, or cultures thereof.

199. The composition of claim 134, comprising at least three microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646, and strains derived therefrom, or cultures thereof.

200. The composition of claim 134, comprising at least four microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, and S2646, and strains derived therefrom, or cultures thereof.

DETAILED DESCRIPTION

A. Definitions

Figure 1:
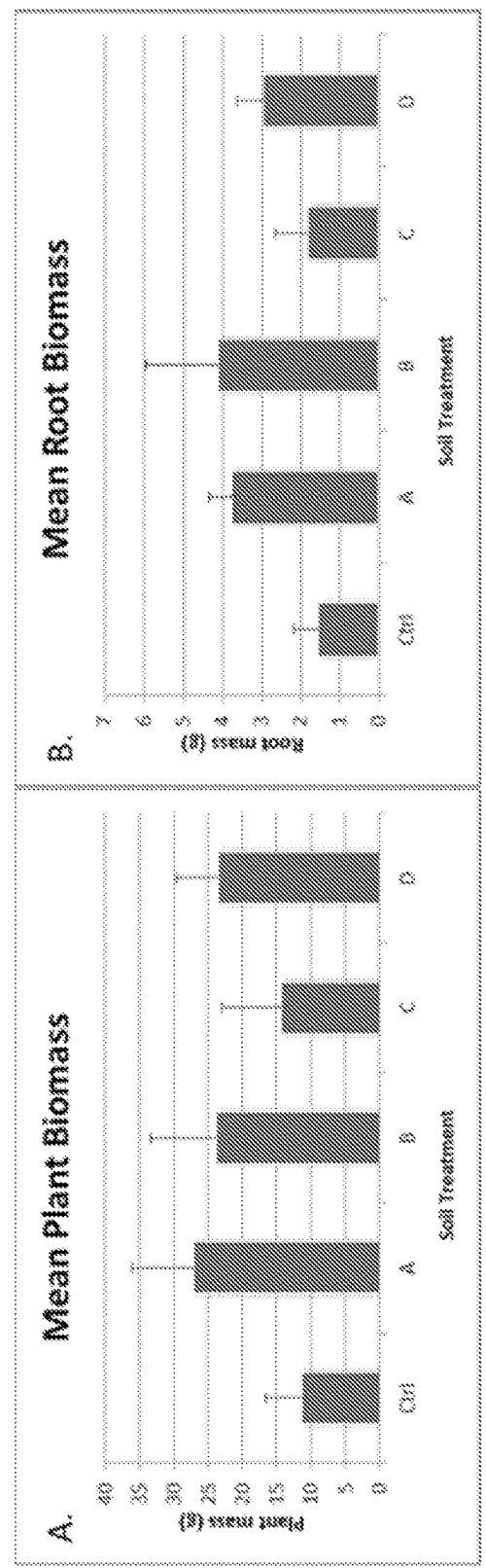
FIG. 1A shows the mean sweet corn plant biomass of each treatment (n=3; +/− standard deviation) of sweet corn seed treated with microbial consortia A-D in sterile soil.
FIG. 1B shows the mean sweet corn root biomass of each treatment (n=3; +/− standard deviation) of sweet corn seed treated with microbial consortia A-D in sterile soil.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed by those skilled in the art.

The singular form "a", "an", and "the" include plural references unless the context clearly dictates otherwise. For example, the term "a cell" includes one or more cells, including mixtures thereof.

As used herein, an isolated strain of a microbe is a strain that has been removed from its natural milieu. As such, the term "isolated" does not necessarily reflect the extent to which the microbe has been purified. But, in different embodiments, an "isolated" culture has been purified at least 2× or 5× or 10× or 50× or 100× from the raw material from which it is isolated. As a non-limiting example, if a culture is isolated from soil as raw material, the organism can be isolated to an extent that its concentration in a given quantity of purified or partially purified material (e.g., soil) is at least 2× or 5× or 10× or 50× or 100× of that in the original raw material.

A "substantially pure culture" of the strain of microbe refers to a culture which contains substantially no other microbes than the desired strain or strains of microbe. In other words, a substantially pure culture of a strain of microbe is substantially free of other contaminants, which can include microbial contaminants as well as undesirable chemical contaminants.

As used herein, a "biologically pure" strain is intended to mean the strain separated from materials with which it is normally associated in nature. A strain associated with other strains, or with compounds or materials that it is not normally found with in nature, is still defined as "biologically pure." A monoculture of a particular strain is, of course, "biologically pure." In different embodiments, a "biologically pure" culture has been purified at least 2× or 5× or 10× or 50× or 100× or 1000× or higher (to the extent considered feasible by a skilled person in the art) from the material with which it is normally associated in nature. As a non-limiting example, if a culture is normally associated with soil, the organism can be biologically pure to an extent that its concentration in a given quantity of purified or partially purified material with which it is normally associated (e.g. soil) is at least 2× or 5× or 10× or 50× or 100×, or 1000× or higher (to the extent considered feasible by a skilled person in the art) that in the original unpurified material.

As used herein, the term "enriched culture" of an isolated microbial strain refers to a microbial culture wherein the total microbial population of the culture contains more than 50%, 60%, 70%, 80%, 90%, or 95% of the isolated strain.

The term "culturing", as used herein, refers to the propagation of organisms on or in media of various kinds. Suitable media are known to a person with ordinary skill in the art.

A "composition" as used herein means a combination of an active agent (e.g., a PGPM or microbial strain described herein) and at least one other compound, carrier, or composition, which can be inert (for example, a detectable agent or label or liquid carrier) or active, such as, but not limited to, a fertilizer, nutrient, or pesticide. A microbial composition refers to a composition comprising at least one microbial species.

Ribosomes, which are comprised of numerous ribosomal proteins and three ribosomal RNA (rRNA) molecules, are a key component of protein synthesis. The 16S subunit rRNA, which is encoded by the 16S rRNA gene, has been the focus of much attention in microbial phylogenetic studies. The 16S rRNA gene sequence is highly conserved between taxonomic groups, yet also possesses regions that are highly polymorphic. Moreover, the rate of change in the RNA sequence is thought to have been relatively constant over evolutionary time, enabling scientists to determine the relative relatedness of different organisms.

An "effective amount", as used herein, is an amount sufficient to effect beneficial and/or desired results. An effective amount can be administered in one or more administrations. In terms of treatment, inhibition or protection, an effective amount is that amount sufficient to ameliorate, stabilize, reverse, slow or delay progression of the target infection, abiotic stress, or disease state. The expression "effective microorganism" used herein in reference to a microorganism is intended to mean that the subject strain exhibits a degree of promotion of plant health, growth and/or yield or a degree of inhibition of a pathogenic disease that exceeds, at a statistically significant level, that of an untreated control. In some instances, the expression "an effective amount" is used herein in reference to that quantity of microbial treatment which is necessary to obtain a beneficial or desired result relative to that occurring in an untreated control under suitable conditions of treatment as described herein. For example, the expression "an agriculturally effective amount" is used herein in reference to that quantity of microbial treatment which is necessary to obtain an agriculturally beneficial or desired result relative to that occurring in an untreated control under suitable conditions of treatment as described herein. The effective amount of an agricultural formulation or composition that should be applied for the improvement of plant health, growth and/or yield, for the control of, e.g., insects, plant diseases, or weeds, can be readily determined via a combination of general knowledge of the applicable field.

A "nutrient" as used herein means a compound or composition that is able to provide one or more nutrient elements to plants. In some embodiments, a nutrient provides one or more nutrient elements selected from nitrogen (N), phosphorus (P), potassium (K), calcium (Ca), magnesium (Mg), sulfur (S), iron (Fe), manganese (Mn), zinc (Zn), copper (Cu), nickel (Ni), boron (B) and molybdenum (Mo) to the plants. In some embodiments, a nutrient as used herein provides at least one of nitrogen (N), phosphorus (P) and potassium (K) to the plants. In some embodiments, a nutrient provides at least one of calcium (Ca), magnesium (Mg) and sulfur (S) to the plants. In some embodiments, a nutrient of the embodiments of this application provides at least one of iron (Fe), manganese (Mn), zinc (Zn), copper (Cu), nickel (Ni), boron (B) and molybdenum (Mo) to the plants. In some embodiments, a nutrient is a compound or composition that promotes the plant uptake of one or more nutrient elements selected from nitrogen (N), phosphorus (P), potassium (K), calcium (Ca), magnesium (Mg), sulfur (S), iron (Fe), manganese (Mn), zinc (Zn), copper (Cu), nickel (Ni), boron (B) and molybdenum (Mo), from the soil.

A "fertilizer" as used herein means a compound or composition that is added to plants or soil to improve plant health, growth and/or yield. In some embodiments, a fertilizer improves plant health, growth and/or yield by providing a nutrient (such as the ones described herein) to the plant. Fertilizers include, but are not limited to, inorganic fertilizers, organic (or natural) fertilizers, granular fertilizers and liquid fertilizers. Granular fertilizers are solid granules, while liquid fertilizers are made from water soluble powders or liquid concentrates that mix with water to form a liquid fertilizer solution. In some embodiments, plants can quickly take up most water-soluble fertilizers, while granular fertilizers may need a while to dissolve or decompose before plants can access their nutrients. High-tech granular fertilizers have "slow-release," "timed-release," or "controlled-release" properties, synonymous terms meaning that they release their nutrients slowly over a period of time. Organic fertilizer comes from an organic source such as, but not limited to, compost, manure, blood meal, cottonseed meal, feather meal, crab meal, or others, as opposed to synthetic sources. There are also some natural fertilizers that are not organic, such as Greensand, which contain potassium, iron, calcium, and other nutrients. These are considered suitable for organic gardening because they are not synthesized, but come from natural mineral-rich deposits in the earth. Organic fertilizers depend on the microbes in the soil to break them down into digestible bits for plants. In some embodiments, organic fertilizers encourage soil microbes, earthworms, and other flora more than synthetic fertilizers do, because most organic fertilizers don't add excess salts and acid to the soil. Inorganic fertilizers are also known as synthetic or artificial fertilizers. Inorganic fertilizers are manufactured.

A "bacteriostatic" compound or agent, or a bacteriostat (abbreviated Bstatic), is a biological or chemical agent that stops bacteria from growing and reproducing, while not necessarily harming them otherwise. An "acaricide" means a compound or composition that increases the mortality of, or materially inhibits the growth, reproduction, or spread of undesired acarids, including but not limited to dust mites. A "bactericide" means a compound or composition that increases the mortality of, or materially inhibits the growth, reproduction, or spread of undesired bacteria, such as (but not limited to) those unfavorable for the plant growth. A "fungicidal" refers to a compound or composition that increases the mortality of, or materially inhibits the growth, reproduction, or spread of undesired fungi, such as (but not limited to) those unfavorable for the plant growth. A "nematicide" refers to a compound or composition that increases the mortality of, or materially inhibits the growth, reproduction, or spread of undesired nematodes. A "insecticide" refers to a compound or composition that increases the mortality of, or materially inhibits the growth, reproduction, or spread of undesired insects, such as (but not limited to) those that are harmful for the plant growth. A "microbicide" refers to a compound or composition that increases the mortality of, or materially inhibits the growth, reproduction, or spread of undesired microbes, such as (but not limited to) those that are harmful for the plant growth. A "pesticide" refers to a compound or composition that increases the mortality of, or materially inhibits the growth, reproduction, or spread of undesired pests, such as (but not limited to) those that are harmful for the plant growth.

A "carrier" as used herein refers to a substance or a composition that support the survival of the microbes. Such carriers may be either organic or non-organic.

"Seed priming" or "priming of seed" means controlling the hydration level within seeds so that the metabolic activity necessary for germination can occur but elongation by the embryonic axis, i.e. usually radicle emergence, is prevented. Different physiological activities within the seed occur at different moisture levels (Leopold and Vertucci, 1989, Moisture as a regulator of physiological reactions in seeds. In: Seed Moisture, eds. P. C. Stanwood and M. B. McDonald. CSSA Special Publication Number 14. Madison, Wis.: Crop Science Society of America, pp. 51-69; Taylor, 1997, Seed storage, germination and quality. In: The Physiology of Vegetable Crops, ed. H. C. Wien. Wallingford, U.K.: CAB International, pp. 1-36). The last physiological activity in the germination process is radicle emergence. The initiation of radicle emergence requires a high seed water content. By limiting seed water content, all the metabolic steps necessary for germination can occur without the irreversible act of radicle emergence. Prior to radicle emergence, the seed is considered desiccation tolerant, thus the primed seed moisture content can be decreased by drying. After drying, primed seeds can be stored until time of sowing. For example, in some embodiments, a plant seed is exposed or placed in contact with a microbial strain or a culture thereof, or a composition according to the embodiments of this application during the hydration treatment of seed priming. In some embodiments, the exposure or contact of a plant seed with the microbial strain or a culture thereof or a composition of the embodiments of this application, during the priming process improves seed germination performance, later plant health, plant growth, and/or final plant yield.

As used herein, an "endophyte" is an endosymbiont that lives within a plant for at least part of its life. Endophytes may be transmitted either vertically (directly from parent to offspring) or horizontally (from individual to unrelated individual). In some embodiments, vertically-transmitted fungal endophytes are asexual and transmit from the maternal plant to offspring via fungal hyphae penetrating the host's seeds. Bacterial endophytes can also be transferred vertically from seeds to seedlings (Ferreira et al., FEMS Microbiol. Lett. 287:8-14, 2008). In some embodiments, horizontally-transmitted endophytes are typically sexual, and transmit via spores that can be spread by wind and/or insect vectors. Microbial endophytes of crop plants have received considerable attention with respect to their ability to control disease and insect infestation, as well as their potential to promoting plant growth. For instance, some microbial strains described herein are able to establish as endophytes in plants that come in contact with them. Such microbial strains are microbial endophytes.

The term "pathogen" as used herein refers to an organism such as an alga, an arachnid, a bacterium, a fungus, an insect, a nematode, a parasitic plant, a protozoan, a yeast, or a virus capable of producing a disease in a plant or animal. The term "phytopathogen" as used herein refers to a pathogenic organism that infects a plant. A "pathogenic disease" is a disease, such as a plant disease, that is caused by at least one pathogen. A "phytopathogenic disease" is a disease, such as a plant disease, that is caused by at least one phytopathogen. Some pathogens that may cause plant pathogenic diseases include, but are not limited to, *Colletotrichum, Fusarium, Gibberella, Monographella, Penicillium,* and *Stagnospora* organisms.

"Percentage of sequence identity", as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e. g. BLAST). The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (Add. APL. Math. 2:482, 1981), by the global homology alignment algorithm of Needleman and Wunsch (J Mol. Biol. 48:443, 1970), by the search for similarity method of Pearson and Lipman (Proc. Natl. Acad. Sci. USA 85:2444, 1988), by heuristic implementations of these algorithms (NCBI BLAST, WU-BLAST, BLAT, SIM, BLASTZ), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, preferably at least 70%, preferably at least 80%>, preferably at least 85%, preferably at least 90%>, preferably at least 95%, and preferably at least 96%>, 97%, 98% or 99% sequence identity compared to a reference sequence using the programs. In addition, pairwise sequence homology or sequence similarity, as used, refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Query nucleic acid and amino acid sequences can be searched against subject nucleic acid or amino acid sequences residing in public or proprietary databases. Such searches can be done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST can be used: Filter options set to "default", the Comparison Matrix set to "BLOSUM62", the Gap Costs set to "Existence: 11, Extension: 1", the Word Size set to 3, the Expect (E threshold) set to 1e-3, and the minimum length of the local alignment set to 50% of the query sequence length. Sequence identity and similarity may also be determined using GenomeQuest™ software (Gene-IT, Worcester Mass. USA).

As used herein, "progeny" includes descendants of a particular plant or plant line. Progeny of an instant plant include seeds formed on $F_1, F_2, F_3, F_4, F_5, F_6$ and subsequent generation plants, or seeds formed on $BC_1, BC_2, BC_3,$ and subsequent generation plants, or seeds formed on $F_1BC_1, F_1BC_2, F_1BC_3,$ and subsequent generation plants. The designation $F_1$ refers to the progeny of a cross between two parents that are genetically distinct. The designations $F_2, F_3, F_4, F_5,$ and $F_6$ refer to subsequent generations of self- or sib-pollinated progeny of an $F_1$ plant. Backcrossing is a crossing of a hybrid with one of its parents or an individual genetically similar to its parent, in order to achieve offspring with a genetic identity which is closer to that of the parent. It is used in horticulture, animal breeding and in production of gene knockout organisms. Backcrossed hybrids are sometimes described with acronym "BC", for example, an $F_1$ hybrid crossed with one of its parents (or a genetically similar individual) can be termed a $BC_1$ hybrid, and a further cross of the $BC_1$ hybrid to the same parent (or a genetically similar individual) produces a $BC_2$ hybrid.

As used herein in reference to a nucleic acid and polypeptide, the term "variant" is used herein to denote a polypeptide, protein or polynucleotide molecule with some differences, generated synthetically or naturally, in their amino acid or nucleic acid sequences as compared to a reference polypeptide or polynucleotide, respectively. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.).

The term "variant", when used herein in reference to a microorganism, is a microbial strain having identifying characteristics of the species to which it belongs, while having at least one nucleotide sequence variation or identifiably different trait with respect to the parental strain, where the trait is genetically based (heritable).

"PGPM" refers to plant-growth promoting microorganisms (or microbes). In some embodiments, PGPMs not only can promote plant health, growth and/or yield, but also can survive and multiply in microhabitats associated with the root surface, in competition with other microbiota, and/or are able to colonize the root, at least for the time needed to express their plant promotion and/or protection activities. In some embodiments, microbial strains whose 16S rRNA gene comprises a nucleic acid sequence selected from the SEQ ID Nos.: 1-164, are PGPMs.

The microbial strains (PGPMs), isolates, cultures, compositions or synthetic consortia promote or enhance plant health, growth or yield, or have plant growth-promoting activity. The term "plant growth-promoting activity", as used herein, encompasses a wide range of improved plant properties, including, for example without limitation, improved nitrogen fixation, improved root development, increased leaf area, increased plant yield, increased seed germination, increased photosynthesis, or an increase in accumulated biomass of the plant. In some embodiments, the microbial strains, isolates, cultures, compositions or synthetic consortia as described herein improves stress tolerance (e.g., tolerance to drought, flood, salinity, heat, pest), improves nutrient uptake, plant heath and vigor, improves root development, increases leaf area, increases plant yield, increases seed germination, or an increase in accumulated biomass of the plant. In some embodiments, the microbial strains, isolates, cultures, compositions or synthetic consortia as described herein increase the size or mass of a plant or parts thereof, as compared to a control plant, or parts thereof or as compared to a predetermined standard. In some embodiments, the microbial strains, isolates, cultures, compositions or synthetic consortia as described herein promote plant growth by promoting seed germination, as compared to a control seed. In some embodiments, the microbial strains, isolates, cultures, compositions or synthetic consortia as described herein improve the health, vigor and yield of a plant, as compared to a control plant.

As used herein, the term "yield" refers to the amount of harvestable plant material or plant-derived product, and is normally defined as the measurable produce of economic value of a crop. For crop plants, "yield" also means the amount of harvested material per acre or unit of production. Yield may be defined in terms of quantity or quality. The harvested material may vary from crop to crop, for example, it may be seeds, above ground biomass, roots, fruits, cotton fibers, any other part of the plant, or any plant-derived product which is of economic value.

The term "yield" also encompasses yield potential, which is the maximum obtainable yield. Yield may be dependent on a number of yield components, which may be monitored by certain parameters. These parameters are well known to persons skilled in the art and vary from crop to crop. The term "yield" also encompasses harvest index, which is the ratio between the harvested biomass over the total amount of biomass.

In some embodiments, the microbial strains, isolates, cultures and compositions according to the embodiments of this application lead to plant growth improvement that is an at least 2% increase, at least 5% increase, at least 10% increase, at least 25% increase, at least 50% increase, at least 75% increase, or at least a 100% increase in the property being measured. Thus, as non-limiting examples, the microbial strains, isolates, cultures and compositions according to the embodiments of this application may produce an above stated percentage increase in nitrogen fixation, or an above stated increase in total root weight, or in leaf area or in plant product yield (e.g., an above stated percentage increase in plant product weight), or an increased percentage of seeds that germinate within 10 days or 14 days or 30 days, or rate of photosynthesis (e.g., determined by $CO_2$ consumption) or accumulated biomass of the plant (e.g., determined by weight and/or height of the plant). The plant product is the item—usually but not necessarily—a food item produced by the plant.

A "control plant", as used herein, provides a reference point for measuring changes in phenotype of the subject plant, and may be any suitable plant cell, seed, plant component, plant tissue, plant organ or whole plant. A control plant may comprise, for example (but not limited to), (a) a wild-type plant or cell, i.e., of the same genotype as the starting material for the genetic alteration which resulted in the subject plant or cell; (b) a plant or cell of the genotype as the starting material but which has been transformed with a null construct (i.e., a construct which has no known effect on the trait of interest, such as a construct comprising a reporter gene); (c) a plant or cell which is a non-transformed segregant among progeny of a subject plant or cell; (d) a plant or cell which is genetically identical to the subject plant or cell but which is not exposed to the same treatment (e.g., inoculant treatment) as the subject plant or cell; (e) the subject plant or cell itself, under conditions in which the gene of interest is not expressed; or (f) the subject plant or cell itself, under conditions in which it has not been exposed to a particular treatment such as, for example, an inoculant or combination of inoculants and/or other chemicals.

"Inoculant" as used herein refers to any culture or preparation that comprises at least one microorganism. In some embodiments, an inoculant (sometimes as microbial inoculant, or soil inoculant) is an agricultural amendment that uses beneficial microbes (including, but not limited to endophytes) to promote plant health, growth and/or yield. Many of the microbes suitable for use in an inoculant form symbiotic relationships with the target crops where both parties benefit (mutualism).

Competitive fitness refers to the fitness of the microbes to compete with their neighbors for space and resources. Fitness means the ability or propensity of a given genotype (e.g., a 16S rRNA gene sequence) to both survive and reproduce in a given environment.

Biofertilizers designate the biological products which contain microorganisms providing direct and/or indirect gains in plant health, growth and/or yield.

A bioreactor refers to any device or system that supports a biologically active environment. As described herein a bioreactor is a vessel in which microorganisms including the microorganism of the embodiments of this application can be grown.

A greenhouse as used herein refers to both a typical greenhouse or a grow room. A grow room typically has normal walls and ceilings, optionally has windows, has normal indoor type of floor, optionally has floor drain, has artificial light source, and has the infrastructure to be used for other purpose than growing plants. A typical greenhouse has walls and ceilings that allow light to penetrate (e.g., walls/ceilings made of glass, plastic or other types of suitable materials), has concrete, dirt, gravel or similar type of floor, has natural/ambient light, but can have additional artificial lights.

All publications, patents and published patent applications referred to in this application are specifically incorporated by reference herein.

The discussion of the general methods given herein is intended for illustrative purposes only. Other alternative methods and embodiments will be apparent to those of skill in the art upon review of this disclosure.

B. Plant Growth-Promoting Microorganisms

Diverse plant-associated microorganisms, including, but not limited to, many rhizobacterial species, can positively impact plant health and physiology in a variety of ways. These beneficial microbes are generally referred to as PGPMs, such as plant growth-promoting bacteria (PGPB) or plant growth-promoting rhizosphere (PGPR). To date, isolated strains of over two dozen genera of microorganisms have been reported to have plant growth-promoting activity and/or biocontrol activity, and new genera and species with similar activities are still being discovered. Additionally, within some bacterial genera, multiple species and subspecies of biocontrol agents have been identified and can be found across multiple spatial scales, from the global level to farm level, and even on single plants. Furthermore, it has been reported that some individual microbial isolates may display biocontrol and/or plant growth-promoting activity not only on the plants or crops from which they were obtained but also on other crops. This indicates the generalist nature of some genotypes, especially those with a wide geographic distribution. If introduced in sufficient numbers and active for a sufficient duration, a single microbial population can have a significant impact on plant health.

The embodiments disclosed include new microbial strains that are PGPMs. In some embodiments, the 16S rRNA gene of the microbial strain comprises a nucleotide sequence selected from SEQ ID Nos.: 1-164. In some embodiments, the microbial strain comprises a 16S rRNA gene comprising a nucleotide sequence selected from SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, and 159. In some embodiments, the 16S rRNA gene of the microbial strain comprises a nucleotide sequence selected from SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 159. In some embodiments, the 16S rRNA gene of the microbial strain comprises a nucleotide sequence selected from SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159. In some embodiments, the 16S rRNA gene of the microbial strain comprises a nucleotide sequence selected from SEQ ID Nos.: 133, 134 and 138. In some embodiments, the 16S rRNA gene of the microbial strain comprises a nucleotide sequence selected from SEQ ID Nos.: 113, 123, 126, 131, and 149. In some embodiments, the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 5, 7, 25, 28, 39, 44, 47, 52, 56, 63, 68, 71, 78, 82, 111, 114, 119, 124, 127, 133, 134, 138, 141, 143, 145, 150, 155, and 158. In some embodiments, the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159. In some embodiments, the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 113, 123, 126, 131, and 149. In some embodiments, the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 133, 134 and 138. Some embodiments provide a genus of plant growth-promoting microorganisms comprising any of the DNA sequences described herein and which enhances the health, growth and/or yield of a plant, as described herein.

In some embodiments, the microbial strain is selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, S2646, or a strain derived from any one of these strains. Some embodiments also provide isolates and cultures of the microbial strains as described herein, and compositions and synthetic consortia comprising various combinations of those microbial strains, isolates or cultures.

PGPMs may demonstrate plant growth-promoting activity, which encompasses a wide range of improved plant properties, including, for example without limitation, improved nitrogen fixation, improved root development, increased leaf area, increased plant yield, increased nutrient availability or uptake, increased seed germination, increased photosynthesis, or an increase in accumulated biomass of the plant. In some embodiments, the improvement is an at least 2% increase, at least 5% increase, at least 10% increase, at least 25% increase, at least 50% increase, at least 75% increase, or at least a 100% increase in the property being measured. Thus, as non-limiting examples, the microbial strains, isolates, cultures or compositions of the embodiments of this application may produce an above-stated percentage increase in nitrogen fixation, or an above stated increase in total root weight, or in leaf area or in plant product yield (e.g., an above stated percentage increase in plant product weight), or an increased percentage of seeds that germinate within 10 days or 14 days or 30 days, or rate of photosynthesis (e.g., determined by $CO_2$ consumption) or accumulated biomass of the plant (e.g., determined by weight of the plant). The plant product is the item—usually but not necessarily—a food item produced by the plant. The yield can be determined using any convenient method, for example, bushels or pounds of plant product produced per acre of planting.

In some embodiments, the PGPMs, when applied to seed, plant surfaces, plant parts, or soil, colonizes rhizosphere and/or the interior of the plant and promotes growth of the host plant. In some embodiments, PGPMs are biofertilizers. In some embodiments, the PGPMs are microbial fertilizers, which supply the plant with nutrients and thereby can promote plant growth in the absence of pathogen pressure. In some embodiments, the PGPMs may directly promote plant growth and/yield through mechanisms, including, but not limited to, ability to produce or change the concentration of plant hormones; asymbiotic nitrogen fixation; and/or solubilization of mineral phosphate and other nutrients.

In some embodiments, PGPMs may affect the plant growth and development as phytostimulators. For example, some PGPMs described herein have the ability to produce or change the concentration of plant hormones, including, but not limited to the five classical phytohormones, i.e., auxin, ethylene, abscisic acid, cytokinin, and gibberellin. Some PGPMs may also produce enzymes or secondary metabolites that affect phytohormone production in plants. In some embodiments, PGPMs may have the ability to produce or change the concentration of other hormones as well as certain volatile organic compounds (VOCs) and the cofactor pyrrolquinoline quinone (PQQ), thereby stimulating plant growth and/or yield.

In some embodiments, PGPMs may affect the plant growth and development by modifying nutrient availability or uptake. The PGPMs may alter nutrient uptake rates, for example, by direct effects on roots, by effects on the environment which in turn modify root behavior, and by competing directly for nutrients. Some factors by which PGPMs described herein may play a role in modifying the nutrient use efficiency in soils include, for example, root geometry, nutrient solubility, nutrient availability by producing plant congenial ion form, partitioning of the nutrients in plant and utilization efficiency. For example, a low level of soluble phosphate can limit the growth of plants. Some plant growth-promoting microbes are capable of solubilizing phosphate from either organic or inorganic bound phosphates, thereby facilitating plant growth.

In some embodiments, PGPMs may affect the plant growth and development as plant stress controllers. For example, some PGPMs may control and/or reduce several types of plant stress, including, but not limited to, stress from the effects of phytopathogenic bacteria, stress from polyaromatic hydrocarbons, stress from heavy metal such as $Ca^{2+}$ and $Ni^{2+}$, and stress from salt and severe weather conditions (e.g., drought or flood).

In some embodiments, PGPMs may promote plant health, growth and/or yield directly by controlling phytopathogens or pests in plants. In some embodiments, PGPMs described herein exhibit one or more mechanisms of biological disease control, most of which involve competition and production of metabolites that affect the pathogen directly. Examples of such metabolites include antibiotics, cell wall-degrading enzymes, siderophores, and HCN. It is noteworthy to state that different mechanisms may be found in a single PGPM strain and act simultaneously. In some embodiments, PGPMs may affect the plant growth and development by producing extracellular siderophores. Some PGPMs described herein may secrete low molecular weight, high affinity ferric-chelating microbial cofactors that specifically enhance their acquisition of iron by binding to membrane bound siderophore receptors. Siderophores are small, high-affinity chelators that bind Fe, making it more (or less) available to certain member of natural microflora. For example, a siderophore may make Fe more available to a plant or microbe that possesses the ability to recognize and import the specific siderophore molecular structure. Many different siderophore types and structures exist with different Fe-binding affinities. Furthermore, exchange of Fe from a siderophore with low Fe-binding affinity to one with higher Fe-binding affinity is known to occur which may further influence Fe availability to any given organism. One of the siderophores produced by some pseudomonad PGPMs is known as pseudobactin that inhibits the growth of *Erwinia cartovora* (causal organism for soft-rot of potato) (see, e.g., Kloepper et al. Current Microbiol. 4: 317-320, 1980). Additions of pseudobactin to the growth medium inhibited soft-rot infection and also reduced the number of pathogenic fungi in the potato plant along with a significant increase in potato yield. Most evidence to support the siderophore theory of biological control by PGPM comes from work with the pyoverdines, one class of siderophores that comprises the fluorescent pigments of fluorescent pseudomonads (Demange et al. in Iron Transport in Microbes, Plants and Animals, pp 167-187, 1987). According to the siderophore theory, pyoverdines demonstrate certain functional strain specificity which is due to selective recognition of outer membrane siderophore receptors (Bakker et al. Soil Biology and Biochemistry 19: 443-450, 1989). Production of siderophore(s) may modulate the fitness and/or growth of other strains. In addition to inhibiting certain strains (e.g., *Erwinia*), production of siderophore(s) can also support the fitness/growth of other microbial strains that possess receptors for a given siderophore but are unable to synthesize the molecule themselves.

In some embodiments, the PGPMs may act indirectly on the plant by increasing the competitive fitness of a second microbial strain (e.g., another PGPM) by, e.g., providing nutrients, metabolites and/or siderophores (and/or by any other benefiting mechanism as described herein) to the second microbial strain. In some embodiments, the PGPMs may act indirectly on the plant by increasing the competitive fitness of a second microbial strain (e.g., another PGPM) by, e.g., providing nutrients, metabolites and/or siderophores (and/or by any other benefiting mechanism as described herein) to the second microbial strain, and/or by decreasing the competitive fitness of a third microbial strain that inhibits, competes with, or excludes or otherwise has a negative impact on the fitness of the second microbial strain.

In some embodiments, the PGPMs are biocontrol agents of plant diseases by activating chemical and/or physical defenses of the host plants, i.e., inducing induced systemic resistance (ISR) or systemic acquired resistance (SAR). In some embodiments, induction of resistance promoted by PGPMs of the present embodiments is active and signaling in the route of salicylic acid with induction of proteins related to the pathogenesis (PR-proteins) or route of the jasmonic acid and ethylene. Sometimes, when the PGPMs colonize the root system, constituents of the microorganism cell molecules act as a biochemical signal, and the genes that encode for the synthesis of the PR-proteins are activated. In addition to PR-proteins, plants produce other enzymes of the defense, including peroxidases, phenylalanine ammonialyse (PAL), and polyphenoloxidase (PPO). Peroxidase and PPO are catalysts in the formation of lignin. PAL and other enzymes are involved in the formation of phytoalexins. In some embodiments, the PGPMs described herein induce plant resistance to diseases by increasing peroxidases, PPO and/or PAL production.

In some embodiments, the PGPMs of the embodiments of this application promote the plant health, growth and/or yield via one or more of the mechanisms as described herein.

In some embodiments, the PGPMs of the embodiments of this application are biofertilizers or biocontrol agents, which are compatible with organic farming.

Other aspects of the present embodiments contemplate isolated and/or cultured PGPMs. In one aspect, an embodiment provides isolated microbial strains (or PGPMs), isolated cultures thereof, biologically pure cultures thereof, and enriched cultures thereof. In some embodiments, the microbial isolate or culture comprises a microbial strain, wherein the 16S rRNA gene of the microbial strain comprises a nucleotide sequence selected from SEQ ID Nos.: 1-164. In some embodiments, the microbial isolate or culture comprises a microbial strain, wherein the 16S rRNA gene of the microbial strain comprises a nucleotide sequence selected from SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, and 159. In some embodiments, the microbial isolate or culture comprises a microbial strain, wherein the 16S rRNA gene of the microbial strain comprises a nucleotide sequence selected from SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158. In some embodiments, the microbial isolate or culture comprises a microbial strain, wherein the 16S rRNA gene of the microbial strain comprises a nucleotide sequence selected from SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159. In some embodiments, the microbial isolate or culture comprises a microbial strain, wherein the 16S rRNA gene of the microbial strain comprises a nucleotide sequence selected from SEQ ID Nos.: 113, 123, 126, 131, and 149. In some embodiments, the microbial isolate or culture comprises a microbial strain, wherein the 16S rRNA gene of the microbial strain comprises a nucleotide sequence selected from SEQ ID Nos.: 133, 134 and 138. In some embodiments, the microbial isolate or culture comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158. In some embodiments, the microbial isolate or culture comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, and 159. In some embodiments, the microbial isolate or culture comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 113, 123, 126, 131, and 149. In some embodiments, the microbial isolate or culture comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 133, 134 and 138.

Some embodiments provide a microbial isolate or culture thereof comprising a microbial strain selected from: P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328 and S2646, or a strain derived from any one of these strains. The microbial isolates or cultures promote the plant health, growth and/or yield, e.g., via one or more of the mechanisms as described herein.

C. Microbiological Compositions

Embodiments of this application provide a microbial composition that comprises a PGPM or microbial strain, such as a microbial strain selected from those described herein, or a culture thereof. In some embodiments, the microbial composition comprises a microbial strain, wherein the 16S rRNA gene of said strain comprises a sequence selected from the group consisting of SEQ ID Nos.: 1-164, or a culture thereof.

In some embodiments, the microbial composition comprises a microbial strain, wherein the 16S rRNA gene of said strain comprises a sequence selected from the group consisting of SEQ ID Nos.: 5, 6, 7, 8, 25, 26, 28, 29, 39, 40, 44, 45, 47, 48, 52, 53, 56, 57, 63, 64, 68, 69, 71, 72, 78, 79, 82, 83, 111, 112, 113, 114, 115, 119, 120, 123, 124, 125, 126, 127, 128, 131, 132, 133, 134, 135, 138, 139, 140, 141, 142, 143, 144, 145, 146, 149, 150, 151, 155, 156, and 159, or a culture thereof. In some embodiments, the microbial composition comprises a microbial strain, wherein the 16S rRNA gene of said strain comprises a sequence selected from the group consisting of SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158, or a culture thereof. In some embodiments, the microbial composition comprises a microbial strain, wherein the 16S rRNA gene of said strain comprises a sequence selected from the group consisting of SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159, or a culture thereof. In some embodiments, the microbial composition comprises a microbial strain, wherein the 16S rRNA gene of said strain comprises a sequence selected from the group consisting of SEQ ID Nos.: 113, 123, 126, 131, and 149, or a culture thereof. In some embodiments, the microbial composition comprises a microbial strain, wherein the 16S rRNA gene of said strain comprises a sequence selected from the group consisting of SEQ ID Nos.: 133, 134 and 138, or a culture thereof. In some embodiments, the microbial composition comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 5, 7, 25, 28, 39, 44, 47, 52, 56, 63, 68, 71, 78, 82, 111, 114, 119, 124, 127, 133, 134 138, 141, 143, 145, 150, 155, and 158, or a culture thereof. In some embodiments, the microbial composition comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 6, 8, 26, 29, 40, 45, 48, 53, 57, 64, 69, 72, 79, 83, 112, 115, 120, 125, 128, 132, 135, 139, 140, 142, 144, 146, 151, 156, and 159, or a culture thereof. In some embodiments, the microbial composition comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 113, 123, 126, 131, and 149, or a culture thereof. In some embodiments, the microbial composition comprises a microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 133, 134 and 138, or a culture thereof. In some embodiments of the above compositions, the microbial composition optionally further comprises a second microbial strain whose 16S rRNA gene sequence comprises a sequence selected from the group consisting of SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163, and 164, or a culture thereof. In some embodiments of the above compositions, the microbial composition further comprises a second microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163 and 164 or a culture thereof.

In some embodiments, the microbial composition comprises at least two microbial strains, wherein the 16S rRNA gene of each of said microbial strains comprises a sequence independently selected from the group consisting of SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163, and 164, or cultures thereof. In some embodiments, the microbial composition comprises at least two microbial strains, wherein the 16S rRNA gene of each of the microbial strains independently comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 1, 2, 3, 4, 9, 10, 11, 12, 13, 14, 15, 16, 17, 18, 19, 20, 21, 22, 23, 24, 27, 30, 31, 32, 33, 34, 35, 36, 37, 38, 41, 42, 43, 46, 49, 50, 51, 54, 55, 58, 59, 60, 61, 62, 65, 66, 67, 70, 73, 74, 75, 76, 77, 80, 81, 84, 85, 86, 87, 88, 89, 90, 91, 92, 93, 94, 95, 96, 97, 98, 99, 100, 101, 102, 103, 104, 105, 106, 107, 108, 109, 110, 116, 117, 118, 121, 122, 129, 130, 136, 137, 147, 148, 152, 153, 154, 157, 160, 161, 162, 163, and 164, or cultures thereof.

In some embodiments, the microbial composition comprises at least one microbial strain, wherein the 16S rRNA gene of said microbial strain comprises a sequence independently selected from the group consisting of SEQ ID Nos.: 1, 2, 3, 4, 9, 10, 11, 12, 14, 15, 16, 17, 18, 20, 21, 24, 27, 30, 31, 33, 34, 35, 38, 41, 42, 43, 46, 51, 54, 55, 58, 59, 60, 61, 62, 65, 66, 67, 77, 81, 84, 85, 86, 87, 88, 92, 95, 96, 106, 107, 109, 110, 116, 117, 118, 122, 130, 136, 137, 147, 148, 153, 154, 157, 160, and 161, or cultures thereof. In some embodiments, the microbial composition comprises at least two microbial strains, wherein the 16S rRNA gene of each of said microbial strains comprises a sequence independently selected from the group consisting of SEQ ID Nos.: 1, 2, 3, 4, 9, 10, 11, 12, 14, 15, 16, 17, 18, 20, 21, 24, 27, 30, 31, 33, 34, 35, 38, 41, 42, 43, 46, 51, 54, 55, 58, 59, 60, 61, 62, 65, 66, 67, 77, 81, 84, 85, 86, 87, 88, 92, 95, 96, 106, 107, 109, 110, 116, 117, 118, 122, 130, 136, 137, 147, 148, 153, 154, 157, 160, and 161, or cultures thereof. In some embodiments, the microbial composition comprises at least one microbial strain, wherein the 16S rRNA gene of the microbial strain comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 1, 2, 3, 4, 9, 10, 11, 12, 14, 15, 16, 17, 18, 20, 21, 24, 27, 30, 31, 33, 34, 35, 38, 41, 42, 43, 46, 51, 54, 55, 58, 59, 60, 61, 62, 65, 66, 67, 77, 81, 84, 85, 86, 87, 88, 92, 95, 96, 106, 107, 109, 110, 116, 117, 118, 122, 130, 136, 137, 147, 148, 153, 154, 157, 160, and 161, or cultures thereof. In some embodiments, the microbial composition comprises at least two microbial strains, wherein the 16S rRNA gene of each of the microbial strains independently comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 1, 2, 3, 4, 9, 10, 11, 12, 14, 15, 16, 17, 18, 20, 21, 24, 27, 30, 31, 33, 34, 35, 38, 41, 42, 43, 46, 51, 54, 55, 58, 59, 60, 61, 62, 65, 66, 67, 77, 81, 84, 85, 86, 87, 88, 92, 95, 96, 106, 107, 109, 110, 116, 117, 118, 122, 130, 136, 137, 147, 148, 153, 154, 157, 160, and 161, or cultures thereof.

In some embodiments, the microbial composition comprises at least two microbial strains, wherein the 16S rRNA gene of each of said microbial strains comprises a sequence independently selected from the group consisting of SEQ ID Nos.: 13, 19, 22, 23, 32, 36, 37, 49, 50, 70, 73, 74, 75, 76, 80, 89, 90, 91, 93, 94, 97, 98, 99, 100, 101, 102, 103, 104, 105, 108, 121, 129, 152, 162, 163 and 164, or cultures thereof. In some embodiments, the microbial composition comprises at least two microbial strains, wherein the 16S rRNA gene of each of the microbial strains independently comprises a nucleotide sequence that exhibits at least 85%, at least 90%, at least 91%, at least 92%, at least 93%, at least 94%, at least 95%, at least 96%, at least 97%, at least 98%, at least 99%, or at least 99.5% sequence identity to any one of the nucleotide sequences as set forth in SEQ ID Nos.: 13, 19, 22, 23, 32, 36, 37, 49, 50, 70, 73, 74, 75, 76, 80, 89, 90, 91, 93, 94, 97, 98, 99, 100, 101, 102, 103, 104, 105, 108, 121, 129, 152, 162, 163 and 164, or cultures thereof.

In some embodiments, the microbial composition comprises one or more microbial strains, wherein the 16S rRNA gene of each of said strains comprises a sequence independently selected from SEQ ID Nos.: 1, 2, 4, 5, 6, 10, 12, 50, 55, 56, 57, or a culture thereof.

In some embodiments, the microbial composition comprises one or more microbial strains, wherein the 16S rRNA gene of each of said strains comprises a sequence independently selected from SEQ ID Nos.: 6 and 57, or a culture thereof. In some embodiments, the microbial composition comprises at least two microbial strains, wherein the 16S rRNA genes of said at least two strains comprise sequences of SEQ ID Nos.: 6 and 57, respectively, or cultures thereof.

In some embodiments, the microbial composition comprises one or more microbial strains, wherein the 16S rRNA gene of each of said strains comprises a sequence independently selected from SEQ ID Nos.: 2, 5, 10, 12, 50, 55, and 56, or a culture thereof. In some embodiments, the microbial composition comprises two or more microbial strains, wherein the 16S rRNA gene of each of said strains comprises a sequence independently selected from SEQ ID Nos.: 2, 5, 10, 12, 50, 55, and 56, or cultures thereof. In some embodiments, the microbial composition comprises one or more microbial strains, wherein the 16S rRNA gene of each of said strains comprises a sequence independently selected from SEQ ID Nos.: 5 and 56, and optionally further comprises one or more additional microbial strains, wherein the 16S rRNA gene of each of said additional strains comprises a sequence independently selected from the group consisting of SEQ ID Nos.: 2, 10, 12, 50, and 55, or cultures thereof. In some embodiments, the microbial composition comprises at least seven (7) microbial strains, wherein the 16S rRNA genes of said at least seven strains comprise sequences of SEQ ID Nos.: 2, 5, 10, 12, 50, 55, and 56, respectively, or cultures thereof.

In some embodiments, the microbial composition comprises one or more microbial strains, wherein the 16S rRNA gene of each of said strains comprises a sequence independently selected from SEQ ID Nos.: 1, 4, 9, 11, 49, and 54, or a culture thereof. In some embodiments, the microbial composition comprises two or more microbial strains, wherein the 16S rRNA gene of each of said strains comprises a sequence independently selected from SEQ ID Nos.: 1, 4, 9, 11, 49, and 54, or cultures thereof. In some embodiments, the microbial composition comprises at least six (6) microbial strains, wherein the 16S rRNA genes of said at least six strains comprise sequences of SEQ ID Nos.: 1, 4, 9, 11, 49, and 54, respectively, or cultures thereof.

In some embodiments, the microbial composition comprises one or more microbial strains, wherein the 16S rRNA gene of each of said strains comprises a sequence independently selected from SEQ ID Nos.: 34, 35, 46, 47, 48, 65, 66, 67, 68, 69, 70, 71, 72, 73, and 74, or a culture thereof.

In some embodiments, the microbial composition comprises one or more microbial strains, wherein the 16S rRNA gene of each of said strains comprises a sequence independently selected from SEQ ID Nos.: 48, 69, and 72, or a culture thereof. In some embodiments, the microbial composition comprises two or more microbial strains, wherein the 16S rRNA gene of each of said strains comprises a sequence independently selected from SEQ ID Nos.: 48, 69, and 72, or cultures thereof. In some embodiments, the microbial composition comprises at least three (3) microbial strains, wherein the 16S rRNA genes of said at least three strains comprise sequences of SEQ ID Nos.: 48, 69 and 72, respectively, or cultures thereof.

In some embodiments, the microbial composition comprises one or more microbial strains, wherein the 16S rRNA gene of each of said strains comprises a sequence independently selected from SEQ ID Nos.: 35, 47, 66, 68, 71, 73, and 74, or a culture thereof. In some embodiments, the microbial composition comprises two or more microbial strains, wherein the 16S rRNA gene of each of said strains comprises a sequence independently selected from SEQ ID Nos.: 35, 47, 66, 68, 71, 73, and 74, or cultures thereof. In some embodiments, the microbial composition comprises one or more microbial strains, wherein the 16S rRNA gene of each of said strains comprises a sequence independently selected from SEQ ID Nos.: 47, 68 and 71, and wherein said composition optionally further comprises one or more additional microbial strains, wherein the 16S rRNA gene of each of said additional strains comprises a sequence independently selected from the group consisting of SEQ ID Nos.: 35, 66, 73 and 74, or cultures thereof. In some embodiments, the microbial composition comprises at least seven (7) microbial strains, wherein the 16S rRNA genes of said at least seven strains comprise sequences of SEQ ID Nos.: 35, 47, 66, 68, 71, 73, and 74, respectively, or cultures thereof.

In some embodiments, the microbial composition comprises one or more microbial strains, wherein the 16S rRNA gene of each of said strains comprises a sequence independently selected from SEQ ID Nos.: 34, 46, 65, 67, and 70, or a culture thereof. In some embodiments, the microbial composition comprises two or more microbial strains, wherein the 16S rRNA gene of each of said strains comprises a sequence independently selected from SEQ ID Nos.: 34, 46, 65, 67, 70, or cultures thereof. In some embodiments, the microbial composition comprises at least five (5) microbial strains, wherein the 16S rRNA genes of said at least five strains comprise sequences of SEQ ID Nos.: 34, 46, 65, 67, and 70, respectively, or cultures thereof.

In some embodiments, the microbial composition comprises one or more microbial strains, wherein the 16S rRNA gene of each of said strains comprises a sequence independently selected from SEQ ID Nos.: 20, 21, 22, 23, 24, 25, 26, 30, 31, 32, 33, 41, 42, 62, 63, and 64, or a culture thereof.

In some embodiments, the microbial composition comprises one or more microbial strains, wherein the 16S rRNA gene of each of said strains comprises a sequence independently selected from SEQ ID Nos.: 26 and 64, or a culture thereof. In some embodiments, the microbial composition comprises at least two (2) microbial strains, wherein the 16S rRNA genes of said at least two strains comprise sequences of SEQ ID Nos.: 26 and 64, respectively, or cultures thereof.

In some embodiments, the microbial composition comprises one or more microbial strains, wherein the 16S rRNA gene of each of said strains comprises a sequence independently selected from SEQ ID Nos.: 21, 22, 23, 25, 31, 33, 42, and 63, or a culture thereof. In some embodiments, the microbial composition comprises two or more microbial strains, wherein the 16S rRNA gene of each of said strains comprises a sequence independently selected from SEQ ID Nos.: 21, 22, 23, 25, 31, 33, 42, and 63, or cultures thereof. In some embodiments, the microbial composition comprises one or more microbial strains, wherein the 16S rRNA gene of each of said strains comprises a sequence independently selected from SEQ ID Nos.: 25 and 63, and wherein said composition optionally further comprises one or more additional microbial strains, wherein the 16S rRNA gene of each of said additional strains comprises a sequence independently selected from the group consisting of SEQ ID Nos.: 21, 22, 23, 31, 33, and 42, or cultures thereof. In some embodiments, the microbial composition comprises at least eight (8) microbial strains, wherein the 16S rRNA genes of said at least eight strains comprise sequences of SEQ ID Nos.: 21, 22, 23, 25, 31, 33, 42, and 63, respectively, or cultures thereof.

In some embodiments, the microbial composition comprises one or more microbial strains, wherein the 16S rRNA gene of each of said strains comprises a sequence independently selected from SEQ ID Nos.: 20, 24, 30, 32, 41, and 62, or a culture thereof. In some embodiments, the microbial composition comprises two or more microbial strains, wherein the 16S rRNA gene of each of said strains comprises a sequence independently selected from SEQ ID Nos.: 20, 24, 30, 32, 41, and 62, or cultures thereof. In some embodiments, the microbial composition comprises at least six (6) microbial strains, wherein the 16S rRNA genes of said at least six strains comprise sequences of SEQ ID Nos.: 20, 24, 30, 32, 41, and 62, respectively, or cultures thereof.

In some embodiments, the microbial composition comprises one or more microbial strains, wherein the 16S rRNA gene of each of said strains comprises a sequence independently selected from SEQ ID Nos.: 18, 19, 36, 37, 75, and 76, or a culture thereof.

In some embodiments, the microbial composition comprises one or more microbial strains, wherein the 16S rRNA gene of each of said strains comprises a sequence independently selected from SEQ ID Nos.: 19, 37, and 76, or a culture thereof. In some embodiments, the microbial composition comprises two or more microbial strains, wherein the 16S rRNA gene of each of said strains comprises a sequence independently selected from SEQ ID Nos.: 19, 37, and 76, or cultures thereof. In some embodiments, the microbial composition comprises at least three (3) microbial strains, wherein the 16S rRNA genes of said at least three strains comprise sequences of SEQ ID Nos.: 19, 37, and 76, respectively, or cultures thereof.

In some embodiments, the microbial composition comprises one or more microbial strains, wherein the 16S rRNA gene of each of said strains comprises a sequence independently selected from SEQ ID Nos.: 18, 36, and 75, or a culture thereof. In some embodiments, the microbial composition comprises two or more microbial strains, wherein the 16S rRNA gene of each of said strains comprises a sequence independently selected from SEQ ID Nos.: 18, 36, and 75, or cultures thereof. In some embodiments, the microbial composition comprises at least three (3) microbial strains, wherein the 16S rRNA genes of said at least three strains comprise sequences of SEQ ID Nos.: 18, 36, and 75, respectively, or cultures thereof.

In some embodiments, the microbial composition comprises one or more microbial strains, wherein the 16S rRNA gene of each of said strains comprises a sequence independently selected from SEQ ID Nos.: 11, 13, 58, 59, 60, and 61, or a culture thereof.

In some embodiments, the microbial composition comprises one or more microbial strains, wherein the 16S rRNA gene of each of said strains comprises a sequence independently selected from SEQ ID Nos.: 13, 59, and 61, or a culture thereof. In some embodiments, the microbial composition comprises two or more microbial strains, wherein the 16S rRNA gene of each of said strains comprises a sequence independently selected from SEQ ID Nos.: 13, 59, and 61, or cultures thereof. In some embodiments, the microbial composition comprises at least three (3) microbial strains, wherein the 16S rRNA genes of said at least three strains comprise sequences of SEQ ID Nos.: 13, 59, and 61, respectively, or cultures thereof.

In some embodiments, the microbial composition comprises one or more microbial strains, wherein the 16S rRNA gene of each of said strains comprises a sequence independently selected from SEQ ID Nos.: 11, 58, and 60, or a culture thereof. In some embodiments, the microbial composition comprises two or more microbial strains, wherein the 16S rRNA gene of each of said strains comprises a sequence independently selected from SEQ ID Nos.: 11, 58, and 60, or cultures thereof. In some embodiments, the microbial composition comprises at least three (3) microbial strains, wherein the 16S rRNA genes of said at least three strains comprise sequences of SEQ ID Nos.: 11, 58, and 60, respectively, or cultures thereof.

In some embodiments, the microbial composition comprises one or more microbial strains, wherein the 16S rRNA gene of each of said strains comprises a sequence independently selected from SEQ ID Nos.: 27, 38, 39, 40, 43, 44, 45, and 77, or a culture thereof.

In some embodiments, the microbial composition comprises one or more microbial strains, wherein the 16S rRNA gene of each of said strains comprises a sequence independently selected from SEQ ID Nos.: 40 and 45, or a culture thereof. In some embodiments, the microbial composition comprises at least two (2) microbial strains, wherein the 16S rRNA genes of said at least two strains comprise sequences of SEQ ID Nos.: 40 and 45, respectively, or cultures thereof.

In some embodiments, the microbial composition comprises one or more microbial strains, wherein the 16S rRNA gene of each of said strains comprises a sequence independently selected from SEQ ID Nos.: 39, 44, and 77, or a culture thereof. In some embodiments, the microbial composition comprises two or more microbial strains, wherein the 16S rRNA gene of each of said strains comprises a sequence independently selected from SEQ ID Nos.: 39, 44, and 77, or cultures thereof. In some embodiments, the microbial composition comprises one or more microbial strains, wherein the 16S rRNA gene of each of said strains comprises a sequence independently selected from SEQ ID Nos.: 39 and 44, and wherein said composition optionally further comprises one additional microbial strains, wherein the 16S rRNA gene of said additional strain comprises a sequence independently selected from the group consisting of SEQ ID No.: 77, or cultures thereof. In some embodiments, the microbial composition comprises at least three microbial strains, wherein the 16S rRNA genes of said at least three strains comprise sequences of SEQ ID Nos.: 39, 44, and 77, respectively, or cultures thereof.

In some embodiments, the microbial composition comprises one or more microbial strains, wherein the 16S rRNA gene of each of said strains comprises a sequence independently selected from SEQ ID Nos.: 27, 38, and 43, or a culture thereof. In some embodiments, the microbial composition comprises two or more microbial strains, wherein the 16S rRNA gene of each of said strains comprises a sequence independently selected from SEQ ID Nos.: 27, 38, and 43, or cultures thereof. In some embodiments, the microbial composition comprises at least three microbial strains, wherein the 16S rRNA genes of said at least eight strains comprise sequences of SEQ ID Nos.: 27, 38, and 43, respectively, or cultures thereof.

In some embodiments, the microbial composition comprises one or more microbial strains, wherein the 16S rRNA gene of each of said strains comprises a sequence independently selected from SEQ ID Nos.: 1, 3, 4, 7, 8, 51, 52, 53, 134, and 135, or a culture thereof.

In some embodiments, the microbial composition comprises one or more microbial strains, wherein the 16S rRNA gene of each of said strains comprises a sequence independently selected from SEQ ID Nos.: 8, 53, and 135, or a culture thereof. In some embodiments, the microbial composition comprises two or more microbial strains, wherein the 16S rRNA gene of each of said strains comprises a sequence independently selected from SEQ ID Nos.: 8, 53, and 135, or a culture thereof. In some embodiments, the microbial composition comprises at least three microbial strains, wherein the 16S rRNA genes of said at least three strains comprise sequences of SEQ ID Nos.: 8, 53, and 135, respectively, or cultures thereof.

In some embodiments, the microbial composition comprises one or more microbial strains, wherein the 16S rRNA gene of each of said strains comprises a sequence independently selected from SEQ ID Nos.: 3, 7, 52, and 134, or a culture thereof. In some embodiments, the microbial composition comprises two or more microbial strains, wherein the 16S rRNA gene of each of said strains comprises a sequence independently selected from SEQ ID Nos.: 3, 7, 52, and 134, or cultures thereof. In some embodiments, the microbial composition comprises one or more microbial strains, wherein the 16S rRNA gene of each of said strains comprises a sequence independently selected from SEQ ID Nos.: 7, 52, and 134, and wherein said composition optionally further comprises an additional microbial strains wherein the 16S rRNA gene of said additional strain comprises a sequence independently selected from the group consisting of SEQ ID No.: 3, or cultures thereof. In some embodiments, the microbial composition comprises at least four microbial strains, wherein the 16S rRNA genes of said at least four strains comprise sequences of SEQ ID Nos.: 3, 7, 52, and 134, respectively, or cultures thereof.

In some embodiments, the microbial composition comprises one or more microbial strains, wherein the 16S rRNA gene of each of said strains comprises a sequence independently selected from SEQ ID Nos.: 1, 4, and 51, or a culture thereof. In some embodiments, the microbial composition comprises two or more microbial strains, wherein the 16S rRNA gene of each of said strains comprises a sequence independently selected from SEQ ID Nos.: 1, 4, and 51, or cultures thereof. In some embodiments, the microbial composition comprises at least three microbial strains, wherein the 16S rRNA genes of said at least three strains comprise sequences of SEQ ID Nos.: 1, 4, and 51, respectively, or cultures thereof.

In some embodiments, the microbial composition comprises one or more microbial strains, wherein the 16S rRNA gene of each of said strains comprises a sequence independently selected from SEQ ID Nos.: 14, 16, 78, 79, and 80, or a culture thereof.

In some embodiments, the microbial composition comprises a microbial strain, wherein the 16S rRNA gene of said strain comprises a sequence that is SEQ ID No.: 79, or a culture thereof.

In some embodiments, the microbial composition comprises one or more microbial strains, wherein the 16S rRNA gene of each of said strains comprises a sequence independently selected from SEQ ID Nos.: 78 and 80, or a culture thereof. In some embodiments, the microbial composition comprises at least two microbial strains, wherein the 16S rRNA genes of said at least two strains comprise sequences of SEQ ID Nos.: 78 and 80, respectively, or cultures thereof.

In some embodiments, the microbial composition comprises one or more microbial strains, wherein the 16S rRNA gene of each of said strains comprises a sequence independently selected from SEQ ID Nos.: 14 and 16, or a culture thereof. In some embodiments, the microbial composition comprises at least two microbial strains, wherein the 16S rRNA genes of said at least two strains comprise sequences of SEQ ID Nos.: 14 and 16, respectively, or cultures thereof.

In some embodiments, the microbial composition comprises one or more microbial strains, wherein the 16S rRNA gene of each of said strains comprises a sequence independently selected from SEQ ID Nos.: 43, 44, 45, 81, 82, 83, 84, 145 and 146, or a culture thereof.

In some embodiments, the microbial composition comprises one or more microbial strains, wherein the 16S rRNA gene of each of said strains comprises a sequence independently selected from SEQ ID Nos.: 45, 83, and 146 or a culture thereof. In some embodiments, the microbial composition comprises at least two (2) microbial strains, wherein the 16S rRNA genes of said at least two strains comprise sequences of SEQ ID Nos.: 45, 83, and 146 respectively, or cultures thereof.

In some embodiments, the microbial composition comprises one or more microbial strains, wherein the 16S rRNA gene of each of said strains comprises a sequence independently selected from SEQ ID Nos.: 44, 82 and 145, or a culture thereof. In some embodiments, the microbial composition comprises two or more microbial strains, wherein the 16S rRNA gene of each of said strains comprises a sequence independently selected from SEQ ID Nos.: 44, 82, and 145, or cultures thereof. In some embodiments, the microbial composition comprises one or more microbial strains, wherein the 16S rRNA gene of each of said strains comprises a sequence independently selected from SEQ ID Nos.: 44 and 82, and wherein said composition optionally further comprises one additional microbial strains, wherein the 16S rRNA gene of said additional strain comprises a sequence independently selected from the group consisting of SEQ ID No.: 85, or cultures thereof. In some embodiments, the microbial composition comprises at least three microbial strains, wherein the 16S rRNA genes of said at least three strains comprise sequences of SEQ ID Nos.: 44, 82 and 145, respectively, or cultures thereof.

In some embodiments, the microbial composition comprises one or more microbial strains, wherein the 16S rRNA gene of each of said strains comprises a sequence independently selected from SEQ ID Nos.: 43, 81 and 84, or a culture thereof. In some embodiments, the microbial composition comprises two or more microbial strains, wherein the 16S rRNA gene of each of said strains comprises a sequence independently selected from SEQ ID Nos.: 43, 81, and 84, or cultures thereof. In some embodiments, the microbial composition comprises at least three microbial strains, wherein the 16S rRNA genes of said at least eight strains comprise sequences of SEQ ID Nos.: 43, 81 and 84, respectively, or cultures thereof.

In some embodiments, the microbial composition comprises one or more microbial strains, wherein the 16S rRNA gene of each of said strains comprises a sequence independently selected from SEQ ID Nos.: 24, 86, 87, and 88, or a culture thereof.

In some embodiments, the microbial composition comprises one or more microbial strains, wherein the 16S rRNA gene of each of said strains comprises a sequence independently selected from SEQ ID Nos.: 87 and 88, or a culture thereof. In some embodiments, the microbial composition comprises at least two microbial strains, wherein the 16S rRNA genes of said at least two strains comprise sequences of SEQ ID Nos.: 87 and 88, respectively, or cultures thereof.

In some embodiments, the microbial composition comprises one or more microbial strains, wherein the 16S rRNA gene of each of said strains comprises a sequence independently selected from SEQ ID Nos.: 24 and 86, or a culture thereof. In some embodiments, the microbial composition comprises at least two microbial strains, wherein the 16S rRNA genes of said at least two strains comprise sequences of SEQ ID Nos.: 24 and 86, respectively, or cultures thereof.

In some embodiments, the microbial composition comprises one or more microbial strains, wherein the 16S rRNA gene of each of said strains comprises a sequence independently selected from SEQ ID Nos.: 51, 52, 53, 81, 82, and 83, or a culture thereof.

In some embodiments, the microbial composition comprises one or more microbial strains, wherein the 16S rRNA gene of each of said strains comprises a sequence independently selected from SEQ ID Nos.: 53 and 83, or a culture thereof. In some embodiments, the microbial composition comprises at least two (2) microbial strains, wherein the 16S rRNA genes of said at least two strains comprise sequences of SEQ ID Nos.: 53 and 83, respectively, or cultures thereof.

In some embodiments, the microbial composition comprises one or more microbial strains, wherein the 16S rRNA gene of each of said strains comprises a sequence independently selected from SEQ ID Nos.: 52 and 82, or a culture thereof. In some embodiments, the microbial composition comprises at least two microbial strains, wherein the 16S rRNA genes of said at least two strains comprise sequences of SEQ ID Nos.: 52 and 82, respectively, or cultures thereof.

In some embodiments, the microbial composition comprises one or more microbial strains, wherein the 16S rRNA gene of each of said strains comprises a sequence independently selected from SEQ ID Nos.: 51 and 81, or a culture thereof. In some embodiments, the microbial composition comprises at least two microbial strains, wherein the 16S rRNA genes of said at least two strains comprise sequences of SEQ ID Nos.: 51 and 81, respectively, or cultures thereof.

In some embodiments, the microbial composition comprises one or more microbial strains, wherein the 16S rRNA gene of each of said strains comprises a sequence independently selected from SEQ ID Nos.: 51, 52, 53, 75, 76, 81, 82, 83, 84, 145 and 146, or a culture thereof.

In some embodiments, the microbial composition comprises one or more microbial strains, wherein the 16S rRNA gene of each of said strains comprises a sequence independently selected from SEQ ID Nos.: 53, 83, and 146, or a culture thereof. In some embodiments, the microbial composition comprises two or more microbial strains, wherein the 16S rRNA gene of each of said strains comprises a sequence independently selected from SEQ ID Nos.: 53, 83, and 146, or a culture thereof. In some embodiments, the microbial composition comprises at least three microbial strains, wherein the 16S rRNA genes of said at least three strains comprise sequences of SEQ ID Nos.: 53, 83, and 146, respectively, or cultures thereof.

In some embodiments, the microbial composition comprises one or more microbial strains, wherein the 16S rRNA gene of each of said strains comprises a sequence independently selected from SEQ ID Nos.: 52, 76, 82 and 145, or a culture thereof. In some embodiments, the microbial composition comprises two or more microbial strains, wherein the 16S rRNA gene of each of said strains comprises a sequence independently selected from SEQ ID Nos.: 52, 76, 82, and 145, or cultures thereof. In some embodiments, the microbial composition comprises one or more microbial strains, wherein the 16S rRNA gene of each of said strains comprises a sequence independently selected from SEQ ID Nos.: 52, 82, and 145, and wherein said composition optionally further comprises an additional microbial strains wherein the 16S rRNA gene of said additional strain comprises a sequence independently selected from the group consisting of SEQ ID No.: 76, or cultures thereof. In some embodiments, the microbial composition comprises at least four microbial strains, wherein the 16S rRNA genes of said at least four strains comprise sequences of SEQ ID Nos.: 52, 76, 82 and 145, respectively, or cultures thereof.

In some embodiments, the microbial composition comprises one or more microbial strains, wherein the 16S rRNA gene of each of said strains comprises a sequence independently selected from SEQ ID Nos.: 51, 75, 81, and 84, or a culture thereof. In some embodiments, the microbial composition comprises two or more microbial strains, wherein the 16S rRNA gene of each of said strains comprises a sequence independently selected from SEQ ID Nos.: 51, 75, 81, and 84, or cultures thereof. In some embodiments, the microbial composition comprises at least four microbial strains, wherein the 16S rRNA genes of said at least four strains comprise sequences of SEQ ID Nos.: 51, 75, 81, and 84, respectively, or cultures thereof.

In some embodiments, the microbial composition comprises one or more microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, P0042_A8 or S2167, P0042_D5 or S2165, P0042_B2 or S2168, P0042_B12 or S2189, P0042_C2 or S2173, P0042_D10 or S2172, P0044_A3 or S2476, P0018_A11, P0044_A5, P0047_E2, P0047_C1, P0038_D2 or S2166, P0042_E1, P0047_E8, P0018_A1, S2159_P0058_B9, S2161_P0054_E8, S2164_P0054_F4, P0057_A3 or S2160, S2142_P0061_E11, S2163_P0019_A12, P0147_D10 or S2291, P0147_G10 or S2292, P0160_F7 or S2351, P0140_C10 or S2300, S2387, P0157_G5 or S2303, P0160_E1 or S2374, P0134_G7 or S2280, S2384, S2275, S2278, S2373, S2370, S2293, S2382, P0132_A12, P0132_C12, P0140_D9, P0173_H3 or S2404, S2385, S2197, S2285, S2477, S2376, S2420, S2424, S2445, S2333, S2329, S2327, S2330, S2423, S2435, S2158, S2437, S2332, S2521, S2228, S2473, P0156_G2, P0154_G3, S2487, S2488, S2421, P0105_C5, P0154_H3, P0156_G1, S1112, S2669, S2375, S2651, S2652, S2653, S2654, S2655, S2656, S2668, S2644, S2328, S2646, and any combination thereof, and strains derived therefrom, or cultures thereof. In some embodiments, the microbial composition comprises at least two of the strains disclosed herein. In another embodiment, the microbial composition comprises a plurality of strains disclosed herein.

In some embodiments, the microbial composition comprises one or more microbial strains selected from P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, and strains derived therefrom, or cultures thereof. In some embodiments, the microbial composition comprises P0032_C7, P0048_B9 or S2198, P0050_F5 or S2199, P0035_B2 or S2145, P0020_B1, P0047_A1 or S2284, P0033_E1 or S2177, P0032_A8 or S2181, P0049_E7, or strains derived therefrom, or cultures thereof.

In some embodiments, the microbial composition comprises one or more microbial strains selected from P0042_A8 or S2167, P0042_D5 or S2165, P0042_B2 or S2168, P0042_B12 or S2189, P0042_C2 or S2173, P0042_D10 or S2172, P0044_A3 or S2476, and strains derived therefrom, or cultures thereof. In some embodiments, the microbial composition comprises P0042_A8 or S2167, P0042_C2 or S2173, P0042_D10 or S2172, P0044_A3 or S2476, P0042_B12 or S2189, P0042_B2 or S2168, and P0042_D5 or S2165, or strains derived therefrom, or cultures thereof.

In some embodiments, the microbial composition comprises one or more microbial strains selected from P0018_A11, P0044_A5, P0047_E2, P0047_C1, P0038_D2 or S2166, P0042_E1, P0047_E8, P0018_A1, and strains derived therefrom, or cultures thereof. In some embodiments, the microbial composition comprises P0044_A5, P0038_D2 or S2166, P0018_A11, P0047_E2, P0018_A1, P0047_C1, P0042_E1, and P0047_E8, or strains derived therefrom, or cultures thereof.

In some embodiments, the microbial composition comprises one or more microbial strains selected from S2159_P0058_B9, S2161_P0054_E8, S2164_P0054_F4, P0057_A3 or S2160, S2142_P0061_E11, S2163_P0019_A12, and strains derived therefrom, or cultures thereof. In some embodiments, the microbial composition comprises S2142_P0061_E11, S2161_P0054_E8, S2164_P0054_F4, P0057_A3 or S2160, S2159_P0058_B9, and S2163_P0019_A12, or strains derived therefrom, or cultures thereof.

In some embodiments, the microbial composition comprises one or more microbial strains selected from P0147_D10 or S2291; P0147_G10 or S2292; PS160_F7 or S2351, and strains derived therefrom, or cultures thereof. In some embodiments, the microbial composition comprises P0147_D10 or S2291; P0147_G10 or S2292; and PS160_F7 or S2351, or strains derived therefrom, or cultures thereof.

In some embodiments, the microbial composition comprises one or more microbial strains selected from P0140_C10 or S2300; S2387; P0157_G5 or S2303, and strains derived therefrom, or cultures thereof. In some embodiments, the microbial composition comprises P0140_C10 or S2300; S2387; and P0157_G5 or S2303, or strains derived therefrom, or cultures thereof.

In some embodiments, the microbial composition comprises one or more microbial strains selected from P0160_E1 or S2374; P0134_G7 or S2280; S2384, and strains derived therefrom, or cultures thereof. In some embodiments, the microbial composition comprises P0160_E1 or S2374; P0134_G7 or S2280; and S2384, or strains derived therefrom, or cultures thereof.

In some embodiments, the microbial composition comprises one or more microbial strains selected from S2275; S2278, and strains derived therefrom, or cultures thereof. In some embodiments, the microbial composition comprises S2275 and S2278, or strains derived therefrom, or cultures thereof.

In some embodiments, the microbial composition comprises one or more microbial strains selected from P0157_G5 or S2303; S2373; S2375, and strains derived therefrom, or cultures thereof. In some embodiments, the microbial composition comprises P0157_G5 or S2303; S2373; and S2375, or strains derived therefrom, or cultures thereof.

In some embodiments, the microbial composition comprises one or more microbial strains selected from S2293; S2382, and strains derived therefrom, or cultures thereof. In some embodiments, the microbial composition comprises S2293 and S2382, or strains derived therefrom, or cultures thereof.

In some embodiments, the microbial composition comprises one or more microbial strains independently selected from S2385 and S2373, and strains derived therefrom, or cultures thereof. In some embodiments, the microbial composition comprises S2385 and S2375, or strains derived therefrom, or cultures thereof.

In some embodiments, the microbial composition comprises one or more microbial strains independently selected from S2385, S2669, S2373 and S2375, and strains derived therefrom, or cultures thereof. In some embodiments, the microbial composition comprises S2385, S2669, S2373 and S2375, or strains derived therefrom, or cultures thereof. In some embodiments, the microbial composition comprises on or more microbial strains independently selected from S2385, S2669, S2373, S2375, S2293 and S2644, and strains derived therefrom, or cultures thereof. In some embodiments, the microbial composition comprises S2385, S2669, S2373, S2375, S2293 and S2644, or strains derived therefrom, or cultures thereof.

In another embodiment provides a composition comprising a synthetic microbial consortium. In some embodiments, a synthetic consortium comprises: (a) a first set of microbes comprising one or more microbes that promote plant health, growth, and/or yield; and (b) a second set of microbes comprising one or more microbes that increase (directly or indirectly) the competitive fitness of one or more of the microbes of the first set of microbes in step (a); wherein the first and the second sets of microbes are combined into a single mixture as a synthetic consortium. In one embodiment, the synthetic consortium further comprises microbial strains not found together in nature. In another embodiment, the synthetic consortium comprises microbial strains not found in comparable concentrations relative to one another in nature. In some embodiments of a synthetic consortium, one or more microbes of the first set of microbes ((a) above) enhance nutrient availability and/or nutrient uptake of a plant. In some embodiments of a synthetic consortium, one or more microbes in the first set of microbes ((a) above) modulate plant hormone levels. In some embodiments of a synthetic consortium, one or more microbes in the first set of microbes ((a) above) demonstrate one or more of the activities selected from nitrogen fixation, IAA production, ACC deaminase activity, phosphate solubilization, and/or iron solubilization (and/or any other activities from which plant health, growth, and/or yield may be benefited). In some embodiments of a synthetic consortium, one or more microbes of the first set of microbes ((a) above) inhibit or suppress a plant pathogen (e.g., as a biological pesticide such as one selected from those described herein). In some embodiments of a synthetic consortium, one or more microbes in the second set of microbes ((b) above) directly increase the competitive fitness of one or more microbes in the first set of microbes ((a) above). In some embodiments, one or more microbes in the second set of microbes produce a metabolite that enhances the competitive fitness of one or more microbes in the first set of microbes. For example, one or more microbes in the second set of microbes produce a siderophore that enhances iron acquisition of one or more of the microbes in the first set of microbes. In some embodiments of a synthetic consortium, one or more microbes in the second set of microbes ((b) above) decrease the competitive fitness of a microorganism that is distinct from the microbes of the first or the second sets of microbes ((a) or (b) above), and potentially detrimental to (e.g., by inhibiting, competing with, excluding, or otherwise having a negative impact on) the fitness of one or more microbes in the first set of microbes ((a) above). In some embodiments of a synthetic consortium, one or more microbes in the second set of microbes ((b) above) produce a metabolite that is bactericidal, bacteriostatic or otherwise modulates growth of a microorganism that is distinct from the microbes of the first and the second sets of microbes, and that is detrimental to (e.g., by inhibiting, competing with, excluding, or otherwise having a negative impact on) the fitness of one or more microbes in the first set of microbes ((a) above). For example, one or more of the microbes in the second set of microbes ((b) above) produce a siderophore that inhibits the growth or fitness of a microorganism that is potentially detrimental to one or more microbes in the first set ((a) above). Thus, the function of the second set of microbes is to directly or indirectly increase the fitness or competitive fitness of the first set of microbes. In some embodiments of a synthetic consortium, the first and second set of microbes are combined and supplemented with an inert formulary component. In some embodiments, the synthetic consortium and compositions thereof promotes or enhances the health, growth and/or yield of a plant. In some embodiments, the synthetic consortium or a composition thereof according to the present application is applied to a plant (or a part thereof), a seed, or a seedling.

In some embodiments, the microbial compositions described herein, such as any of the microbial compositions described above, further comprise an agriculturally effective amount of an additional substance, compound or composition, such as, but not limited to, a nutrient, a fertilizer, an acaricide, a bactericide, a fungicide, an insecticide, a microbicide, a nematicide, a pesticide, or a combination thereof.

In some embodiments, the compositions are chemically inert; hence they are compatible with substantially any other constituents of the application schedule. The compositions may also be used in combination with plant growth affecting substances, such as fertilizers, plant growth regulators, and the like, provided that such compounds or substances are biologically compatible. The compositions may also be used in combination with biologically compatible pesticidal active agents as, for example, herbicides, nematocides, fungicides, insecticides, and the like.

In some embodiments, the microbial strains and compositions may furthermore be in the form of a mixture with synergists. Synergists are compounds by which the activity of the active compositions is increased without it being necessary for the synergist added to be active itself.

In some embodiments, the microbial strains and compositions may furthermore be in the form of a mixture with inhibitors (e.g., preservatives) which reduce the degradation of the active compositions after application in the habitat of the plant, on the surface of parts of plants or in plant tissues.

The active microbial strains and compositions may be used as a mixture with known fertilizers, acaricides, bactericides, fungicides, insecticides, microbicides, nematicides, pesticides, or combinations of any thereof, for example in order to widen the spectrum of action or to prevent the development of resistances to pesticides in this way. In many cases, synergistic effects, i.e., the activity of the mixture can exceed the activity of the individual components. A mixture with other known active compounds, such as growth regulators, safeners and/or semiochemicals is also contemplated.

In some embodiments, the compositions may include at least one chemical or biological fertilizer. The amount of at least one chemical or biological fertilizer employed in the compositions may vary depending on the final formulation as well as the size of the plant and seed to be treated. In some embodiments, the at least one chemical or biological fertilizer employed is about 0.1% w/w to about 80% w/w based on the entire formulation. In some embodiments, the at least one chemical or biological fertilizer is present in an amount of about 1% w/w to about 60%>w/w and in some embodiments about 10%>w/w to about 50% w/w.

The microbiological compositions optionally further include at least one biological fertilizer. Exemplary biological fertilizers that are suitable for use herein and can be included in a microbiological composition according to the embodiments of this application for promoting plant growth and/or yield include microbes, animals, bacteria, fungi, genetic material, plant, and natural products of living organisms. In these compositions, the microorganism is isolated prior to formulation with an additional organism. For example, microbes such as but not limited to species of *Achromobacter, Ampelomyces, Aureobasidium, Azospirillum, Azotobacter, Bacillus, Beauveria, Bradyrhizobium, Candida, Chaetomium, Cordyceps, Cryptococcus, Dabaryomyces, Delftia, Erwinia, Exophilia, Gliocladium, Herbaspirillum, Lactobacillus, Mariannaea, Microccocus, Paecilomyces, Paenibacillus, Pantoea, Pichia, Rhizobium, Saccharomyces, Sporobolomyces, Stenotrophomonas, Talaromyces,* and *Trichoderma* can be provided in a composition with the microorganisms. Use of the microbiological compositions according to the present embodiments in combination with the microbial microorganisms disclosed in U.S. Patent Appl. Publication Nos. US20030172588A1, US20030211119A1, US20130276493, US20140082770; U.S. Pat. Nos. 7,084,331; 7,097,830; 7,842,494; PCT Appl. Nos. WO2010109436A1, WO2013158900, and WO2013090628 is also contemplated.

In some embodiments, the compositions may include at least one chemical or biological pesticide, acaricide, bactericide, fungicide, insecticide, microbicide, nematicide, or a combination thereof. The amount of at least one chemical or biological pesticide, acaricide, bactericide, fungicide, insecticide, microbicide, nematicide, or a combination thereof employed in the compositions can vary depending on the final formulation as well as the size of the plant and seed to be treated. In some embodiments, the at least one chemical or biological pesticide, acaricide, bactericide, fungicide, insecticide, microbicide, nematicide, or a combination thereof employed is about 0.1% w/w to about 80% w/w based on the entire formulation. In some embodiments, the at least one chemical or biological pesticide, acaricide, bactericide, fungicide, insecticide, microbicide, nematicide, or a combination thereof is present in an amount of about 1% w/w to about 60%>w/w and most preferably about 10%>w/w to about 50% w/w.

A variety of chemical pesticides is apparent to one of skill in the art and may be used. Exemplary chemical pesticides include those in the carbamate, organophosphate, organochlorine, and pyrethroid classes. Also included are chemical control agents such as, but not limited to, benomyl, borax, captafol, captan, chorothalonil, formulations containing copper; formulations containing dichlone, dicloran, iodine, zinc; fungicides such as but not limited to blastididin, cymoxanil, fenarimol, flusilazole, folpet, imazalil, ipordione, maneb, manocozeb, metalaxyl, oxycarboxin, myclobutanil, oxytetracycline, PCNB, pentachlorophenol, prochloraz, propiconazole, quinomethionate, sodium aresenite, sodium DNOC, sodium hypochlorite, sodium phenylphenate, streptomycin, sulfur, tebuconazole, terbutrazole, thiabendazole, thiophanate-methyl, triadimefon, tricyclazole, triforine, validimycin, vinclozolin, zineb, and ziram.

In some embodiments, the compositions include at least one biological pesticide. Exemplary biological pesticides that are suitable for use herein and can be included in a microbiological composition for preventing a plant pathogenic disease include microbes, animals, bacteria, fungi, genetic material, plant, and natural products of living organisms. In these compositions, the microorganism is isolated prior to formulation with an additional organism. For example, microbes such as but not limited to species of *Anthrobacter, Ampelomyces, Aureobasidium, Bacillus, Beauveria, Candida, Chaetomium, Cordyceps, Cryptococcus, Dabaryomyces, Erwinia, Exophilia, Gliocladium, Mariannaea, Paecilomyces, Paenibacillus, Pantoea, Pichia, Pseudomonas, Sporobolomyces, Streptomyces, Talaromyces*, and *Trichoderma* can be provided in a composition with the microorganisms disclosed herein, with fungal strains of the *Muscodor* genus being preferred. Use of the microbiological compositions in combination with the microbial antagonists disclosed in U.S. Pat. Nos. 7,518,040; 7,601,346; and 6,312,940 is also contemplated.

Examples of fungi that may be combined with microbial strains and compositions in a composition include, without limitation, *Muscodor* species, *Aschersonia aleyrodis, Beauveria bassiana* ("white muscarine"), *Beauveria brongniartii, Chladosporium herbarum, Cordyceps clavulata, Cordyceps en tomorrhiza, Cordyceps facis, Cordyceps gracilis, Cordyceps melolanthae, Cordyceps militaris, Cordyceps myrmecophila, Cordyceps ravenelii, Cordyceps sinensis, Cordyceps sphecocephala, Cordyceps subsessilis, Cordyceps unilateralis, Cordyceps variabilis, Cordyceps washingtonensis, Culicinomyces clavosporus, Entomophaga grylli, Entomophaga maimaiga, Entomophaga muscae, Entomophaga praxibulli, Entomophthora plutellae, Fusarium lateritium, Glomus* species, *Hirsutella citriformis, Hirsutella thompsoni, Metarhizium anisopliae* ("green muscarine"), *Metarhizium flaviride, Muscodor albus, Neozygitesfloridana, Nomuraea rileyi, Paecilomyces farinosus, Paecilomyces fumosoroseus, Pandora neoaphidis, Tolypocladium cylindrosporum, Verticillium lecanii, Zoophthora radicans*, and mycorrhizal species such as *Laccaria bicolor*. Other mycopesticidal species will be apparent to those skilled in the art.

In still another embodiment, the PGPM compositions, consortia and methods disclosed herein can be used to treat transgenic seed. A transgenic seed refers to the seed of plants containing at least one heterologous gene that allows the expression of a polypeptide or protein not naturally found in the plant. The heterologous gene in transgenic seed can originate, for example, from microorganisms of the species *Bacillus, Rhizobium, Pseudomonas, Serratia, Trichoderma, Clavibacter, Glomus* or *Gliocladium*.

A further embodiment relates to a method of increasing the durability of plant pest compositions comprising providing a plant protection composition to a plant or planted area, and providing the PGPM compositions, consortia and methods described herein to the plant or planted area, wherein the PGPM compositions, consortia and methods described herein have a different mode of action than the plant protection composition.

The present disclosure further provides compositions that contain at least one of the isolated microbial strains or cultures thereof, such as any one of those described herein, and a carrier. The carrier may be any one or more of a number of carriers that confer a variety of properties, such as increased stability, wettability, dispersibility, etc. Wetting agents such as natural or synthetic surfactants, which can be nonionic or ionic surfactants or a combination thereof, can be included in a composition of the embodiments. Emulsions, such as water-in-oil emulsions can also be used to formulate a composition that includes at least one isolated microorganism of the present embodiments (see, for example, U.S. Pat. No. 7,485,451, incorporated by reference herein). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products (e.g., ground grain or beans, broth or flour derived from grain or beans), starch, sugar, or oil. The carrier may be an agricultural carrier. In certain preferred embodiments, the carrier is a seed, and the composition may be applied or coated onto the seed or allowed to saturate the seed.

In some embodiments, the agricultural carrier may be soil or plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material ("yard waste"), compost, or wood from building site refuse, sawdust or small fibers from recycling of paper, fabric, or wood. Other suitable agricultural carriers are known to those skilled in the art.

In some embodiments, the carrier suitable for the compositions described herein is an organic carrier. The organic carriers include, but are not limited to, peat, turf, talc, lignite, kaolinite, pyrophyllite, zeolite, montmorillonite, alginate, press mud, sawdust, and vermiculite. Talc is a natural mineral referred as steatite or soapstone composed of various minerals in combination with chloride and carbonate. Chemically it is referred as magnesium silicate and available as powder form from industries suited for wide range of applications. Talc has relative hydrophobicity, low moisture equilibrium, chemical inertness, reduced moisture absorption and it prevents the formation of hydrate bridges which enable longer storage periods. Peat (turf) is a carbonized vegetable tissue formed in wet conditions by decomposition of various plants and mosses. Peat is formed by the slow decay of successive layers of aquatic and semi aquatic plants, such as sedges, reeds, rushes, and mosses. Press mud is a byproduct of sugar industries. Vermiculite is a light mica-like mineral used to improve aeration and moisture retention. In some embodiments, compositions with organic carriers as described herein are suitable for organic farming. Other suitable organic carriers are known to those skilled in the art.

The microbiological compositions that comprise isolated microbial strains or cultures thereof may be in a variety of forms, including, but not limited to, still cultures, whole cultures, stored stocks of cells, mycelium and/or hyphae (particularly glycerol stocks), agar strips, stored agar plugs in glycerol/water, freeze dried stocks, and dried stocks such as lyophilisate or mycelia dried onto filter paper or grain seeds. As defined herein, "isolated culture" or grammatical equivalents as used in this disclosure and in the art is understood to mean that the referred to culture is a culture fluid, pellet, scraping, dried sample, lyophilisate, or section (for example, hyphae or mycelia); or a support, container, or medium such as a plate, paper, filter, matrix, straw, pipette or pipette tip, fiber, needle, gel, swab, tube, vial, particle, etc. that contains a single type of organism. An isolated culture of a microbial antagonist is a culture fluid or a scraping, pellet, dried preparation, lyophilisate, or section of the microorganism, or a support, container, or medium that contains the microorganism, in the absence of other organisms.

In some embodiments, the compositions are in a liquid form. For example, in the liquid form, e.g., solutions or suspensions, the microorganisms of the present embodiments may be mixed or suspended in water or in aqueous solutions. Suitable liquid diluents or carriers include water, aqueous solutions, petroleum distillates, or other liquid carriers.

In some embodiments, the compositions are in a solid form. For example, solid compositions can be prepared by dispersing the microorganisms of the embodiments in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

In one embodiment, the microbial composition promotes plant health, growth and/or yield via one or more mechanisms by which PGPMs function, as described herein. In some embodiments, the compositions contemplated herein enhance the growth and yield of crop plants by acting as microbial fertilizers, biocontrol agents of plant diseases, and/or inducers of plant resistance. The compositions, similarly to other biofertilizer agents, may have a high margin of safety because they typically do not burn or injure the plant.

As described throughout the present application, enhancing plant growth and plant yield may be effected by application of one or more of the compositions to a host plant or parts of the host plant. The compositions can be applied in an amount effective to enhance plant growth or yield relative to that in an untreated control. The active constituents are used in a concentration sufficient to enhance the growth of the target plant when applied to the plant. As will be apparent to a skilled person in the art, effective concentrations may vary depending upon various factors such as, for example, (a) the type of the plant or agricultural commodity; (b) the physiological condition of the plant or agricultural commodity; (c) the concentration of pathogens affecting the plant or agricultural commodity; (d) the type of disease injury on the plant or agricultural commodity; (e) weather conditions (e.g., temperature, humidity); and (f) the stage of plant disease. Typical concentrations are those higher than $1\times10^2$ CFU/mL of carrier. In some embodiments, concentrations range from about $1\times10^2$ to about $1\times10^{10}$ CFU/mL, such as the concentrations ranging from $1\times10^5$ to $1\times10^9$ CFU/mL. In some embodiments, concentrations are those of from about 1 to about 100 mg dry bacterial mass per milliliter of carrier (liquid composition) or per gram of carrier (dry formulation). In some embodiments, the concentrations range from $1\times10^2$ to about $1\times10^{10}$ cell/mL, such as the concentrations ranging from $1\times10^5$ to $1\times10^9$ cell/mL of the composition or carrier.

In some embodiments, the amount of one or more of the microorganisms in the compositions may vary depending on the final formulation as well as size or type of the plant or seed utilized. Preferably, the one or more microorganisms in the compositions are present in about 0.01% w/w to about 80% w/w of the entire formulation. In some embodiments, the dry weights of one or more microorganisms employed in the compositions is about 0.01%, 0.1%, 1%, 5% w/w to about 65% w/w and most preferably about 1% w/w to about 60% w/w by weight of the entire formulation.

The microbiological compositions may be applied to the target plant (or part(s) thereof) using a variety of conventional methods such as dusting, coating, injecting, rubbing, rolling, dipping, spraying, or brushing, or any other appropriate technique which does not significantly injure the target plant to be treated. Exemplary methods include, but are not limited to, the inoculation of growth medium or soil with suspensions of microbial cells and the coating of plant seeds with microbial cells and/or spores.

Also provided are methods of treating a plant by application of any of a variety of customary formulations in an effective amount to either the soil (i.e., in-furrow), a portion of the plant (i.e., drench) or on the seed before planting (i.e., seed coating or dressing). Customary formulations include solutions, emulsifiable concentrate, wettable powders, suspension concentrate, soluble powders, granules, suspension-emulsion concentrate, natural and synthetic materials impregnated with active compound, and very fine control release capsules in polymeric substances. In certain embodiments, the microbial compositions are formulated in powders that are available in either a ready-to-use formulation or are mixed together at the time of use. In either embodiment, the powder may be admixed with the soil prior to or at the time of planting. In an alternative embodiment, one or both of either the plant growth-promoting agent or biocontrol agent is a liquid formulation that is mixed together at the time of treating. One of ordinary skill in the art understands that an effective amount of the inventive compositions depends on the final formulation of the composition as well as the size of the plant or the size of the seed to be treated.

Depending on the final formulation and method of application, one or more suitable additives can also be introduced to the compositions. Adhesives such as carboxymethylcellulose and natural and synthetic polymers in the form of powders, granules, or latexes, such as gum arabic, chitin, polyvinyl alcohol and polyvinyl acetate, as well as natural phospholipids, such as cephalins and lecithins, and synthetic phospholipids, trehalose, mannitol, sorbitol, myo-inositol, sophorose, maltotriose, glucose, (+)-galactose, methyl-beta-D-galactopyranoside can be added to the present compositions.

In some embodiments, the compositions are formulated n a single, stable solution, or emulsion, or suspension. For solutions, the active chemical compounds are typically dissolved in solvents before the biological agent is added. Suitable liquid solvents include petroleum based aromatics, such as xylene, toluene or alkylnaphthalenes, aliphatic hydrocarbons, such as cyclohexane or paraffins, for example petroleum fractions, mineral and vegetable oils, alcohols, such as butanol or glycol as well as their ethers and esters, ketones, such as methyl ethyl ketone, methyl isobutyl ketone or cyclohexanone, strongly polar solvents, such as dimethylformamide and dimethyl sulphoxide. For emulsion or suspension, the liquid medium is water. In one embodiment, the chemical agent and biological agent are suspended in separate liquids and mixed at the time of application. In a preferred embodiment of suspension, the chemical agent and biological agent are combined in a ready-to-use formulation that exhibits a reasonably long shelf-life. In use, the liquid can be sprayed or can be applied foliarly as an atomized spray or in-furrow at the time of planting the crop. The liquid composition can be introduced in an effective amount on the seed (i.e., seed coating or dressing) or to the soil (i.e., in-furrow) before germination of the seed or directly to the soil in contact with the roots by utilizing a variety of techniques known in the art including, but not limited to, drip irrigation, sprinklers, soil injection or soil drenching. Optionally, stabilizers and buffers can be added, including alkaline and alkaline earth metal salts and organic acids, such as citric acid and ascorbic acid, inorganic acids, such as hydrochloric acid or sulfuric acid. Biocides can also be added and can include formaldehydes or formaldehyde-releasing agents and derivatives of benzoic acid, such as p-hydroxybenzoic acid.

D. Microbial Consortia

One embodiment provides a microbial consortium comprising two or more microbial strains, wherein the microbial consortium promotes or enhances plant health, growth, and/or yield.

One embodiment, provides a method for identifying at least one microbial strain that is associated with plant health, growth and/or yield, said method comprising the steps of:
(1) providing a plurality of plant rhizosphere samples;
(2) isolating a plurality of genomic DNAs from each of the samples provided in step (1);
(3) determining the sequences of a plurality of 16S rRNA gene segments from each plurality of genomic DNAs isolated in step (2);
(4) determining the abundance (absolute or relative) of each of said 16S rRNA gene segments in each plurality of 16S rRNA gene segments whose sequences were determined in step (3);
(5) determining the plant biomass or the abundance of a parameter associated therewith (e.g., plant weight, plant height, root size/length, etc.) or the plant yield for each of the plants from which the rhizosphere samples of step (1) were collected;
(6) correlating the abundance of each 16S rRNA gene segment determined in step (4) with the plant biomass or the abundance of a parameter associated therewith (e.g., plant weight, plant height, root size/length, etc.) or the plant yield determined in step (5);
(7) selecting at least one 16S rRNA gene segment whose abundance correlates to the plant biomass or the abundance of a parameter associated therewith (e.g., plant weight, plant height, root size/length, etc.) or the plant yield, as determined in step (6); and
(8) identifying at least one microbial strain from the plurality of plant rhizosphere samples in step (1) that comprises the at least one 16S rRNA gene segment selected in step (7).

Individual microbial strains may also be combined to produce a consortium based on their compatibility and function. Some embodiments provide a microbial consortium comprising two or more microbial strains identified by the methods as described herein.

Furthermore, it is recognized that certain different species of microbes tend to coincide or co-localize in nature due to their close and long-term physical and/or biochemical interactions. Certain microbial strains may work together as a consortium to support, and/or (directly or indirectly) promote plant health, growth and/or yield. For example, biological control of plant pathogens in disease suppressible soil is due to the existence of mixture of microbial antagonists. Furthermore, due to the physical and/or biochemical interactions, when working together as a consortium, some co-localizing microbial strains often demonstrate various synergistic effects as compared to them working alone.

Another embodiment provides a method for assembling a microbial consortium comprising two or more microbial strains that are associated with plant health, growth and/or yield, said method comprising the steps of:
(1) providing a plurality of plant rhizosphere samples;
(2) isolating a plurality of genomic DNAs from each of the samples provided in step (1);
(3) determining the sequences of a plurality of 16S rRNA gene segments from each plurality of genomic DNAs isolated in step (2);
(4) determining the abundance (absolute or relative) of each of said 16S rRNA gene segments in each plurality of 16S rRNA gene segments whose sequences were determined in step (3);
(5) determining the plant biomass or the abundance of a parameter associated therewith (e.g., plant weight, plant height, root size/length, etc.) or the plant yield for each of the plants from which the rhizosphere samples of step (1) were collected;
(6) correlating the abundance of each 16S rRNA gene segment determined in step (4) with the plant biomass or the abundance of a parameter associated therewith (e.g., plant weight, plant height, root size/length, etc.) or the plant yield determined in step (5);
(7) selecting at least one 16S rRNA gene segment whose abundance correlates to the plant biomass or the abundance of a parameter associated therewith (e.g., plant weight, plant height, root size/length, etc.) or the plant yield, as determined in step (6);
(8) correlating the abundance of the at least one 16S rRNA gene segment selected in step (7) with the abundances of the other of the plurality of 16S rRNA gene segments whose sequences were determined in step (3) across said plurality of samples;
(9) identifying one or more 16S rRNA gene segments whose abundances correlate with the abundance of the at least one 16S rRNA gene segment selected in step (7) across said plurality of samples;
(10) identifying two or more microbial strains, which comprises the 16S rRNA gene segments identified in steps (7) and (9), respectively; and

(11) assembling said two or more microbial strains identified in step (10) into a microbial consortium by combining said strains into a single mixture.

One embodiment provides a method for identifying a microbial consortium comprising two or more microbial strains, which promote plant health, growth and/or yield, based on 16S rRNA profiling. In some embodiments of this method, plants and the associated rhizosphere samples are first collected. Microbial 16S rRNA sequence tags are then determined for each plant rhizosphere sample using known methods (Patin et al. 2013 Microb. Ecol. 65:709-719). Pearson correlation values are then determined for the relative or percent abundance of each 16S rRNA sequence tag and the normalized weight (or height) of the corresponding plant, across a plurality of samples from plant fields. Bacterial 16S rRNA sequence tags with the highest correlation to either plant weight or height are then identified. The 16S rRNA sequence tags with the highest correlation to plant performance (normalized plant height or weight) are selected to identify other microbes that potentially shared functional interactions and thus, constituted consortia. To identify potential consortium members, distribution of the 16S rRNA sequence tags best correlated to plant performance are compared with every other sequence tag in the data set to identify co-distributing sequences. A ranked list of Pearson correlations of these comparisons is created and is expected to reveal candidate consortium members.

In another aspect, one embodiment provides a method of preparing a synthetic microbial consortium, comprising:
(a) selecting a first set of microbes comprising one or more microbes that promote plant health, growth, and/or yield;
(b) selecting a second set of microbes comprising one or more microbes that increase (directly or indirectly) the competitive fitness of one or more of the microbes of the first set of microbes in step (a); and
(c) combining the first and the second sets of microbes into a single mixture as a synthetic consortium.

In some embodiments of a synthetic consortium, one or more microbes of the first set of microbes ((a) above) enhance nutrient availability and/or nutrient uptake of a plant. In some embodiments of a synthetic consortium, one or more microbes in the first set of microbes ((a) above) modulate plant hormone levels. In some embodiments of a synthetic consortium, one or more microbes in the first set of microbes ((a) above) demonstrate one or more of the activities selected from nitrogen fixation, IAA production, ACC deaminase activity, phosphate solubilization, and/or iron solubilization (and/or any other activities from which plant health, growth, and/or yield may be benefited). In some embodiments of a synthetic consortium, one or more microbes of the first set of microbes ((a) above) inhibit or suppress a plant pathogen (e.g., as a biological pesticide such as one selected from those described herein). In some embodiments of a synthetic consortium, one or more microbes in the second set of microbes ((b) above) directly increase the competitive fitness of one or more microbes in the first set of microbes ((a) above). In some embodiments, one or more microbes in the second set of microbes produce a metabolite that enhances the competitive fitness of one or more microbes in the first set of microbes. For example, one or more microbes in the second set of microbes produce a siderophore that enhances iron acquisition of one or more of the microbes in the first set of microbes. In some embodiments of a synthetic consortium, one or more microbes in the second set of microbes ((b) above) decrease the competitive fitness of a microorganism that is distinct from the microbes of the first or the second sets of microbes ((a) or (b) above), and are potentially detrimental to (e.g., by inhibiting, competing with, excluding, or otherwise having a negative impact on) the fitness of one or more microbes in the first set of microbes ((a) above). In some embodiments of a synthetic consortium, one or more microbes in the second set of microbes ((b) above) produce a metabolite that is bactericidal, bacteriostatic or otherwise modulates growth of a microorganism that is distinct from the microbes of the first and the second sets of microbes, and potentially detrimental to (e.g., by inhibiting, competing with, excluding, or otherwise having a negative impact on) the fitness of one or more microbes in the first set of microbes ((a) above). For example, one or more of the microbes in the second set of microbes ((b) above) produce a siderophore that inhibits the growth or fitness of a microorganism that is potentially detrimental to one or more microbes in the first set ((a) above). In some embodiments of a synthetic consortium, the second set of microbes ((b) above) are supplemented with an inert formulary component. In some embodiments, the synthetic consortium and compositions thereof promote or enhance plant health, plant growth and/or plant yield. In some embodiments, the synthetic consortium or a composition thereof according to the present application is applied to a plant (or a part thereof), a seed, or a seedling.

Another embodiment contemplates a microbial consortium identified or prepared by a method according to any of the methods described above. The present embodiments further contemplate a method of promoting plant health, growth, and/or yield using a microbial consortium identified or constructed by a method according to the according to any of the methods described above.

E. Seed Coating Formulations

In one aspect, the microbial strains, cultures and/or compositions described herein are formulated as a seed treatment. In some embodiments, seeds can be partially, or substantially uniformly coated with one or more layers of the microbial strains, cultures, and/or compositions disclosed herein using conventional methods, including but not limited to mixing, spraying or a combination thereof through the use of treatment application equipment that is specifically designed and manufactured to accurately, safely, and efficiently apply seed treatment products to seeds.

In some embodiments, seeds can be coated using a coating technology such as, but not limited to, rotary coaters, drum coaters, fluidized bed techniques, spouted beds, rotary mists or a combination thereof. Liquid seed treatments such as those of the present embodiments can be applied, for example, via either a spinning "atomizer" disk or a spray nozzle which evenly distributes the seed treatment onto the seed as it moves though the spray pattern. In certain embodiments, the seed is then mixed or tumbled for an additional period of time to achieve additional treatment distribution and drying. The seeds can be primed or unprimed before coating with the compositions to increase the uniformity of germination and emergence. In an alternative embodiment, a dry powder formulation can be metered onto the moving seed and allowed to mix until completely distributed.

Other aspects provide seeds treated with the subject microbial compositions. One embodiment provides seeds having at least part of the surface area coated with a microbiological composition according to the present embodiments. In one embodiment, the microorganism-treated seeds have a microbial spore concentration or microbial cell concentration from about $10^5$ to about $10^9$ per seed. The seeds may also have more spores or microbial cells per seed. The microbial spores and/or cells can be coated freely onto the seeds or, preferably, they can be formulated in a liquid or solid composition before being coated onto the seeds. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, the microbial compositions contain functional agents capable of protecting seeds from the harmful effects of selective herbicides such as activated carbon, nutrients (fertilizers), and other agents capable of improving the germination and quality of the products or a combination thereof.

Seed coating methods and compositions that are known in the art can be particularly useful when they are modified by the addition of one of the compositions disclosed herein. Such coating methods and apparatus for their application are disclosed in, for example but not limited to, U.S. Pat. Nos. 5,918,413; 5,554,445; 5,389,399; 4,759,945; and 4,465,017. Seed coating compositions are disclosed, for example, in U.S. Pat. Appl. No. US20100154299, U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, which are all incorporated herein by reference.

A variety of additives can be added to the seed treatment formulations comprising the compositions disclosed herein. Binders can be added and include those composed preferably of an adhesive polymer that can be natural or synthetic without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arables; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

Any of a variety of colorants may be employed, including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. Other additives that can be added include trace nutrients such as salts of iron, manganese, boron, copper, cobalt, nickel, molybdenum and zinc. A polymer or other dust control agent can be applied to retain the treatment on the seed surface.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrans; alginates; sugars; molasses; polyvinyl pyrrolidones; polysaccharides; proteins; fats; oils; gum arables; gelatins; syrups; and starches. More examples can be found in, for example, U.S. Pat. No. 7,213,367 and U.S. Pat. Appln. No. US20100189693, incorporated herein by reference.

Various additives, such as adherents, dispersants, surfactants, and nutrient and buffer ingredients, can also be included in the seed treatment formulation. Other seed treatment additives include, but are not limited to, coating agents, wetting agents, buffering agents, and polysaccharides. At least one agriculturally acceptable carrier may be added to the seed treatment formulation such as water, solids or dry powders. The dry powders can be derived from a variety of materials such as calcium carbonate, gypsum, vermiculite, talc, humus, activated charcoal, and various phosphorous compounds.

In some embodiments, the seed coating composition can comprise at least one filler which is an organic or inorganic, natural or synthetic component with which the active components are combined to facilitate its application onto the seed. In certain embodiments, the filler is an inert solid such as clays, natural or synthetic silicates, silica, resins, waxes, solid fertilizers (for example, ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminum or magnesium silicates.

The seed treatment formulation may further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; biological fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed or alternatively, may be added as part of the seed coating composition of the embodiments.

In some embodiments, the amount of the composition or other ingredients used in the seed treatment should not inhibit germination of the seed, or cause phytotoxic damage to the seed.

The formulation that is used to treat the seed in the compositions of this application may be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is about 0.5% to about 99% by weight (w/w), 5%-40% or as otherwise formulated by those skilled in the art.

In some embodiments, other conventional inactive or inert ingredients may be incorporated into the seed treatment formulation. Such inert ingredients include, but are not limited to, conventional sticking agents; dispersing agents such as methylcellulose, for example, serve as combined dispersant/sticking agents for use in seed treatments; polyvinyl alcohol; lecithin, polymeric dispersants (e.g., polyvinylpyrrolidone/vinyl acetate); thickeners (e.g., clay thickeners to improve viscosity and reduce settling of particle suspensions); emulsion stabilizers; surfactants; antifreeze compounds (e.g., urea), dyes, colorants, and the like. Further inert ingredients useful in the embodiments of this application can be found in McCutcheon's, vol. 1, "Emulsifiers and Detergents," MC Publishing Company, Glen Rock, N.J., U.S.A., 1996. Additional inert ingredients useful in the embodiments of this application can be found in McCutcheon's, vol. 2, "Functional Materials," MC Publishing Company, Glen Rock, N.J., U.S.A., 1996.

The coating formulations of this application may be applied to seeds by a variety of methods, including, but not limited to, mixing in a container (e.g., a bottle or bag), mechanical application, tumbling, spraying, and immersion. A variety of active or inert material can be used for contacting seeds with the microbial compositions, such as conventional film-coating materials including but not limited to water-based film coating materials such as SEPIRET™ (Seppic, Inc., N.J.) and OPACOAT™ (Berwind Pharm. Services, P.A.)

The amount of a composition according to the embodiments of this application that is used for the treatment of the seed will vary depending upon the type of seed and the type of active ingredients, but the treatment will comprise contacting the seeds with an agriculturally effective amount of the inventive composition. As discussed herein, an effective amount means that amount of the inventive composition that is sufficient to affect beneficial or desired results. An effective amount can be administered in one or more administrations.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively, may be added in the coating layer.

The seed coating formulations of the embodiments of this application may be applied to the seeds using a variety of techniques and machines, such as fluidized bed techniques, the roller mill method, rotostatic seed treaters, and drum coaters. Other methods, such as spouted beds may also be useful. The seeds may be pre-sized before coating. In some embodiments, after coating, the seeds are dried and then transferred to a sizing machine for sizing. Such procedures are known to a skilled artisan.

The microorganism-treated seeds may also be enveloped with a film overcoating to protect the coating. Such overcoatings are known in the art and may be applied using fluidized bed and drum film coating techniques, as well as any other suitable methods known in the art.

In another embodiment, microbial strains, isolates, cultures, and/or compositions of this application can be introduced onto a seed by use of solid matrix priming. For example, a quantity of an inventive composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Solid matrix materials which are useful in may include polyacrylamide, starch, clay, silica, alumina, soil, sand, polyurea, polyacrylate, or any other material capable of absorbing or adsorbing the composition for a time and releasing that composition into or onto the seed. It is useful to make sure that the composition and the solid matrix material are compatible with each other. For example, the solid matrix material should be chosen so that it can release the composition at a reasonable rate, for example over a period of minutes, hours, days, or months.

In some embodiments, any plant seed capable of germinating to form a plant may be treated with the compositions contemplated herein. Suitable seeds include, but are not limited to, those of cereals, coffee, cole crops, fiber crops, flowers, fruits, legume, oil crops, trees, tuber crops, vegetables, as well as other plants of the monocotyledonous and dicotyledonous species. In some embodiments, crop seeds are coated include, but are not limited to, bean, carrot, corn, cotton, grasses, lettuce, peanut, pepper, potato, rapeseed, rice, rye, *sorghum*, soybean, sugarbeet, sunflower, tobacco, and tomato seeds. In certain embodiments, barley or wheat (spring wheat or winter wheat) seeds are coated with the present compositions.

F. Methods for Preparing the Composition

Cultures of the microorganisms may be prepared for use in the compositions of the present application using techniques known in the art, including, but not limited to, standard static drying and liquid fermentation. Growth is commonly effected in a bioreactor. A bioreactor may be any appropriate shape or size for growing the microorganisms (PGPMs). A bioreactor may range in size and scale from 10 mL to liters to cubic meters and may be made of stainless steel or any other appropriate material as known and used in the art. The bioreactor may be a batch type bioreactor, a fed batch type or a continuous-type bioreactor (e.g., a continuous stirred reactor). For example, a bioreactor may be a chemostat as known and used in the art of microbiology for growing and harvesting microorganisms. A bioreactor may be obtained from any commercial supplier (See also Bioreactor System Design, Asenjo & Merchuk, CRC Press, 1995). For small scale operations, a batch bioreactor may be used, for example, to test and develop new processes, and for processes that cannot be converted to continuous operations.

Microorganisms or PGPMs grown in a bioreactor may be suspended or immobilized. Growth in the bioreactor is generally under aerobic conditions at suitable temperatures and pH for growth. Cell growth can be achieved at temperatures between 5 and 40° C., with the preferred temperature being in the range of 15 to 30° C., 15 to 28° C., 20 to 30° C., or 15 to 25° C. The pH of the nutrient medium can vary between 4.0 and 9.0, but the preferred operating range is usually slightly acidic to neutral at pH 4.0 to 7.0, or 4.5 to 6.5, or pH 5.0 to 6.0. Typically, maximal cell yield is obtained in 18-96 hours after inoculation.

Optimal conditions for the cultivation of the microorganisms of this application may depend upon the particular strain. However, by virtue of the conditions applied in the selection process and general requirements of most microorganisms, a person of ordinary skill in the art would be able to determine essential nutrients and conditions. The microorganisms or PGPMs would typically be grown in aerobic liquid cultures on media which contain sources of carbon, nitrogen, and inorganic salts that can be assimilated by the microorganism and supportive of efficient cell growth. Exemplary (but not limiting) carbon sources are hexoses such as glucose, but other sources that are readily assimilated such as amino acids, may be substituted. Many inorganic and proteinaceous materials may be used as nitrogen sources in the growth process. Exemplary (but not limiting) nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. In some embodiments, potato dextrose liquid medium for fungal strains and R2A broth premix for bacterial strains is used.

G. Methods for Using the Microbial Strains, Cultures, and/or Compositions

Other aspects provide a method for treating a plant seed, comprising a step of exposing or contacting said plant seed with a microbial strain, isolate, culture, and/or composition as described herein.

Other aspects provide a method for enhancing the growth or yield of a plant, said method comprising applying an effective amount of a microbial strain, isolate, culture, and/or composition as described herein to the plant or to the plant's surroundings. Another aspect, provides a method for preventing, inhibiting or treating the development of a pathogenic disease of a plant, said method comprising applying an effective amount of a microbial strain, isolate, culture and/or composition as described herein to the plant or to the plant's surroundings. In some embodiments of the methods, the microbial strain is grown in a growth medium or soil of a host plant prior to or concurrent with the host plant growth in said growth medium or soil. In some embodiments, the microbial strain is established as an endophyte on said plant. In some embodiments of the above method, a microbial strain (PGPM) is applied to the plant (or a part thereof) or to the plant's surroundings (e.g., immediate soil layer or rhizosphere) in a culture or a composition at a concentration that is at least 2×, 5×, 10×, 100×, 500×, or 1000× the concentration of the same microbial strain found or detected in an untreated control plant (or a part thereof) or the control plant's surroundings, respectively. In some embodiments, upon or after application, the concentration of the microbial strain (PGPM) in the treated plant (or a part thereof) or the plant's surroundings (e.g., immediate soil layer or rhizosphere) is at least 2×, 5×, 10×, 100×, 500×, or 1000× the concentration of the same microbial strain found or detected in an untreated control plant (or a part thereof) or the control plant's surroundings. In some embodiments of the above method, a microbial strain (PGPM) is applied to the plant (or a part thereof) or to the plant's surroundings (e.g., immediate soil layer or rhizosphere) in a culture or a composition at a concentration that is higher than $1 \times 10^2$ CFU/mL. In some embodiments, concentration ranges from about $1 \times 10^2$ to about $1 \times 10^{10}$ CFU/mL, such as the concentrations ranging from $1 \times 10^5$ to $1 \times 10^9$ CFU/mL. In some embodiments, application of a microbial strain (PGPM) to the plant (or a part thereof) or to the plant's surroundings (e.g., immediate soil layer or rhizosphere) in a culture or a composition at a concentration that is at least $1 \times 10^6$ CFU/mL leads to a concentration of the microbial strain in the treated plant, plant part or the plant's surroundings that is at least 2× the amount of the strain found in the untreated plant or its surroundings. Table 1 summarizes the mean and medians of the relative abundance of microbial strains P0032_C7, P0160_E1 or S2374, P0048_B9 or S2198, P0050_F5 or S2199, P0035_B2 or S2145, P0134_G7 or S2280, P0020_B1, S2370, S2375, S2445, S2333, S2329, S2376, S2327, S2330, P0047_A1 or S2284, P0147_D10 or S2291, S2423, S2278, P0132_A12 or S2420, P0132_C12, P0105_C5, P0154_H3, S1112, S2435, S2159_P0058_B9, P0018_A11, P0044_A5, P0047_E2, S2487, S2488, P0047_C1, S2382, P0140_D9, S2387, S2158, P0038_D2 or S2166, S2424, P0042_E1, P0042_A8 or S2167, S2293, S2421, P0154_G3, S2161_P0054_E8, S2164_P0054_F4, P0057_A3 or S2160, P0140_C10 or S2300, P0047_E8, P0157_G5 or S2303, P0042_D5 or S2165, S2373, S2473, P0033_E1 or S2177, P0173_H3 or S2404, S2384, S2385, S2521, P0032_A8 or S2181, P0049_E7, S2197, S2477, P0147_G10 or S2292, P0160_F7 or S2351, P0018_A1, P0042_B2 or S2168, P0042_B12 or S2189, S2228, S2285, P0042_C2 or S2173, P0042_D10 or S2172, P0044_A3 or S2476, S2142_P0061_E11, S2163_P0019_A12, S2669, S2473, P00156 G2, S2651, S2652, S2653, S2654, S2655, S2656, S2668, S2644, and S2646 as found in untreated control corn plants and corresponding plant rhizosphere. In some embodiments of the above methods, the concentration of a PGPM applied to the plant or detected upon/after such application is at least 2×, 5×, 10×, 100×, 500×, or 1000× the mean concentration for the same microbial strain as listed in Table 1.

TABLE 1

Summary of the means and medians of the relative abundance of microbial strains from 274 soil samples:

| Isolate name | Relative % Abundance | | |
|---|---|---|---|
| | Mean | Median | Std Dev |
| P0032_C7, P0160_E1 or S2374 | 0.034 | 0.018 | 0.042 |
| P0048_B9 or S2198, P0050_F5 or S2199, P0035_B2 or S2145, P0134_G7 or S2280 | 0.016 | 0.009 | 0.019 |
| P0020_B1 | 0.106 | 0.008 | 0.224 |
| S2370, S2375 | 0.064 | 0.010 | 0.112 |
| S2445 | 0.004 | 0.000 | 0.009 |
| S2333 | 0.015 | 0.005 | 0.023 |
| S2329 | 0.069 | 0.042 | 0.115 |
| S2376 | 0.613 | 0.278 | 0.674 |
| S2327 | 0.030 | 0.009 | 0.047 |
| S2330 | 0.019 | 0.001 | 0.039 |
| P0047_A1 or S2284, P0147_D10 or S2291 | 0.025 | 0.016 | 0.031 |
| S2423 | 0.016 | 0.001 | 0.043 |
| S2278, P0132_A12, S2420 | 0.070 | 0.011 | 0.153 |
| P0132_C12, P0105_C5, P0154_H3, S2646 | 0.022 | 0.001 | 0.075 |
| S1112 | 0.001 | 0.000 | 0.004 |
| S2435 | 0.003 | 0.000 | 0.018 |
| S2159_P0058_B9 | 0.007 | 0.000 | 0.043 |
| P0018_A11, P0044_A5, P0047_E2, S2487, S2488 | 0.068 | 0.052 | 0.061 |
| P0047_C1, S2382 | 0.052 | 0.017 | 0.101 |
| P0140_D9, S2387 | 0.034 | 0.005 | 0.074 |
| S2158 | 0.074 | 0.045 | 0.103 |
| P0038_D2 or S2166, S2424 | 0.029 | 0.016 | 0.042 |
| P0042_E1 | 0.022 | 0.000 | 0.053 |
| P0042_A8 or S2167 | 0.009 | 0.000 | 0.076 |
| S2293 | 0.005 | 0.001 | 0.010 |
| S2421 | 0.002 | 0.000 | 0.005 |
| P0154_G3 | 0.002 | 0.000 | 0.005 |
| S2161_P0054_E8, S2164_P0054_F4, P0057_A3 or S2160 | 0.001 | 0.000 | 0.002 |
| P0140_C10 or S2300 | 0.079 | 0.001 | 0.201 |
| P0047_E8 | 0.050 | 0.009 | 0.099 |
| P0157_G5 or S2303 | 0.009 | 0.001 | 0.019 |
| P0042_D5 or S2165 | 0.018 | 0.003 | 0.040 |
| S2373 | 0.033 | 0.001 | 0.074 |
| S2437 | 0.015 | 0.003 | 0.027 |
| P0033_E1 or S2177 | 0.007 | 0.002 | 0.014 |
| P0173_H3 or S2404, S2384, S2385 | 0.010 | 0.004 | 0.015 |
| S2521 | 0.011 | 0.004 | 0.024 |
| P0032_A8 or S2181, P0049_E7, S2197, S2477, S2285 | 0.023 | 0.007 | 0.039 |
| P0147_G10 or S2292 | 0.026 | 0.001 | 0.058 |
| P0160_F7 or S2351 | 0.006 | 0.000 | 0.014 |

TABLE 1-continued

Summary of the means and medians of the relative abundance of microbial strains from 274 soil samples:

| Isolate name | Relative % Abundance | | |
|---|---|---|---|
| | Mean | Median | Std Dev |
| P0018_A1 | 0.009 | 0.002 | 0.013 |
| P0042_B2 or S2168 | 0.005 | 0.000 | 0.009 |
| P0042_B12 or S2189 | 0.001 | 0.000 | 0.003 |
| S2228 | 0.023 | 0.002 | 0.072 |
| P0042_C2 or S2173, P0042_D10 or S2172, P0044_A3 or S2476 | 0.005 | 0.001 | 0.010 |
| S2142_P0061_E11, S2163_P0019_A12, S2669 | 0.002 | 0.000 | 0.008 |
| S2473 | 0.004 | 0.000 | 0.018 |
| P0156_G2 | 0.000 | 0.000 | 0.001 |
| S2651, S2652, S2653 | 0.018 | 0.026 | 0.008 |
| S2654 | 0.020 | 0.056 | 0.000 |
| S2655 | 0.029 | 0.039 | 0.011 |
| S2656 | 0.002 | 0.003 | 0.000 |
| S2668 | 0.007 | 0.022 | 0.000 |
| S2644 | 0.027 | 0.043 | 0.010 |

In some embodiments of the above method, the microbial strain is established as an endophyte on the plant and the seed offspring of the plant after application. In some embodiments of this aspect, the microbial endophyte introduced into the plant may be an endophytic microorganism having a plant growth-promoting activity, a biological control activity, or a combination of both activities. A variety of methods previously found effective for the introduction of a microbial endophyte into cereal grass species are known in the art. Examples of such methods include those described in U.S. Pat. Appl. No. 20030195117A1, U.S. Pat. Appl. No. 20010032343A1, and U.S. Pat. No. 7,084,331, incorporated herein by reference. In some embodiments, the microbial strain, isolate, culture, and/or composition is applied to one or more places selected from the soil, a seed, a root, a flower, a leaf, a fruit, a portion of the plant or the whole plant. In this aspect, the microbial strain, culture or composition may be delivered to the plant by any of the delivery system described herein.

Examples of phytopathogenic diseases that are suitable for applications of the methods and materials include, but are not limited to, diseases caused by a broad range of pathogenic fungi. The methods of the present embodiments are preferably applied against pathogenic fungi that are important or interesting for agriculture, horticulture, plant biomass for the production of biofuel molecules and other chemicals, and/or forestry. In some embodiments, the pathogenic fungi are pathogenic *Pseudomonas* species (e.g., *Pseudomonas solanacearum*), *Xylella fastidiosa*; *Ralstonia solanacearum*, *Xanthomonas campestris*, *Erwinia amylovora*, *Fusarium* species, *Phytophthora* species (e.g., *P. infestans*), *Botrytis* species, *Leptosphaeria* species, powdery mildews (Ascomycota) and rusts (Basidiomycota), etc.

Non-limiting examples of plant pathogens of interest include, for instance, *Acremonium strictum*, *Agrobacterium tumefaciens*, *Alternaria alternate*, *Alternaria solani*, *Aphanomyces euteiches*, *Aspergillus fumigatus*, *Athelia rolfsii*, *Aureobasidium pullulans*, *Bipolaris zeicola*, *Botrytis cinerea*, *Calonectria kyotensis*, *Cephalosporium maydis*, *Cercospora medicaginis*, *Cercospora sojina*, *Colletotrichum coccodes*, *Colletotrichum fragariae*, *Colletotrichum graminicola*, *Coniella diplodiella*, *Coprinopsis psychromorbida*, *Corynespora cassiicola*, *Curvularia pallescens*, *Cylindrocladium crotalariae*, *Diplocarpon earlianum*, *Diplodia gossyina*, *Diplodia* spp., *Epicoccum nigrum*, *Erysiphe dehoracearum*, *Fusarium graminearum*, *Fusarium oxysporum*, *Fusarium oxysporum* f. sp. *tuberosi*, *Fusarium proliferatum* var. *proliferatum*, *Fusarium solani*, *Fusarium verticillioides*, *Ganoderma boninense*, *Geotrichum candidum*, *Glomerella tucumanensis*, *Guignardia bidwellii*, *Kabatiella zeae*, *Leptosphaerulina briosiana*, *Leptotrochila medicaginis*, *Macrophomina*, *Macrophomina phaseolina*, *Magnaporthe grisea*, *Magnaporthe oryzae*, *Microsphaera manshurica*, *Monilinia fructicola*, *Mycosphaerella fijiensis*, *Mycosphaerella fragariae*, *Nigrospora oryzae*, *Ophiostoma ulmi*, *Pectobacterium carotovorum*, *Pellicularia sasakii* (*Rhizoctonia solani*), *Peronospora manshurica*, *Phakopsora pachyrhizi*, *Phoma foveata*, *Phoma medicaginis*, *Phomopsis longicolla*, *Phytophthora cinnamomi*, *Phytophthora erythroseptica*, *Phytophthora fragariae*, *Phytophthora infestans*, *Phytophthora medicaginis*, *Phytophthora megasperma*, *Phytophthora palmivora*, *Podosphaera leucotricha*, *Pseudopeziza medicaginis*, *Puccinia graminis* subsp. *Tritici* (UG99), *Puccinia sorghi*, *Pyricularia grisea*, *Pyricularia oryzae*, *Pythium ultimum*, *Pythium aphanidermatum*, *Rhizoctonia solani*, *Rhizoctonia zeae*, *Rosellinia* sp., *Sclerotinia sclerotiorum*, *Sclerotinina trifoliorum*, *Sclerotium rolfsii*, *Septoria glycines*, *Septoria lycopersici*, *Setomelanomma turcica*, *Sphaerotheca macularis*, *Spongospora subterranea*, *Stemphylium* sp, *Synchytrium endobioticum*, *Thecaphora* (*Angiosorus*), *Thielaviopsis*, *Tilletia indica*, *Trichoderma viride*, *Ustilago maydis*, *Verticillium alboatrum*, *Verticillium dahliae*, *Verticillium dahliae*, *Xanthomonas axonopodis*, or *Xanthomonas oryzae* pv. *oryzae*.

In some embodiments, the methods and materials are useful in suppressing the development of the pathogens *Aspergillus fumigatus*, *Botrytis cinerea*, *Cerpospora betae*, *Colletotrichum* sp., *Curvularia* spp., *Fusarium* sp., *Ganoderma boninense*, *Geotrichum candidum*, *Gibberella* sp., *Monographella* sp., *Mycosphaerella fijiensis*, *Phytophthora palmivora*, *Phytophthora ramorum*, *Penicillium* sp., *Pythium ultimum*, *Pythium aphanidermatum*, *Rhizoctonia solani*, *Rhizopus* spp., *Schizophyllum* spp., *Sclerotinia sclerotiorum*, *Stagnospora* sp., *Verticillium dahliae*, or *Xanthomonas axonopodis*. In some embodiments, the methods and materials may be used to suppress the development of several plant pathogens of commercial importance, including *Fusarium graminearum* NRRL-5883, *Monographella nivalis* ATCC MYA-3968, *Gibberella zeae* ATCC-16106, *Stagnospora nodorum* ATCC-26369, *Colletotrichum graminicola* ATCC-34167, and *Penicillium* sp. pathogens.

In some embodiments, the method for enhancing the growth or yield of a plant, including any of such methods descried herein, further comprises a step of processing soil before planting a plant, a plant seed or a plant seedling in said soil. In some embodiments, the soil is fully or partially sterilized in the soil processing step. In some embodiments, the soil processing method comprises making a microwave radiator move into soil, and thereafter radiating microwaves from the microwave radiator to soil to be processed. Examples of such a method can be found, e.g., in US 20060283364. In some embodiments, the soil is fully or partially sterilized by autoclaving (e.g., at 121° C., 1 h or other similar conditions) or by gamma (γ)-irradiation (50 kGy). In some embodiments, the soil is fully or partially sterilized by heating, steaming or gassing with ethylene oxide. In some embodiments, the soil is partially or fully sterilized by soil solarization. Soil solarization is an environmentally friendly method of using solar power for soil processing (e.g., sterilization) by mulching the soil and covering it with tarp, usually with a plastic (e.g. transparent polyethylene) cover, to trap solar energy. Other suitable soil processing methods are known to those skilled in the art.

In some embodiments, the method for enhancing the growth or yield of a plant comprises (a) processing the soil before planting the plant, plant seed or seedling thereof in said soil; (b) planting the plant, plant seed or seedling thereof in the soil processed in step (a); and (3) applying an effective amount of a microbial strain, isolate, culture, and/or composition as described herein to the plant, plant seed or seedling, or surroundings thereof. In some embodiments, the soil is fully sterilized. In some embodiments, the soil is partially sterilized. In some embodiments, the soil is processed by autoclaving in step (a).

H. Delivery Systems

Microbial stains, isolates or cultures thereof, or microbial compositions may be delivered through several means. In some embodiments, they are delivered by seed treatment, seed priming, seedling dip, soil application, foliar spray, fruit spray, hive insert, sucker treatment, sett treatment, and a multiple delivery system.

In some embodiments, the microbial strains, cultures thereof or compositions comprising the same, as described herein, may be delivered by direct exposure or contact with a plant seed. In some embodiments, the seed can be coated with a microbial strain (or an isolate or a culture thereof) or a composition thereof. Seed treatment with PGPMs may be effective against several plant diseases.

In some embodiments, the microbial strains, isolates, cultures or compositions, as described herein, can be delivered by direct exposure or contact with a plant seed during seed priming process. Priming with PGPMs may increase germination and improve seedling establishment.

Such priming procedures may initiate the physiological process of germination, but prevents the emergence of plumule and radicle. It has been recognized that initiation of the physiological process helps in the establishment and proliferation of the PGPMs on the spermosphere.

In some embodiments, the microbial strains, isolates, cultures thereof or compositions comprising the same, as described herein, can be delivered by seedling dip. Plant pathogens often enter host plants through root. In some embodiments, protection of rhizosphere region by prior colonization with PGPMs prevents the establishment of a host-parasite relationship.

In some embodiments, the microbial strains, isolates, cultures or compositions, as described herein, can be delivered by direct application to soil. Soil is the repertoire of both beneficial and pathogenic microbes. In some embodiments, delivering PGPMs to soil can suppress the establishment of pathogenic microbes.

In some embodiments, the microbial strains, isolates, cultures or compositions, as described herein, can be delivered by foliar spray or fruit spray. In some embodiments, delivering PGPMs directly to plant foliage or fruit can suppress pathogenic microbes contributing to various foliar diseases or post-harvest diseases.

In some embodiments, the microbial strains, isolates, cultures or compositions are delivered by hive insert. Honey bees and bumble bees serve as a vector for the dispersal of biocontrol agents of diseases of flowering and fruit crops. In some embodiments, a dispenser can be attached to the hive and loaded with the PGPMs, optionally in combination with other desired agents.

In some embodiments, the microbial strains, isolates, cultures or compositions are delivered by sucker treatment or sett treatment. PGPMs can plant a vital role in the management of soilborne diseases of vegetatively propagated crops. The delivery of PGPMs varies depending upon the crop. For crops such as banana, PGPMs may be delivered through sucker treatment (e.g., sucker dipping). For crops such as sugarcane, PGPMs may be delivered through sett treatment (e.g., sett dipping).

In some embodiments, the microbial strains, isolates, cultures or compositions are delivered by a multiple delivery system comprising two or more of the delivery systems as described herein.

I. Plant Varieties and Seed Offspring Infected with a Microbial Strain

Also provided, in other aspects of the present embodiments is an artificially infected plant created by artificially introducing a microbial endophyte disclosed herein into the plant. In some embodiments of this aspect, the microbial endophyte introduced into the plant may be an endophytic microorganism having a plant growth-promoting activity, a biological control activity, or a combination of both activities. In some embodiments, the microbial strain is established as an endophyte in the plant or a progeny thereof (e.g., the seed offspring) that is exposed to or treated with a microbial (endophytic) strain, isolate, culture or composition thereof as described herein. Accordingly, another embodiment provides a seed of the artificially infected plant, comprising the microbial endophyte disclosed herein.

A variety of methods previously found effective for the introduction of a microbial endophyte into cereal grass species are known in the art. Examples of such methods include those described in U.S. Pat. Appl. No. 20030195117A1, U.S. Pat. Appl. No. 20010032343A1, and U.S. Pat. No. 7,084,331, among others.

In some embodiments, after artificial infection, a DNA sequence of the isolated endophytic microorganism is amplified by PCR and the endophyte is confirmed by carrying out a homology search for the DNA sequence amplified. In some embodiments, a foreign gene that expresses an identifiable means is introduced into the above-mentioned endophytic microorganism, and the presence of the colonization of the above-mentioned endophytic microorganism infecting the plant is confirmed by the above-identifiable means using the foreign gene.

J. Suitable Plants

In principle, the methods and compositions of this application may be deployed for any plant species. Monocotyledonous as well as dicotyledonous plant species are particularly suitable. The methods and compositions are preferably used with plants that are important or interesting for agriculture, horticulture, for the production of biomass used in producing liquid fuel molecules and other chemicals, and/or forestry.

In still another embodiment, the PGPM compositions, consortia and methods disclosed herein can be used to treat transgenic seed. A transgenic seed refers to the seed of plants containing at least one heterologous gene that allows the expression of a polypeptide or protein not naturally found in the plant. The heterologous gene in transgenic seed can originate, for example, from microorganisms of the species *Bacillus, Rhizobium, Pseudomonas, Serratia, Trichoderma, Clavibacter, Glomus* or *Gliocladium*.

Thus, embodiments of this application have use over a broad range of plants, preferably higher plants pertaining to the classes of Angiospermae and Gymnospermae. Plants of the subclasses of the Dicotylodenae and the Monocotyledonae are particularly suitable. Dicotyledonous plants belong to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

The methods and compositions may be used in plants that are important or interesting for agriculture, horticulture, biomass for the production of biofuel molecules and other chemicals, and/or forestry. Non-limiting examples include, for instance, *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Arundo donax* (giant reed), *Secale cereale* (rye), *Salix* spp. (willow), *Eucalyptus* spp. (eucalyptus), *Triticosecale* spp. (triticum—wheat×rye), *Bambuseae* (Bamboo), *Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassava), *Lycopersicon esculentum* (tomato), *Lactuca saliva* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (Huperzia serrata), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (petunia), *Poinsettia pulcherrima* (poinsettia), *Nicotiana tabacum* (tobacco), *Lupinus albus* (lupin), *Uniola paniculata* (oats), *Agrostis* spp. (bentgrass), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), *Phleum pratense* (timothy), and conifers. Of interest are plants grown for energy production, so called energy crops, such as cellulose-based energy crops like *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* spp. (triticum—wheat×rye), and *Bambuseae* (Bamboo); and starch-based energy crops like *Zea mays* (corn) and *Manihot esculenta* (cassava); and sugar-based energy crops like *Saccharum* sp. (sugarcane), *Beta vulgaris* (sugarbeet), and *Sorghum bicolor* (L.) *Moench* (sweet sorghum); and biofuel-producing energy crops like *Glycine max* (soybean), *Brassica napus* (canola), *Helianthus annuus* (sunflower), *Carthamus tinctorius* (safflower), *Jatropha curcas* (Jatropha), *Ricinus communis* (castor), *Elaeis guineensis* (African oil palm), *Elaeis oleifera* (American oil palm), *Cocos nucifera* (coconut), *Camelina sativa* (wild flax), *Pongamia pinnata* (Pongam), *Olea europaea* (olive), *Linum usitatissimum* (flax), *Crambe abyssinica* (Abyssinian-kale), and *Brassica juncea.*

In some embodiments, the methods and compositions may be used in corn, including but not limited to, flour corn (*Zea mays* var. *amylacea*), popcorn (*Zea mays* var. *everta*), dent corn (*Zea mays* var. *indentata*), flint corn (*Zea mays* var. *indurate*), sweet corn (*Zea mays* var. *saccharata* and *Zea mays* var. *rugosa*), waxy corn (*Zea mays* var. *ceratina*), amylomaize (*Zea mays*), pod corn (*Zea mays* var. *tunicata* Larrañaga ex A. St. Hil.), and striped maize (*Zea mays* var. *japonica*). In some embodiments, the methods and compositions are used in sweetcorn.

This disclosure will be better understood from the Examples which follow. However, one skilled in the art will readily appreciate that the specific methods and results discussed are merely illustrative of the disclosure as described more fully in the embodiments.

EXAMPLES

Example 1 Collection of Soil Samples and Sequencing of Soil Microorganisms

Soil samples were collected from agricultural fields. For instance, soil samples were collected from corn and soy fields on two continents. Samples were collected in Orbost, Victoria and Lowood, Queensland, Australia in February 2014, from Brentwood, Calif., USA in April 2014 and from Lynn, Ind., USA in June 2014. The present application contemplates PGPMs identified and isolated from any suitable types of environmental materials, such as samples collected from, without limitation, soil, rock, plants, animals, organic debris, water, aerosols, etc. From each field V3-V5 stage corn plants were selected, removed from the ground and soil collected. For each plant height and weight was recorded, soil attached to the roots were collected for cultivation and DNA extraction, and bulk soil surrounding the root structure was collected for soil chemistry analysis and archiving.

Root associated soil samples (about 0.5 g) were collected in triplicate from the rhizosphere of corn plants for DNA extraction and sequencing. Samples were placed into 2-mL screw-cap centrifuge tubes containing a sterile ceramic bead matrix consisting of one 4-mm glass bead (GSM-40), 1.0 g of 1.4- to 1.6-mm zirconium silicate beads (SLZ-15) and 0.75 g of 0.070- to 0.125-mm zirconium silicate beads (BSLZ-1) obtained from Cero Glass (Columbia, Tenn.). Samples were kept cool and transported to the laboratory for DNA extraction.

Samples were mechanically lysed using a FastPrep FP 120 instrument (Bio-101, Vista, Calif.) at 6.5 m/s for 45 s in 1 ml phosphate buffer (200 mM sodium phosphate, 200 mM NaCl, 20 mM EDTA, pH 8.0) and 10% SDS (sodium dodecyl sulfate). Lysed samples were centrifuged at 13,000×g for 5 min at 4° C. to separate the supernatant with DNA and particulate matter. Supernatants were transferred into new 1.5-mL centrifuge tubes and further purified by adding 500 µl phenol-chloroform-isoamyl alcohol (25:24:1) and centrifuging at 13,200×g for 5 min at room temperature. The separated aqueous phase containing the DNA was collected for final purification on QIAprep Plasmid Spin columns (Qiagen, Valencia, Calif.) following manufacturer's instructions.

Genomic DNA was prepared for pyro-sequencing a 600-bp portion of the 16S rRNA gene covering hypervariable regions 5-8 (V5-V8). Samples were amplified by PCR using universal fusion primers incorporating universal primer pair TX9/1391R, the 'A' and 'B' 454 pyro-sequencing adapters and a sample specific variable length nucleotide barcode sequence (TX9-A-BCxx, 5'-CCATCTCATCCCTGCGT-GTCTCCGACTCAGxxxxxxGGATTAGAWACCCBGG-TAGT-3'; 1391R-B-Adap, 5'-[BioTEG]CCTATCCCCTGT-GTGCCTTGGCAGTCTCAGGACGGGCRGTGWGT-RCA-3'). All samples were PCR cycle titrated to determine the lowest number of cycles needed for sufficient product and to reduce the incidence of PCR errors. Thermocycling conditions were as follows: initial 94° C. for 1 min, sample specific number of cycles of 94° C. for 30 s, 55° C. for 45 s and 68° C. for 1 min, final extension at 68° C. for 1 min. After titration, a 200 µl reaction was prepared containing the following: 40 µl template (1 ng/µl), 20 µl HiFi Buffer (Invitrogen, Carlsbad, Calif.), 10 µl 8 mM TX9-A-BCxx, 10 µl 8 mM 1391R-B-Adap, 10 µl 4 mM dNTP (NEB, Ipswich, Mass.), 8 µl 50 mM MgSO4 (Invitrogen, Carlsbad, Calif.), 8 µl 10 mg/ml BSA (Invitrogen, Carlsbad, Calif.), 0.8 µl HiFi Platinum Taq (Invitrogen, Carlsbad, Calif.), and 93.2 µl sterile milliQ water. Each reaction was amplified in 4×50 µl replicates to minimize PCR errors and combined before purification. Amplicon products were purified on a 0.9% agarose gel and recovered with a QIAquick gel extraction kit (Qiagen, Valencia, Calif.) following manufacturer's instructions. Final products were quantified using SYBR green (Invitrogen, Carlsbad, Calif.).

The barcoded amplicon products were multiplexed into libraries of 8 for sequencing using the standard 454 Life Sciences Lib-L emulsion PCR protocol and Titanium chemistry (Margulies, M. et al. 2005. Genome sequencing in microfabricated high-density picoliter reactors. Nature 437: 376-380) with the default 454 shotgun processing pipeline.

All sequences retained by the GS FLX Instrument quality filters were subjected to additional in-house sorting by sample, trimming and quality control (QC) filters. Sequences passing the GS FLX signal processing step were trimmed within the conserved region adjacent to V5V6 region of the 16S rRNA gene using a series of trimming rules. Trim targets were defined using the expected barcode location relative to the primer end position (5' trim point), and a defined trimming region 230-290 bases from 5' trim point (3' trim point for V5V6). Sequences shorter than 120 basepairs were rejected. Once the sequences are trimmed they were filtered based on quality. All bases must have a minimum Q-score of 20 (Q20); if a sequence had a base with a score less than Q20 the whole sequence was rejected. Also, 90% of the bases in a sequence must have a score of Q25 or greater or the sequence is rejected. The sequences trimmed that passed the quality filtering were then used to generate the data tables for analysis.

Example 2 Identification of Microbial Consortia

The corn plants for sampling were at the V3-V5 stage of development and were chosen based upon being either under- or over-performing plants based on visual inspection and comparison with neighboring plants. Under-performing plants were chosen based upon being equal or smaller in size to neighboring plants which collectively presented as smaller in size with the average size of plants across the entire field. Over-performing plants were chosen based upon being greater in size than the average size of plants across the general area or entire field. Another criterion for choosing an over-performing plant was that its immediate neighbors were also over-performing relative to the size of plants in the general area or entire field. Plants were collected in pairs that each included an under- and over-performing plant that were located within 5 meters of one another. Between 6-18 pairs of plants were collected from each field.

Prior to sampling, the height of each plant was determined by extending the upper leaves vertically to the highest point and measuring this level. The weight of the plant was determined post-sampling by removing the entire above soil portion of the plant and transferring into a sealed Ziploc quart size bag. The sealed bags were used to minimize variability due to water evaporation from the plant post-harvest. The weight of the plant was determined within approximately 1 hour after collection.

Corn root-associated soil samples were conducted by digging up the corn plants with a shovel and carefully excavating roots with a sterile stainless steel spatula. Soil clinging to the roots was removed directly into 2 ml centrifuge tubes containing beads for cell lysis.

DNA extraction and profiling were performed as described in Example 1. (See Patin et al. Microb. Ecol. 65:709-719, 2013).

In order to compare microbial communities associated with corn roots from plants from different fields, the heights and weights of each plant collected from the same field were normalized. A number of different normalization methods were deployed that included Z-scores, interpolation of the values between 0-1 and percent rank. The reason for normalizing the values was to enable comparison of plants between fields that, in some cases, were of different sizes as a result of different planting dates, soil types, weather, etc.

Approximately 100,000 V5V6 16S rRNA sequence tags were determined for each sample. Pearson correlation values were determined for the percent abundance of each 16S rRNA sequence tag and the normalized corn plant weight (or height) across about 150 samples from 4 fields in Victoria and Queensland, Australia comprising either sweet corn or field corn. Bacterial 16S rRNA sequence tags with the highest correlation to either plant weight or height were identified. The four 16S rRNA sequence tags with the highest correlation to plant performance (normalized plant height or weight) were selected to identify other microbes that potentially shared functional interactions and thus, constituted consortia. To identify potential consortium members, distribution of the 16S rRNA sequence tags best correlated to plant performance were compared with every other sequence tag in the data set to identify co-distributing sequences. A ranked list of Pearson correlations of these comparisons was created and revealed candidate consortium members for each of the four plant performance-correlated sequence tags.

Cultivation screens were also performed from the same samples where the root-associated microbial communities were resolved by 16S rRNA gene profiling. Approximately 20,000 isolates were recovered by cultivating on seven different solid medium formulations. The identity of the isolates was determined by PCR-amplifying a portion of the 16S rRNA gene comprising the v5-v8 variable regions. The sequences were trimmed to the same V5V6 region as used for the 16S rRNA gene profiles conducted above. This step allowed for cross indexing between the cultivation and 16S rRNA gene profiling data.

Cultivated strains corresponding to the four best plant performance correlated sequence tags and their best co-distributing sequence tags were recovered and tested for their ability to increase plant performance.

Example 3 Isolation of Soil Microorganisms

Rhizosphere soil samples were collected in sterile vials and stored on ice. Once transported back to the laboratory, samples were stored at 4° C. For isolation of microbial strains from soil samples, 0.5 gram of soil was transferred to a new, sterile vial, and diluted with 25 mL of VL55 base medium (Sait et al, 2002). Diluted soil solutions were shaken at room temperature for 20 minutes on a plate shaker set to 180 rpm. Soil solutions were then sonicated using a probe sonicator set to 90% power output (Fisher Scientific FB120110). Following sonication, soil particulates were allowed to settle and the supernatant solution, referred to as "soil extract", was collected and transferred to sterile vial(s). The soil extract was serial diluted in VL55 base medium and plated onto solid media for isolation of single colonies.

All samples were plated onto a large media panel containing a variety of carbon sources. The majority of media used VL55 base with additional growth substrates and solidified with 0.8% gellan. Carbon sources and final concentrations added to VL55 media included xylan (0.05%), pectin (0.05%), alginate (0.05%), D-glucose (0.5 mM), D-galactose (0.5 mM), D-xylose (0.5 mM), L-arabinose (0.5 mM), D-galacturonate (0.5 mM), D-glucuronate (0.5 mM), L-ascorbate (0.5 mM), D-gluconate (0.5 mM), n-acetyl-glucosamine (2 mM), an amino acid mixture (Hudson et al, 1989; Joseph et al, 2003), and 5%-10% sterile rumen fluid. Additional media included dilute nutrient broth (0.08 g/L) solidified with 0.8% gellan, M9 glucose agar (Teknova M1260), and a nitrogen-free medium containing 0.2 g/L $KH_2PO_4$, 0.8 g/L $K_2HPO_4$, 0.2 g/L $MgSO_4$ $7H_2O$, 0.1 g/L NaCl, 0.02 g/L $CaCl_2$ $2H_2O$, 0.005 g/L $FeSO_4$ $7H_2O$, 0.002 g/L $NaMoO_4$ $2H_2O$, 0.01 $MnCl_2$ $4H_2O$, 2.0 g/L sodium lactate, 2.0 g/L sodium citrate, 2.0 g/L sucrose, 2.0 g/L D-xylose, and 2.0 g/L malic acid. All versions of media were also made with the antifungal compound nystatin (100 U/mL final concentration).

Isolation media plates were incubated at 26° C. for a period ranging from 1 to 12 weeks, and single colonies were picked using sterile toothpicks onto fresh plates in 96 well array format. Media plates with arrayed colonies were incubated at 26° C. for another 3-14 days. Array plate colonies were transferred to liquid media in deep well plates using a sterile 96-pin transfer tool. Deep well plates contained 1 mL of liquid versions of the media described above. Liquid plates were incubated until visible cell growth was observed. DNA was then extracted from liquid cultures using a 96-well microbial DNA isolation kit (MPBio #119696200 or MoBio #10196) and subsequently used as a template for PCR to amplify the 16S rRNA gene. A lysozyme and proteinase K pretreatment step was used prior to the kit DNA extraction in order to increase efficiency of cell lysis. Purified PCR products were sequenced for strain identification. Isolate strains of interest were re-streaked onto new plates and colony purified. DNA was extracted once more from colony purified strains and the identity confirmed.

Example 4. Isolation of Plant Endophyte Microorganisms

Corn plants grown following the methods described in Example 7, were harvested and used to isolate endophyte microorganisms.

The crown area of the corn plant, typically located an inch below the soil surface, was cut under sterile conditions with a sterile scalpel. Immediately after sampling, the outside surface of the crown was washed with a bleach (20%), tween 80 (0.1%) and deionized water (79.9%) solution and rinsed with sterilized deionized water or Dulbecco Phosphate Buffered saline solution (PBS). The crown was washed and rinsed twice, after which the first mm at the base of the crown was removed in a sterile petri dish using a sterile scalpel. Endophyte microorganism were then isolated either by stamping the crown (see Method 1 below), or by plating a crown extract (see Method 2 below), on a selection of seven solid media plates from the media panel described in Example 3.

Method 1: Crown Stamp

After removing the first mm of the crown, the newly exposed area was pressed directly (stamped) onto the surface of one of each solid media plate in the panel.

Method 2: Crown Extract

Under sterile conditions, the center section of the crown was sliced with a sterile scalpel and cut up into small pieces. These pieces, along with a small volume of PBS (1 or 2 mL), were added to a sterile Potter-Elvehjem tissue grinder and homogenized with a minimum of 20 strokes. The supernatant of this crown extract was then plated (100 µL of solution per plate) and spread evenly with either sterile glass beads or a sterile disposable plastic spreader.

The plates were then incubated and microorganisms isolated following the methods described in Example 3.

The same or similar methods as described herein could be used for isolation of endophytes from other crop and plant types (Zinnel et. al. 2002. Isolation and characterization of endophytic colonizing bacteria from agronomic crops and prairie plants. Applied and Environmental Microbiology 68(5): 2198-2208). The same or similar methods as described herein could also be used for isolation of endophytes from other plant sections, including, for example, seeds, plant reproductive tissue, vegetative tissue, regenerative tissues, plant parts, or progeny of the non-naturally occurring plant varieties.

Example 5 Biochemical Characteristics of the Microbial Isolates

The isolated microbes were further tested for properties important in their interaction with plants. The studied properties included production of IAA-Auxin, siderophores and ACC-Deaminase, nitrogen fixation and solubilization of inorganic phosphates. The results of these bacterial activity assays are presented below and in Table 2.

TABLE 2

Results of five biochemical assays. IAA: Indole Actic Acid production measured by absorbance where value >0.082 is above background (see in bold). Sidero: Siderophore production measured by observation of color change on a scale of 1-3 from minimal to significant. PO4: Inorganic phosphate solubilization measured by observation of halo on a scale of 1-3 from minimal to significant. N-fix: Molecular nitrogen fixation measured by observation of growth on a scale of 1-3 from minimal to significant. ACC: ACC deaminase production measured by observation of growth on a scale of 1-3 from minimal to significant.

| Taxon Internal Isolate Names | BIOCHEMICAL ASSAYS | | | | |
| --- | --- | --- | --- | --- | --- |
|  | IAA | Sidero | PO4 | N-fix | ACC |
| P0047_E8 | 0.063 | 0 | 1 | 0 | 0 |
| P0057_A3 or S2160 | 0.125 | 1 | 1 | 1 | 0 |
| P0105_C5 | 0.084 | 1 | 0 | 0 | 0 |
| P0132_A12 | 0.084 | 0 | 3 | 0 | 0 |
| P0132_C12 | 0.083 | 0 | 3 | 0 | 0 |
| P0147_G10 or S2292 | 0.083 | 0 | 0 | 0 | 0 |
| P0154_H3 | 0.079 | 1 | 1 | 0 | 0 |
| P0156_G1 | 0.067 | 0 | 0 | 1 | 0 |
| P0156_G2 | 0.079 | 0 | 0 | 1 | 1 |
| P0157_G5 or S2303 | 0.147 | 0 | 0 | — | 0 |
| P0160_E1 or S2374 | 0.107 | 0 | 0 | 1 | 1 |
| P0160_F7 or S2351 | 0.099 | 0 | 1 | 1 | 1 |
| P0173_H3 or S2404 | 0.076 | — | 0 | 1 | 1 |
| S2142_P0061_E11 | 0.049 | 1 | 1 | 1 | 1 |
| S2158 | 0.078 | 0 | 0 | 1 | 0 |
| S2159_P0058_B9 | 0.112 | 1 | 1 | 2 | 0 |
| S2161_P0054_E8 | 0.129 | 1 | 1 | 1 | 0 |
| S2163_P0019_A12 | 0.051 | 1 | 3 | 1 | 1 |
| S2164_P0054_F4 | 0.118 | 1 | 1 | 1 | 0 |
| S2228 | 0.070 | 1 | 0 | 0 | 0 |
| S2275 | 0.077 | 1 | 2 | 0 | 0 |
| S2278 | 0.078 | 1 | 2 | 0 | 0 |
| S2370 | 0.071 | 0 | 0 | 1 | 0 |
| S2382 | 0.068 | 0 | 0 | 2 | 2 |
| S2420 | 0.068 | 0 | 0 | 2 | 0 |
| S2421 | 0.065 | 0 | 0 | 2 | 2 |
| S2423 | 0.083 | 0 | 0 | 3 | 1 |
| S2424 | 0.069 | 0 | 0 | 0 | 2 |
| S2437 | 0.088 | 0 | 0 | 0 | 0 |
| S2477 | 0.070 | 0 | 0 | 3 | 2 |
| S2487 | 0.064 | 0 | 1 | 3 | 2 |
| S2488 | 0.056 | 0 | 0 | 0 | 3 |
| S2669 | 0.053 | 0 | 3 | 0 | 0 |
| S2375 | 0.077 | 0 | 0 | 1 | 1 |
| S2653 | 0.096 | 0 | 0 | 0 | 0 |
| S2654 | 0.077 | 0 | 0 | 1 | 1 |
| S2656 | 0.127 | 0 | 0 | 1 | 1 |
| S2644 | 0.127 | 0 | 0 | 1 | 1 |

Indole Acetic Acid (IAA) Production:

Auxins are a class of plant hormones that have been shown to dramatically affect plant growth in a variety of ways. The main Auxin that has been identified as a phytohormone is Indole 3-Acetic Acid, 'IAA'. IAA is often produced biosynthetically from Tryptophan. This analysis used a liquid growth medium containing Tryptophan to quantify the amount of IAA produced by our microbial isolates.

This assay was typically performed in standard 96-well plate format as detailed herein. 250 µL of medium containing 80 mg/L Difco Nutrient Broth and 100 mg/L Trytophan were transferred with a standard 96-channel pipette apparatus to each well of a 96-well cell culture plate. Bacterial isolate cultures were then transferred via a sterile 96-pin transfer tool and the resulting cultures were typically stored at 26° C. for 2-4 days. The culture plates were centrifuged (20° C., 4000 rpm, 10 min) and subsequently, 33 µL of the supernatant solution were removed from each well and transferred to a clean 96-well assay plate. Each well in this assay plate was mixed with 200 µL of a modified Salkowsky Reagent (Appl. Environmental Microbio. 1995, 61, 793.), held in the dark at room temperature for 10 minutes and subsequently analyzed by standard Beer-Lambert type absorbance-concentration analysis using 535 nm wavelength radiation.

The following isolates were positive for IAA production: P0160_E1 or S2374, P0132_A12, P0132_C12, S2159_P0058_B9, S2161_P0054_E8, S2164_P0054_F4, P0057_A3 or S2160, P0157_G5 or S2303, P0160_F7 or S2351, P0147_G10 or S2292, S2437, S2423, P0105_C5, S2653, S2656 and 2644.

Inorganic Phosphate Solubilization:

The microbial isolates were screened for their ability to solubilize inorganic phosphate using a modified PVK-Agarose-Calcium Phosphate solid medium (Pikovskaya R. I.

1948 Mobilization of phosphorus in soil in connection with the vital activity of some microbial species. Microbiologia 17: 362-370, and Nautiyal C. S. 1999 An efficient microbiological growth medium for screening phosphate solubilizing microorganisms (FEMS Microbiology Letters 170: 265-270) consisted of the following components.

PVK-Calcium Phosphate Medium with Agarose; Ingredients Per 1 L: 10 g Glucose, 5 g $Ca_3(PO_4)_2$, 0.5 g $(NH_4)_2SO_4$, 0.2 g NaCl, 0.1 g $MgSO_4.7H_2O$, 0.2 g KCl, 0.5 g Yeast Extract, 0.002 g $MnSO_4$—$H_2O$, 0.002 g $FeSO_4.7H_2O$, 7 g Agarose.

Initially, the resulting medium is opaque white due to the presence of insoluble calcium phosphate. After transfer of the isolates to the PVK-plate and subsequent storage at 26° C. for 2-3 weeks, the appearance of a clear, translucent spot or 'halo' is indicative of the isolates' ability to solubilize inorganic phosphate. The phosphate solubilizing activity of the bacteria was rated on a 1-3× system, where 3× indicates significant growth whereas 1× suggests minimal, yet observable phosphate solubilization.

The following isolates were positive for phosphate solubilization: P0132_A12, P0132_C12, S2159_P0058_B9, S2161_P0054_E8, S2164_P0054_F4, P0057_A3 or S2160, P0047_E8, P0160_F7 or S2351, S2142_P0061_E11, S2163_P0019_A12, S2278, S2275, S2487, P0154_H3 and S2669.

Siderophore Production:

The microbial isolates were screened for their ability to produce Siderophores by the method of Schwynn and Neilands' Chrome Azurol S (CAS) assay (Anal. Biochem. 1987, 160, 47). The medium consisted of 80 mg/L Difco Nutrient Broth, 8 g/L Gellan Gum Powder and the CAS reagent dye solution. The blue-colored solid plates and CAS reagent solution were prepared as described by Schwyn et. al. (vide supra). The isolates were transferred to the blue plates which were subsequently stored at 26° C. for 2-3 weeks. Production of siderophores is indicated by a color change from blue to orange in a circular or 'halo' shape around the siderophore producing microbes. The siderophore production activity of the bacteria was rated on a 1-3× system, where 3× indicates significant siderophore production whereas 1× suggests minimal, yet observable siderophore production.

The following isolates were positive for siderophore production: S2159_P0058_B9, S2161_P0054_E8, S2164_P0054_F4, P0057_A3 or S2161, S2142_P0061_E11, S2163_P0019_A12, S2278, S2275, S222, P0105_C5, and P0154_H3.

Molecular Nitrogen Fixation:

Microbial isolates were transferred via a 96-pin transfer tool onto solid medium plates with no intentionally added Nitrogen source. The components of the medium per liter are as follows: 0.2 g $MgSO_4 \times 7H_2O$, 0.1 g NaCl, 0.2 g $KH_2PO_4$, 0.8 g $K_2HPO_4$-3H2O, Gellan Gum Powder 8 g, 10 mL 25% HCl, 1.5 g $FeCl_2 \times 4H_2O$, 0.19 g $CoCl_2 \times 6H_2O$, 0.1 g $MnCl_2 \times 4H_2O$, 0.07 g $ZnCl_2$, 6 mg $H_3BO_3$, 36 mg $Na_2MoO_4 \times 2H_2O$, 24 mg $NiCl_2 \times 6H_2O$, 2 mg $CuCl_2 \times 2H_2O$, 20 mg $CaCl_2$-$2H_2O$, 5 mg $FeSO_4$-$7H_2O$, 2 mg $NaMoO_4$-$2H_2O$, 10 mg $MnCl_2$-$4H_2O$, 2 g Sodium lactate (60% w/w aq.), 2 g Sodium citrate, 2 g sucrose, 2 g xylose, 2 g malic acid. $CaCl_2$ (10%, 5 mL) was added after sterilization and prior to dispensing the medium onto the plates to aid in solidification of the plate media.

Normally, plates were stored at 26° C. for 2-3 weeks. The appearance of any growth of the isolates is indicative of their ability to 'fix' molecular nitrogen. The growth of the bacteria was rated on a 1-3× system, where 3× indicates significant growth whereas 1× suggests minimal, yet observable growth.

The following isolates were positive for nitrogen fixation: P0160_E1 or S2374, S2159_P0058_B9, S2164_P0054_F4, P0057_A3 or S2160, P0173_H3 or S2404, P0160_F7 or S2351, S2164_P0061_E11, S2163_P0019_A12, S2161_P0054_E8, P0156_G2, P0156_G1, S2487, S2423, S2477, S2420, S2382, S2421, S2158, S2370, S2375, S2654, S2656, and S2644.

ACC Deaminase Production:

The ability of the microbial isolates to produce the ACC-Deaminase Enzyme was carried out using Nitrogen Free medium plates (described above for the Nitrogen Fixation assay) which were subsequently coated with ACC. To each plate was added 1 mL of a 30 mM aqueous ACC solution which was spread evenly around the plate surface with glass beads and dried at room temperature. Isolates were transferred to the ACC-coated plates and the resulting plates were stored at 26° C. for 2-3 weeks; the appearance of any growth of the isolates is indicative of their ability to metabolise ACC by the ACC-Deaminase enzyme. The growth of the bacteria was rated on a 1-3× system, where 3× indicates significant growth whereas 1× suggests minimal, yet observable growth.

The following isolates were 'positive' for ACC-Deaminase production: P0160_E1 or S2374, P0173_H3 or S2404, P0160_F7 or S2351, S2142_P0061_E11, S2163_P0019_A12, P0156_G2, S2488, S2487, S2477, S2382, S2421, S2424, S2423, S2375, S2654, S2656, and S2644.

Example 6 Germination and Seedling Early Growth Tests

Germination

Corn kernels (Test I untreated sweet corn; Test II—Blue River untreated field corn) were sterilized in a solution of 20% bleach for 5 minutes. Bleached corn was then washed 10× in sterile pH 7.0 phosphate buffer. A final wash was performed using sterile deionized water. Kernels were then placed on pre-sterilized filter paper within a 150 mm petri dish (~75 kernels per dish). Five milliliters of sterile deionized water was added to each petri dish to dampen the filter paper. Petri dishes were stored in a dark growth chamber for three days. On day three, sprouted kernels were sorted and the largest germinated sprouts were used for seedling growth in subsequent steps. In all steps, sterile tweezers were used to transfer kernels and all work was carried out in a biosafety hood.

Inoculation

Previously isolated and sequence confirmed microbial strains were grown to high cell density in shaking flasks at 26° C. In Test I, cells were centrifuged and pellets were washed with sterile 1×M9 salts (Sigma-Aldrich M6030). Cells were then resuspended in M9 salts at a density equal to an optical density of 0.1. For Test II, cells were prepared in a similar manner but were washed and resuspended in a sterile saline solution (NaCl 3.0 g/L, $MgSO_4$ $7H_2O$ 0.197 g/L, $CaCl_2$ $2H_2O$ 0.176 g/L) to an optical density of 0.1.

Figure 6:
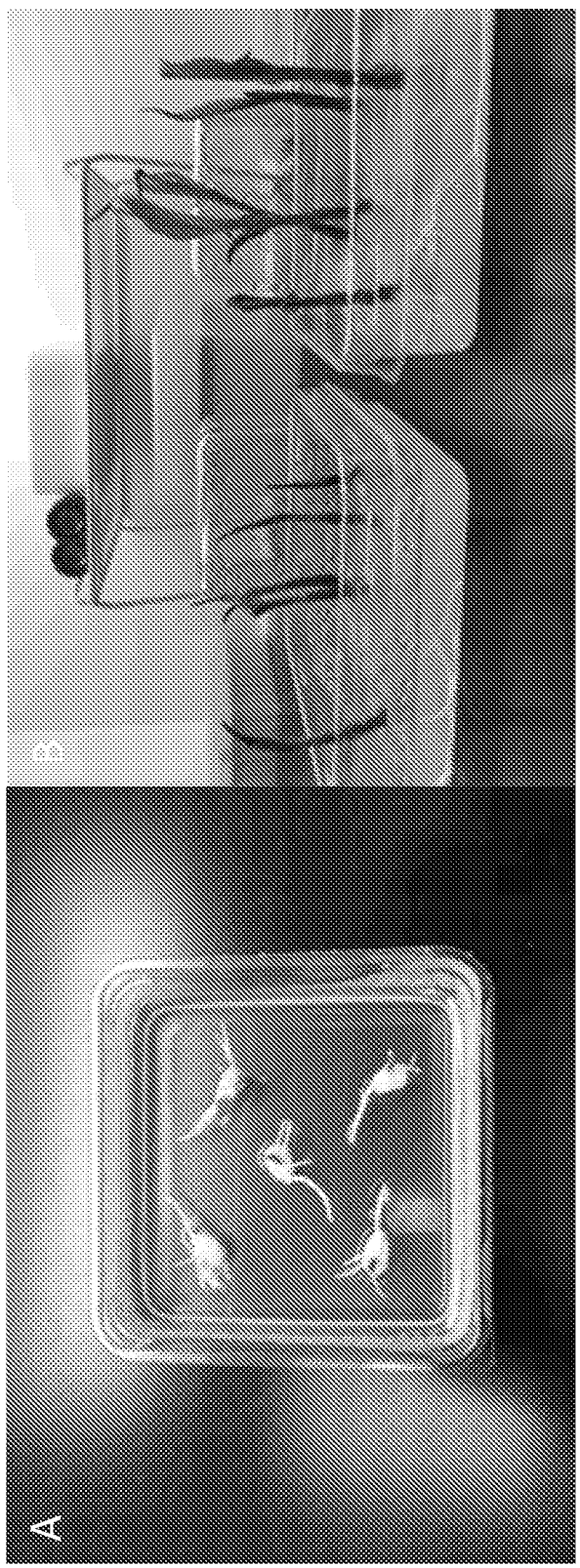
FIG. 6 shows Test II seedling growth in PlantCon containers using MS/Phytagel medium. A) Sprouted seeds transferred to PlantCon on day three. B) Example of seedling growth in PlantCon container at day five.

Using sterile tweezers, germinated seeds were transferred to sterile PlantCon containers (MPBio #0926722) containing 100 mL of Murashige and Skoog (MS) medium (MPBio #0926233), solidified with 3 g/L Phytagel (Sigma-Aldrich P8169) (FIG. 6). Four seeds were transferred to each container for Test 1 and five seeds were transferred to each container for Test II. After the seeds were evenly spaced apart inside the PlantCon container, 100 µL of microbial strain treatments was pipette directly onto the center of each germinated seed. Each seed within a container received the same treatment. Control treatments received 100 µL of buffer only. PlantCon covers were replaced and the containers were transferred to a growth chamber which maintained a 26° C. constant temperature and a light/dark cycle of 16 and 8 hours, respectively.

Measurements

Figure 7:
FIG. 7 show seedling measurements. On day 7, plants were removed from PlantCon containers. Shoot length and root length were recorded for each plant, and the average value was calculated for each treatment. A) Control (buffer only) treatment in Test II. B) Strain S2330 treatment in Test II.
Figure 8:
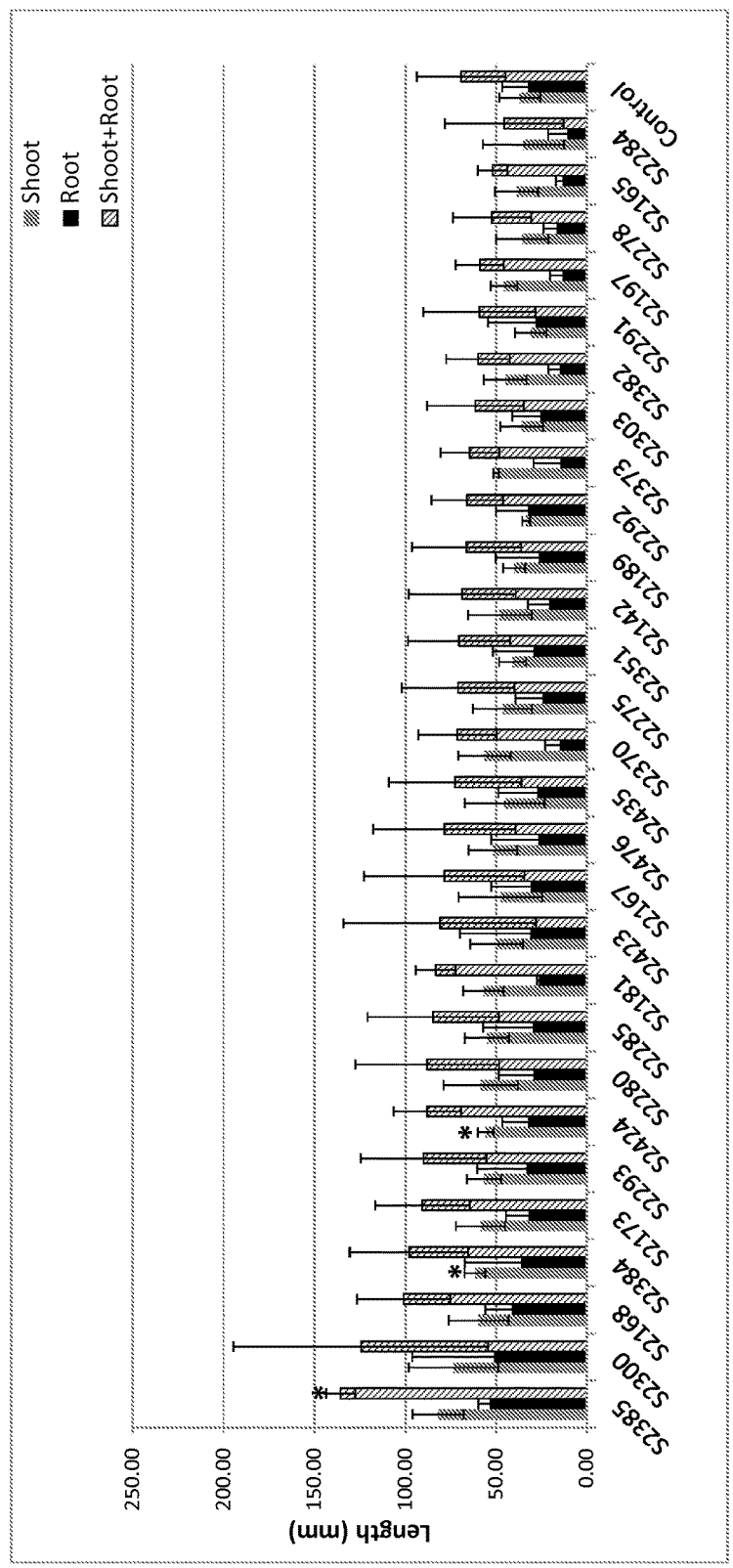
FIG. 8 shows Test I seedling growth results. Average values were plotted for shoot length, root length, and shoot+root length. Error bars are standard deviations (n=2-4). Asterisk indicates significance compared to control treatment (p<0.05).
Figure 9:
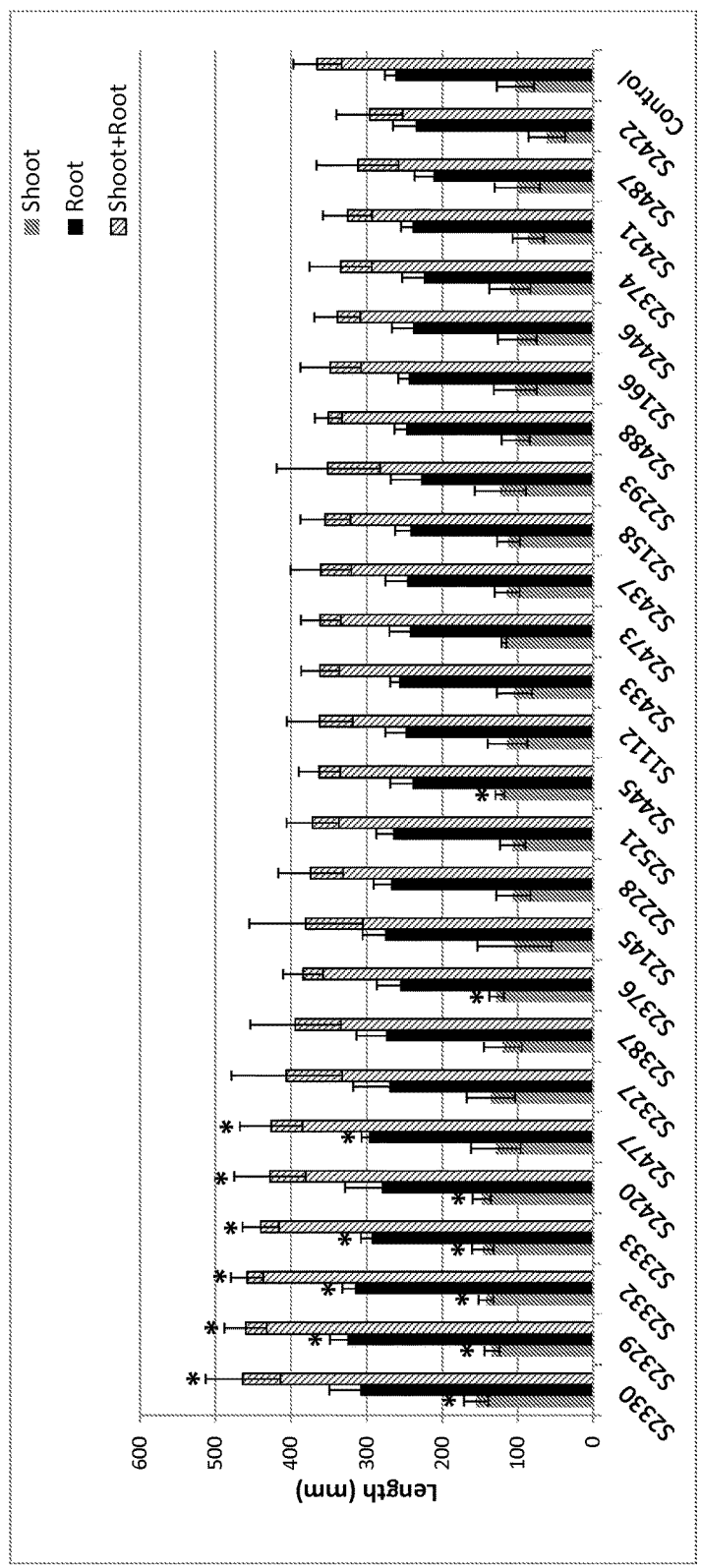
FIG. 9 shows Test II seedling growth results. Average values were plotted for shoot length, root length (sum of three longest roots), and shoot+root length. Error bars are standard deviations (n=5). Asterisk indicates significance compared to control treatment (p<0.05).
Figure 10:
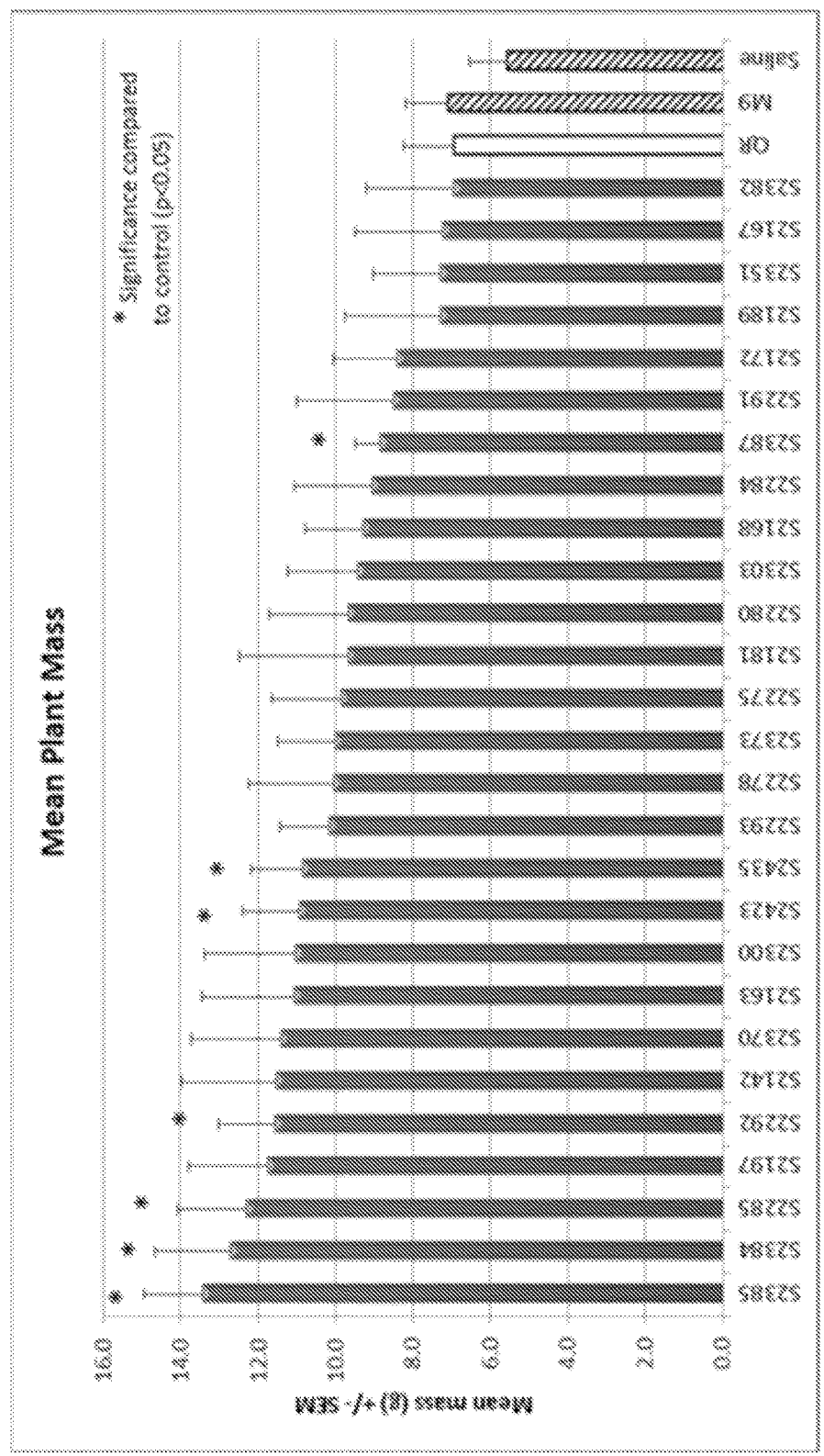
FIG. 10 shows the mean plant mass of treatments equal or greater than the commercial product treatment (white bar: QR) and controls (hashed bar: M9, Saline). Error bars are standard error of mean (SEM; n=3-10). Asterisk indicates significance compared to control treatment (t-test; p<0.05).
Figure 11:
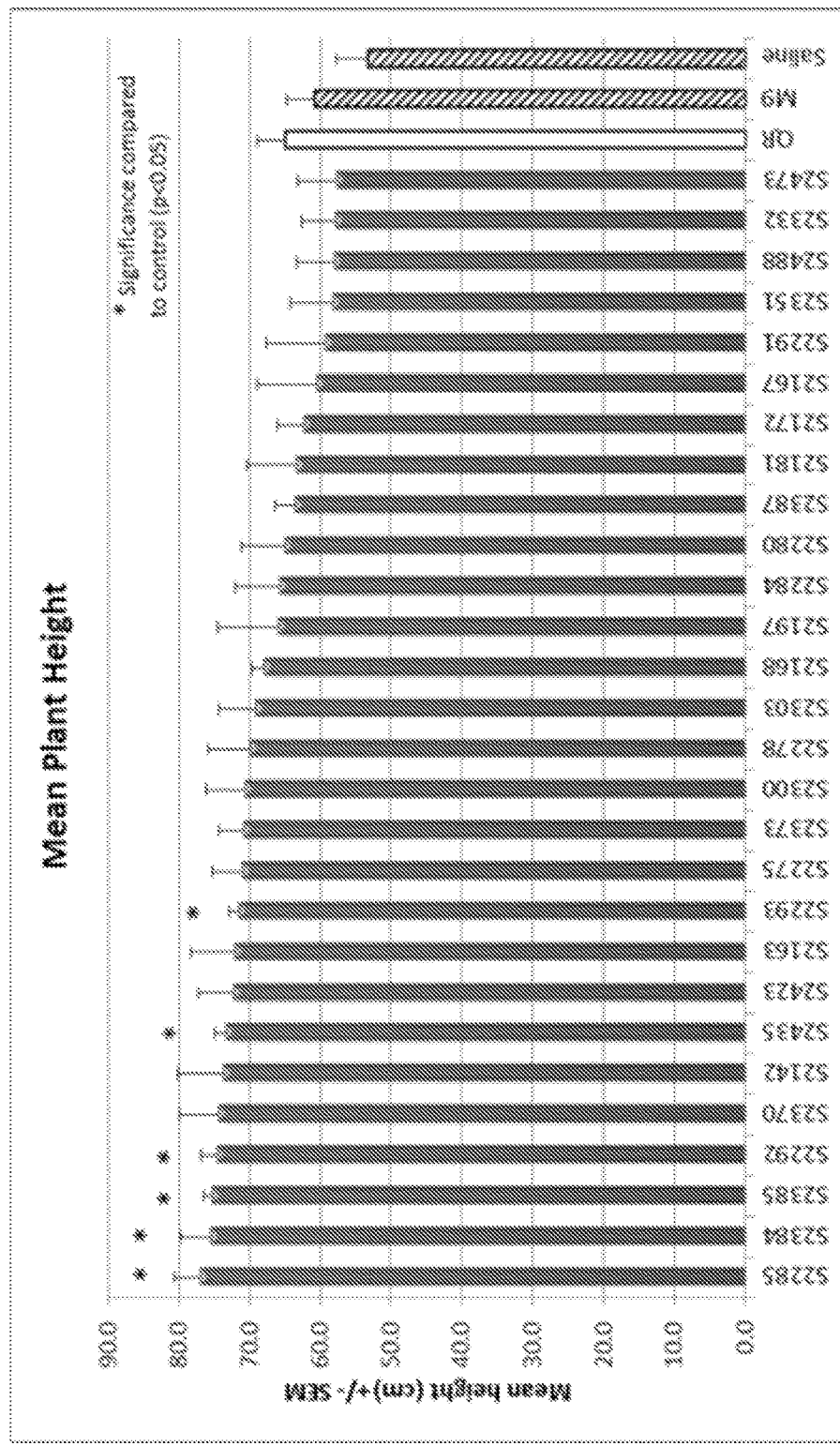
FIG. 11 shows the mean plant height of treatments greater than the mean of the controls (hashed bars: M9 and Saline). Commercial product (white bar: QR). Error bars are standard error of mean (SEM; n=3-10). Asterisk indicates significance compared to control treatment (t-test; p<0.05).
Figure 12:
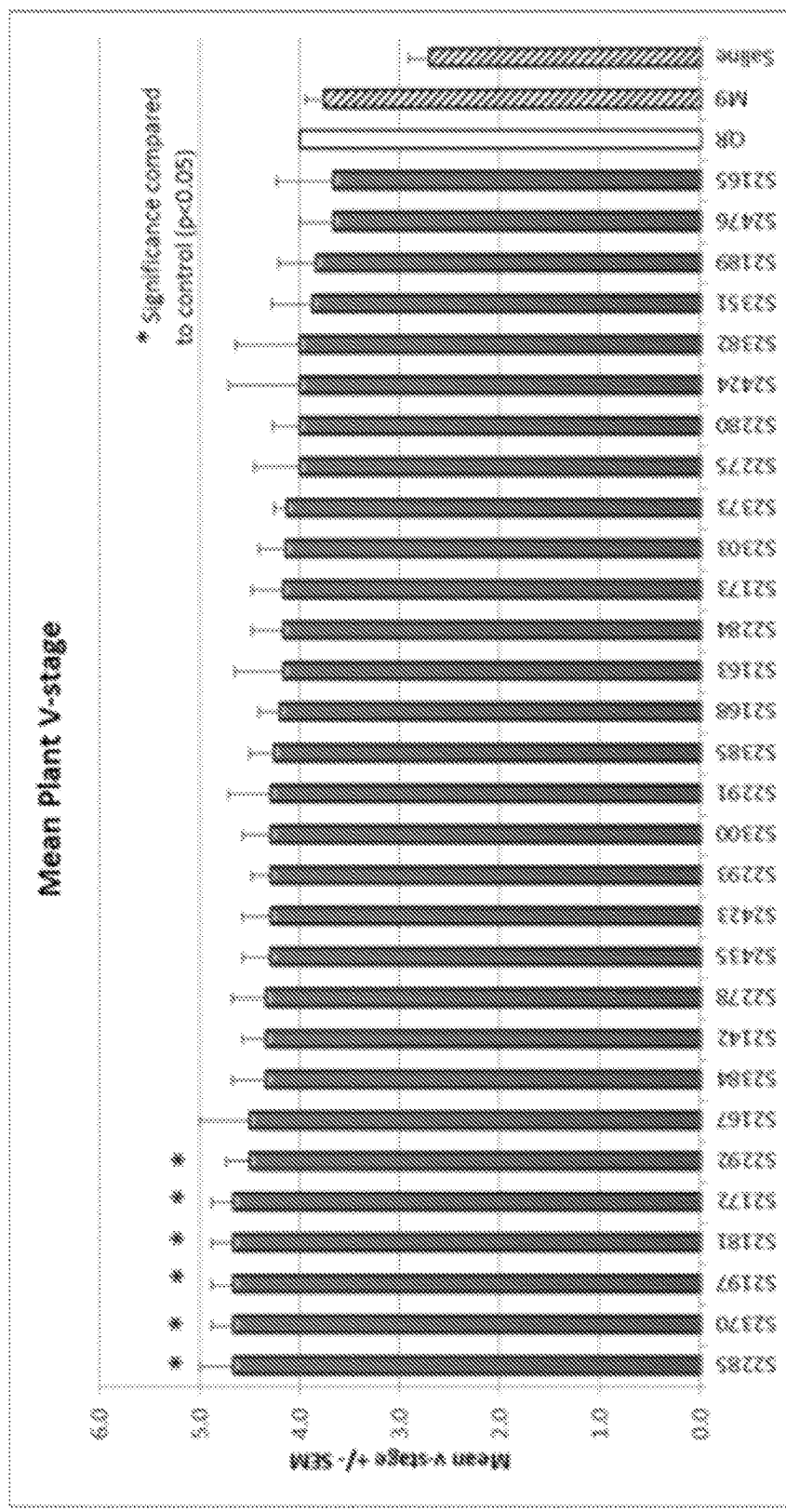
FIG. 12 shows the mean plant V-stage of treatments greater than the mean of the controls (hashed bars: M9, Saline). Commercial product (white bar: QR). Error bars are standard error of mean (SEM; n=3-10). Asterisk indicates significance compared to control treatment (t-test; p<0.05).

On day seven, seedlings were removed from the containers and measured (FIG. 7). A single shoot length was recorded for each seedling. In Test I, a single root length was recorded for each seedling. In Test II, the three longest roots per seedling were measured and sum calculated. An average shoot length value and root length value was calculated from all seedlings in the same container (of the ones that grew). Additionally, the sum of shoot and root values was calculated for each plant and average values calculated for all plants that received the same treatment. Average values per treatment for shoot length, root length, and shoot plus root length were plotted (FIGS. 8 and 9 for Test I and Test II, respectively). A two-sided T-Test was performed and treatments that were significantly higher than the control ($p<0.05$) are indicated on the plots.

Example 7 Enhancement of Biomass Production in Maize in Greenhouse Growth Experiment (1) Greenhouse Experiment 1

A greenhouse experiment was designed to evaluate if four microbial consortia according to the present embodiments could enhance developmental-stage (through V3-V5) plant growth and performance.

31 microbial isolates were obtained using the method of Example 3. These isolates were grown up in individual cultures before testing. Out of the original 31 isolates, 26 isolates were used for the greenhouse experiment. Four (4) microbial consortia (A-D) of the isolates (shown below) were tested. In each consortium, isolates were added so the final concentration of each member of the consortium was $\sim 1 \times 10^9$ cells/ml.

Consortium A: P0035_B2 or S2145, P0032_C7, P0020_B1, P0047_A1 or S2284, P0032_A8 or S2181, P0049_E7, P0033_E1 or S2177.

Consortium B: P0042_A8 or S2167, P0042_C2 or S2173, P0042_D10 or S2172, P0044_A3 or S2476, P0042_B12 or S2189, P0042_B2 or S2168, P0042_D5 or S2165

Consortium C: P0038_D2 or S2166, P0018_A11, P0047_E2, P0018_A1, P0047_C1, P0042_E1, P0047_E8

Consortium D: S2142_P0061_E11, S2161_P0054_E8, S2164_P0054_F4, P0057_A3 or S2160, S2159_P0058_B9, S2163_P0019_A12

Figure 2:
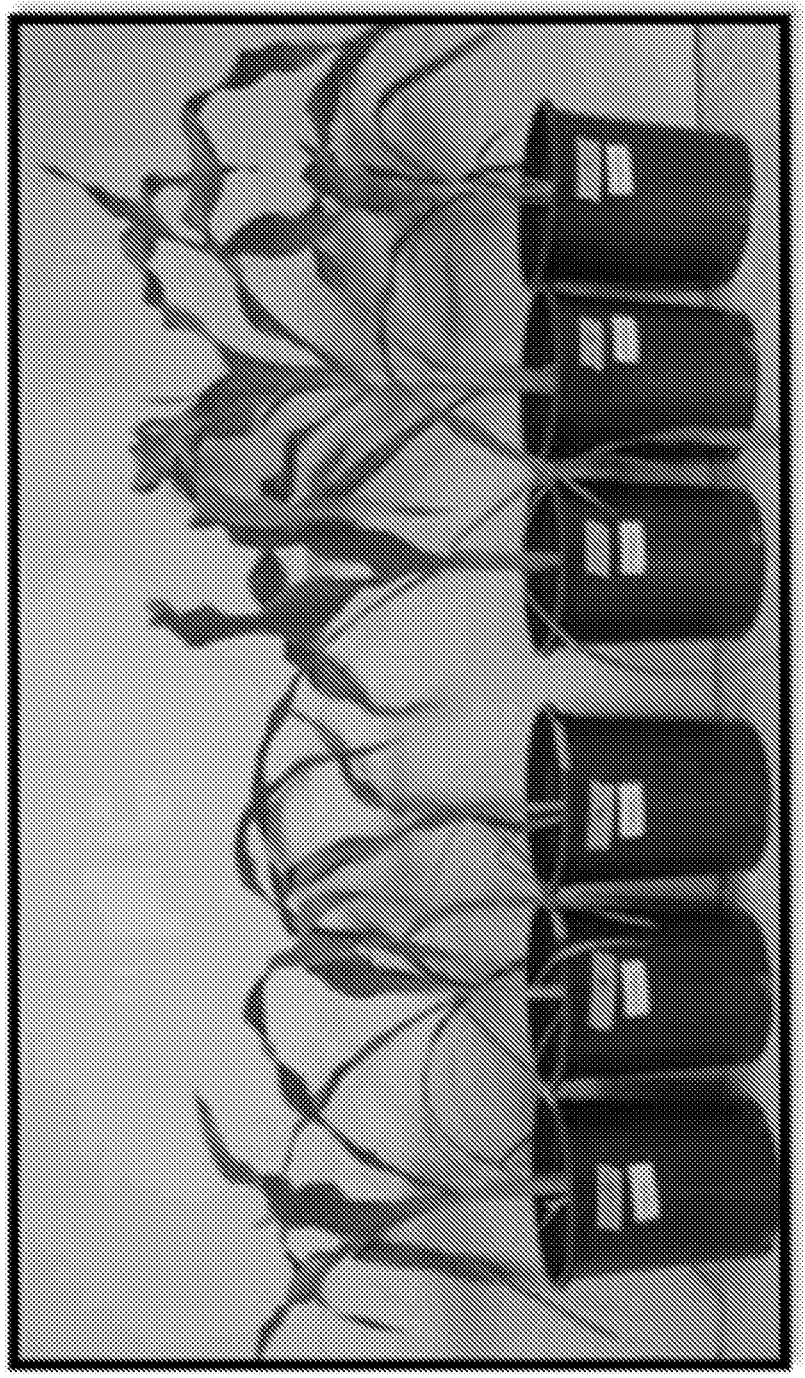
FIG. 2 shows a photo of sweet corn growth of sterile soil control and microbial consortia B (P0042_A8 or S2167, P0042_C2 or S2173, P0042_D10 or S2172, P0044_A3 or S2476, P0042_B12 or S2189, P0042_B2 or S2168, and P0042_D5 or S2165) treatment at 47 days of growth, where the three pots on the left are triplicate control treatments, and the three pots on the right are triplet consortia B treatments.
Figure 3:
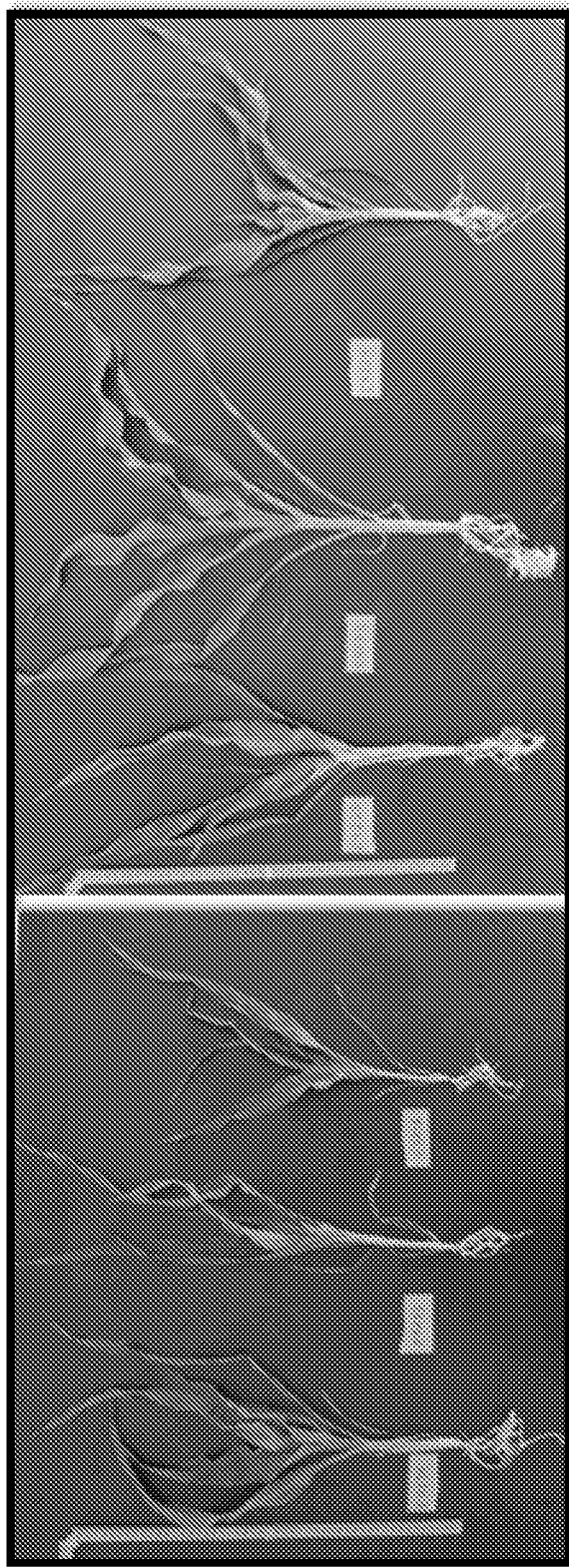
FIG. 3 shows a photo sweet corn growth of sterile soil control and microbial consortia B (P0042_A8 or S2167, P0042_C2 or S2173, P0042_D10 or S2172, P0044_A3 or S2476, P0042_B12 or S2189, P0042_B2 or S2168, and P0042_D5 or S2165) treatment after harvest and soil removal, where the three plants on the left are triplicate control treatments, and the three plants on the right are triplet consortia B treatments.

Agricultural soil was acquired (Brentwood, Calif.) and divided into two parts. The first was kept "live", with the natural microbial community from the field intact with nitrogen ($NO_3$ and $NH_4$), phosphorus (P) and potassium (K) values as follows: $NO_3$ 41 ppm, $NH_4$ 4.7 ppm, P 30.0 ppm, and K 244 ppm. The second was sterilized, by autoclaving at 121° C. for 60 min and had nitrogen ($NO_3$ and $NH_4$), phosphorus (P) and potassium (K) values as follows: $NO_3$ 75 ppm, $NH_4$ 5.1 ppm, P 39.2 ppm, and K 242 ppm. The two experimental soil types (live and sterile) were homogenized by mechanical mixing, added to fill 30 1-gallon pots ⅔ full (15 pots per soil type), watered to saturation and left to drain. After draining, one sweet corn seed per pot was planted at uniform depth for all 30 pots. Treatments (Consortia A-D) and control (MS media) were set up in triplicate, with 1 ml added directly on top of each seed (concentration $5 \times 10^9$-$7 \times 10^9$ cells/ml). Treated seeds were covered with sterile sand (ASTM Graded Sand C778) and left to grow on a 16 hour light/8 hour dark cycle for 47 days. Plants were watered to maintain 60% saturation throughout the experiment. Growth was evaluated by leaf count and weekly photographs comparing control and treatment plants (FIG. 2). At the end of the growth experiment, plant and root biomass was measured to evaluate performance (FIGS. 1A, 1B and 3).

The same or similar methods as described herein are used at larger scales, including outdoor field trials and with isolates or various consortia applied at different concentrations to a range of crop types.

(2) Greenhouse Experiment 2

A greenhouse experiment was designed to evaluate if consortia according to the present embodiments could enhance developmental-stage (through V3-V5) plant growth and performance. The six consortia (E-J) and one single microbe treatment (S2376) were selected using the present embodiments.

Microbial consortia members (15) were obtained using the method of Example 3. These isolates were grown up in individual cultures before being combined into the six consortia defined below. Isolates were added so the final concentration of each member was $\sim 1 \times 10^9$ cells/ml.

Consortium E: P0147_D10 or S2291, P0160_F7 or S2351, P0147_G10 or S2292.

Consortium F: P0140_C10 or S2300, S2387, P0157_G5 or S2303.

Consortium G: S2384, P0160_E1 or S2374, P0134_G7 or S2280.

Consortium H: S2275, S2278.

Consortium I: S2373, S2375, P0157_G5 or S2303.

Consortium J: S2293, S2382.

Figure 4:
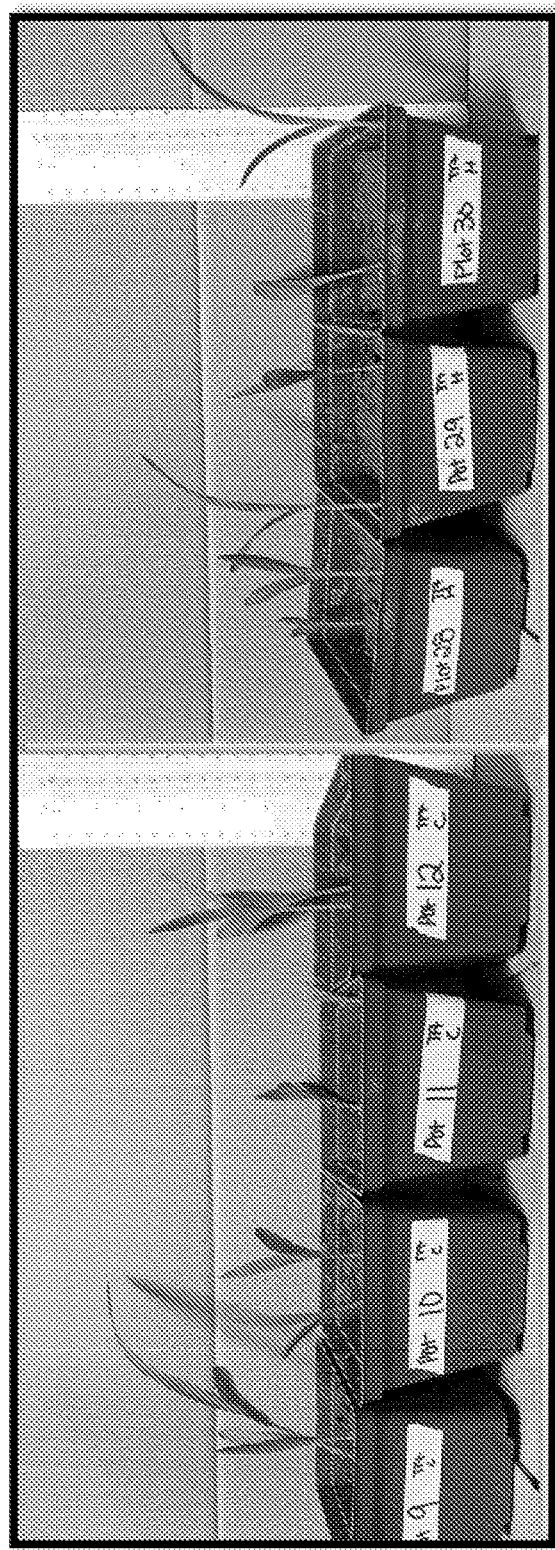
FIG. 4 shows a photo of Treatment G (n=4) and Buffer control (n=3) in live soil after 10 days of growth.
Figure 5:
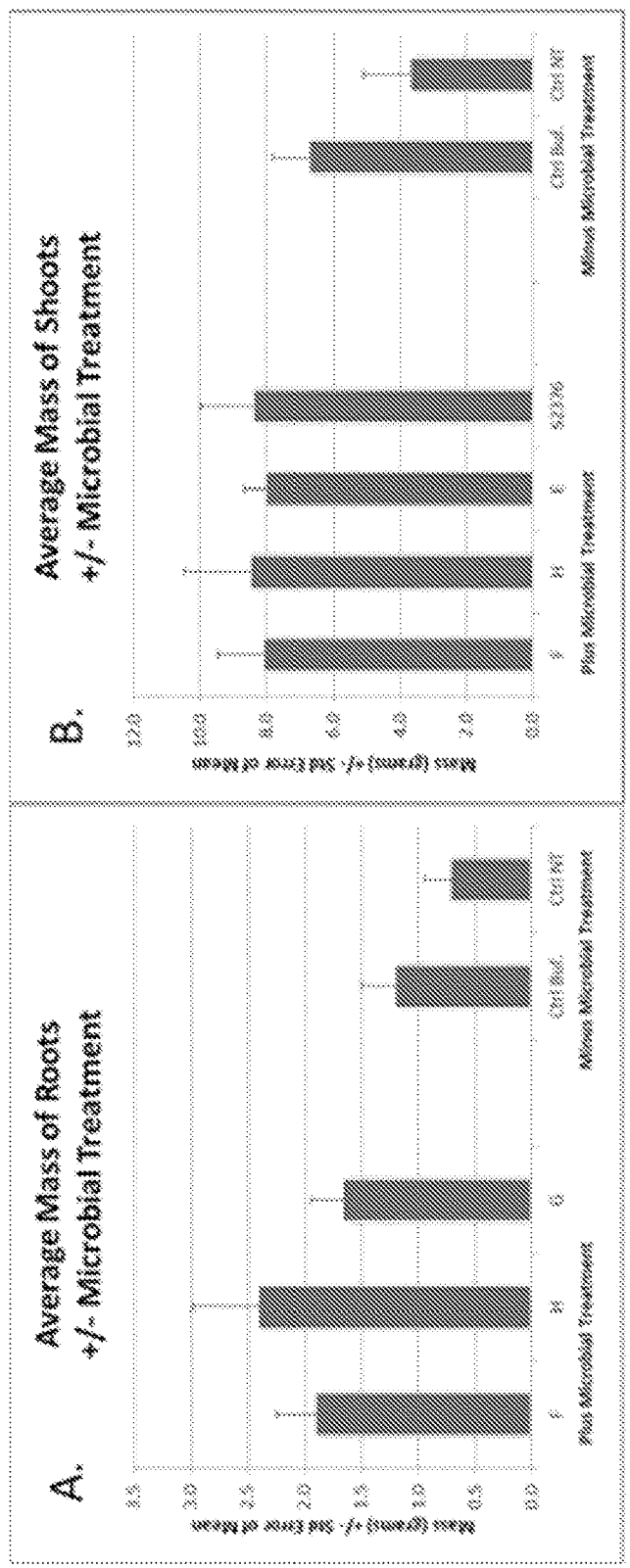
FIG. 5 shows the average mass of roots (n=3) and shoots (n=4) of microbial treatments and controls (Ctrl Buf (n=1) and Ctr NT, n=1), +/− standard error of mean in live soil. A. shows average root mass for treatments F, H, and G and Ctrl Buf and Ctr NT. B. shows average shoot mass for treatments F, H, E and S2376 and Ctrl Buf and Ctr NT.

Agricultural soil was acquired (Brentwood, Calif.) and used to plant two sweet corn seeds in 4" containers. The nitrogen ($NO_3$ and $NH_4$), phosphorus (P) and potassium (K) values of the soil were as follows: $NO_3$ 73 ppm, $NH_4$ 1.6 ppm, P 34.3 ppm, and K 297 ppm. Treatments (Consortia E-J), Single strain S2376 and controls (MS media and no treatment: "NT") were set up in quadruplicate, with 1 ml treatment added directly on top of each seed (concentration $1 \times 10^9$ cells/ml). Treated seeds were covered with soil and left to grow on a 16 hour light/8 hour dark cycle for 30 days. Plants were watered to maintain ~60% saturation throughout the experiment. Growth was evaluated by leaf count and photographs comparing control and treatment plants (FIG. 4). At the end of the growth experiment, plant and root biomass was measured to evaluate performance (FIG. 5).

(3) Greenhouse Experiment 3

A growth experiment was performed to evaluate if single isolates according to the present embodiments could enhance developmental-stage (through V3-V5) plant growth and performance. Thirty-eight isolates were selected for testing in 3 sets of experiments using the present embodiments.

Corn seeds were grown in soil after application of various microbial and/or nutrient treatments. For two experiments agricultural soil was acquired (Brentwood, Calif.) and mixed with 30% w/w plaster sand purchased from a local building materials company (Shamrock's Building Materials, San Rafael, Calif.). After mixing the soil-sand mix was sterilized by autoclaving in 3 kg batches at 121° C. for 4 hours with nitrogen ($NO_3$ and $NH_4$), phosphorus (P) and potassium (K) values as follows: $NO_3$ 88-100 ppm, $NH_4$ 0.5-0.6 ppm, P 24-25.2 ppm, and K 219-239 ppm. For a third experiment the soil was a 60% Cache Creek sand: 20% clay: 20% peat mixture that was steamed to sterilize. After sterilization a small amount of field soil was added to create a soil mix that had a natural field microbial community.

In two experiments, 4" pots were filled with sterile soil from four different batches to homogenize and then thoroughly wetted with large-grain-filtered, UV-sterilized water from the irrigation system. A bench-top drill press was used to create holes with uniform depth in the pots and one Blue River untreated field corn seed was placed pedicel down into the bottom of the hole with forceps to ensure uniform seed orientation. In a third experiment, 4" pots were filled with the soil mix and one seed (Blue River untreated field corn) per pot were placed on their side and pressed 1.25" into the dry soil with a wooden dowel for consistent seed placement.

The 38 microbial isolates, obtained using the method of Example 3 or 4, were grown up in individual cultures to an optical density of 0.1 (~$1\times10^8$ cell/ml) and used as single treatments. 1 ml of the treatment was dispensed directly onto the seeds. In one experiment, one treatment was a commercially available microbial product (QuickRoots©, TJ Technologies Inc. "QR") added to 8 pots following manufacturer instructions. In two experiments, each treatment was added to 8 pots, with the control buffer (M9 media or saline) added to 20 pots and after treatment application the seed was covered with soil from around the hole using sterile spatulas. In a third experiment, the treatments were added to 5 sets of 50 pots. Each set of 50 pots also received 1 mL of a nitrogen fertilizer amount ($NH_4Cl$: 2 mM, 0.2 mM, 0.02 mM, 0.002 mM and 0), applied in a circle 1.5-2" around the seed. The pots were then gently shaken to cover the seed with soil and watered by hand with reverse-osmosis sterilized water.

In all experiments the pots were assigned randomized locations in the greenhouse. In all experiments stake emitters were placed in each pot for watering. In the first two experiments the water source was large-grain-filtered and UV-sterilized, and 15-20 ml was applied per pot twice per day. A photoperiod of 16 light:8 dark was maintained using 1000 watt lights hung approximately 5 feet above the pots. The experiments continued until the signs of senescence in lower leaves (~3 weeks). In a third experiment the water source was deionized by reverse-osmosis and 15-20 ml was applied per pot twice per day. The experiment took place under ambient sunlight between Aug. 28 and Sep. 12, 2014.

Growth was evaluated by height from the base of the stem to the tip of the longest leaf and chlorophyll using a Minolta SPAD meter during the course of the experiments. At the end of two experiments, all plants were photographed by treatment and the plant mass and V-stage were additionally measured. Average values per treatment for plant mass, plant height, V-stage and chlorophyll were plotted (FIGS. 10, 11, 12 and 13, respectively). A two-sided T-test was performed and treatments that were significantly higher than the control ($p<0.05$ or $p<0.001$) are indicated on the plots.

(4) Field Trial 1

A 0.8 acre field in the form of 6 rows 2200 feet long was divided into 84 plots. The field's soil is designated as Capay Clay, Wet. Nitrogen levels in the field were 30-50 ppm, Phosphorous was 20-70 ppm, and Potassium was 230-300 ppm according to soil analysis from several points in the field. In-furrow pre-plant fertilizer was applied, and a second application was made when corn was about V4. Each plot consisted of 6 rows spaced 33" apart, and was 25' long, with 1' between each plot. The two outer rows of the entire experimental section were left unseeded and received no treatments. The four remaining rows were seeded with fungicide-treated sweet corn variety 3674 and treated.

The four inner rows were first hoed to make a furrow, followed by hand seeding placing one kernel every 7 inches along the furrow. Each plot was seeded with 42 seeds per row for a total of 168 seeds per plot. Of the 84 total plots, 2 plots were given no treatment, 4 plots were given a control buffer treatment (sterile 1×M9 salts; Sigma-Aldrich M6030) and 78 plots received microbial treatments in M9 buffer. One milliliter of liquid treatment (consortia or single strains) was applied directly onto each seed and was then covered with soil by hand. After all planting was completed sprinklers were used to water in seeds. Since the field trial was surrounded by grower's fields, the trial was treated the same as the rest of the field for the entirety of the growing season, and was harvested Oct. 14, 2014. To eliminate the possibility of edge effects affecting outcome, only the 2 inner rows (of the 4 planted and treated for each plot) were harvested.

The liquid treatments consisted of 6 consortia and 5 single strains (P0147_D10 or S2291, P0140_C10 or S2300, S2384, S2373, S2376) each applied at three different cell concentrations. All microbial isolates were obtained using the method of Example 3 and grown up in individual cultures. Consortia members were combined to so the final concentration of each member was either: $1\times10^9$, $1\times10^8$ or $1\times10^7$ cells/ml.

Consortium E: P0147_D10 or S2291, P0160_F7 or S2351, P0147_G10 or S2292.

Consortium F: P0140_C10 or S2300, S2387, P0157_G5 or S2303.

Consortium G: S2384, P0160_E1 or S2374, P0134_G7 or S2280.

Consortium H: S2275, S2278.

Consortium I: S2373, S2375, P0157_G5 or S2303.

Consortium J: S2293, S2382.

Figure 14:
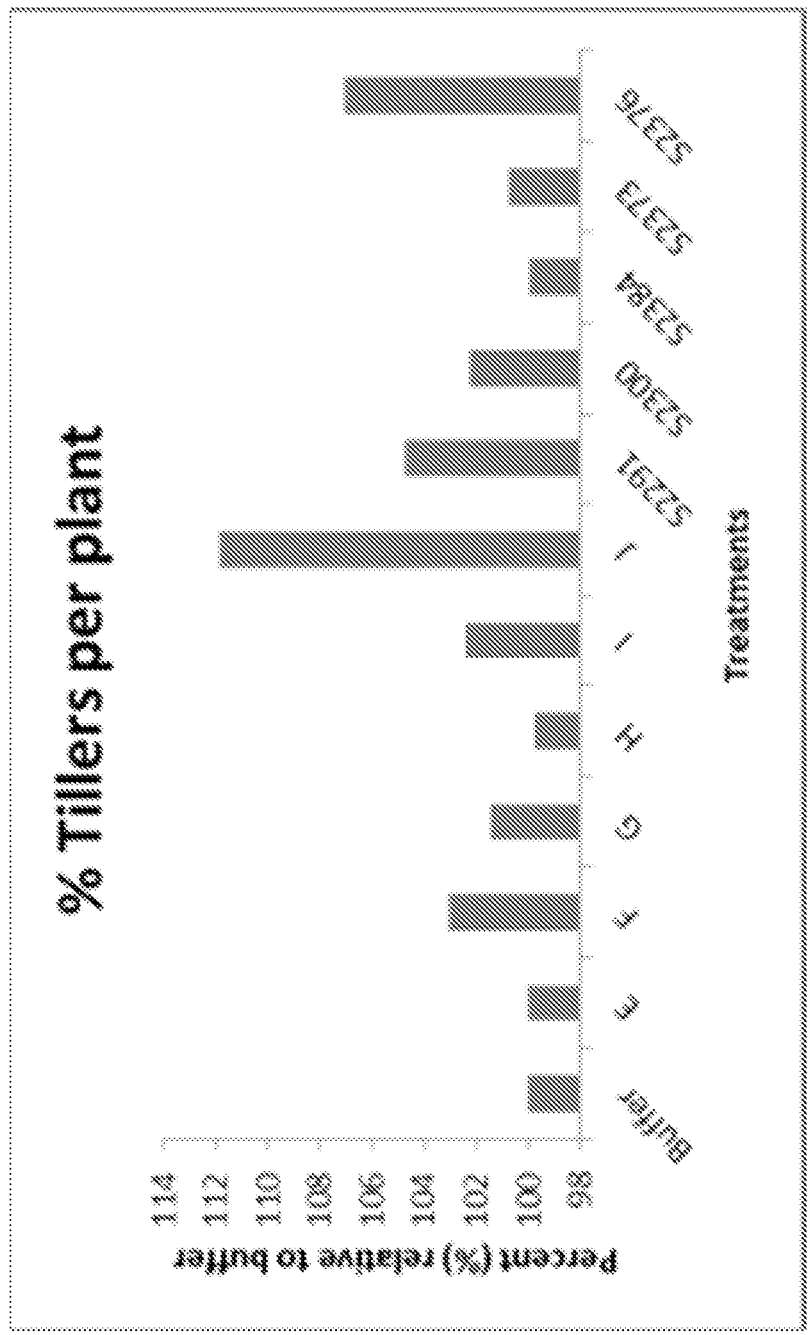
FIG. 14 shows the percent tillers per microbe treated sweet corn plant relative to buffer control for 11 treatments (Consortia E, F, G, H, I and J; single strain S2291, S2300, S2384, S2373 and S2376).
Figure 15:
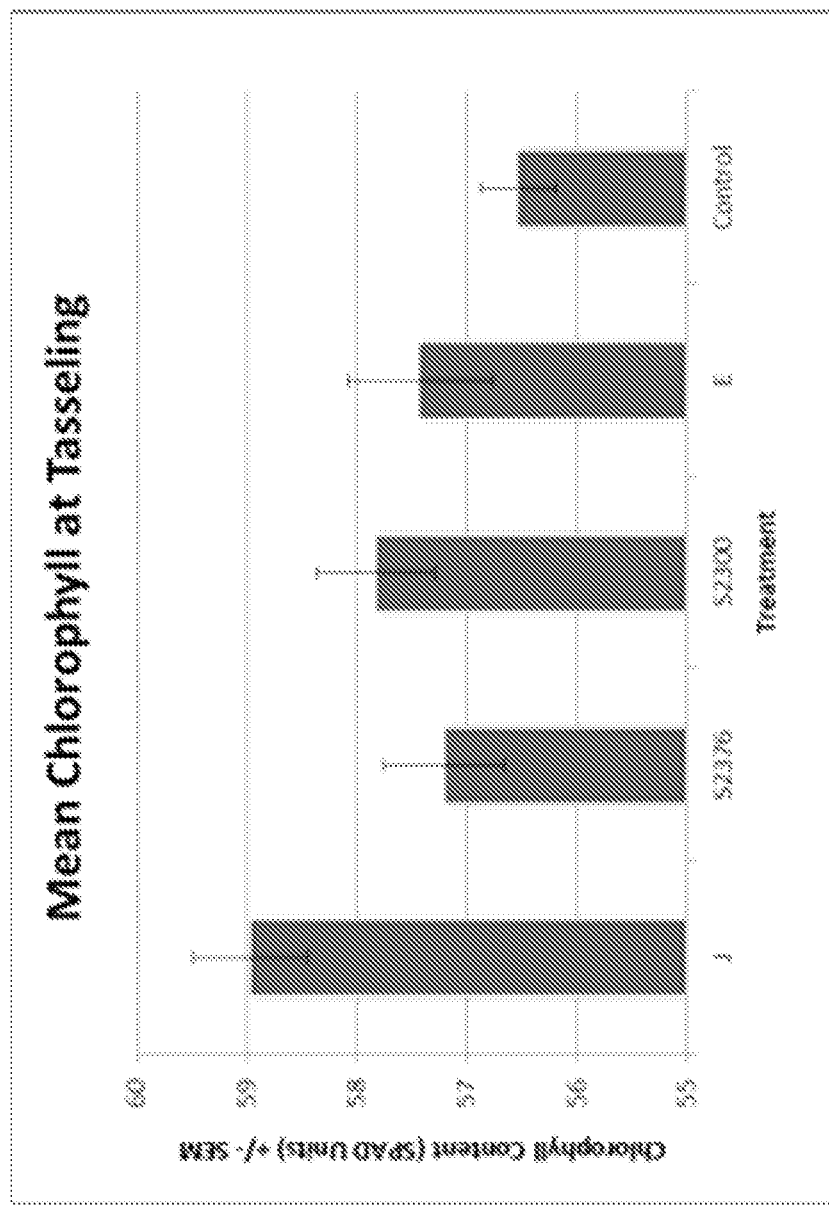
FIG. 15 shows the mean chlorophyll at tasseling of treatments S2376, S2300, E, J and buffer control, +/− standard error of the mean (SEM).

Tillers were counted on each corn plant one month after the seeds were planted. For each treatment and single strain, the number of tillers per plant is represented in percent relative to buffer (FIG. 14). Chlorophyll was measured from 10 plots at the start of tasseling (FIG. 15).

Figure 13:
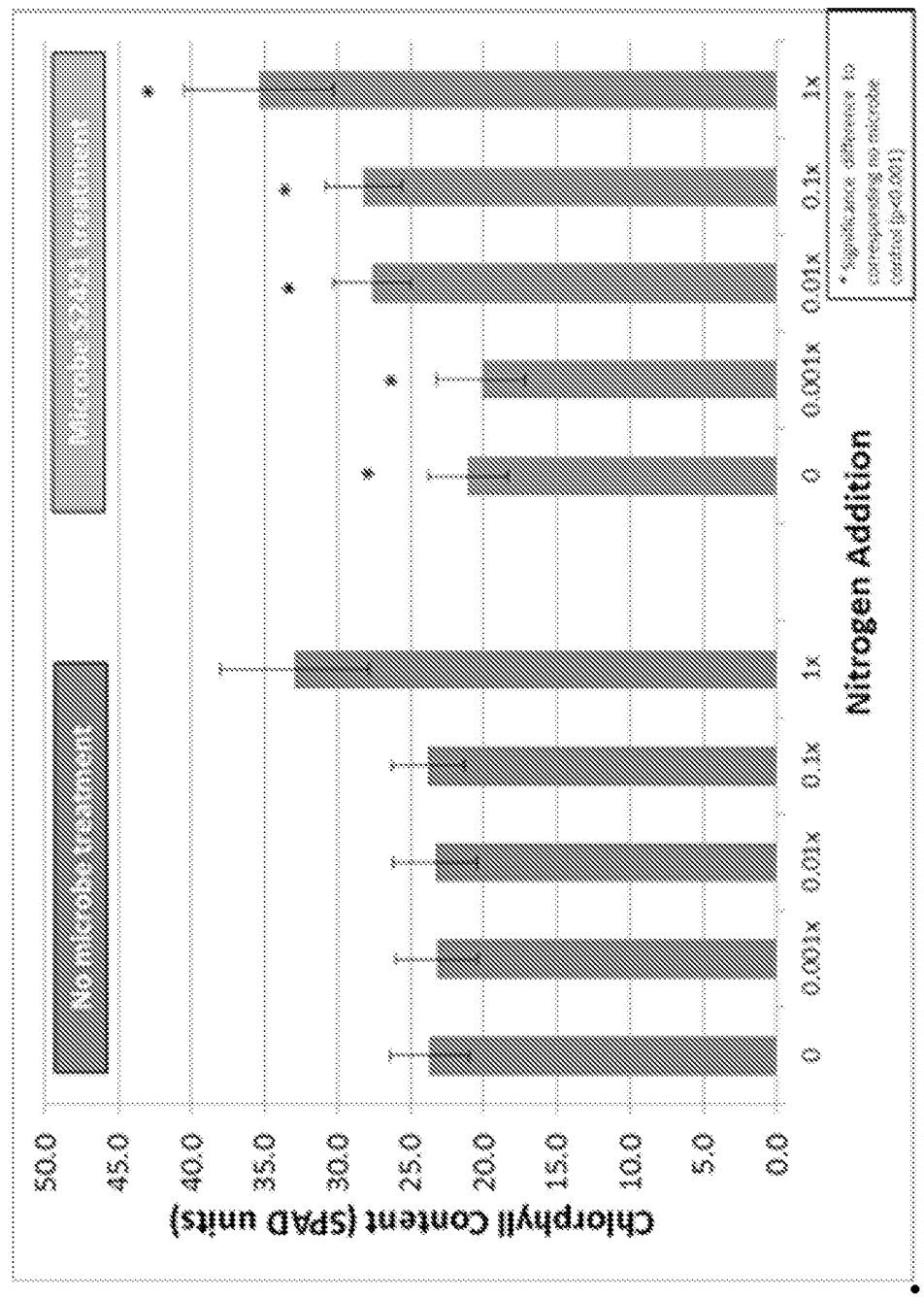
FIG. 13 shows the mean chlorophyll content (SPAD units; +/− standard deviation; n=43-49) for two treatments (no microbe control and S2421) over a range of nitrogen fertilization ($NH_4Cl$: 2 mM, 0.2 mM, 0.02 mM, 0.002 mM and 0). Asterisk indicates significant difference (p<0.001) to its corresponding un-inoculated control.
Figure 16:
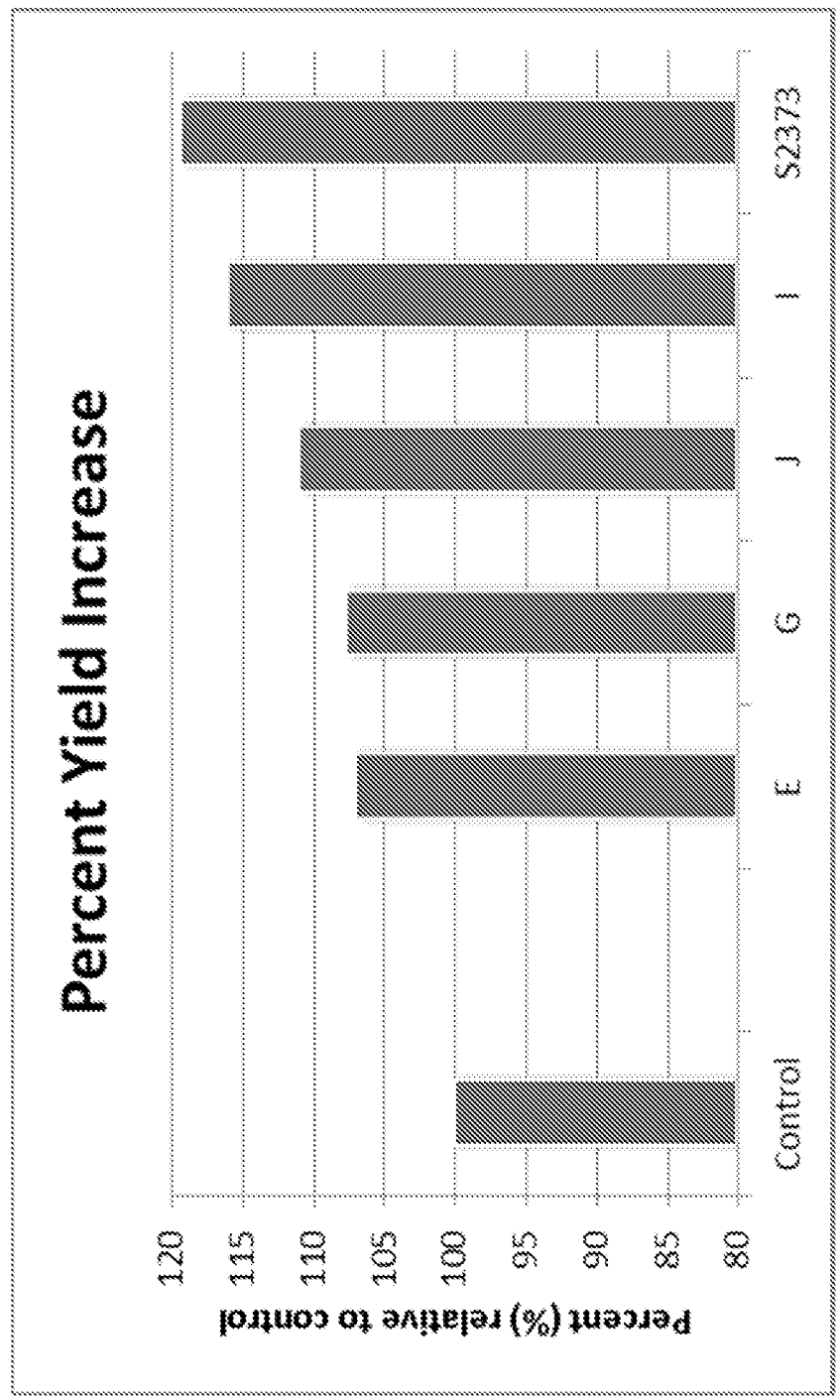
FIG. 16 shows the percent yield increase of sweet corn, in marketable ears per acre for single strain treatment S2373 and consortia treatments E, G, I, and J.

Mean chlorophyll content (SPAD units) and standard error of the mean (SEM) is shown for four treatments and control (FIG. 13). At harvest the number of marketable ears per acre was counted for each treatment. The percent yield increase relative to the control treatment is shown in FIG. 16.

(5) Greenhouse Experiment 4

Figure 17:
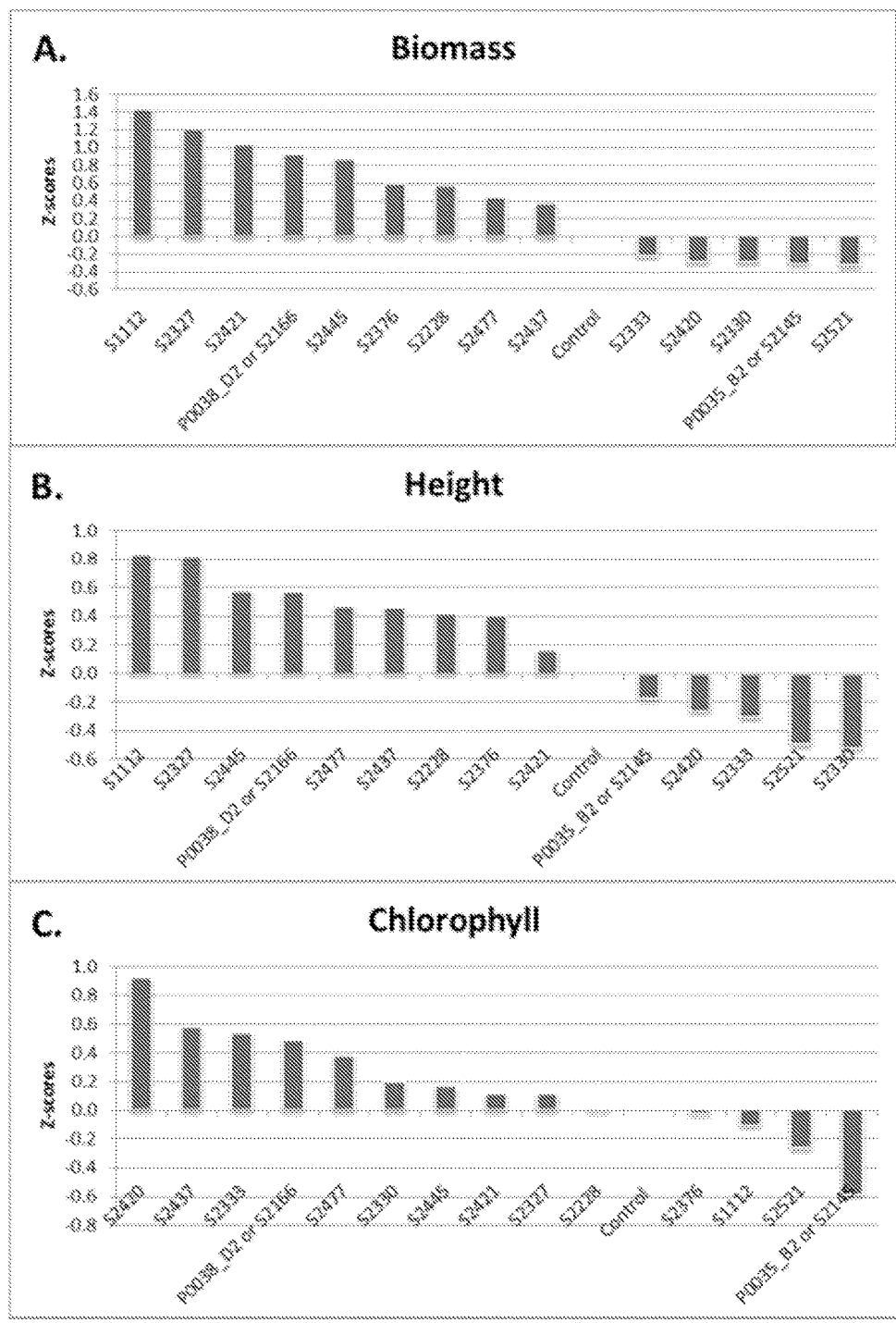
FIG. 17 shows the z-scores (standard deviations) of the single strain treatment effect relative to buffer controls for A) Plant Biomass, B) Plant Height and C) Chlorophyll of youngest true leaf, in a field corn growth experiment in sterilized soil.
Figure 18:
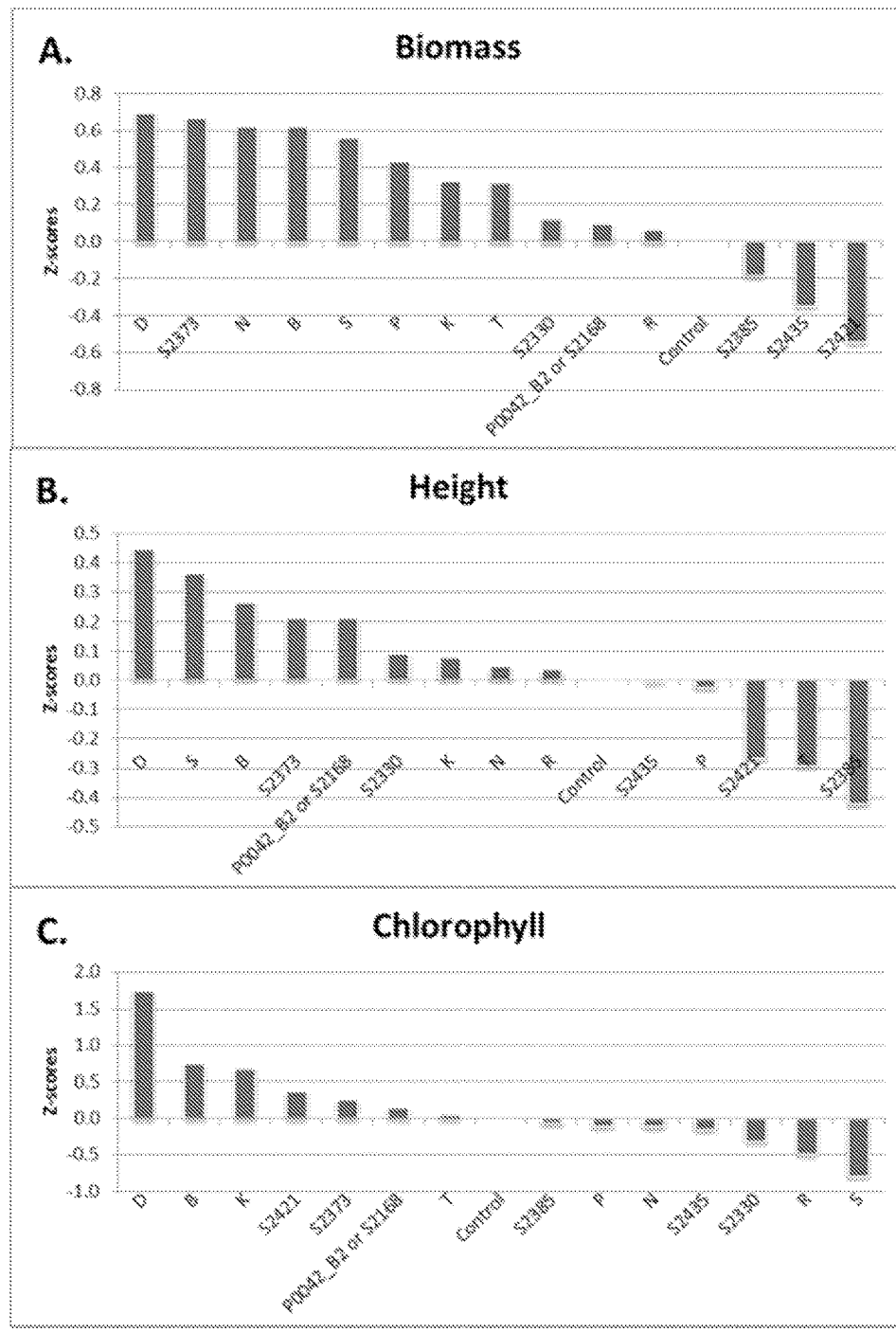
FIG. 18 shows the z-scores (standard deviations) of the single strain or consortia treatment effect relative to buffer controls for A) Plant Biomass, B) Plant Height and C) Chlorophyll of youngest true leaf, in a field corn growth experiment in sterilized soil.
Figure 19:
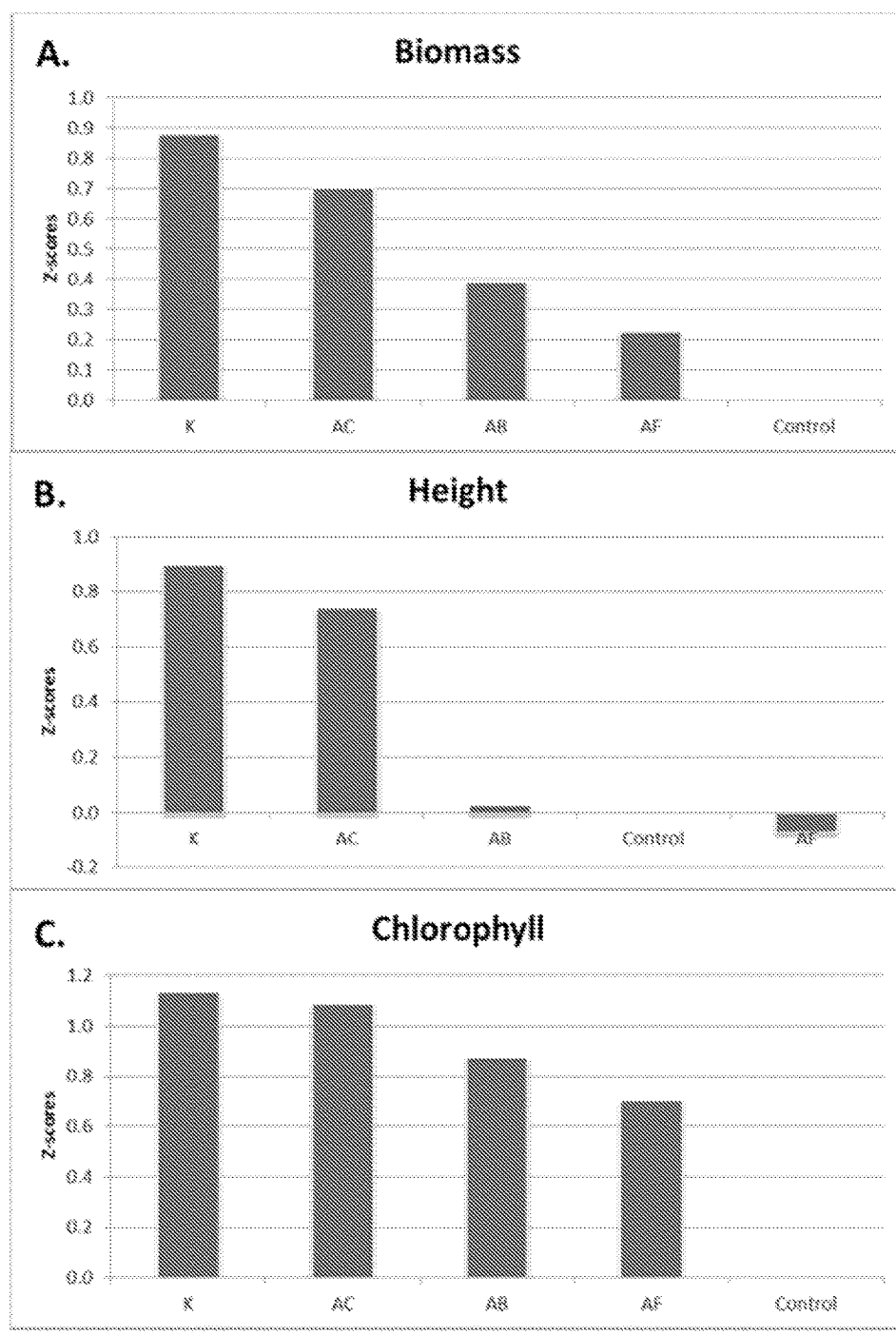
FIG. 19 shows the z-scores (standard deviations) of the consortia treatment effect relative to buffer controls for A) Plant Biomass, B) Plant Height and C) Chlorophyll of youngest true leaf, in a field corn growth experiment in sterilized soil.

Additional growth experiments were performed using the methods described in Example 7.1-7.3. Twenty-one single isolates and 23 synthetic consortia were evaluated for plant growth and performance enhancing effects in three sets of experiments. The results from 19 single isolates and 11 consortia, defined below, are presented in FIGS. 17-19. Microbial treatment data is presented as z-scores, or standard deviations, relative to the control treatment for plant biomass, plant above soil height and chlorophyll reading of the youngest true leaf (i.e. highest v-stage leaf with a collar) at the time of harvest.

Consortium B: P0042_A8 or S2167, P0042_C2 or S2173, P0042_D10 or S2172, P0044_A3 or S2476, P0042_B12 or S2189, P0042_B2 or S2168, P0042_D5 or S2165.

Consortium D: S2142_P0061_E11, S2161_P0054_E8, S2164_P0054_F4, P0057_A3 or S2160, S2159_P0058_B9, S2163_P0019_A12.

Consortium K: S2385 and S2373.

Consortium N: S2327 (or SEQ ID Nos.: 99 or 100), S2329 (or SEQ ID Nos.: 97 or 98), S2330 (or SEQ ID Nos.: 101 or 102), S2332 (or SEQ ID Nos.: 113, 114 or 115), S2333 (or SEQ ID Nos.: 95 or 96) and S2328 (or SEQ ID Nos.: 162 or 163).

Consortium P: S2373 (or SEQ ID Nos.: 81, 82, or 83) and P0042_B2 or S2168 (or SEQ ID Nos.: 65 or 66).

Consortium R: S2385 (or SEQ ID Nos.: 51, 52 or 53) and P0042_B2 or S2168 (or SEQ ID Nos.: 65 or 66).

Consortium S: S2385 (or SEQ ID Nos.: 51, 52 or 53) and S2421 (or SEQ ID Nos.: 136 or 137).

Consortium T: S2385 (or SEQ ID Nos.: 51, 52 or 53) and S2330 (or SEQ ID Nos.: 101 or 102).

Consortium AB: S2159_P0058_B9 (or SEQ ID Nos.: 18 or 19), S2161_P0054_E8 (or SEQ ID Nos.: 36 or 37) and S2163_P0019_A12 (or SEQ ID Nos. 75 or 76).

Consortium AC: S2373 (or SEQ ID Nos.: 81, 82, or 83), S2385 (or SEQ ID Nos.: 51, 52 or 53), P0147_D10 or S2291 (or SEQ ID Nos.: 11 or 13), S2293 (or SEQ ID Nos.: 86 or 87), S2382 (or SEQ ID Nos.: 24 or 88), S2487 (or SEQ ID Nos.: 20 or 129), S2644 (or SEQ ID Nos.: 160 or 161), P0042_A8 or S2167 (or SEQ ID Nos.: 34 or 35), P0038_D2 or S2166 (or SEQ ID Nos.: 30 or 31), P0042_D10 or S2172 (or SEQ ID Nos.: 70, 73 or 74), S2159_P0058_B9 (or SEQ ID Nos.: 18 or 19), S2161_P0054_E8 (or SEQ ID Nos.: 36 or 37), and S2163_P0019_A12 (or SEQ ID Nos. 75 or 76).

Consortium AF: S2373 (or SEQ ID Nos.: 81, 82, or 83), S2385 (or SEQ ID Nos.: 51, 52 or 53) and S2646 (or SEQ ID Nos.: 16 or 164).

Example 8 Enhancement of Biomass Production in *Arabidopsis* in Laboratory Growth Experiments (1) Experiment 1—Dicot Growth Test Sterilized *Arabidopsis* Col-1 seeds were cold stratified in 0.1% agarose at 4° C. for 7 days. Commercially available potting soil (Miracle-Gro®) was sterilized via autoclave and used to fill 72-plug trays. Trays were than saturated with UV-sterile tap water and allowed to drain. Dilute seeds were then placed on the surface of sterile potting soil using a sterile transfer pipette. Approximately 5-10 seeds were added to each plug. Microbial isolates were obtained using the method of Example 3 and treatments prepared as described in Example 7. Briefly, each strain was freshly grown to high cell density in its preferred medium, and then washed 1× in VL55 buffer. Strains were then combined according to treatments and resuspended in VL55 buffer at a total concentration of 1 OD, or approximately $1 \times 10^9$ cells/mL.

Treatments included 2 single strains (S2373 and S1112) and 5 consortia (defined below). 1 mL of each treatment was added to each plug. Control plugs received 1 mL of VL55 buffer only. Plug trays were placed in a growth chamber at 26° C. and at a 16/8 hour light/dark cycle. Plants were watered 3 times per week using a bottom watering technique.

Figure 20:
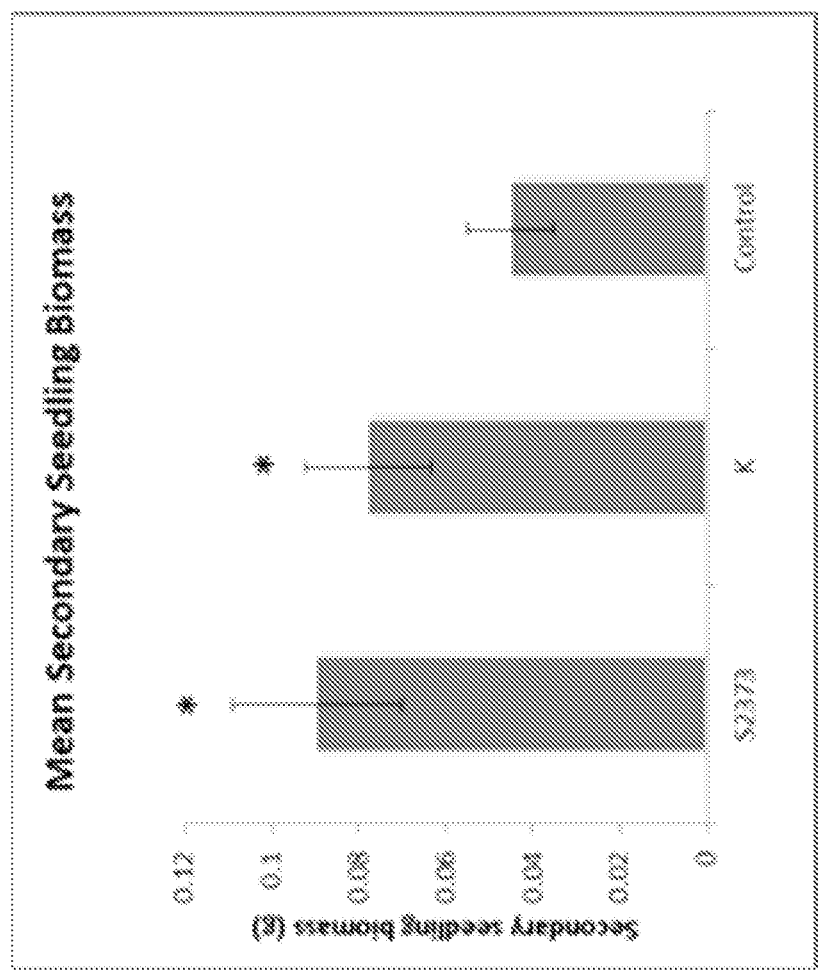
FIG. 20 shows *Arabidopsis* biomass of secondary seedlings treated with single strain S2373 and consortium K. Seedlings trimmed on day 20. Asterisk denotes significance (t-test, $p<0.05$).
Figure 21:
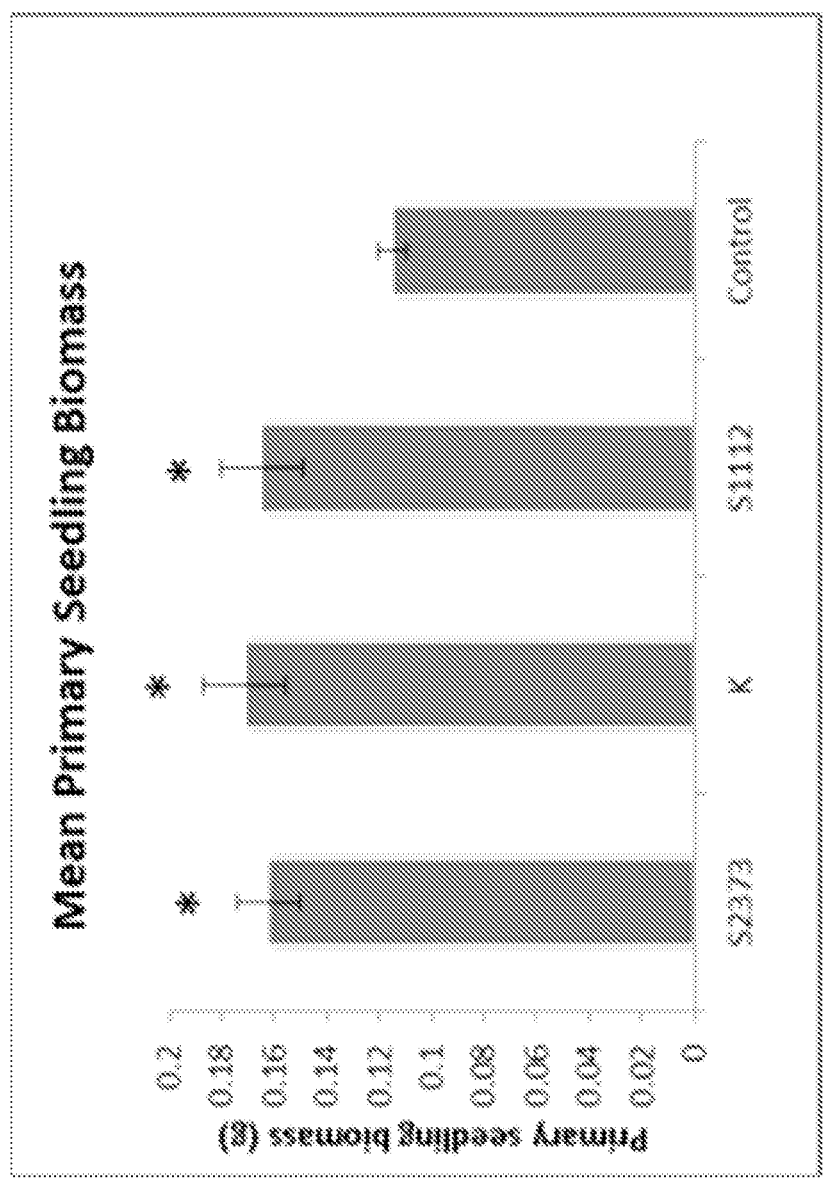
FIG. 21 shows *Arabidopsis* biomass of primary seedlings treated with single strains S2373, S1112 and consortium K. Seedlings trimmed on day 25. Asterisk denotes significance (t-test, $p<0.05$).

*Arabidopsis* seedlings were then allowed to grow for 20 days. At this point, plugs with more than one seedling were pruned so that the largest seedling remained. Smaller seedlings are referred to as "secondary seedlings". Freshly trimmed secondary seedlings were weighed for biomass measurement. The average total biomass per plug for each treatment was calculated and compared to controls (FIG. 20). On day 25, the last and largest seedling was sampled and weighed ("primary seedling"). Average biomass of the single plants were compared to the controls (FIG. 21).

Two tailed T-test using unequal variance was used to assess statistical significance. The results of secondary and primary seedling biomass compared to control are shown in FIGS. 20 and 21 for significant treatments ($p<0.05$; indicated with an asterisk).

Consortium I: S2373, S2375, P0157_G5 or S2303.
Consortium J: S2293, S2382.
Consortium K: S2385 and S2373.
Consortium S: S2385 (or SEQ ID Nos.: 51, 52 or 53) and S2421 (or SEQ ID Nos.: 136 or 137).
Consortium AB: S2159_P0058_B9 (or SEQ ID Nos.: 18 or 19), S2161_P0054_E8 (or SEQ ID Nos.: 36 or 37) and S2163_P0019_A12 (or SEQ ID Nos. 75 or 76).

(2) Experiment 2—Triple-Stress Assay

*Arabidopsis* plants were grown in a combination of three abiotic stresses with and without microbial treatments. Specifically, plants were grown in conditions of simultaneous drought stress, heat stress and high light stress. One single strain treatments (S2373) and three consortia (Consortium K, I and S) were evaluated for positive growth and/or positive decay parameters (i.e. increased resistance to stressors) as described below.

Methods:

Phase 1 Screen:

Wild type columbia line *Arabidopsis* seeds ware soaked in water and incubated at 4° C. for 3 days in the dark. Cold shocked seeds were planted in controlled density and spacing on soil. Specifically, 9 plants in a 3×3 grid were grown per 5.5 inch square pot with 8 pots per flat. For microbiological treatment testing, one flat consisted of 4 pots treated and 4 pots of non-treated seeds. Thus 36 treated plants are directly compared to 36 untreated plants.

For 14 days, plants were grown under non-stressed conditions involving: (a) Soil: Metromix 360; (b) Fertilizer: Osmocote and Peter's; (c) Light Regime: 16 hours light/8 hours dark; (d) Light Intensity: 150 μE; (e) Temperature Regime: 22 C day/20 C night; and (f) Humidity: 50% Relative Humidity. On the last day of non-stressed growth, flats were brought to 100% soil water capacity and imaged and analyzed to get total green area pixel count using a LemnaTec Scanalyzer.

The flats were then transferred to "triple stress" conditions consisting of: (a) no additional watering; (b) Light Regime: 16 hours light/8 hours dark; (c) Light Intensity: 350 μE (d) Temperature Regime: 22° C. day with a 32° C. pulse for 4 hours in the middle of the day/20° C. night; and (f) Humidity: 50% Relative Humidity. Flats under these conditions were imaged daily for 14 days.

From the LemnaTec data, growth area, growth slope and maximum day area, decay area and decay slope are determined and compared to control treatments. Parameters for microbe treatments which have a reproducible effect relative to the control treatments are considered to "trend positive" and move on to further testing. Results are shown in Table 3, where "+" indicates a treatment had a positive effect on the parameter.

TABLE 3

Results from LemnaTec growth analysis

| Parameter | S2373 | K | I | S |
|---|---|---|---|---|
| Growth Area | + | − | + | − |
| Growth slope | + | + | + | + |
| Max Day Area | + | − | + | − |
| Decay Area | + | − | − | − |
| Decay Slope | + | − | − | − |

Example 9 Suppression of Plant Pathogens by Microbe Treatments

Two single strains (S2373 and S1112) and three consortia (K, I and S) were tested for suppression response to the plant pathogen *Pythium aphanidermatum* in a soybean assay. Assays were performed in a 24 well round bottom microplate (Whatman/GE, Cat#7701-5102). Prior to assay setup, each well was filled with 3 ml of a sand:soil (1:1) mixture and autoclaved. Zoospores were harvested from 5-7 day old *Pythium aphanidermatum* V8 agar plates following successive washing with water. Released zoospores were counted with a haemocytometer and resuspended to a final concentration of 50 zoospores/ml in sterile water. Twelve replicates were run per treatment with delivery of assay components per well as indicated below in Table 4.

Following assay set up, each plate was sealed in a plastic bag and incubated overnight at 25° C. in the dark. At this time, each well received a single soybean seed which was covered with an additional 3 ml of sand/soil mixture and was watered with 1.2 ml sterile water. Plates were then placed in a tray containing moistened paper towels, covered with a plastic dome and placed in a plant growth chamber incubator at 25° C. with 16 hour light:8 hour dark cycle.

Figure 22:
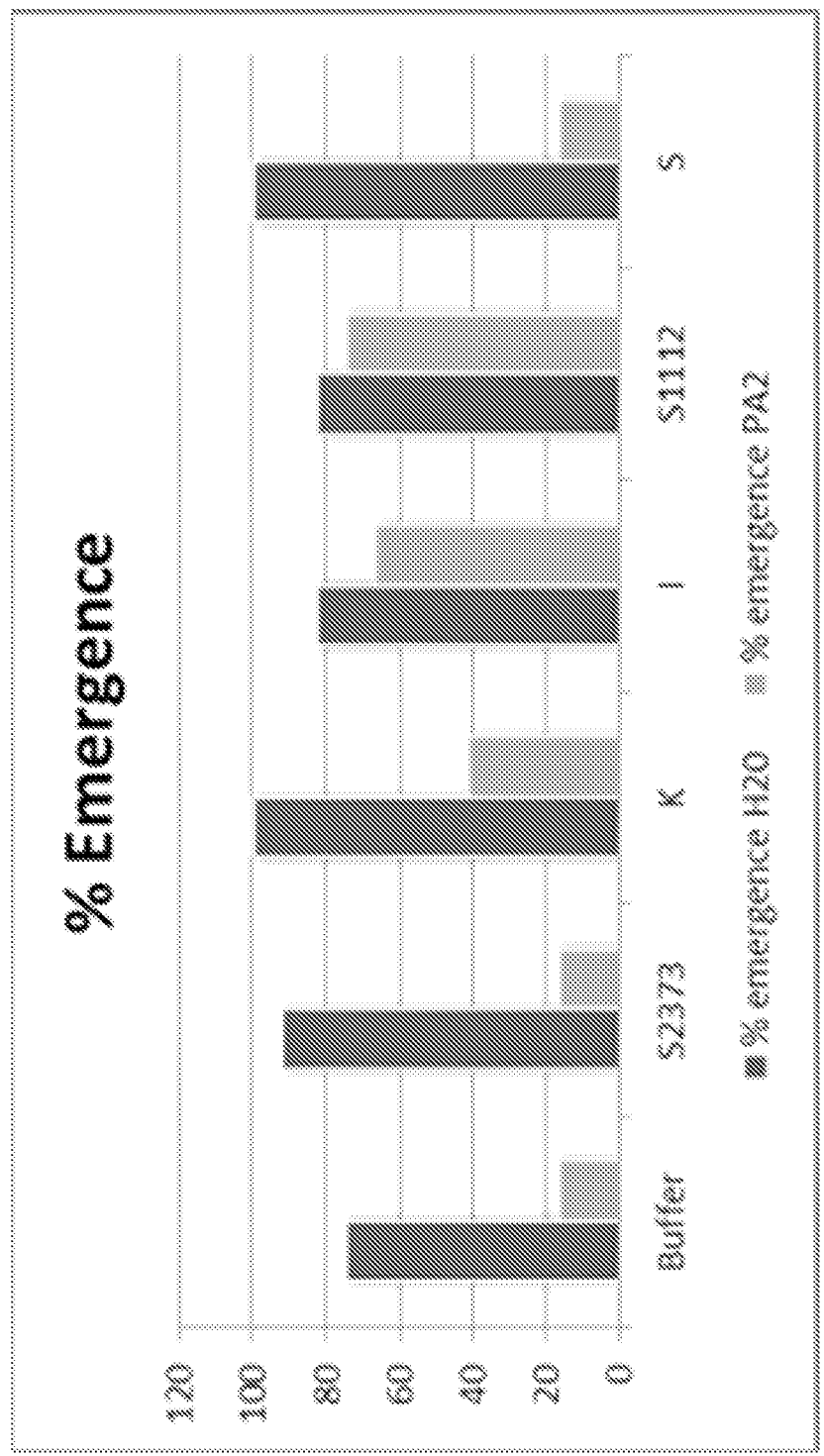
FIG. 22 shows percent emergence of soybean seedlings after 6 days under control (water/$H_2O$) and disease (*Pythium aphanidermatum*/PA2) conditions with 5 microbial treatments (S2373, S1112, consortia K, I and S).
Figure 23:
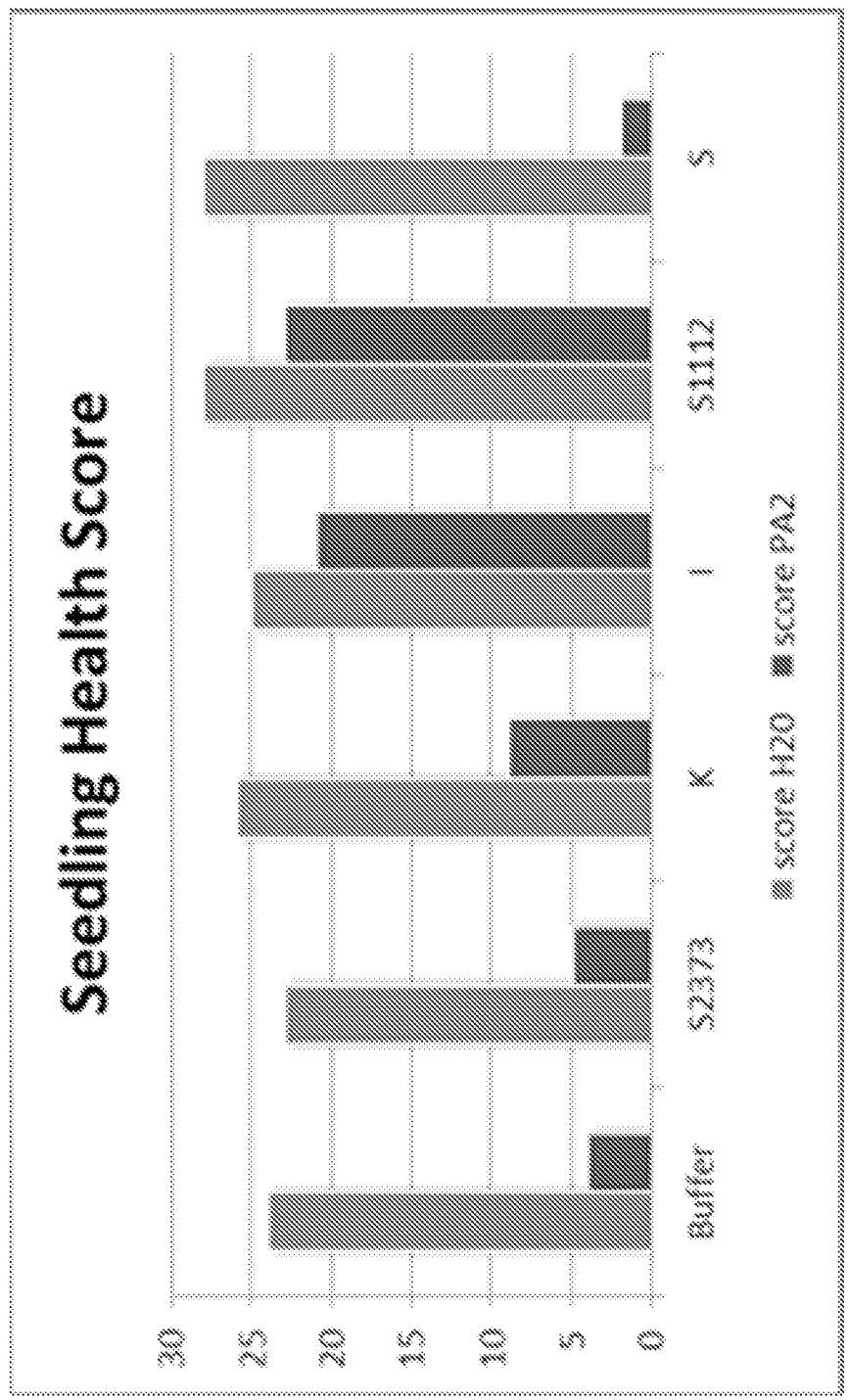
FIG. 23 shows plant health score of soybean seedlings after 6 days under control (water/$H_2O$) and disease (*Pythium aphanidermatum*/PA2) conditions with 5 microbial treatments (S2373, S1112, consortia K, I and S). Each of 12 replicate plants scored on a scale of 0 (diseased) to 3 (healthy) and the sum per treatment reported (max score 36).

Plants were scored at 6 days following seed planting for percent germination or emergence (FIG. 22), as well as seedling height/vigor using the scale below with the total score for all replicates recorded (FIG. 23; max score of 36):

0: no emergence or extreme rotting of emerged cotyledons;

1: <30% height relative to no pathogen control; v. poor root mass relative to control;

2: 30-60% height relative to no pathogen control; poor root mass relative to control; and 3: >60% height relative to no pathogen control; good root mass relative to control.

TABLE 4

Assay composition per treatment.

| Treatment | Buffer | Microbe ($1.5 \times 10^9$ cfu/ml) | H20 | *P. aphanidermatum* (50 zoospores/ml) |
|---|---|---|---|---|
| Buffer only + water | 0.125 | none | 0.875 | none |
| Buffer only + pathogen | 0.125 | none | 0.375 | 0.50 |
| S2373 + water | | 0.125 | 0.875 | none |
| Consortia K + water | | 0.125 | 0.875 | none |
| Consortia I + water | | 0.125 | 0.875 | none |
| S1112 + water | | 0.125 | 0.875 | none |
| Consortia S + water | | 0.125 | 0.875 | none |
| S2373 + pathogen | | 0.125 | 0.375 | 0.50 |
| Consortia K + pathogen | | 0.125 | 0.375 | 0.50 |
| Consortia I + pathogen | | 0.125 | 0.375 | 0.50 |
| S1112 + pathogen | | 0.125 | 0.375 | 0.50 |
| Consortia S + pathogen | | 0.125 | 0.375 | 0.50 |

What is claimed is:

1. A composition comprising a plant seed and one or more microbial strains, wherein at least one microbial strain comprises strain S2373, NRRL Deposit No. B-67109, and wherein the 16S sequence of the strain S2373 comprises any one of SEQ ID Nos: 81, 82, or 83.

2. The composition of claim 1, further comprising at least one different microbial strain, wherein the 16S sequence of the one different microbial strain comprises any one of SEQ ID Nos: 1-164.

3. The composition of claim 1, further comprising an agriculturally effective amount of a compound or composition selected from the group consisting of a nutrient, a fertilizer, an acaricide, a bactericide, a fungicide, an insecticide, a microbicide, a nematicide, and a pesticide.

4. The composition of claim 1, further comprising a carrier.

5. The composition of claim 4, wherein said carrier is selected from peat, turf, talc, lignite, kaolinite, pyrophyllite, zeolite, montmorillonite, alginate, press mud, sawdust, perlite, mica, silicas, quartz powder, calcium bentonite, vermiculite and mixtures thereof.

6. The composition of claim 1, wherein the composition is prepared as a formulation selected from the group consisting of an emulsion, a colloid, a dust, a granule, a pellet, a powder, a spray, and a solution.

7. A plant seed having a coating comprising the composition of claim 1.

8. The composition of claim 1, wherein the plant seed is a transgenic plant seed.

9. The composition of claim 1, wherein the composition further comprises a biocontrol agent selected from the group consisting of a bacteria, a fungus, a yeast, a protozoa, a virus, an entomopathogenic nematode, a botanical extract, a protein, a nucleic acid, a secondary metabolite, and an inoculant.

\* \* \* \* \*

SEQUENCE LISTING

```
<160> NUMBER OF SEQ ID NOS: 164

<210> SEQ ID NO 1
<211> LENGTH: 250
<212> TYPE: DNA
<213> ORGANISM: Unknown
<220> FEATURE:
<223> OTHER INFORMATION: 16S DNA Tag

<400> SEQUENCE: 1
cacaccgtaa acgttgggcg ctaggtgtgg gactcattcc acgagttccg tgccgcagct      60
aacgcattaa gcgccccgcc tggggagtac ggccgcaagg ctaaaactca aaggaattga     120
cgggggcccg cacaagcggc ggagcatgcg gattaattcg atgcaacgcg aagaacctta     180
cctaggtttg acatatacga gaagcctcta gagatagagg tctctttgga cactcgtata     240
caggtggtgc                                                            250

<210> SEQ ID NO 2
<211> LENGTH: 586
<212> TYPE: DNA
<213> ORGANISM: Unknown
<220> FEATURE:
<223> OTHER INFORMATION: 16S DNA Tag

<400> SEQUENCE: 2
cacaccgtaa acgttgggcg ctaggtgtgg gactcattcc acgagttccg tgccgcagct      60
aacgcattaa gcgccccgcc tggggagtac ggccgcaagg ctaaaactca aaggaattga     120
cgggggcccg cacaagcggc ggagcatgcg gattaattcg atgcaacgcg aagaacctta     180
```

```
cctaggtttg acatatacga gaagcctcta gagatagagg tctctttgga cactcgtata      240
caggtggtgc atggctgtcg tcagctcgtg tcgtgagatg ttgggttaag tcccgcaacg      300
agcgcaaccc tcgtcttatg ttgccagcac gtaatggtgg ggactcataa gagactgccg      360
gggtcaactc ggaggaaggt ggggatgacg tcaagtcatc atgccccttta tgcctagggc     420 ttcacgcatg ctacaatggc cggtacaaag gctgcgaaa tcgcaagatg gagcgaatcc      480
caaaaagccg gtctcagttc ggattggggt ctgcaactcg accccatgaa gtcggagtcg     540
ctagtaatcg cagatcagca acgctgcggt gaatacgttc ccgggc                    586
```

```
<210> SEQ ID NO 3
<211> LENGTH: 586
<212> TYPE: DNA
<213> ORGANISM: Unknown
<220> FEATURE:
<223> OTHER INFORMATION: 16S DNA Tag

<400> SEQUENCE: 3
cacaccgtaa acgttgggcg ctaggtgtgg gactcattcc acgagttccg tgccgcagct      60
aacgcattaa gcgccccgcc tgggagtac ggccgcaagg ctaaaactca aaggaattga     120
cgggggcccg cacaagcggc ggagcatgcg gattaattcg atgcaacgcg aagaaccta    180 cctaggtttg acatatacga gaagcctcta gagatagagg tctctttgga cactcgtata     240
caggtggtgc atggctgtcg tcagctcgtg tcgtgagatg ttgggttaag tcccgcaacg     300
agcgcaaccc tcgtcttatg ttgccagcac gtcatggtgg ggactcataa gagactgccg    360
gggtcaactc ggaggaaggt ggggatgacg tcaagtcatc atgccccttta tgcctagggc    420 ttcacgcatg ctacaatggc cggtacaaag gctgcgaaa tcgcaagatg gagcgaatcc     480
caaaaagccg gtctcagttc ggattggggt ctgcaactcg accccatgaa gtcggagtcg    540
ctagtaatcg cagatcagca acgctgcggt gaatacgttc ccgggc                   586
```

```
<210> SEQ ID NO 4
<211> LENGTH: 250
<212> TYPE: DNA
<213> ORGANISM: Unknown
<220> FEATURE:
<223> OTHER INFORMATION: 16S DNA Tag

<400> SEQUENCE: 4
cacaccgtaa acgttgggcg ctaggtgtgg gactcattcc acgagttccg tgccgcagct      60
aacgcattaa gcgccccgcc tgggagtac ggccgcaagg ctaaaactca aaggaattga     120
cgggggcccg cacaagcggc ggagcatgcg gattaattcg atgcaacgcg aagaaccta    180 cctaggtttg acatatacga gaagcctcta gagatagagg tctctttgga cacttgtata     240
caggtggtgc                                                           250
```

```
<210> SEQ ID NO 5
<211> LENGTH: 588
<212> TYPE: DNA
<213> ORGANISM: Unknown
<220> FEATURE:
<223> OTHER INFORMATION: 16S DNA Tag

<400> SEQUENCE: 5
cacaccgtaa acgttgggcg ctaggtgtgg gactcattcc acgagttccg tgccgcagct      60
aacgcattaa gcgccccgcc tgggagtac ggccgcaagg ctaaaactca aaggaattga     120
cgggggcccg cacaagcggc ggagcatgcg gattaattcg atgcaacgcg aagaaccta    180
```
cctaggtttg acatatacga gaagcctcta gagatagagg tctctttgga cacttgtata    240
caggtggtgc atggctgtcg tcagctcgtg tcgtgagatg ttgggttaag tcccgcaacg    300
agcgcaaccc tcgtcttatg ttgccagcgg gtaatgccgg ggactcataa gagactgccg    360
gggtcaactc ggaggaaggt ggggatgacg tcaagtcatc atgccccta tgcctagggc     420 ttcacgcatg ctacaatggc cggtacaaag gctgcgaaa tcgcaagatg gagcgaatcc     480
caaaaagccg gtctcagttc ggattggggt ctgcaactcg accccatgaa gtcggagtcg    540
ctagtaatcg cagatcagca acgctgcggt gaatacgttc ccgggcct                 588

<210> SEQ ID NO 6
<211> LENGTH: 94
<212> TYPE: DNA
<213> ORGANISM: Unknown
<220> FEATURE:
<223> OTHER INFORMATION: 16S DNA Tag

<400> SEQUENCE: 6
gtatacaggt ggtgcatggc tgtcgtcagc tcgtgtcgtg agatgttggg ttaagtcccg    60
caacgagcgc aaccctcgtc ttatgttgcc agcg                                94

<210> SEQ ID NO 7
<211> LENGTH: 588
<212> TYPE: DNA
<213> ORGANISM: Unknown
<220> FEATURE:
<223> OTHER INFORMATION: 16S DNA Tag

<400> SEQUENCE: 7
cacaccgtaa acgttgggcg ctaggtgtgg gactcattcc acgagttccg tgccgcagct    60
aacgcattaa gcgccccgcc tggggagtac ggccgcaagg ctaaaactca aaggaattga    120
cgggggcccg cacaagcggc ggagcatgcg gattaattcg atgcaacgcg aagaaccta    180 cctaggtttg acatatacga gaagcctcta gagatagagg tctctttgga cacttgtata    240
caggtggtgc atggctgtcg tcagctcgtg tcgtgagatg ttgggttaag tcccgcaacg    300
agcgcaaccc tcgtcttatg ttgccagcac gtcatggtgg ggactcataa gagactgccg    360
gggtcaactc ggaggaaggt ggggatgacg tcaagtcatc atgccccta tgcctagggc     420 ttcacgcatg ctacaatggc cggtacaaag gctgcgata ccgcaaggtg gagcgaatcc    480
caaaaagccg gtctcagttc ggattggggt ctgcaactcg accccatgaa gtcggagtcg    540
ctagtaatcg cagatcagca acgctgcggt gaatacgttc ccgggcct                 588

<210> SEQ ID NO 8
<211> LENGTH: 245
<212> TYPE: DNA
<213> ORGANISM: Unknown
<220> FEATURE:
<223> OTHER INFORMATION: 16S DNA Tag

<400> SEQUENCE: 8
tagaggtctc tttggacact tgtatacagg tggtgcatgg ctgtcgtcag ctcgtgtcgt    60
gagatgttgg gttaagtccc gcaacgagcg caaccctcgt cttatgttgc cagcacgtca    120
tggtggggac tcataagaga ctgccggggt caactcggag gaaggtgggg atgacgtcaa    180
gtcatcatgc cccttatgcc tagggcttca cgcatgctac aatggccggt acaagggct    240 gcgat                                                                245

<210> SEQ ID NO 9
<211> LENGTH: 250
<212> TYPE: DNA
<213> ORGANISM: Unknown
<220> FEATURE:
<223> OTHER INFORMATION: 16S DNA Tag

<400> SEQUENCE: 9
cacgccctaa acgatgcgaa ctggatgttg ggagcaacta ggctctcagt atcgaagcta      60
acgcgttaag ttcgccgcct ggggagtacg gtcgcaagac tgaaactcaa aggaattgac     120
gggggcccgc acaagcggtg gagtatgtgg tttaattcga tgcaacgcgc agaaccttac     180
ctggccttga catccacgga acccttgaga gatcgagggg tgccttcggg aaccgtgaga     240
caggtgctgc                                                             250

<210> SEQ ID NO 10
<211> LENGTH: 588
<212> TYPE: DNA
<213> ORGANISM: Unknown
<220> FEATURE:
<223> OTHER INFORMATION: 16S DNA Tag

<400> SEQUENCE: 10
cacgccctaa acgatgcgaa ctggatgttg ggagcaacta ggctctcagt atcgaagcta      60
acgcgttaag ttcgccgcct ggggagtacg gtcgcaagac tgaaactcaa aggaattgac     120
gggggcccgc acaagcggtg gagtatgtgg tttaattcga tgcaacgcgc agaaccttac     180
ctggccttga catccacgga acccttgaga gatcgagggg tgccttcggg aaccgtgaga     240
caggtgctgc atggctgtcg tcagctcgtg tcgtgagatg ttgggttaag tcccgcaacg     300
agcgcaaccc ttgtccttag ttgccagcac gtaatggtgg gaactctaag gagaccgccg     360
gtgacaaacc ggaggaaggt ggggatgacg tcaagtcatc atggccctta cggccagggc     420
tacacacgta ctacaatggt ggggacagag ggctgcgatc ccgcgagggt gagccaatcc     480
cagaaacccc atctcagtcc ggatcggagt ctgcaactcg actccgtgaa gtcggaatcg     540
ctagtaatcg cagatcagca ttgctgcggt gaatacgttc ccgggcct                  588

<210> SEQ ID NO 11
<211> LENGTH: 252
<212> TYPE: DNA
<213> ORGANISM: Unknown
<220> FEATURE:
<223> OTHER INFORMATION: 16S DNA Tag

<400> SEQUENCE: 11
cacgccgtaa acgatggaag ctagccgttg gcaagtttac ttgtcggtgg cgcagctaac      60
gcattaagct tcccgcctgg ggagtacggt cgcaagatta aaactcaaag gaattgacgg     120
gggcccgcac aagcggtgga gcatgtggtt taattcgaag caacgcgcag aaccttacca     180
gcccttgaca tcccggtcgc ggtttccaga gatggatacc ttcagttcgg ctggaccggt     240
gacaggtgct gc                                                          252

<210> SEQ ID NO 12
<211> LENGTH: 587
<212> TYPE: DNA
<213> ORGANISM: Unknown
<220> FEATURE:
<223> OTHER INFORMATION: 16S DNA Tag

<400> SEQUENCE: 12

```
cacgccgtaa acgatggaag ctagccgttg gcaagtttac ttgtcggtgg cgcagctaac      60
gcattaagct tcccgcctgg ggagtacggt cgcaagatta aaactcaaag gaattgacgg     120
gggcccgcac aagcggtgga gcatgtggtt taattcgaag caacgcgcag aaccttacca     180
gcccttgaca tcccggtcgc ggtttccaga gatggatacc ttcagttcgg ctggaccggt     240
gacaggtgct gcatggctgt cgtcagctcg tgtcgtgaga tgttgggtta agtcccgcaa     300
cgagcgcaac cctcgccctt agttgccagc attcagttgg gcactctaag gggactgccg     360
gtgataagcc gagaggaagg tggggatgac gtcaagtcct catggcccct acgggctggg     420
ctacacacgt gctacaatgg tggtgacagt gggcagcgag accgcgaggt cgagctaatc     480
tccaaaagcc atctcagttc ggattgcact ctgcaactcg agtgcatgaa gttggaatcg     540
ctagtaatcg cggatcagca tgccgcggtg aatacgttcc cgggcct                  587
```

<210> SEQ ID NO 13
<211> LENGTH: 587
<212> TYPE: DNA
<213> ORGANISM: Unknown
<220> FEATURE:
<223> OTHER INFORMATION: 16S DNA Tag

<400> SEQUENCE: 13

```
cacgccgtaa acgatggaag ctagccgttg gcaagtttac ttgtcggtgg cgcagctaac      60
gcattaagct tcccgcctgg ggagtacggt cgcaagatta aaactcaaag gaattgacgg     120
gggcccgcac aagcggtgga gcatgtggtt taattcgaag caacgcgcag aaccttacca     180
gcccttgaca tcccggtcgc ggtttccaga gatggatacc ttcagttcgg ctggaccggt     240
gacaggtgct gcatggctgt cgtcagctcg tgtcgtgaga tgttgggtta agtcccgcaa     300
cgagcgcaac cctcgccctt agttgccatc attcagttgg gcactctaag gggactgccg     360
gtgataagcc gagaggaagg tggggatgac gtcaagtcct catggcccct acgggctggg     420
ctacacacgt gctacaatgg tggtgacagt gggcagcgag accgcgaggt cgagctaatc     480
tccaaaagcc atctcagttc ggattgcact ctgcaactcg agtgcatgaa gttggaatcg     540
ctagtaatcg cggatcagca tgccgcggtg aatacgttcc cgggcct                  587
```

<210> SEQ ID NO 14
<211> LENGTH: 249
<212> TYPE: DNA
<213> ORGANISM: Unknown
<220> FEATURE:
<223> OTHER INFORMATION: 16S DNA Tag

<400> SEQUENCE: 14

```
cacgccgtaa acgatgtcaa ctagccgttg ggagccttga gctcttagtg gcgcagctaa      60
cgcattaagt tgaccgcctg gggagtacgg ccgcaaggtt aaaactcaaa tgaattgacg     120
ggggcccgca caagcggtgg agcatgtggt ttaattcgaa gcaacgcgaa gaaccttacc     180
aggccttgac atccaatgaa ctttccagag atggattggt gccttcggga acattgagac     240
aggtgctgc                                                             249
```

<210> SEQ ID NO 15
<211> LENGTH: 586
<212> TYPE: DNA
<213> ORGANISM: Unknown
<220> FEATURE:
<223> OTHER INFORMATION: 16S DNA Tag

```
<400> SEQUENCE: 15
cacgccgtaa acgatgtcaa ctagccgttg ggagccttga gctcttagtg gcgcagctaa      60
cgcattaagt tgaccgcctg gggagtacgg ccgcaaggtt aaaactcaaa tgaattgacg     120
ggggcccgca caagcggtgg agcatgtggt ttaattcgaa gcaacgcgaa gaaccttacc     180
aggccttgac atccaatgaa ctttccagag atggattggt gccttcggga acattgagac     240
aggtgctgca tggctgtcgt cagctcgtgt cgtgagatgt tgggttaagt cccgtaacga     300
gcgcaaccct tgtccttagt taccagcacg ttatggtggg cactctaagg agactgccgg     360
tgacaaaccg gaggaaggtg gggatgacgt caagtcatca tggcccttac ggcctgggct     420
acacacgtgc tacaatggtc ggtacagagg gttgccaagc cgcgaggtgg agctaatccc     480
acaaaaccga tcgtagtccg gatcgcagtc tgcaactcga ctgcgtgaag tcggaatcgc     540
tagtaatcgc gaatcagaat gtcgcggtga atacgttccc gggcct                   586

<210> SEQ ID NO 16
<211> LENGTH: 249
<212> TYPE: DNA
<213> ORGANISM: Unknown
<220> FEATURE:
<223> OTHER INFORMATION: 16S DNA Tag

<400> SEQUENCE: 16
cacgccgtaa acgatgtcaa ctagccgttg ggagccttga gctcttagtg gcgcagctaa      60
cgcattaagt tgaccgcctg gggagtacgg ccgcaaggtt aaaactcaaa tgaattgacg     120
ggggcccgca caagcggtgg agcatgtggt ttaattcgaa gcaacgcgaa gaaccttacc     180
aggccttgac atccaatgaa ctttccagag atggattggt gccttcggga gcattgagac     240
aggtgctgc                                                            249

<210> SEQ ID NO 17
<211> LENGTH: 574
<212> TYPE: DNA
<213> ORGANISM: Unknown
<220> FEATURE:
<223> OTHER INFORMATION: 16S DNA Tag

<400> SEQUENCE: 17
cacgccgtaa acgatgtcaa ctagccgttg ggagccttga gctcttagtg gcgcagctaa      60
cgcattaagt tgaccgcctg gggagtacgg ccgcaaggtt aaaactcaaa tgaattgacg     120
ggggcccgca caagcggtgg agcatgtggt ttaattcgaa gcaacgcgaa gaaccttacc     180
aggccttgac atccaatgaa ctttccagag atggattggt gccttcggga gcattgagac     240
aggtgctgca tggctgtcgt cagctcgtgt cgtgagatgt tgggttaagt cccgtaacga     300
gcgcaaccct tgtccttagt taccagcacg ttatggtggg cactctaagg agactgccgg     360
tgacaaaccg gaggaaggtg gggatgacgt caagtcatca tggcccttac ggcctgggct     420
acacacgtgc tacaatggtc ggtacagagg gttgccaagc cgcgaggtgg agctaatccc     480
acaaaaccga tcgtagtccg gatcgcagtc tgcaactcga ctgcgtgaag tcggaatcgc     540
tagtaatcgc gaatcagaat gtcgcggtga atac                                574

<210> SEQ ID NO 18
<211> LENGTH: 249
<212> TYPE: DNA
<213> ORGANISM: Unknown
<220> FEATURE:
<223> OTHER INFORMATION: 16S DNA Tag
```

<400> SEQUENCE: 18

```
cacgccgtaa acgatgtcga cttggaggtt gtgcccttga ggcgtggctt ccggagctaa      60
cgcgttaagt cgaccgcctg gggagtacgg ccgcaaggtt aaaactcaaa tgaattgacg     120
ggggcccgca caagcggtgg agcatgtggt ttaattcgat gcaacgcgaa gaaccttacc     180
tactcttgac atccagagaa ctttccagag atggattggt gccttcggga actctgagac     240
aggtgctgc                                                             249
```

<210> SEQ ID NO 19
<211> LENGTH: 585
<212> TYPE: DNA
<213> ORGANISM: Unknown
<220> FEATURE:
<223> OTHER INFORMATION: 16S DNA Tag

<400> SEQUENCE: 19

```
cacgccgtaa acgatgtcga cttggaggtt gtgcccttga ggcgtggctt ccggagctaa      60
cgcgttaagt cgaccgcctg gggagtacgg ccgcaaggtt aaaactcaaa tgaattgacg     120
ggggcccgca caagcggtgg agcatgtggt ttaattcgat gcaacgcgaa gaaccttacc     180
tactcttgac atccagagaa ctttccagag atggattggt gccttcggga actctgagac     240
aggtgctgca tggctgtcgt cagctcgtgt tgtgaaatgt tgggttaagt cccgcaacga     300
gcgcaaccct tatcctttgt tgccagcggt ccggccggga actcaaagga gactgccagt     360
gataaactgg aggaaggtgg ggatgacgtc aagtcatcat ggcccttacg agtagggcta     420
cacacgtgct acaatggcgc atacaaagag aagcgacctc gcgagagcaa gcggacctca     480
taaagtgcgt cgtagtccgg attggagtct gcaactcgac tccatgaagt cggaatcgct     540
agtaatcgta gatcagaatg ctacggtgaa tacgttcccg ggcct                     585
```

<210> SEQ ID NO 20
<211> LENGTH: 249
<212> TYPE: DNA
<213> ORGANISM: Unknown
<220> FEATURE:
<223> OTHER INFORMATION: 16S DNA Tag

<400> SEQUENCE: 20

```
cacgccgtaa acggtgggaa ctaggtgttg gcgacattcc acgtcgtcgg tgccgcagct      60
aacgcattaa gttccccgcc tggggagtac ggccgcaagg ctaaaactca aggaattga     120
cggggggcccg cacaagcagc ggagcatgtg gcttaattcg acgcaacgcg aagaaccta    180
ccaaggcttg acatacaccg gaaacggcca gagatggtcg ccccttgtg gtcggtgtac     240
aggtggtgc                                                             249
```

<210> SEQ ID NO 21
<211> LENGTH: 585
<212> TYPE: DNA
<213> ORGANISM: Unknown
<220> FEATURE:
<223> OTHER INFORMATION: 16S DNA Tag

<400> SEQUENCE: 21

```
cacgccgtaa acggtgggaa ctaggtgttg gcgacattcc acgtcgtcgg tgccgcagct      60
aacgcattaa gttccccgcc tggggagtac ggccgcaagg ctaaaactca aggaattga     120
cggggggcccg cacaagcagc ggagcatgtg gcttaattcg acgcaacgcg aagaaccta    180
```

```
ccaaggcttg acatacaccg gaaacggcca gagatggtcg ccccttgtg gtcggtgtac    240 aggtggtgca tggctgtcgt cagctcgtgt cgtgagatgt tgggttaagt cccgcaacga    300
gcgcaaccct tgttctgtgt tgccagcatg cccttcgggg tgatggggac tcacaggaga    360
ctgccggggt caactcggag gaaggtgggg acgacgtcaa gtcatcatgc ccttatgtc     420 ttgggctgca cacgtgctac aatggcaggt acaatgagct gcgaagccgt gaggcggagc    480
gaatctcaaa aagcctgtct cagttcggat tggggtctgc aactcgaccc catgaagtcg    540
gagttgctag taatcgcaga tcagcattgc tgcggtgaat acgtt                    585
```

```
<210> SEQ ID NO 22
<211> LENGTH: 585
<212> TYPE: DNA
<213> ORGANISM: Unknown
<220> FEATURE:
<223> OTHER INFORMATION: 16S DNA Tag

<400> SEQUENCE: 22
```

```
cacgccgtaa acggtgggaa ctaggtgttg gcgacattcc acgtcgtcgg tgccgcagct    60
aacgcattaa gttccccgcc tggggagtac ggccgcaagg ctaaaactca aaggaattga    120
cgggggcccg cacaagcagc ggagcatgtg gcttaattcg acgcaacgcg aagaaccta    180 ccaaggcttg acatacaccg gaaacggcca gagatggtcg ccccttgtg gtcggtgtac    240 aggtggtgca tggctgtcgt cagctcgtgt cgtgagatgt tgggttaagt cccgcaacga    300
gcgcaaccct tgttctgtgt tgccagcatg cccttcgggg tgatggggac tcacaggaga    360
ctgccggggt caactcggag gaaggtgggg acgacgtcaa gtcatcatgc ccttatgtc     420 ttgggctgca cacgtgctac aatggccggt acaaagagct gcgaagccgt gaggtggagc    480
gaatctcaaa aagccggtct cagttcggat tggggtctgc aactcgaccc catgaagtcg    540
gagttgctag taatcgcaga tcagcattgc tgcggtgaat acgtt                    585
```

```
<210> SEQ ID NO 23
<211> LENGTH: 585
<212> TYPE: DNA
<213> ORGANISM: Unknown
<220> FEATURE:
<223> OTHER INFORMATION: 16S DNA Tag

<400> SEQUENCE: 23
```

```
cacgccgtaa acggtgggaa ctaggtgttg gcgacattcc acgtcgtcgg tgccgcagct    60
aacgcattaa gttccccgcc tggggagtac ggccgcaagg ctaaaactca aaggaattga    120
cgggggcccg cacaagcagc ggagcatgtg gcttaattcg acgcaacgcg aagaaccta    180 ccaaggcttg acatacaccg gaaacggcca gagatggtcg ccccttgtg gtcggtgtac    240 aggtggtgca tggctgtcgt cagctcgtgt cgtgagatgt tgggttaagt cccgcaacga    300
gcgcaaccct tgttctgtgt tgccagcatg cccttcgggg tgatggggac tcacaggaga    360
ctgccggggt caactcggag gaaggtgggg acgacgtcaa gtcatcatgc ccttatgtc     420 ttgggctgca cacgtgctac aatggccggt acaaagagct gcgaaaccgt gaggtggagc    480
gaatctcaaa aagccggtct cagttcggat tggggtctgc aactcgaccc catgaagtcg    540
gagttgctag taatcgcaga tcagcattgc tgcggtgaat acgtt                    585
```

```
<210> SEQ ID NO 24
<211> LENGTH: 249
<212> TYPE: DNA
<213> ORGANISM: Unknown
```

```
<220> FEATURE:
<223> OTHER INFORMATION: 16S DNA Tag

<400> SEQUENCE: 24
cacgccgtaa acggtgggaa ctaggtgttg gcgacattcc acgtcgtcgg tgccgcagct      60
aacgcattaa gttccccgcc tggggagtac ggccgcaagg ctaaaactca aggaattga     120 cgggggcccg cacaagcagc ggagcatgtg gcttaattcg acgcaacgcg aagaacctta    180
ccaaggcttg acatacgccg gaaagcatca gagatggtgc ccccttgtg gtcggtgtac     240 aggtggtgc                                                             249

<210> SEQ ID NO 25
<211> LENGTH: 594
<212> TYPE: DNA
<213> ORGANISM: Unknown
<220> FEATURE:
<223> OTHER INFORMATION: 16S DNA Tag

<400> SEQUENCE: 25
cacgccgtaa acggtgggaa ctaggtgttg gcgacattcc acgtcgtcgg tgccgcagct      60
aacgcattaa gttccccgcc tggggagtac ggccgcaagg ctaaaactca aggaattga     120 cgggggcccg cacaagcagc ggagcatgtg gcttaattcg acgcaacgcg aagaacctta    180
ccaaggcttg acatacgccg gaaagcatca gagatggtgc ccccttgtg gtcggtgtac     240 aggtggtgca tggctgtcgt cagctcgtgt cgtgagatgt tgggttaagt cccgcaacga    300
gcgcaaccct tgtcctgtgt tgccagcatg cccttcgggg tgatgggac tcacaggaga     360 ccgccggggt caactcggag gaaggtgggg acgacgtcaa gtcatcatgc ccttatgtc     420 ttgggctgca cacgtgctac aatggccggt acaatgagct gcgataccgt gaggtggagc    480
gaatctcaaa aagccggtct cagttcggat tgggtctgc aactcgaccc catgaagtcg     540
gagttgctag taatcgcaga tcagcattgc tgcggtgaat acgttcccgg gcct           594

<210> SEQ ID NO 26
<211> LENGTH: 303
<212> TYPE: DNA
<213> ORGANISM: Unknown
<220> FEATURE:
<223> OTHER INFORMATION: 16S DNA Tag

<400> SEQUENCE: 26
caacgcgaag aaccttacca aggcttgaca tacgccggaa agcatcagag atggtgcccc      60
ccttgtggtc ggtgtacagg tggtgcatgg ctgtcgtcag ctcgtgtcgt gagatgttgg    120
gttaagtccc gcaacgagcg caaccttgt cctgtgttgc cagcatgccc ttcggggtga     180 tgggactca caggagaccg ccggggtcaa ctcggaggaa ggtggggacg acgtcaagtc     240
atcatgcccc ttatgtcttg gctgcacac gtgctacaat ggccggtaca atgagctgcg     300
ata                                                                   303

<210> SEQ ID NO 27
<211> LENGTH: 249
<212> TYPE: DNA
<213> ORGANISM: Unknown
<220> FEATURE:
<223> OTHER INFORMATION: 16S DNA Tag

<400> SEQUENCE: 27
cacgccgtaa acggtgggca ctaggtgtgg gcaacattcc acgttgtccg tgccgcagct      60
```

```
aacgcattaa gtgccccgcc tgggagtac ggccgcaagg ctaaaactca aaggaattga    120
cgggggcccg cacaagcggc ggagcatgtg gcttaattcg acgcaacgcg aagaaccta    180 ccaaggcttg acatacaccg gaaacgtctg gagacaggcg ccccttgtg gtcggtgtac    240 aggtggtgc                                                          249

<210> SEQ ID NO 28
<211> LENGTH: 581
<212> TYPE: DNA
<213> ORGANISM: Unknown
<220> FEATURE:
<223> OTHER INFORMATION: 16S DNA Tag

<400> SEQUENCE: 28
cacgccgtaa acggtgggca ctaggtgtgg gcaacattcc acgttgtccg tgccgcagct    60
aacgcattaa gtgccccgcc tgggagtac ggccgcaagg ctaaaactca aaggaattga    120
cgggggcccg cacaagcggc ggagcatgtg gcttaattcg acgcaacgcg aagaacctta    180
ccaaggcttg acatacaccg gaaacgtctg gagacaggcg ccccttgtg gtcggtgtac    240 aggtggtgca tggctgtcgt cagctcgtgt cgtgagatgt tgggttaagt cccgcaacga    300
gcgcaaccct tgtcccgtgt tgccagcaag cccttcgggg tgttggggac tcacgggaga    360 ccgccgggt caactcggag gaggtgggga cgacgtcaag tcatcatgcc ccttatgtct    420
tgggctgcac acgtgctaca atggccgta caatgagctg cgataccgca aggtggagcg    480
aatctcaaaa agccggtctc agttcggatt ggggtctgca actcgacccc atgaagtcgg    540
agtcgctagt aatcgcagat cagcattgct gcggtgaata c                      581

<210> SEQ ID NO 29
<211> LENGTH: 164
<212> TYPE: DNA
<213> ORGANISM: Unknown
<220> FEATURE:
<223> OTHER INFORMATION: 16S DNA Tag

<400> SEQUENCE: 29
gcccccttgt ggtcggtgta caggtggtgc atggctgtcg tcagctcgtg tcgtgagatg    60
ttgggttaag tcccgcaacg agcgcaaccc ttgtcccgtg ttgccagcaa gcccttcggg    120
gtgttgggga ctcacgggag accgccgggg tcaactcgga ggag                   164

<210> SEQ ID NO 30
<211> LENGTH: 250
<212> TYPE: DNA
<213> ORGANISM: Unknown
<220> FEATURE:
<223> OTHER INFORMATION: 16S DNA Tag

<400> SEQUENCE: 30
catgccgtaa acgttgggca ctaggtgtgg gggacattcc acgttttccg cgccgtagct    60
aacgcattaa gtgccccgcc tgggagtac ggccgcaagg ctaaaactca aaggaattga    120
cgggggcccg cacaagcggc ggagcatgcg gattaattcg atgcaacgcg aagaacctta    180
ccaaggcttg acatgaaccg gaaagacctg gaaacaggtg ccccgcttgc ggtcggttta    240
caggtggtgc                                                         250

<210> SEQ ID NO 31
<211> LENGTH: 569
<212> TYPE: DNA
<213> ORGANISM: Unknown
```

<220> FEATURE:
<223> OTHER INFORMATION: 16S DNA Tag

<400> SEQUENCE: 31

```
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaacctta     180
ccaaggcttg acatgaaccg gaaagacctg gaaacaggtg ccccgcttgc ggtcggttta     240
caggtggtgc atggttgtcg tcagctcgtg tcgtgagatg ttgggttaag tcccgcaacg     300
agcgcaaccc tcgttctatg ttgccagcac gtgatggtgg ggactcatag gagactgccg     360
gggtcaactc ggaggaaggt ggggacgacg tcaaatcatc atgccccta tgtcttgggc     420
ttcacgcatg ctacaatggc cggtacaaag ggttgcgata ctgtgaggtg gagctaatcc     480
caaaaagccg gtctcagttc ggattggggt ctgcaactcg acccatgaa gtcggagtcg     540
ctagtaatcg cagatcagca acgctgcgg                                       569
```

<210> SEQ ID NO 32
<211> LENGTH: 250
<212> TYPE: DNA
<213> ORGANISM: Unknown
<220> FEATURE:
<223> OTHER INFORMATION: 16S DNA Tag

<400> SEQUENCE: 32

```
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaacctta     180
ccaaggcttg acatgaaccg gtaagacctg gaaacaggtc ccccacttgt ggtcggttta     240
caggtggtgc                                                            250
```

<210> SEQ ID NO 33
<211> LENGTH: 576
<212> TYPE: DNA
<213> ORGANISM: Unknown
<220> FEATURE:
<223> OTHER INFORMATION: 16S DNA Tag

<400> SEQUENCE: 33

```
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaacctta     180
ccaaggcttg acatgaaccg gtaagacctg gaaacaggtc ccccacttgt ggtcggttta     240
caggtggtgc atggttgtcg tcagctcgtg tcgtgagatg ttgggttaag tcccgcaacg     300
agcgcaaccc tcgttccatg ttgccagcgc gttatggcgg ggactcatgg gagactgccg     360
gggtcaactc ggaggaaggt ggggacgacg tcaaatcatc atgccccta tgtcttgggc     420
ttcacgcatg ctacaatggc cggtacaaag ggttgcgata ctgtgaggtg gagctaatcc     480
caaaaagccg gtctcagttc ggattggggt ctgcaactcg acccatgaa gtcggagtcg     540
ctagtaatcg cagatcagca acgctgcggt gaatac                               576
```

<210> SEQ ID NO 34
<211> LENGTH: 250
<212> TYPE: DNA

```
<213> ORGANISM: Unknown
<220> FEATURE:
<223> OTHER INFORMATION: 16S DNA Tag

<400> SEQUENCE: 34
catgccgtaa acgttgggca ctaggtgtgg gggacattcc acgttttccg cgccgtagct    60
aacgcattaa gtgccccgcc tggggagtac ggccgcaagg ctaaaactca aaggaattga   120
cgggggcccg cacaagcggc ggagcatgcg gattaattcg atgcaacgcg aagaacctta   180
ccaaggcttg acatgaaccg gtaagacctg gaaacaggtc ccccgcttgc ggtcggttta   240
caggtggtgc                                                          250

<210> SEQ ID NO 35
<211> LENGTH: 588
<212> TYPE: DNA
<213> ORGANISM: Unknown
<220> FEATURE:
<223> OTHER INFORMATION: 16S DNA Tag

<400> SEQUENCE: 35
catgccgtaa acgttgggca ctaggtgtgg gggacattcc acgttttccg cgccgtagct    60
aacgcattaa gtgccccgcc tggggagtac ggccgcaagg ctaaaactca aaggaattga   120
cgggggcccg cacaagcggc ggagcatgcg gattaattcg atgcaacgcg aagaacctta   180
ccaaggcttg acatgaaccg gtaagacctg gaaacaggtc ccccgcttgc ggtcggttta   240
caggtggtgc atggttgtcg tcagctcgtg tcgtgagatg ttgggttaag tcccgcaacg   300
agcgcaaccc tcgttctatg ttgccagcac gtgatggtgg ggactcatag gagactgccg   360
gggtcaactc ggaggaaggt ggggacgacg tcaaatcatc atgccccta tgtcttgggc   420 ttcacgcatg ctacaatggc cggtacaaag ggttgcgata ctgtgaggtg gagctaatcc   480
caaaaagccg gtctcagttc ggattggggt ctgcaactcg accccatgaa gtcggagtcg   540
ctagtaatcg cagatcagca acgctgcggt gaatacgttc ccgggcct                588

<210> SEQ ID NO 36
<211> LENGTH: 249
<212> TYPE: DNA
<213> ORGANISM: Unknown
<220> FEATURE:
<223> OTHER INFORMATION: 16S DNA Tag

<400> SEQUENCE: 36
cacgccgtaa acgatgtcga cttggaggtt gttcccttga ggagtggctt ccggagctaa    60
cgcgttaagt cgaccgcctg gggagtacgg ccgcaaggtt aaaactcaaa tgaattgacg   120
ggggcccgca caagcggtgg agcatgtggt ttaattcgat gcaacgcgaa gaaccttacc   180
tactcttgac atccagagaa cttttccaga gatggattgg gccttcggga actctgagac   240
aggtgctgc                                                           249

<210> SEQ ID NO 37
<211> LENGTH: 586
<212> TYPE: DNA
<213> ORGANISM: Unknown
<220> FEATURE:
<223> OTHER INFORMATION: 16S DNA Tag

<400> SEQUENCE: 37
cacgccgtaa acgatgtcga cttggaggtt gttcccttga ggagtggctt ccggagctaa    60
cgcgttaagt cgaccgcctg gggagtacgg ccgcaaggtt aaaactcaaa tgaattgacg   120
```

```
gggccccgca caagcggtgg agcatgtggt ttaattcgat gcaacgcgaa gaaccttacc    180
tactcttgac atccagagaa ctttccagag atggattggg gccttcggga actctgagac    240
aggtgctgca tggctgtcgt cagctcgtgt tgtgaaatgt tgggttaagt cccgcaacga    300
gcgcaaccct tatcctttgt tgccagcgcg tgatggcggg aactcaaagg agactgccgg    360
tgataaaccg gaggaaggtg gggatgacgt caagtcatca tggcccttac gagtagggct    420
acacacgtgc tacaatggcg catacaaaga gaagcgacct cgcgagagca agcggacctc    480
acaaagtgcg tcgtagtccg gatcggagtc tgcaactcga ctccgtgaag tcggaatcgc    540
tagtaatcgt ggatcagaat gccacggtga atacgttccc gggcct              586

<210> SEQ ID NO 38
<211> LENGTH: 249
<212> TYPE: DNA
<213> ORGANISM: Unknown
<220> FEATURE:
<223> OTHER INFORMATION: 16S DNA Tag

<400> SEQUENCE: 38
cacgccgtaa acggtgggaa ctaggtgttg gcgacattcc acgtcgtcgg tgccgcagct     60
aacgcattaa gttccccgcc tggggagtac ggccgcaagg ctaaaactca aaggaattga    120
cgggggcccg cacaagcagc ggagcatgtg gcttaattcg acgcaacgcg aagaaccttta   180 ccaaggcttg acatacaccg gaaaaccctg gagacagggt cccccttgtg gtcggtgtac    240
aggtggtgc                                                             249

<210> SEQ ID NO 39
<211> LENGTH: 591
<212> TYPE: DNA
<213> ORGANISM: Unknown
<220> FEATURE:
<223> OTHER INFORMATION: 16S DNA Tag

<400> SEQUENCE: 39
cacgccgtaa acggtgggaa ctaggtgttg gcgacattcc acgtcgtcgg tgccgcagct     60
aacgcattaa gttccccgcc tggggagtac ggccgcaagg ctaaaactca aaggaattga    120
cgggggcccg cacaagcagc ggagcatgtg gcttaattcg acgcaacgcg aagaaccttta   180 ccaaggcttg acatacaccg gaaaaccctg gagacagggt cccccttgtg gtcggtgtac    240
aggtggtgca tggctgtcgt cagctcgtgt cgtgagatgt tgggttaagt cccgcaacga    300
gcgcaaccct tgttctgtgt tgccagcatg cccttcgggg tgatgggggac tcacaggaga   360 ctgccggggt caactcggag gaaggtgggg acgacgtcaa gtcatcatgc cccttatgtc    420
ttgggctgca cacgtgctac aatggcaggt acaatgagct gcgatgccgc gaggcggagc    480
gaatctcaaa aagcctgtct cagttcggat tggggtctgc aactcgaccc catgaagtcg    540
gagttgctag taatcgcaga tcagcattgc tgcggtgaat acgttcccgg g             591

<210> SEQ ID NO 40
<211> LENGTH: 259
<212> TYPE: DNA
<213> ORGANISM: Unknown
<220> FEATURE:
<223> OTHER INFORMATION: 16S DNA Tag

<400> SEQUENCE: 40
accggaaaac cctggagaca gggtcccccct tgtggtcggt gtacaggtgg tgcatggctg     60
```

```
tcgtcagctc gtgtcgtgag atgttgggtt aagtcccgca acgagcgcaa cccttgttct    120
gtgttgccag catgcccttc ggggtgatgg ggactcacag gagactgccg gggtcaactc    180
ggaggaaggt ggggacgacg tcaagtcatc atgcccctta tgtcttgggc tgcacacgtg    240
ctacaatggc aggtacaat                                                  259

<210> SEQ ID NO 41
<211> LENGTH: 249
<212> TYPE: DNA
<213> ORGANISM: Unknown
<220> FEATURE:
<223> OTHER INFORMATION: 16S DNA Tag

<400> SEQUENCE: 41
cacgccgtaa acggtgggca ctaggtgtgg gcaacattcc acgttgtccg tgccgcagct     60
aacgcattaa gtgccccgcc tggggagtac ggccgcaagg ctaaaactca aaggaattga    120
cgggggcccg cacaagcggc ggagcatgtg gcttaattcg acgcaacgcg aagaacctta    180
ccaaggcttg acatacaccg gaaagcatta gagatagtgc ccccttgtg gtcggtgtac     240 aggtggtgc                                                             249

<210> SEQ ID NO 42
<211> LENGTH: 593
<212> TYPE: DNA
<213> ORGANISM: Unknown
<220> FEATURE:
<223> OTHER INFORMATION: 16S DNA Tag

<400> SEQUENCE: 42
cacgccgtaa acggtgggca ctaggtgtgg gcaacattcc acgttgtccg tgccgcagct     60
aacgcattaa gtgccccgcc tggggagtac ggccgcaagg ctaaaactca aaggaattga    120
cgggggcccg cacaagcggc ggagcatgtg gcttaattcg acgcaacgcg aagaacctta    180
ccaaggcttg acatacaccg gaaagcatta gagatagtgc ccccttgtg gtcggtgtac     240 aggtggtgca tggctgtcgt cagctcgtgt cgtgagatgt tgggttaagt cccgcaacga    300
gcgcaaccct tgtcccgtgt tgccagcagg cccttgtggt gctggggact cacgggagac    360
cgccggggtc aactcggagg aaggtgggga cgacgtcaag tcatcatgcc ccttatgtct    420
tgggctgcac acgtgctaca atggccgta caatgagctg cgataccgtg aggtggagcg    480
aatctcaaaa agccggtctc agttcggatt ggggtctgca actcgacccc atgaagtcgg    540
agtcgctagt aatcgcagat cagcattgct gcggtgaata cgttcccggg cct           593

<210> SEQ ID NO 43
<211> LENGTH: 252
<212> TYPE: DNA
<213> ORGANISM: Unknown
<220> FEATURE:
<223> OTHER INFORMATION: 16S DNA Tag

<400> SEQUENCE: 43
cacgccgtaa actatgagag ctagccgtcg gcaagtttac ttgtcggtgg cgcagctaac     60
gcattaagct ctccgcctgg ggagtacggt cgcaagatta aaactcaaag gaattgacgg    120
gggcccgcac aagcggtgga gcatgtggtt taattcgaag caacgcgcag aaccttacca    180
gcccttgaca tcccggtcgc ggtttccaga gatggaaacc ttcagttcgg ctggaccggt    240
gacaggtgct gc                                                         252
```

<210> SEQ ID NO 44
<211> LENGTH: 587
<212> TYPE: DNA
<213> ORGANISM: Unknown
<220> FEATURE:
<223> OTHER INFORMATION: 16S DNA Tag

<400> SEQUENCE: 44

```
cacgccgtaa actatgagag ctagccgtcg gcaagtttac ttgtcggtgg cgcagctaac    60
gcattaagct ctccgcctgg ggagtacggt cgcaagatta aaactcaaag gaattgacgg   120
gggcccgcac aagcggtgga gcatgtggtt taattcgaag caacgcgcag aaccttacca   180
gcccttgaca tcccggtcgc ggtttccaga gatggaaacc ttcagttcgg ctggaccggt   240
gacaggtgct gcatggctgt cgtcagctcg tgtcgtgaga tgttgggtta agtcccgcaa   300
cgagcgcaac cctcgccctt agttgccagc attcagttgg gcactctaag gggactgccg   360
gtgataagcc gagaggaagg tggggatgac gtcaagtcct catggccctt acgggctggg   420
ctacacacgt gctacaatgg tggtgacagt gggcagcgag accgcgaggt cgagctaatc   480
tccaaaagcc atctcagttc ggattgcact ctgcaactcg agtgcatgaa gttggaatcg   540
ctagtaatcg cagatcagca tgctgcggtg aatacgttcc cgggcct                 587
```

<210> SEQ ID NO 45
<211> LENGTH: 263
<212> TYPE: DNA
<213> ORGANISM: Unknown
<220> FEATURE:
<223> OTHER INFORMATION: 16S DNA Tag

<400> SEQUENCE: 45

```
tccgcctggg gagtacggtc gcaagattaa aactcaaagg aattgacggg ggcccgcaca    60
agcggtggag catgtggttt aattcgaagc aacgcgcaga accttaccag cccttgacat   120
cccggtcgcg gtttccagag atggaaacct tcagttcggc tggaccggtg acaggtgctg   180
catggctgtc gtcagctcgt gtcgtgagat gttgggttaa gtcccgcaac gagcgcaacc   240
ctcgccctta gttgccagca ttc                                           263
```

<210> SEQ ID NO 46
<211> LENGTH: 250
<212> TYPE: DNA
<213> ORGANISM: Unknown
<220> FEATURE:
<223> OTHER INFORMATION: 16S DNA Tag

<400> SEQUENCE: 46

```
catgccgtaa acgttgggca ctaggtgtgg gggacattcc acgttttccg cgccgtagct    60
aacgcattaa gtgccccgcc tgggagtac ggccgcaagg ctaaaactca aggaattga    120
cgggggcccg cacaagcggc ggagcatgcg gattaattcg atgcaacgcg aagaaccttta   180
ccaaggcttg acatgaaccg gaaacgcctg gaaacaggtg ccccgcttgc ggtcggttta   240
caggtggtgc                                                         250
```

<210> SEQ ID NO 47
<211> LENGTH: 588
<212> TYPE: DNA
<213> ORGANISM: Unknown
<220> FEATURE:
<223> OTHER INFORMATION: 16S DNA Tag

<400> SEQUENCE: 47

```
catgccgtaa acgttgggca ctaggtgtgg gggacattcc acgttttccg cgccgtagct        60
aacgcattaa gtgccccgcc tggggagtac ggccgcaagg ctaaaactca aaggaattga       120
cgggggcccg cacaagcggc ggagcatgcg gattaattcg atgcaacgcg aagaacctta       180
ccaaggcttg acatgaaccg gaaacgcctg gaaacaggtg ccccgcttgc ggtcggttta       240
caggtggtgc atggttgtcg tcagctcgtg tcgtgagatg ttgggttaag tcccgcaacg       300
agcgcaaccc tcgttctatg ttgccagcac gtgatggtgg ggactcatag gagactgccg       360
gggtcaactc ggaggaaggt ggggacgacg tcaaatcatc atgcccctta tgtcttgggc       420
ttcacgcatg ctacaatggc cggtacaaag ggttgcgata ctgtgaggtg gagctaatcc       480
caaaaagccg gtctcagttc ggattgggt ctgcaactcg accccatgaa gtcggagtcg        540
ctagtaatcg cagatcagca acgctgcggt gaatacgttc ccgggcct                    588

<210> SEQ ID NO 48
<211> LENGTH: 290
<212> TYPE: DNA
<213> ORGANISM: Unknown
<220> FEATURE:
<223> OTHER INFORMATION: 16S DNA Tag

<400> SEQUENCE: 48
aaacgcctgg aaacaggtgc cccgcttgcg gtcggtttac aggtggtgca tggttgtcgt       60
cagctcgtgt cgtgagatgt tgggttaagt cccgcaacga gcgcaaccct cgttctatgt      120
tgccagcacg tgatggtggg gactcatagg agactgccgg ggtcaactcg gaggaaggtg      180
gggacgacgt caaatcatca tgccccttat gtcttgggct tcacgcatgc tacaatggcc      240
ggtacaaagg gttgcgatac tgtgaggtgg agctaatccc aaaaagccgg                 290

<210> SEQ ID NO 49
<211> LENGTH: 250
<212> TYPE: DNA
<213> ORGANISM: Unknown
<220> FEATURE:
<223> OTHER INFORMATION: 16S DNA Tag

<400> SEQUENCE: 49
cacgccgtaa acgttgggcg ctagatgtgg ggaccattcc acggtttccg tgtcgcagct       60
aacgcattaa gcgccccgcc tggggagtac ggccgcaagg ctaaaactca aaggaattga      120
cgggggcccg cacaagcggc ggagcatgcg gattaattcg atgcaacgcg aagaacctta      180
ccaaggcttg acatatacga gaacgggcca gaaatggtca actctttgga cactcgtaaa      240
caggtggtgc                                                            250

<210> SEQ ID NO 50
<211> LENGTH: 588
<212> TYPE: DNA
<213> ORGANISM: Unknown
<220> FEATURE:
<223> OTHER INFORMATION: 16S DNA Tag

<400> SEQUENCE: 50
cacgccgtaa acgttgggcg ctagatgtgg ggaccattcc acggtttccg tgtcgcagct       60
aacgcattaa gcgccccgcc tggggagtac ggccgcaagg ctaaaactca aaggaattga      120
cgggggcccg cacaagcggc ggagcatgcg gattaattcg atgcaacgcg aagaacctta      180
ccaaggcttg acatatacga gaacgggcca gaaatggtca actctttgga cactcgtaaa      240
caggtggtgc atggttgtcg tcagctcgtg tcgtgagatg ttgggttaag tcccgcaacg       300
```

```
agcgcaaccc tcgttctatg ttgccagcac gtaatggtgg gaactcatag gagactgccg    360
gggtcaactc ggaggaaggt ggggatgacg tcaaatcatc atgcccctta tgtcttgggc    420
ttcacgcatg ctacaatggc cggtacaaag gctgcaata ccgtaaggtg gagcgaatcc    480
caaaaagccg gtctcagttc ggattgaggt ctgcaactcg acctcatgaa gtcggagtcg    540
ctagtaatcg cagatcagca acgctgcggt gaatacgttc ccgggcct                 588

<210> SEQ ID NO 51
<211> LENGTH: 248
<212> TYPE: DNA
<213> ORGANISM: Unknown
<220> FEATURE:
<223> OTHER INFORMATION: 16S DNA Tag

<400> SEQUENCE: 51
cacaccgtaa acgttgggcg ctaggtgtgg gactcattcc acgagttccg tgccgcagct    60
aacgcattaa gcgccccgcc tgggagtac ggccgcaagg ctaaaactca aaggaattga     120
cgggggcccg cacaagcggc ggagcatgcg gattaattcg atgcaacgcg aagaaccta    180 cctaggtttg acatataggg aaatctgcta gagatagcag gtccgtaagg gctctataca    240
ggtggtgc                                                             248

<210> SEQ ID NO 52
<211> LENGTH: 586
<212> TYPE: DNA
<213> ORGANISM: Unknown
<220> FEATURE:
<223> OTHER INFORMATION: 16S DNA Tag

<400> SEQUENCE: 52
cacaccgtaa acgttgggcg ctaggtgtgg gactcattcc acgagttccg tgccgcagct    60
aacgcattaa gcgccccgcc tgggagtac ggccgcaagg ctaaaactca aaggaattga     120
cgggggcccg cacaagcggc ggagcatgcg gattaattcg atgcaacgcg aagaaccta    180 cctaggtttg acatataggg aaatctgcta gagatagcag gtccgtaagg gctctataca    240
ggtggtgcat ggctgtcgtc agctcgtgtc gtgagatgtt gggttaagtc cgcaacgag     300 cgcaaccctc gtcttatgtt gccagcacgt catggtgggg actcataaga gactgccggg    360
gtcaactcgg aggaaggtgg ggatgacgtc aagtcatcat gccccttatg cctagggctt    420
cacgcatgct acaatggccg gtacaaaggg ctgcgaaatc gcaagatgga gcgaatccca    480
aaaagccggt ctcagttcgg attggggtct gcaactcgac cccatgaagt cggagtcgct    540
agtaatcgca gatcagcaac gctgcggtga atacgttccc gggcct                   586

<210> SEQ ID NO 53
<211> LENGTH: 223
<212> TYPE: DNA
<213> ORGANISM: Unknown
<220> FEATURE:
<223> OTHER INFORMATION: 16S DNA Tag

<400> SEQUENCE: 53
caggtccgta agggctctat acaggtggtg catggctgtc gtcagctcgt gtcgtgagat    60
gttgggttaa gtcccgcaac gagcgcaacc ctcgtcttat gttgccagca cgtcatggtg    120
gggactcata agagactgcc ggggtcaact cggaggaagg tggggatgac gtcaagtcat    180
catgcccctt atgcctaggg cttcacgcat gctacaatgg ccg                      223
```

<210> SEQ ID NO 54
<211> LENGTH: 252
<212> TYPE: DNA
<213> ORGANISM: Unknown
<220> FEATURE:
<223> OTHER INFORMATION: 16S DNA Tag

<400> SEQUENCE: 54

```
cacgccgtaa acgatggaag ctagccgttg gcaagtttac ttgtcggtgg cgcagctaac     60
gcattaagct tcccgcctgg ggagtacggt cgcaagatta aaactcaaag gaattgacgg    120
gggcccgcac aagcggtgga gcatgtggtt taattcgaag caacgcgcag aaccttacca    180
gcccttgaca tcccggtcgc ggtttccaga aatggatacc ttcagttcgg ctggaccggt    240
gacaggtgct gc                                                        252
```

<210> SEQ ID NO 55
<211> LENGTH: 587
<212> TYPE: DNA
<213> ORGANISM: Unknown
<220> FEATURE:
<223> OTHER INFORMATION: 16S DNA Tag

<400> SEQUENCE: 55

```
cacgccgtaa acgatggaag ctagccgttg gcaagtttac ttgtcggtgg cgcagctaac     60
gcattaagct tcccgcctgg ggagtacggt cgcaagatta aaactcaaag gaattgacgg    120
gggcccgcac aagcggtgga gcatgtggtt taattcgaag caacgcgcag aaccttacca    180
gcccttgaca tcccggtcgc ggtttccaga aatggatacc ttcagttcgg ctggaccggt    240
gacaggtgct gcatggctgt cgtcagctcg tgtcgtgaga tgttgggtta agtcccgcaa    300
cgagcgcaac cctcgccctt agttgccatc attcagttgg gcactctaag gggactgccg    360
gtgataagcc gagaggaagg tggggatgac gtcaagtcct catggccctt acgggctggg    420
ctacacacgt gctacaatgg tggtgacagt gggcagcgag accgcgaggt cgagctaatc    480
tccaaaagcc atctcagttc ggattgcact ctgcaactcg agtgcatgaa gttggaatcg    540
ctagtaatcg cggatcagca tgccgcggtg aatacgttcc cgggcct                  587
```

<210> SEQ ID NO 56
<211> LENGTH: 582
<212> TYPE: DNA
<213> ORGANISM: Unknown
<220> FEATURE:
<223> OTHER INFORMATION: 16S DNA Tag

<400> SEQUENCE: 56

```
cacgccgtaa acgatggaag ctagccgttg gcaagtttac ttgtcggtgg cgcagctaac     60
gcattaagct tcccgcctgg ggagtacggt cgcaagatta aaactcaaag gaattgacgg    120
gggcccgcac aagcggtgga gcatgtggtt taattcgaag caacgcgcag aaccttacca    180
gcccttgaca tcccggtcgc ggtttccaga aatggatacc ttcagttcgg ctggaccggt    240
gacaggtgct gcatggctgt cgtcagctcg tgtcgtgaga tgttgggtta agtcccgcaa    300
cgagcgcaac cctcgccctt agttgccatc attcagttgg gcactctaag gggactgccg    360
gtgataagcc gagaggaagg tggggatgac gtcaagtcct catggccctt acgggctggg    420
ctacacacgt gctacaatgg tggtgacagt gggcagcgag accgcgaggt cgagctaatc    480
tccaaaagcc atctcagttc ggattgcact ctgcaactcg agtgcatgaa gttggaatcg    540
ctagtaaatc gcggatcagc atgccgcggg gaatacgttc cc                       582
```

<210> SEQ ID NO 57
<211> LENGTH: 78
<212> TYPE: DNA
<213> ORGANISM: Unknown
<220> FEATURE:
<223> OTHER INFORMATION: 16S DNA Tag

<400> SEQUENCE: 57

| | | |
|---|---|---|
| cgagctaatc tccaaaagcc atctcagttc ggattgcact ctgcaactcg agtgcatgaa | 60 |
| gttggaatcg ctagtaaa | 78 |

<210> SEQ ID NO 58
<211> LENGTH: 252
<212> TYPE: DNA
<213> ORGANISM: Unknown
<220> FEATURE:
<223> OTHER INFORMATION: 16S DNA Tag

<400> SEQUENCE: 58

| | |
|---|---|
| cacgccgtaa acgatggaag ctagccgttg gcaagtttac ttgtcggtgg cgcagctaac | 60 |
| gcattaagct tcccgcctgg ggagtacggt cgcaagatta aaactcaaag gaattgacgg | 120 |
| gggcccgcac aagcggtgga gcatgtggtt taattcgaag caacgcgcag aaccttacca | 180 |
| gcccttgaca tcccggtcgc ggtttccaga gatggaaacc ttcagttcgg ctggaccggt | 240 |
| gacaggtgct gc | 252 |

<210> SEQ ID NO 59
<211> LENGTH: 576
<212> TYPE: DNA
<213> ORGANISM: Unknown
<220> FEATURE:
<223> OTHER INFORMATION: 16S DNA Tag

<400> SEQUENCE: 59

| | |
|---|---|
| cacgccgtaa acgatggaag ctagccgttg gcaagtttac ttgtcggtgg cgcagctaac | 60 |
| gcattaagct tcccgcctgg ggagtacggt cgcaagatta aaactcaaag gaattgacgg | 120 |
| gggcccgcac aagcggtgga gcatgtggtt taattcgaag caacgcgcag aaccttacca | 180 |
| gcccttgaca tcccggtcgc ggtttccaga gatggaaacc ttcagttcgg ctggaccggt | 240 |
| gacaggtgct gcatggctgt cgtcagctcg tgtcgtgaga tgttgggtta agtcccgcaa | 300 |
| cgagcgcaac cctcgccctt agttgccagc attcagttgg gcactctaag gggactgccg | 360 |
| gtgataagcc gagaggaagg tggggatgac gtcaagtcct catggccctt acgggctggg | 420 |
| ctacacacgt gctacaatgg tggtgacagt gggcagcgag accgcgaggt cgagctaatc | 480 |
| tccaaaagcc atctcagttc ggattgcact ctgcaactcg agtgcatgaa gttggaatcg | 540 |
| ctagtaatcg cggatcagca tgccgcggtg aatacg | 576 |

<210> SEQ ID NO 60
<211> LENGTH: 252
<212> TYPE: DNA
<213> ORGANISM: Unknown
<220> FEATURE:
<223> OTHER INFORMATION: 16S DNA Tag

<400> SEQUENCE: 60

| | |
|---|---|
| cacgccgtaa acgatggaag ctagccgttg gcaagtttac ttgtcggtgg cgcagctaac | 60 |
| gcattaagct tcccgcctgg ggagtacggt cgcaagatta aaactcaaag gaattgacgg | 120 |

| | |
|---|---|
| gggcccgcac aagcggtgga gcatgtggtt taattcgaag caacgcgcag aaccttacca | 180 |
| gcccttgaca tcccggtcgc ggtttccaga gatggaaatc ttcagttcgg ctggaccggt | 240 |
| gacaggtgct gc | 252 |

<210> SEQ ID NO 61
<211> LENGTH: 577
<212> TYPE: DNA
<213> ORGANISM: Unknown
<220> FEATURE:
<223> OTHER INFORMATION: 16S DNA Tag

<400> SEQUENCE: 61

| | |
|---|---|
| cacgccgtaa acgatggaag ctagccgttg gcaagtttac ttgtcggtgg cgcagctaac | 60 |
| gcattaagct tcccgcctgg ggagtacggt cgcaagatta aaactcaaag gaattgacgg | 120 |
| gggcccgcac aagcggtgga gcatgtggtt taattcgaag caacgcgcag aaccttacca | 180 |
| gcccttgaca tcccggtcgc ggtttccaga gatggaaatc ttcagttcgg ctggaccggt | 240 |
| gacaggtgct gcatggctgt cgtcagctcg tgtcgtgaga tgttgggtta agtcccgcaa | 300 |
| cgagcgcaac cctcgccctt agttgccagc attcagttgg gcactctaag ggactgccg | 360 |
| gtgataagcc gagaggaagg tggggatgac gtcaagtcct catggccctt acgggctggg | 420 |
| ctacacacgt gctacaatgg tggtgacagt gggcagcgag accgcgaggt cgagctaatc | 480 |
| tccaaaagcc atctcagttc ggattgcact ctgcaactcg agtgcatgaa gttggaatcg | 540 |
| ctagtaatcg cggatcagca tgccgcggtg aatacgt | 577 |

<210> SEQ ID NO 62
<211> LENGTH: 249
<212> TYPE: DNA
<213> ORGANISM: Unknown
<220> FEATURE:
<223> OTHER INFORMATION: 16S DNA Tag

<400> SEQUENCE: 62

| | |
|---|---|
| cacgccgtaa acgttgggaa ctaggtgttg gcgacattcc acgtcgtcgg tgccgcagct | 60 |
| aacgcattaa gttccccgcc tggggagtac ggccgcaagg ctaaaactca aggaattga | 120 |
| cgggggcccg cacaagcagc ggagcatgtg gcttaattcg acgcaacgcg aagaacctta | 180 |
| ccaaggcttg acatataccg gaaacggcta gagatagtcg ccccttgtg gtcggtatac | 240 |
| aggtggtgc | 249 |

<210> SEQ ID NO 63
<211> LENGTH: 593
<212> TYPE: DNA
<213> ORGANISM: Unknown
<220> FEATURE:
<223> OTHER INFORMATION: 16S DNA Tag

<400> SEQUENCE: 63

| | |
|---|---|
| cacgccgtaa acgttgggaa ctaggtgttg gcgacattcc acgtcgtcgg tgccgcagct | 60 |
| aacgcattaa gttccccgcc tggggagtac ggccgcaagg ctaaaactca aggaattga | 120 |
| cgggggcccg cacaagcagc ggagcatgtg gcttaattcg acgcaacgcg aagaacctta | 180 |
| ccaaggcttg acatataccg gaaacggcta gagatagtcg ccccttgtg gtcggtatac | 240 |
| aggtggtgca tggttgtcgt cagctcgtgt cgtgagatgt tgggttaagt cccgcaacga | 300 |
| gcgcaaccct tgttctgtgt tgccagcatg cctttcgggg tgatgggac tcacaggaga | 360 |
| ctgccggggt caactcggag gaaggtgggg acgacgtcaa atcatcatgc cccttatgtc | 420 |

```
ttgggctgca cacgtgctac aatggtcggt acaaagggct gcaatgccgc gaggcggagc    480
gaatcccaaa aagccggcct cagttcggat tggggtctgc aactcgaccc catgaagttg    540
gagttgctag taatcgcaga tcagcatgct gcggtgaata cgttcccggg cct           593
```

<210> SEQ ID NO 64
<211> LENGTH: 106
<212> TYPE: DNA
<213> ORGANISM: Unknown
<220> FEATURE:
<223> OTHER INFORMATION: 16S DNA Tag

<400> SEQUENCE: 64

```
agactgccgg ggtcaactcg gaggaaggtg gggacgacgt caaatcatca tgccccttat    60
gtcttgggct gcacacgtgc tacaatggtc ggtacaaagg gctgca                   106
```

<210> SEQ ID NO 65
<211> LENGTH: 251
<212> TYPE: DNA
<213> ORGANISM: Unknown
<220> FEATURE:
<223> OTHER INFORMATION: 16S DNA Tag

<400> SEQUENCE: 65

```
catgccgtaa acgttgggca ctaggtgtgg gggacattcc acgttttccg cgccgtagct    60
aacgcattaa gtgccccgcc tggggagtac ggccgcaagg ctaaaactca aaggaattga    120
cgggggcccg cacaagcggc ggagcatgcg gattaattcg atgcaacgcg aagaacctta    180
ccaaggcttg acatgaaccg gaccgccgca gaaatgtggt ttccccttcg gggctggttt    240
acaggtggtg c                                                        251
```

<210> SEQ ID NO 66
<211> LENGTH: 588
<212> TYPE: DNA
<213> ORGANISM: Unknown
<220> FEATURE:
<223> OTHER INFORMATION: 16S DNA Tag

<400> SEQUENCE: 66

```
catgccgtaa acgttgggca ctaggtgtgg gggacattcc acgttttccg cgccgtagct    60
aacgcattaa gtgccccgcc tggggagtac ggccgcaagg ctaaaactca aaggaattga    120
cgggggcccg cacaagcggc ggagcatgcg gattaattcg atgcaacgcg aagaacctta    180
ccaaggcttg acatgaaccg gaccgccgca gaaatgtggt ttccccttcg gggctggttt    240
acaggtggtg catggttgtc gtcagctcgt gtcgtgagat gttgggttaa gtcccgcaac    300
gagcgcaacc ctcgttctat gttgccagca cgtgatggtg gggactcata ggagactgcc    360
ggggtcaact cggaggaagg tggggacgac gtcaaatcat catgcccctt atgtcttggg    420
cttcacgcat gctacaatgg ccggtacaaa gggttgcgat actgtgaggt ggagctaatc    480
ccaaaaagcc ggtctcagtt cggattgggg tctgcaactc gaccccatga agtcggagtc    540
gctagtaatc gcagatcagc aacgctgcgg tgaatacgtt cccgggcc                588
```

<210> SEQ ID NO 67
<211> LENGTH: 251
<212> TYPE: DNA
<213> ORGANISM: Unknown
<220> FEATURE:
<223> OTHER INFORMATION: 16S DNA Tag

```
<400> SEQUENCE: 67
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaaccta     180 ccaaggcttg acatggaccg gaccgccgca gaaatgtggt ttccccttg gggctggttt    240 acaggtggtg c                                                         251

<210> SEQ ID NO 68
<211> LENGTH: 588
<212> TYPE: DNA
<213> ORGANISM: Unknown
<220> FEATURE:
<223> OTHER INFORMATION: 16S DNA Tag

<400> SEQUENCE: 68
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaaccta     180 ccaaggcttg acatggaccg gaccgccgca gaaatgtggt ttccccttg gggctggttt    240 acaggtggtg catggttgtc gtcagctcgt gtcgtgagat gttgggttaa gtcccgcaac     300
gagcgcaacc ctcgttctat gttgccagca cgtgatggtg gggactcata ggagactgcc     360
ggggtcaact cggaggaagg tggggacgac gtcaaatcat catgcccctt atgtcttggg    420
cttcacgcat gctacaatgg ccggtacaaa gggttgcgat actgtgaggt ggagctaatc     480
ccaaaaagcc ggtctcagtt cggattgggg tctgcaactc gaccccatga agtcggagtc    540
gctagtaatc gcagatcagc aacgctgcgg aatacgttc ccgggcct                  588

<210> SEQ ID NO 69
<211> LENGTH: 238
<212> TYPE: DNA
<213> ORGANISM: Unknown
<220> FEATURE:
<223> OTHER INFORMATION: 16S DNA Tag

<400> SEQUENCE: 69
gatggtgggg actcatagga gactgccggg gtcaactcgg aggaaggtgg ggacgacgtc      60
aaatcatcat gccccttatg tcttgggctt cacgcatgct acaatggccg gtacaaaggg     120
ttgcgatact gtgaggtgga gctaatccca aaaagccggt ctcagttcgg attgggtct     180 gcaactcgac cccatgaagt cggagtcgct agtaatcgca gatcagcaac gctgcggg      238

<210> SEQ ID NO 70
<211> LENGTH: 251
<212> TYPE: DNA
<213> ORGANISM: Unknown
<220> FEATURE:
<223> OTHER INFORMATION: 16S DNA Tag

<400> SEQUENCE: 70
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaaccta     180 ccaaggcttg acatgaaccg gaccgctgca gaaatgtggt ttccccttg gggctggttt    240 acaggtggtg c                                                         251
```

<210> SEQ ID NO 71
<211> LENGTH: 591
<212> TYPE: DNA
<213> ORGANISM: Unknown
<220> FEATURE:
<223> OTHER INFORMATION: 16S DNA Tag

<400> SEQUENCE: 71

```
catgccgtaa acgttgggca ctaggtgtgg gggacattcc acgttttccg cgccgtagct      60
aacgcattaa gtgccccgcc tggggagtac ggccgcaagg ctaaaactca aggaattga     120
cgggggcccg cacaagcggc ggagcatgcg gattaattcg atgcaacgcg aagaaccttp    180
ccaaggcttg acatgaaccg gaccgctgca gaaatgtggt ttcccctttg gggctggttt    240
acaggtggtg catggttgtc gtcagctcgt gtcgtgagat gttgggttaa gtcccgcaac    300
gagcgcaacc ctcgttctat gttgccagca cgtgatggtg gggactcata ggagactgcc    360
ggggtcaact cggaggaagg tggggacgac gtcaaatcat catgcccctt atgtcttggg    420
cttcacgcat gctacaatgg ccggtacaaa gggttgcgat actgtgaggt ggagctaatc    480
ccaaaaagcc ggtctcagtt cggattgggg tctgcaactc gacccatga agtcggagtc     540
gctagtaatc gcagatcagc aacgctgccg gtgaatacgt tcccggggcc t              591
```

<210> SEQ ID NO 72
<211> LENGTH: 94
<212> TYPE: DNA
<213> ORGANISM: Unknown
<220> FEATURE:
<223> OTHER INFORMATION: 16S DNA Tag

<400> SEQUENCE: 72

```
taatcccaaa aagccggtct cagttcggat tggggtctgc aactcgaccc catgaagtcg     60
gagtcgctag taatcgcaga tcagcaacgc tgcc                                 94
```

<210> SEQ ID NO 73
<211> LENGTH: 589
<212> TYPE: DNA
<213> ORGANISM: Unknown
<220> FEATURE:
<223> OTHER INFORMATION: 16S DNA Tag

<400> SEQUENCE: 73

```
catgccgtaa acgttgggca ctaggtgtgg gggacattcc acgttttccg cgccgtagct      60
aacgcattaa gtgccccgcc tggggagtac ggccgcaagg ctaaaactca aggaattga     120
cgggggcccg cacaagcggc ggagcatgcg gattaattcg atgcaacgcg aagaaccttp    180
ccaaggcttg acatgaaccg gaccgctgca gaaatgtggt ttcccctttg gggctggttt    240
acaggtggtg catggttgtc gtcagctcgt gtcgtgagat gttgggttaa gtcccgcaac    300
gagcgcaacc ctcgttctat gttgccagca cgtgatggtg gggactcata ggagactgcc    360
ggggtcaact cggaggaagg tggggacgac gtcaaatcat catgcccctt atgtcttggg    420
cttcacgcat gctacaatgg ccggtacaaa gggttgcgat actgtgaggt ggagctaatc    480
ccaaaaagcc ggtctcagtt cggattgggg tctgcaactc gacccatga agtcggagtc     540
gctagtaatc gcagatcagc aacgctgcgg tgaatacgtt cccgggcct                589
```

<210> SEQ ID NO 74
<211> LENGTH: 589
<212> TYPE: DNA

<213> ORGANISM: Unknown
<220> FEATURE:
<223> OTHER INFORMATION: 16S DNA Tag

<400> SEQUENCE: 74

```
catgccgtaa acgttgggca ctaggtgtgg gggacattcc acgttttccg cgccgtagct      60
aacgcattaa gtgccccgcc tggggagtac ggccgcaagg ctaaaactca aaggaattga     120
cgggggcccg cacaagcggc ggagcatgcg gattaattcg atgcaacgcg aagaaccttta    180
ccaaggcttg acatgaaccg gaccgctgca gaaatgtggt ttccccttg gggctggttt     240
acaggtggtg catggttgtc gtcagctcgt gtcgtgagat gttgggttaa gtcccgcaac    300
gagcgcaacc ctcgttctat gttgccagca cgtgatggtg gggactcata ggagactgcc    360
ggggtcaact cggaggaagg tggggacgac gtcaaatcat catgccccct atgtcttggg    420
cttcacgcat gctacaatgg ccggtacaaa gggttgcgat actgtgaggt ggagctaatc    480
ccaaaaagcc ggtctcagtt cggattgggg tctgcaactc gacccatga agtcggagtc     540
gctagtaatc gcagatcagc aacgctgcgg tgaatacgtt cccgggcct               589
```

<210> SEQ ID NO 75
<211> LENGTH: 250
<212> TYPE: DNA
<213> ORGANISM: Unknown
<220> FEATURE:
<223> OTHER INFORMATION: 16S DNA Tag

<400> SEQUENCE: 75

```
cacgccctaa acgatgtcaa ctagttgtcg ggtcttcatt gacttggtaa cgtagctaac     60
gcgtgaagtt gaccgcctgg ggagtacggt cgcaagatta aaactcaaag gaattgacgg    120
ggacccgcac aagcggtgga tgatgtggat taattcgatg caacgcgaaa aaccttacct    180
acccttgaca tgtatggaac cctgctgaga ggtgggggtg cccgaaaggg agccataaca    240
caggtgctgc                                                          250
```

<210> SEQ ID NO 76
<211> LENGTH: 580
<212> TYPE: DNA
<213> ORGANISM: Unknown
<220> FEATURE:
<223> OTHER INFORMATION: 16S DNA Tag

<400> SEQUENCE: 76

```
cacgccctaa acgatgtcaa ctagttgtcg ggtcttcatt gacttggtaa cgtagctaac     60
gcgtgaagtt gaccgcctgg ggagtacggt cgcaagatta aaactcaaag gaattgacgg    120
ggacccgcac aagcggtgga tgatgtggat taattcgatg caacgcgaaa aaccttacct    180
acccttgaca tgtatggaac cctgctgaga ggtgggggtg cccgaaaggg agccataaca    240
caggtgctgc atggctgtcg tcagctcgtg tcgtgagatg ttgggttaag tcccgcaacg    300
agcgcaaccc ttgtccctag ttgctacgca agagcactcc agggagactg ccggtgacaa    360
accggaggaa ggtggggatg acgtcaagtc ctcatggccc ttatgggtag gcttcacac    420
gtcatacaat ggtcggaaca gagggtcgcc aaccgcgag ggggagccaa tcccagaaaa    480
ccgatcgtag tccggatcgc actctgcaac tcgagtgcgt gaagctggaa tcgctagtaa    540
tcgcggatca gcatgccgcg gtgaatacgt tcccgggtct                         580
```

<210> SEQ ID NO 77
<211> LENGTH: 594

<212> TYPE: DNA
<213> ORGANISM: Unknown
<220> FEATURE:
<223> OTHER INFORMATION: 16S DNA Tag

<400> SEQUENCE: 77

```
cacgccgtaa acggtgggca ctaggtgtgg gcaacattcc acgttgtccg tgccgcagct    60
aacgcattaa gtgccccgcc tggggagtac ggccgcaagg ctaaaactca aaggaattga   120
cggggggccg cacaagcggc ggagcatgtg gcttaattcg acgcaacgcg aagaacctta   180
ccaaggcttg acatacaccg gaaacgtctg gagacaggcg ccccctttgtg gtcggtgtac   240
aggtggtgca tggctgtcgt cagctcgtgt cgtgagatgt tgggttaagt cccgcaacga   300
gcgcaaccct tgtcccgtgt tgccagcaag cccttcgggg tgttggggac tcacgggaga   360
ccgccggggt caactcggag gaaggtgggg acgacgtcaa gtcatcatgc ccttatgtc    420
ttgggctgca cacgtgctac aatggccggt acaatgagct gcgataccgc aaggtggagc   480
gaatctcaaa aagccggtct cagttcggat tggggtctgc aactcgaccc catgaagtcg   540
gagtcgctag taatcgcaga tcagcattgc tgcggtgaat acgttccgg gcct           594
```

<210> SEQ ID NO 78
<211> LENGTH: 586
<212> TYPE: DNA
<213> ORGANISM: Unknown
<220> FEATURE:
<223> OTHER INFORMATION: 16S DNA Tag

<400> SEQUENCE: 78

```
cacgccgtaa acgatgtcaa ctagccgttg ggagccttga gctcttagtg gcgcagctaa    60
cgcattaagt tgaccgcctg gggagtacgg ccgcaaggtt aaaactcaaa tgaattgacg   120
ggggcccgca caagcggtgg agcatgtggt ttaattcgaa gcaacgcgaa gaaccttacc   180
aggccttgac atccaatgaa cttttccagag atggattggt gccttcggga gcattgagac   240
aggtgctgca tggctgtcgt cagctcgtgt cgtgagatgt tgggttaagt cccgtaacga   300
gcgcaaccct tgtccttagt taccagcacg tgatggtggg cactctaagg agactgccgg   360
tgacaaaccg gaggaaggtg gggatgacgt caagtcatca tggcccttac ggcctgggct   420
acacacgtgc tacaatggtc ggtacagagg gttgccaagc cgcgaggtgg agctaatccc   480
ataaaaccga tcgtagtccg gatcgcagtc tgcaactcga ctgcgtgaag tcggaatcgc   540
tagtaatcgc gaatcagaat gtcgcggtga atacgttccc gggcct                 586
```

<210> SEQ ID NO 79
<211> LENGTH: 439
<212> TYPE: DNA
<213> ORGANISM: Unknown
<220> FEATURE:
<223> OTHER INFORMATION: 16S DNA Tag

<400> SEQUENCE: 79

```
cttagtggcg cagctaacgc attaagttga ccgcctgggg agtacggccg caaggttaaa    60
actcaaatga attgacgggg gcccgcacaa gcggtggagc atgtggttta attcgaagca   120
acgcgaagaa ccttaccagg ccttgacatc caatgaactt tccagagatg gattggtgcc   180
ttcgggagca ttgagacagg tgctgcatgg ctgtcgtcag ctcgtgtcgt gagatgttgg   240
gttaagtccc gtaacgagcg caaccccttgt ccttagttac cagcacgtga tggtgggcac   300
tctaaggaga ctgccggtga caaaccggag gaaggtgggg atgacgtcaa gtcatcatgg   360
```

```
cccttacggc ctgggctaca cacgtgctac aatggtcggt acagagggtt gccaagccgc    420
gaggtggagc taatcccat                                                 439
```

<210> SEQ ID NO 80
<211> LENGTH: 586
<212> TYPE: DNA
<213> ORGANISM: Unknown
<220> FEATURE:
<223> OTHER INFORMATION: 16S DNA Tag

<400> SEQUENCE: 80

```
cacgccgtaa acgatgtcaa ctagccgttg ggagccttga gctcttagtg gcgcagctaa     60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
aggccttgac atccaatgaa ctttccagag atggattggt gccttcggga acattgagac    240
aggtgctgca tggctgtcgt cagctcgtgt cgtgagatgt tgggttaagt cccgtaacga    300
gcgcaaccct tgtccttagt taccagcacg taatggtggg cactctaagg agactgccgg    360
tgacaaaccg gaggaaggtg gggatgacgt caagtcatca tggcccttac ggcctgggct    420
acacacgtgc tacaatggtc ggtacaaagg gttgccaagc cgcgaggtgg agctaatccc    480
ataaaaccga tcgtagtccg gatcgcagtc tgcaactcga ctgcgtgaag tcggaatcgc    540
tagtaatcgc gaatcagaat gtcgcggtga atacgttccc gggcct                  586
```

<210> SEQ ID NO 81
<211> LENGTH: 250
<212> TYPE: DNA
<213> ORGANISM: Unknown
<220> FEATURE:
<223> OTHER INFORMATION: 16S DNA Tag

<400> SEQUENCE: 81

```
cacgccctaa acgatgcgaa ctggatgttg gtctcaactc ggagatcagt gtcgaagcta     60
acgcgttaag ttcgccgcct ggggagtacg gtcgcaagac tgaaactcaa aggaattgac    120
gggggcccgc acaagcggtg gagtatgtgg tttaattcga tgcaacgcga agaaccttac    180
ctggccttga catgtctgga atccctgaga gatcggggag tgccttcggg aaccagaaca    240
caggtgctgc                                                           250
```

<210> SEQ ID NO 82
<211> LENGTH: 588
<212> TYPE: DNA
<213> ORGANISM: Unknown
<220> FEATURE:
<223> OTHER INFORMATION: 16S DNA Tag

<400> SEQUENCE: 82

```
cacgccctaa acgatgcgaa ctggatgttg gtctcaactc ggagatcagt gtcgaagcta     60
acgcgttaag ttcgccgcct ggggagtacg gtcgcaagac tgaaactcaa aggaattgac    120
gggggcccgc acaagcggtg gagtatgtgg tttaattcga tgcaacgcga agaaccttac    180
ctggccttga catgtctgga atccctgaga gatcggggag tgccttcggg aaccagaaca    240
caggtgctgc atggctgtcg tcagctcgtg tcgtgagatg ttgggttaag tcccgcaacg    300
agcgcaaccc ttgtccttag ttgccagcac gtaaaggtgg gaactctaag gagactgccg    360
gtgacaaacc ggaggaaggt ggggatgacg tcaagtcatc atggccctta cggccagggc    420
tacacacgta ctacaatggt cggtacagag ggttgcaata ccgcgaggtg gagccaatcc    480
```

```
cagaaagccg atcccagtcc ggatcgaagt ctgcaactcg acttcgtgaa gtcggaatcg      540
ctagtaatcg cggatcagct atgccgcggt gaatacgttc ccgggcct                  588

<210> SEQ ID NO 83
<211> LENGTH: 121
<212> TYPE: DNA
<213> ORGANISM: Unknown
<220> FEATURE:
<223> OTHER INFORMATION: 16S DNA Tag

<400> SEQUENCE: 83
ggggagtgcc ttcgggaacc agaacacagg tgctgcatgg ctgtcgtcag ctcgtgtcgt      60
gagatgttgg gttaagtccc gcaacgagcg caacccttgt ccttagttgc cagcacgtaa    120
a                                                                    121

<210> SEQ ID NO 84
<211> LENGTH: 250
<212> TYPE: DNA
<213> ORGANISM: Unknown
<220> FEATURE:
<223> OTHER INFORMATION: 16S DNA Tag

<400> SEQUENCE: 84
cacgccctaa acgatgcgaa ctggatgttg gtctcaactc ggagatcagt gtcgaagcta     60
acgcgttaag ttcgccgcct ggggagtacg gtcgcaagac tgaaactcaa aggaattgac    120
gggggcccgc acaagcggtg gagtatgtgg tttaattcga tgcaacgcga agaaccttac    180
ctggccttga catgtccgga atcctgcaga gatgcgggag tgccttcggg aatcggaaca    240
caggtgctgc                                                            250

<210> SEQ ID NO 85
<211> LENGTH: 588
<212> TYPE: DNA
<213> ORGANISM: Unknown
<220> FEATURE:
<223> OTHER INFORMATION: 16S DNA Tag

<400> SEQUENCE: 85
cacgccctaa acgatgcgaa ctggatgttg gtctcaactc ggagatcagt gtcgaagcta     60
acgcgttaag ttcgccgcct ggggagtacg gtcgcaagac tgaaactcaa aggaattgac    120
gggggcccgc acaagcggtg gagtatgtgg tttaattcga tgcaacgcga agaaccttac    180
ctggccttga catgtccgga atcctgcaga gatgcgggag tgccttcggg aatcggaaca    240
caggtgctgc atggctgtcg tcagctcgtg tcgtgagatg ttgggttaag tcccgcaacg    300
agcgcaaccc ttgtccttag ttgccagcga gtaatgtcgg gaactctaag gagactgccg    360
gtgacaaacc ggaggaaggt ggggatgacg tcaagtcatc atggccctta cggccagggc    420
tacacacgta ctacaatggt cggtacagag ggttgcaata ccgcgaggtg gagccaatcc    480
cagaaagccg atcccagtcc ggatcggagt ctgcaactcg actccgtgaa gtcggaatcg    540
ctagtaatcg cggatcagct atgccgcggt gaatacgttc ccgggcct                 588

<210> SEQ ID NO 86
<211> LENGTH: 247
<212> TYPE: DNA
<213> ORGANISM: Unknown
<220> FEATURE:
<223> OTHER INFORMATION: 16S DNA Tag
```

```
<400> SEQUENCE: 86
catgccgtaa acgttgggcg ctaggtgtgg ggaccttcca cggtctccgt gccgcagcta      60
acgcattaag cgccccgcct ggggagtacg gccgcaaggc taaaactcaa aggaattgac     120
gggggcccgc acaagcggcg gagcatgctg attaattcga tgcaacgcga agaaccttac     180
ctgggtttga catataccgg aaagctgcag agatgtagcc ccctttggt cggtatacag      240 gtggtgc                                                               247

<210> SEQ ID NO 87
<211> LENGTH: 585
<212> TYPE: DNA
<213> ORGANISM: Unknown
<220> FEATURE:
<223> OTHER INFORMATION: 16S DNA Tag

<400> SEQUENCE: 87
catgccgtaa acgttgggcg ctaggtgtgg ggaccttcca cggtctccgt gccgcagcta      60
acgcattaag cgccccgcct ggggagtacg gccgcaaggc taaaactcaa aggaattgac     120
gggggcccgc acaagcggcg gagcatgctg attaattcga tgcaacgcga agaaccttac     180
ctgggtttga catataccgg aaagctgcag agatgtagcc ccctttggt cggtatacag      240 gtggtgcatg gctgtcgtca gctcgtgtcg tgagatgttg ggttaagtcc cgcaacgagc     300
gcaaccctcg tcctatgttg ccagcacgta atggtgggga ctcataggag actgccgggg     360
tcaactcgga ggaaggtggg gatgacgtca agtcttcatg cccttatgt ccagggcttc      420 aagcatgcta caatggccgg tacaaagggc tgcgaaaccg caaggtggag cgaatcccaa     480
aaagccggtc tcagttcgga ttggggtctg caactcgacc ccatgaagtc ggagtcgcta     540
gtaatcgcag atcagcaacg ctgcggtgaa tacgttcccg ggcct                     585

<210> SEQ ID NO 88
<211> LENGTH: 594
<212> TYPE: DNA
<213> ORGANISM: Unknown
<220> FEATURE:
<223> OTHER INFORMATION: 16S DNA Tag

<400> SEQUENCE: 88
cacgccgtaa acggtgggaa ctaggtgttg gcgacattcc acgtcgtcgg tgccgcagct      60
aacgcattaa gttccccgcc tggggagtac ggccgcaagg ctaaaactca aggaattga     120 cgggggcccg cacaagcagc ggagcatgtg gcttaattcg acgcaacgcg aagaacctta     180
ccaaggcttg acatacgccg gaaagcatca gagatggtgc ccccttgtg gtcggtgtac     240 aggtggtgca tggctgtcgt cagctcgtgt cgtgagatgt tgggttaagt cccgcaacga     300
gcgcaaccct tgtcctgtgt tgccagcatg cccttcgggg tgatgggac tcacaggaga      360 ccgccgggt caactcggag gaaggtgggg acgacgtcaa gtcatcatgc cccttatgtc      420
ttgggctgca cacgtgctac aatggcaggt acaatgagct gcgataccgt gaggtggagc     480
gaatctcaaa aagcctgtct cagttcggat tggggtctgc aactcgaccc catgaagtcg     540
gagttgctag taatcgcaga tcagcattgc tgcggtgaat acgttcccgg gcct           594

<210> SEQ ID NO 89
<211> LENGTH: 252
<212> TYPE: DNA
<213> ORGANISM: Unknown
<220> FEATURE:
<223> OTHER INFORMATION: 16S DNA Tag
```

<400> SEQUENCE: 89

```
cacgccgtaa acgatgagtg ctaagtgtta gagggtttcc gccctttagt gctgcagcta      60
acgcattaag cactccgcct ggggagtacg ccgcaaggc tgaaactcaa aggaattgac      120
gggggcccgc acaagcggtg gagcatgtgg tttaattcga agcaacgcga agaaccttac    180
caggtcttga catcctctga cactcctaga gataggacgt tccccttcgg gggacagagt    240
gacaggtggt gc                                                        252
```

<210> SEQ ID NO 90
<211> LENGTH: 587
<212> TYPE: DNA
<213> ORGANISM: Unknown
<220> FEATURE:
<223> OTHER INFORMATION: 16S DNA Tag

<400> SEQUENCE: 90

```
cacgccgtaa acgatgagtg ctaagtgtta gagggtttcc gccctttagt gctgcagcta      60
acgcattaag cactccgcct ggggagtacg ccgcaaggc tgaaactcaa aggaattgac      120
gggggcccgc acaagcggtg gagcatgtgg tttaattcga agcaacgcga agaaccttac    180
caggtcttga catcctctga cactcctaga gataggacgt tccccttcgg gggacagagt    240
gacaggtggt gcatggttgt cgtcagctcg tgtcgtgaga tgttgggtta agtcccgcaa    300
cgagcgcaac ccttgatctt agttgccagc attcagttgg gcactctaag gtgactgccg    360
gtgacaaacc ggaggaaggt ggggatgacg tcaaatcatc atgccccta tgacctgggc      420
tacacacgtg ctacaatgga tggtacaaag gcagcaaag ccgcgaggcc tagccaatcc    480
cataaaacca ttctcagttc ggattgtagg ctgcaactcg cctacatgaa gccggaatcg    540
ctagtaatcg cggatcagca tgccgcggtg aatacgttcc cgggcct                587
```

<210> SEQ ID NO 91
<211> LENGTH: 586
<212> TYPE: DNA
<213> ORGANISM: Unknown
<220> FEATURE:
<223> OTHER INFORMATION: 16S DNA Tag

<400> SEQUENCE: 91

```
cacgccgtaa acgatgtcaa ctagccgttg ggagccttga gctcttagtg gcgcagctaa    60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
aggccttgac atccaatgaa ctttccagag atggattggt gccttcggga acattgagac    240
aggtgctgca tggctgtcgt cagctcgtgt cgtgagatgt tgggttaagt cccgtaacga    300
gcgcaaccct tgtccttagt taccagcacg taatggtggg cactctaagg agactgccgg    360
tgacaaaccg gaggaaggtg gggatgacgt caagtcatca tggcccttac ggcctgggct    420
acacacgtgc tacaatggtc ggtacagagg gttgccaagc cgcgaggtgg agctaatccc    480
acaaaaccga tcgtagtccg gatcgcagtc tgcaactcga ctgcgtgaag tcggaatcgc    540
tagtaatcgc gaatcagaat gtcgcggtga atacgttccc gggcct                   586
```

<210> SEQ ID NO 92
<211> LENGTH: 588
<212> TYPE: DNA
<213> ORGANISM: Unknown
<220> FEATURE:

<223> OTHER INFORMATION: 16S DNA Tag

<400> SEQUENCE: 92

| | |
|---|---|
| catgccgtaa acgttgggca ctaggtgtgg gggacattcc acgttttccg cgccgtagct | 60 |
| aacgcattaa gtgccccgcc tggggagtac ggccgcaagg ctaaaactca aaggaattga | 120 |
| cgggggcccg cacaagcggc ggagcatgcg gattaattcg atgcaacgcg aagaacctta | 180 |
| ccaaggcttg acatgaaccg gaaagacctg gaaacaggtg ccccgcttgc ggtcggttta | 240 |
| caggtggtgc atggttgtcg tcagctcgtg tcgtgagatg ttgggttaag tcccgcaacg | 300 |
| agcgcaaccc tcgttctatg ttgccagcac gtgatggtgg ggactcatag gagactgccg | 360 |
| gggtcaactc ggaggaaggt ggggacgacg tcaaatcatc atgcccctta tgtcttgggc | 420 |
| ttcacgcatg ctacaatggc cggtacaaag ggttgcgata ctgtgaggtg gagctaatcc | 480 |
| caaaaagccg gtctcagttc ggattggggt ctgcaactcg accccatgaa gtcggagtcg | 540 |
| ctagtaatcg cagatcagca acgctgcggt gaatacgttc ccgggcct | 588 |

<210> SEQ ID NO 93
<211> LENGTH: 248
<212> TYPE: DNA
<213> ORGANISM: Unknown
<220> FEATURE:
<223> OTHER INFORMATION: 16S DNA Tag

<400> SEQUENCE: 93

| | |
|---|---|
| cacgccgtaa acgatgaatg ccagctgttg gggtgcttgc accgcagtag cgcagctaac | 60 |
| gctttgagca ttccgcctgg ggagtacggt cgcaagatta aaactcaaag gaattgacgg | 120 |
| gggcccgcac aagcggtgga gcatgtggtt taattcgaag caacgcgcag aaccttacca | 180 |
| tcctttgaca tggcgtgtta cccagagaga tttggggtcc acttcggtgg cgcgcacaca | 240 |
| ggtgctgc | 248 |

<210> SEQ ID NO 94
<211> LENGTH: 583
<212> TYPE: DNA
<213> ORGANISM: Unknown
<220> FEATURE:
<223> OTHER INFORMATION: 16S DNA Tag

<400> SEQUENCE: 94

| | |
|---|---|
| cacgccgtaa acgatgaatg ccagctgttg gggtgcttgc accgcagtag cgcagctaac | 60 |
| gctttgagca ttccgcctgg ggagtacggt cgcaagatta aaactcaaag gaattgacgg | 120 |
| gggcccgcac aagcggtgga gcatgtggtt taattcgaag caacgcgcag aaccttacca | 180 |
| tcctttgaca tggcgtgtta cccagagaga tttggggtcc acttcggtgg cgcgcacaca | 240 |
| ggtgctgcat ggctgtcgtc agctcgtgtc gtgagatgtt gggttaagtc ccgcaacgag | 300 |
| cgcaacccac gtccttagtt gccatcattc agttgggcac tctagggaga ctgccggtga | 360 |
| taagccgcga ggaaggtgtg gatgacgtca agtcctcatg gcccttacgg gatgggctac | 420 |
| acacgtgcta caatggcggt gacagtggga cgcgaaggag cgatctggag caaatcccca | 480 |
| aaagccgtct cagttcggat tgcactctgc aactcgagtg catgaaggcg gaatcgctag | 540 |
| taatcgtgga tcagcatgcc acggtgaata cgttcccggg cct | 583 |

<210> SEQ ID NO 95
<211> LENGTH: 250
<212> TYPE: DNA
<213> ORGANISM: Unknown

```
<220> FEATURE:
<223> OTHER INFORMATION: 16S DNA Tag

<400> SEQUENCE: 95
cacgccgtaa acgatgaatg ctaggtgtta ggggtttcga taccettggt gccgaagtta        60 acacattaag cattccgcct ggggagtacg gtcgcaagac tgaaactcaa aggaattgac       120
ggggacccgc acaagcagtg gagtatgtgg tttaattcga agcaacgcga agaaccttac       180
caagtcttga catccctctg aatcctctag agatagaggc ggccttcggg acagaggtga       240
caggtggtgc                                                              250

<210> SEQ ID NO 96
<211> LENGTH: 588
<212> TYPE: DNA
<213> ORGANISM: Unknown
<220> FEATURE:
<223> OTHER INFORMATION: 16S DNA Tag

<400> SEQUENCE: 96
cacgccgtaa acgatgaatg ctaggtgtta ggggtttcga taccettggt gccgaagtta        60 acacattaag cattccgcct ggggagtacg gtcgcaagac tgaaactcaa aggaattgac       120
ggggacccgc acaagcagtg gagtatgtgg tttaattcga agcaacgcga agaaccttac       180
caagtcttga catccctctg aatcctctag agatagaggc ggccttcggg acagaggtga       240
caggtggtgc atggttgtcg tcagctcgtg tcgtgagatg ttgggttaag tcccgcaacg       300
agcgcaaccc ttgattttag ttgccagcag gtaaggctgg gcactctaga atgactgccg       360
gtgacaaacc ggaggaaggc ggggatgacg tcaaatcatc atgcccctta tgacttgggc       420
tacacacgta ctacaatggc tggtacaacg ggaagcgaag ccgcgaggtg gagccaatcc       480
tataaaagcc agtctcagtt cggattgcag gctgcaactc gcctgcatga agtcggaatt       540
gctagtaatc gcggatcagc atgccgcggt gaatacgttc ccgggtct                    588

<210> SEQ ID NO 97
<211> LENGTH: 252
<212> TYPE: DNA
<213> ORGANISM: Unknown
<220> FEATURE:
<223> OTHER INFORMATION: 16S DNA Tag

<400> SEQUENCE: 97
cacgccgtaa acgatgagtg ctaagtgtta gagggtttcc gcccttagt gctgcagcta        60 acgcattaag cactccgcct ggggagtacg gccgcaaggc tgaaactcaa aggaattgac       120
gggggcccgc acaagcggtg gagcatgtgg tttaattcga agcaacgcga agaaccttac       180
caggtcttga catcctctga aaccctaga gatagggctt tccccttcgg gggacagagt       240
gacaggtggt gc                                                           252

<210> SEQ ID NO 98
<211> LENGTH: 587
<212> TYPE: DNA
<213> ORGANISM: Unknown
<220> FEATURE:
<223> OTHER INFORMATION: 16S DNA Tag

<400> SEQUENCE: 98
cacgccgtaa acgatgagtg ctaagtgtta gagggtttcc gcccttagt gctgcagcta        60 acgcattaag cactccgcct ggggagtacg gccgcaaggc tgaaactcaa aggaattgac       120
```

```
gggggcccgc acaagcggtg gagcatgtgg tttaattcga agcaacgcga agaaccttac    180
caggtcttga catcctctga caaccctaga gatagggctt tccccttcgg gggacagagt    240
gacaggtggt gcatggttgt cgtcagctcg tgtcgtgaga tgttgggtta agtcccgcaa    300
cgagcgcaac ccttgatctt agttgccagc attcagttgg gcactctaag gtgactgccg    360
gtgacaaacc ggaggaaggt ggggatgacg tcaaatcatc atgcccctta tgacctgggc    420
tacacacgtg ctacaatgga tggtacaaag ggctgcaaac ctgcgaaggt aagcgaatcc    480
cataaagcca ttctcagttc ggattgcagg ctgcaactcg cctgcatgaa gccggaatcg    540
ctagtaatcg cggatcagca tgccgcggtg aatacgttcc cgggcct              587

<210> SEQ ID NO 99
<211> LENGTH: 250
<212> TYPE: DNA
<213> ORGANISM: Unknown
<220> FEATURE:
<223> OTHER INFORMATION: 16S DNA Tag

<400> SEQUENCE: 99
cacgccgtaa acgatgagtg ctaagtgtta gggggtttcc gccccttagt gctgcagcta    60
acgcattaag cactccgcct ggggagtacg gtcgcaagac tgaaactcaa aggaattgac    120
gggggcccgc acaagcggtg gagcatgtgg tttaattcga agcaacgcga agaaccttac    180
caggtcttga catcctctga caaccctaga gatagggctt tcccttcggg gacagagtga    240
caggtggtgc                                                           250

<210> SEQ ID NO 100
<211> LENGTH: 585
<212> TYPE: DNA
<213> ORGANISM: Unknown
<220> FEATURE:
<223> OTHER INFORMATION: 16S DNA Tag

<400> SEQUENCE: 100
cacgccgtaa acgatgagtg ctaagtgtta gggggtttcc gccccttagt gctgcagcta    60
acgcattaag cactccgcct ggggagtacg gtcgcaagac tgaaactcaa aggaattgac    120
gggggcccgc acaagcggtg gagcatgtgg tttaattcga agcaacgcga agaaccttac    180
caggtcttga catcctctga caaccctaga gatagggctt tcccttcggg gacagagtga    240
caggtggtgc atggttgtcg tcagctcgtg tcgtgagatg ttgggttaag tcccgcaacg    300
agcgcaaccc ttgatcttag ttgccagcat tcagttgggc actctaaggt gactgccggt    360
gacaaaccgg aggaaggtgg ggatgacgtc aaatcatcat gccccttatg acctgggcta    420
cacacgtgct acaatggaca gaacaaaggg ctgcgagacc gcaaggttta gccaatccca    480
caaatctgtt ctcagttcgg atcgcagtct gcaactcgac tgcgtgaagc tggaatcgct    540
agtaatcgcg gatcagcatg ccgcggtgaa tacgttcccg ggcct                  585

<210> SEQ ID NO 101
<211> LENGTH: 250
<212> TYPE: DNA
<213> ORGANISM: Unknown
<220> FEATURE:
<223> OTHER INFORMATION: 16S DNA Tag

<400> SEQUENCE: 101
cacgccgtaa acgatgagtg ctaagtgtta gggggtttcc gccccttagt gctgcagcta    60
acgcattaag cactccgcct ggggagtacg gtcgcaagac tgaaactcaa aggaattgac    120
```

```
ggggcccgc acaagcggtg gagcatgtgg tttaattcga agcaacgcga agaaccttac      180
caggtcttga catcctctga caatcctaga gataggacgt ccccttcggg ggcagagtga      240
caggtggtgc                                                             250

<210> SEQ ID NO 102
<211> LENGTH: 585
<212> TYPE: DNA
<213> ORGANISM: Unknown
<220> FEATURE:
<223> OTHER INFORMATION: 16S DNA Tag

<400> SEQUENCE: 102
cacgccgtaa acgatgagtg ctaagtgtta gggggtttcc gccccttagt gctgcagcta      60
acgcattaag cactccgcct ggggagtacg gtcgcaagac tgaaactcaa aggaattgac      120 ggggcccgc acaagcggtg gagcatgtgg tttaattcga agcaacgcga agaaccttac      180
caggtcttga catcctctga caatcctaga gataggacgt ccccttcggg ggcagagtga      240
caggtggtgc atggttgtcg tcagctcgtg tcgtgagatg ttgggttaag tcccgcaacg      300
agcgcaaccc ttgatcttag ttgccagcat tcagttgggc actctaaggt gactgccggt      360
gacaaaccgg aggaaggtgg ggatgacgtc aaatcatcat gccccttatg acctgggcta      420
cacacgtgct acaatggaca gaacaaaggg cagcgaaacc gcgaggttaa gccaatccca      480
caaatctgtt ctcagttcgg atcgcagtct gcaactcgac tgcgtgaagc tggaatcgct      540
agtaatcgcg gatcagcatg ccgcggtgaa tacgttcccg ggcct                      585

<210> SEQ ID NO 103
<211> LENGTH: 249
<212> TYPE: DNA
<213> ORGANISM: Unknown
<220> FEATURE:
<223> OTHER INFORMATION: 16S DNA Tag

<400> SEQUENCE: 103
cacgccgtaa acgatgtcaa ctagccgttg gaatccttga gatttagtg gcgcagctaa       60 cgcattaagt tgaccgcctg gggagtacgg ccgcaaggtt aaaactcaaa tgaattgacg      120
ggggcccgca caagcggtgg agcatgtggt ttaattcgaa gcaacgcgaa gaaccttacc      180
aggccttgac atgcagagaa cttttccagag atggattggt gccttcggga actctgacac      240
aggtgctgc                                                              249

<210> SEQ ID NO 104
<211> LENGTH: 586
<212> TYPE: DNA
<213> ORGANISM: Unknown
<220> FEATURE:
<223> OTHER INFORMATION: 16S DNA Tag

<400> SEQUENCE: 104
cacgccgtaa acgatgtcaa ctagccgttg gaatccttga gatttagtg gcgcagctaa       60 cgcattaagt tgaccgcctg gggagtacgg ccgcaaggtt aaaactcaaa tgaattgacg      120
ggggcccgca caagcggtgg agcatgtggt ttaattcgaa gcaacgcgaa gaaccttacc      180
aggccttgac atgcagagaa cttttccagag atggattggt gccttcggga actctgacac      240
aggtgctgca tggctgtcgt cagctcgtgt cgtgagatg tgggttaagt cccgtaacga      300
gcgcaaccct tgtccttagt taccagcacg ttatggtggg cactctaagg agactgccgg      360
```

```
tgacaaaccg aggaaggtg gggatgacgt caagtcatca tggcccttac ggcctgggct    420
acacacgtgc tacaatggtc ggtacagagg gttgccaagc cgcgaggtgg agctaatctc    480
acaaaaccga tcgtagtccg gatcgcagtc tgcaactcga ctgcgtgaag tcggaatcgc    540
tagtaatcgc gaatcagaat gtcgcggtga atacgttccc gggcct                   586
```

<210> SEQ ID NO 105
<211> LENGTH: 249
<212> TYPE: DNA
<213> ORGANISM: Unknown
<220> FEATURE:
<223> OTHER INFORMATION: 16S DNA Tag

<400> SEQUENCE: 105

```
cacgccgtaa acgatgtcaa ctagccgttg ggagccttga gctcttagtg gcgcagctaa     60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
aggccttgac atccaatgaa ctttctagag atagattggt gccttcggga acattgagac    240
aggtgctgc                                                            249
```

<210> SEQ ID NO 106
<211> LENGTH: 249
<212> TYPE: DNA
<213> ORGANISM: Unknown
<220> FEATURE:
<223> OTHER INFORMATION: 16S DNA Tag

<400> SEQUENCE: 106

```
cacgccgtaa acgatgtcaa ctagccgttg ggttccttga gaacttagtg gcgcagctaa     60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
tggccttgac atgctgagaa ctttccagag atggattggt gccttcggga actcagacac    240
aggtgctgc                                                            249
```

<210> SEQ ID NO 107
<211> LENGTH: 586
<212> TYPE: DNA
<213> ORGANISM: Unknown
<220> FEATURE:
<223> OTHER INFORMATION: 16S DNA Tag

<400> SEQUENCE: 107

```
cacgccgtaa acgatgtcaa ctagccgttg ggttccttga gaacttagtg gcgcagctaa     60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
tggccttgac atgctgagaa ctttccagag atggattggt gccttcggga actcagacac    240
aggtgctgca tggctgtcgt cagctcgtgt cgtgagatgt tgggttaagt cccgtaacga    300
gcgcaaccct tgtccttagt taccagcacg ttatggtggg aactctaagg agactgccgg    360
tgacaaaccg aggaaggtg gggatgacgt caagtcatca tggcccttac ggccagggct    420
acacacgtgc tacaatggtc ggtacaaagg gttgccaagc cgcgaggtgg agctaatccc    480
ataaaaccga tcgtagtccg gatcgcagtc tgcaactcga ctgcgtgaag tcggaatcgc    540
tagtaatcgt gaatcagaat gtcacggtga atacgttccc gggcct                   586
```

<210> SEQ ID NO 108
<211> LENGTH: 248
<212> TYPE: DNA
<213> ORGANISM: Unknown
<220> FEATURE:
<223> OTHER INFORMATION: 16S DNA Tag

<400> SEQUENCE: 108

| | | | | |
|---|---|---|---|---|
| catgccgtaa acgttgggaa ctaggtgtgg gtctcattcc acgagatccg tgccgcagct | | | | 60 |
| aacgcattaa gttccccgcc tggggagtac ggccgcaagg ctaaaactca aggaattga | | | | 120 |
| cgggggcccg cacaagcggc ggagcatgcg gattaattcg atgcaacgcg aagaacctta | | | | 180 |
| ccaaggcttg acatacaccg gaatcactca gagatgggtg cgtcttcgga ctggtgtaca | | | | 240 |
| ggtggtgc | | | | 248 |

<210> SEQ ID NO 109
<211> LENGTH: 586
<212> TYPE: DNA
<213> ORGANISM: Unknown
<220> FEATURE:
<223> OTHER INFORMATION: 16S DNA Tag

<400> SEQUENCE: 109

| | | | | |
|---|---|---|---|---|
| catgccgtaa acgttgggaa ctaggtgtgg gtctcattcc acgagatccg tgccgcagct | | | | 60 |
| aacgcattaa gttccccgcc tggggagtac ggccgcaagg ctaaaactca aggaattga | | | | 120 |
| cgggggcccg cacaagcggc ggagcatgcg gattaattcg atgcaacgcg aagaacctta | | | | 180 |
| ccaaggcttg acatacaccg gaatcactca gagatgggtg cgtcttcgga ctggtgtaca | | | | 240 |
| ggtggtgcat ggttgtcgtc agctcgtgtc gtgagatgtt gggttaagtc ccgcaacgag | | | | 300 |
| cgcaaccctc gttctatgtt gccagcacgt catggtgggg actcatagga gactgccggg | | | | 360 |
| gtcaactcgg aggaaggtgg ggatgacgtc aaatcatcat gccccttatg tcttgggctt | | | | 420 |
| cacgcatgct acaatggccg gtacaaaggg ctgcgaaacc gcgaggtgga gcaatccca | | | | 480 |
| aaaaaccggt ctcagttcgg attggggtct gcaactcgac cccatgaagt cggagtcgct | | | | 540 |
| agtaatcgca gatcagcaac gctgcggtga atacgttccc gggcct | | | | 586 |

<210> SEQ ID NO 110
<211> LENGTH: 250
<212> TYPE: DNA
<213> ORGANISM: Unknown
<220> FEATURE:
<223> OTHER INFORMATION: 16S DNA Tag

<400> SEQUENCE: 110

| | | | | |
|---|---|---|---|---|
| cacgccctaa acgatgtcaa ctggttgttg ggaaggttcc ttctcagtaa cgtagctaac | | | | 60 |
| gcgtgaagtt gaccgcctgg ggagtacggc cgcaaggttg aaactcaaag gaattgacgg | | | | 120 |
| ggacccgcac aagcggtgga tgatgtggtt taattcgatg caacgcgaaa accttacct | | | | 180 |
| acccttgaca tgtctagaat tttgcagaga tgtgaaagtg ctcgaaagag aactagaaca | | | | 240 |
| caggtgctgc | | | | 250 |

<210> SEQ ID NO 111
<211> LENGTH: 580
<212> TYPE: DNA
<213> ORGANISM: Unknown
<220> FEATURE:
<223> OTHER INFORMATION: 16S DNA Tag

<400> SEQUENCE: 111

```
cacgccctaa acgatgtcaa ctggttgttg ggaaggttcc ttctcagtaa cgtagctaac    60
gcgtgaagtt gaccgcctgg ggagtacggc cgcaaggttg aaactcaaag gaattgacgg   120
ggacccgcac aagcggtgga tgatgtggtt taattcgatg caacgcgaaa aaccttacct   180
acccttgaca tgtctagaat tttgcagaga tgtgaaagtg ctcgaaagag aactagaaca   240
caggtgctgc atggccgtcg tcagctcgtg tcgtgagatg ttgggttaag tcccgcaacg   300
agcgcaaccc ttgtcattag ttgctacgaa agggcactct aatgagactg ccggtgacaa   360
accggaggaa ggtggggatg acgtcaggtc ctcatggccc ttatgggtag gctacacac    420 gtcatacaat ggccggtaca gagggctgcc aacccgcgag gggagccaa tcccagaaaa    480 ccggtcgtag tccggatcgc agtctgcaac tcgactgcgt gaagtcggaa tcgctagtaa   540
tcgcggatca gcttgccgcg gtgaatacgt tccccgggtc                         580

<210> SEQ ID NO 112
<211> LENGTH: 93
<212> TYPE: DNA
<213> ORGANISM: Unknown
<220> FEATURE:
<223> OTHER INFORMATION: 16S DNA Tag

<400> SEQUENCE: 112
ggtcgtagtc cggatcgcag tctgcaactc gactgcgtga agtcggaatc gctagtaatc    60
gcggatcagc ttgccgcggt gaatacgttc ccc                                 93

<210> SEQ ID NO 113
<211> LENGTH: 250
<212> TYPE: DNA
<213> ORGANISM: Unknown
<220> FEATURE:
<223> OTHER INFORMATION: 16S DNA Tag

<400> SEQUENCE: 113
cacgccgtaa acgatgaatg ctaggtgtta ggggtttcga tacccttggt gccgaagtta    60
acacattaag cattccgcct ggggagtacg gtcgcaagac tgaaactcaa aggaattgac   120
ggggacccgc acaagcagtg gagtatgtgg tttaattcga agcaacgcga aaaaccttac   180
caagtcttga catccctctg aatcctctag agatagaggc ggccttcggg acagaggtga   240
caggtggtgc                                                          250

<210> SEQ ID NO 114
<211> LENGTH: 588
<212> TYPE: DNA
<213> ORGANISM: Unknown
<220> FEATURE:
<223> OTHER INFORMATION: 16S DNA Tag

<400> SEQUENCE: 114
cacgccgtaa acgatgaatg ctaggtgtta ggggtttcga tacccttggt gccgaagtta    60
acacattaag cattccgcct ggggagtacg gtcgcaagac tgaaactcaa aggaattgac   120
ggggacccgc acaagcagtg gagtatgtgg tttaattcga agcaacgcga aaaaccttac   180
caagtcttga catccctctg aatcctctag agatagaggc ggccttcggg acagaggtga   240
caggtggtgc atggttgtcg tcagctcgtg tcgtgagatg ttgggttaag tcccgcaacg   300
agcgcaaccc ttgattttag ttgccagcag gtaaggctgg gcactctaga atgactgccg   360
gtgacaaacc ggaggaaggc ggggatgacg tcaaatcatc atgccccttta tgacttgggc   420 tacacacgta ctacaatggc tggtacaacg ggaagcgaag ccgcgaggtg gagccaatcc   480
```

```
tataaaagcc agtctcagtt cggattgcag gctgcaactc gcctgcatga agtcggaatt      540
gctagtaatc gcggatcagc atgccgcggt gaatacgttc ccgggtct                  588
```

<210> SEQ ID NO 115
<211> LENGTH: 84
<212> TYPE: DNA
<213> ORGANISM: Unknown
<220> FEATURE:
<223> OTHER INFORMATION: 16S DNA Tag
<400> SEQUENCE: 115

```
ctgaaactca aaggaattga cggggacccg cacaagcagt ggagtatgtg gtttaattcg      60
aagcaacgcg aaaaacctta ccaa                                            84
```

<210> SEQ ID NO 116
<211> LENGTH: 247
<212> TYPE: DNA
<213> ORGANISM: Unknown
<220> FEATURE:
<223> OTHER INFORMATION: 16S DNA Tag
<400> SEQUENCE: 116

```
cacgccctaa acgatggata ctcgacatac gcgatacaca gtgtgtgtct gagcgaaagc      60
attaagtatc ccacctggga agtacgaccg caaggttgaa actcaaagga attggcgggg     120
gtccgcacaa gcggtggagc atgtggttta attcgatgat acgcgaggaa ccttacctgg     180
gctagaatgc atattgaccg tgggtgaaag ctcactttgt agcaatacac aatttgtaag     240
gtgctgc                                                              247
```

<210> SEQ ID NO 117
<211> LENGTH: 585
<212> TYPE: DNA
<213> ORGANISM: Unknown
<220> FEATURE:
<223> OTHER INFORMATION: 16S DNA Tag
<400> SEQUENCE: 117

```
cacgccctaa acgatggata ctcgacatac gcgatacaca gtgtgtgtct gagcgaaagc      60
attaagtatc ccacctggga agtacgaccg caaggttgaa actcaaagga attggcgggg     120
gtccgcacaa gcggtggagc atgtggttta attcgatgat acgcgaggaa ccttacctgg     180
gctagaatgc atattgaccg tgggtgaaag ctcactttgt agcaatacac aatttgtaag     240
gtgctgcatg gctgtcgtca gctcgtgccg tgaggtgttg ggttaagtcc cgcaacgagc     300
gcaaccccca tcattagttg ccatcaggta aagctgggaa ctctaatgaa actgccgtcg     360
taagacgcga ggaaggaggg gatgatgtca agtcatcatg gcctttatgc ccagggctac     420
acacgtgcta caatggaagg gacaaagagc tgccacttgg cgacaaggcg ctaatctcaa     480 aaacccttc tcagttcaga tcgcagtctg caactcgact gcgtgaagct ggaatcgcta     540
gtaatcgtat atcagcaatg atacggtgaa tacgttcccg gacct                    585
```

<210> SEQ ID NO 118
<211> LENGTH: 247
<212> TYPE: DNA
<213> ORGANISM: Unknown
<220> FEATURE:
<223> OTHER INFORMATION: 16S DNA Tag
<400> SEQUENCE: 118

```
cacaccgtaa acgttgggcg ctaggtgtgg gatccattcc acgggttccg tgccgcagct      60
aacgcattaa gcgccccgcc tggggagtac ggccgcaagg ctaaaactca aaggaattga     120
cgggggcccg cacaagcggc ggagcatgcg gattaattcg atgcaacgcg aagaaccttna    180 cctgggtttg acatatgccg gaaagctcta gagatagagc ccctttagt cggtatacag      240 gtggtgc                                                               247

<210> SEQ ID NO 119
<211> LENGTH: 585
<212> TYPE: DNA
<213> ORGANISM: Unknown
<220> FEATURE:
<223> OTHER INFORMATION: 16S DNA Tag

<400> SEQUENCE: 119
cacaccgtaa acgttgggcg ctaggtgtgg gatccattcc acgggttccg tgccgcagct      60
aacgcattaa gcgccccgcc tggggagtac ggccgcaagg ctaaaactca aaggaattga     120
cgggggcccg cacaagcggc ggagcatgcg gattaattcg atgcaacgcg aagaaccttna    180 cctgggtttg acatatgccg gaaagctcta gagatagagc ccctttagt cggtatacag      240 gtggtgcatg gctgtcgtca gctcgtgtcg tgagatgttg ggttaagtcc cgcaacgagc     300
gcaaccctcg tcctatgttg ccagcgggta atgccgggga ctcataggag actgccgggg    360
tcaactcgga ggaaggtggg gatgacgtca agtcatcatg ccccttatgt ccagggcttc     420
acgcatgcta caatggccgg tacaaagggc tgcgatgctg taaggcggag cgaatcccaa     480
aaagccggtc tcagttcgga ttgggtctg caactcgacc ccatgaagtc ggagtcgcta     540
gtaatcgcag atcagcaacg ctgcggtgaa tacgttcccg ggcct                     585

<210> SEQ ID NO 120
<211> LENGTH: 285
<212> TYPE: DNA
<213> ORGANISM: Unknown
<220> FEATURE:
<223> OTHER INFORMATION: 16S DNA Tag

<400> SEQUENCE: 120
cgggttccgt gccgcagcta acgcattaag cgccccgcct ggggagtacg gccgcaaggc     60
taaaactcaa aggaattgac ggggcccgc acaagcggcg gagcatgcgg attaattcga     120
tgcaacgcga agaaccttac ctgggtttga catatgccgg aaagctctag agatagagcc     180
ccttttagtc ggtatacagg tggtgcatgg ctgtcgtcag ctcgtgtcgt gagatgttgg     240
gttaagtccc gcaacgagcg caaccctcgt cctatgttgc cagcg                     285

<210> SEQ ID NO 121
<211> LENGTH: 248
<212> TYPE: DNA
<213> ORGANISM: Unknown
<220> FEATURE:
<223> OTHER INFORMATION: 16S DNA Tag

<400> SEQUENCE: 121
cacgctgtaa acgatgattg ctagttgtca gccggcatgc cggttggtga cgcagctaac     60
gcattaagca atccgcctgg ggagtacggt cgcaagatta aaactcaaag gaattgacgg     120
gggcccgcac aagcggtgga gcatgtggtt taattcgaag caacgcgcag aaccttacca    180
ccttttgaca tgcctggaca tcatgggaga ccatgctttc tcttcggaga ctgggacaca    240
ggtgctgc                                                              248
```

<210> SEQ ID NO 122
<211> LENGTH: 561
<212> TYPE: DNA
<213> ORGANISM: Unknown
<220> FEATURE:
<223> OTHER INFORMATION: 16S DNA Tag

<400> SEQUENCE: 122

```
cacgctgtaa acgatgattg ctagttgtca gccggcatgc cggttggtga cgcagctaac      60
gcattaagca atccgcctgg ggagtacggt cgcaagatta aaactcaaag gaattgacgg     120
gggcccgcac aagcggtgga gcatgtggtt taattcgaag caacgcgcag aaccttacca     180
ccttttgaca tgcctggaca tcatgggaga ccatgctttc tcttcggaga ctgggacaca     240
ggtgctgcat ggctgtcgtc agctcgtgtc gtgagatgtt gggttaagtc ccgcaacgag     300
cgcaaccctc gctgttagtt gccatcattt agttgggaac tctaacagga ctgccggtgc     360
taagccggag aaggtgggg atgacgtcaa gtcctcatgg cccttacagg gtgggctaca     420
cacgtgctac aatggcgact acagagggca atccctaaa agtcgtctca gttcggatcg     480
tcctctgcaa ctcgagggcg tgaagttgga atcgctagta atcgcggatc agcatgccgc     540
ggtgaatacg ttcccgggcc t                                               561
```

<210> SEQ ID NO 123
<211> LENGTH: 250
<212> TYPE: DNA
<213> ORGANISM: Unknown
<220> FEATURE:
<223> OTHER INFORMATION: 16S DNA Tag

<400> SEQUENCE: 123

```
cacgccgtaa acgatggatg ctagctgtgg ggggtatcga cccccttccgt agcgaagcta     60
acgcgttaag catcccgcct gtggagtacg gccgcaaggc taaaacataa aggaattgac    120
ggggacccgc acaagtggtg gagcgtgttc tttaattcga tgataaacga aaaaccttac    180
cagggtttga catcccaaga attttgtcga aagacgagag tgctttattg aacttggtga    240
cagctgttgc                                                           250
```

<210> SEQ ID NO 124
<211> LENGTH: 572
<212> TYPE: DNA
<213> ORGANISM: Unknown
<220> FEATURE:
<223> OTHER INFORMATION: 16S DNA Tag

<400> SEQUENCE: 124

```
cacgccgtaa acgatggatg ctagctgtgg ggggtatcga cccccttccgt agcgaagcta     60
acgcgttaag catcccgcct gtggagtacg gccgcaaggc taaaacataa aggaattgac    120
ggggacccgc acaagtggtg gagcgtgttc tttaattcga tgataaacga aaaaccttac    180
cagggtttga catcccaaga attttgtcga aagacgagag tgctttattg aacttggtga    240
cagctgttgc atggccgtcg tcagctcgtg tcgtgagatg tttggttaag tccatcaacg    300
agcgcaaccc ttatagttag ttggatttt ctagctagac tgcccggta acggggagga    360
aggaggggat gatgtcaggt cagtattacg cttacatcct gggctagaaa cgcgctacaa    420
tggccggtac aacgggcagc caagccgcaa ggcggagcaa atcccaacaa agccggtccc    480
agttcggatt ggaggctgaa actcgcctcc atgaagtcgg aatcactagt aatcgcaaat    540
```

```
cagcatgttg cggtgaatac gttcccgggt ct                                  572
```

```
<210> SEQ ID NO 125
<211> LENGTH: 92
<212> TYPE: DNA
<213> ORGANISM: Unknown
<220> FEATURE:
<223> OTHER INFORMATION: 16S DNA Tag

<400> SEQUENCE: 125
ttccgtagcg aagctaacgc gttaagcatc ccgcctgtgg agtacggccg caaggctaaa   60
acataaagga attgacgggg acccgcacaa gt                                  92
```

```
<210> SEQ ID NO 126
<211> LENGTH: 250
<212> TYPE: DNA
<213> ORGANISM: Unknown
<220> FEATURE:
<223> OTHER INFORMATION: 16S DNA Tag

<400> SEQUENCE: 126
cacgccgtaa acgatggata ctagctgttg gaggtatcga ccccttcagt agcgaagcta   60
acgcgttaag tatcccgcct gtggagtacg gtcgcaagac taaaacataa aggaattgac  120
ggggacccgc acaagcggtg gagcgtgttc tttaattcga tgataaacga agaaccttac  180
cagggcttga catcccttga attttgtcga aagacgagag tgctttattg agcaaggtga  240
caggtgttgc                                                          250
```

```
<210> SEQ ID NO 127
<211> LENGTH: 572
<212> TYPE: DNA
<213> ORGANISM: Unknown
<220> FEATURE:
<223> OTHER INFORMATION: 16S DNA Tag

<400> SEQUENCE: 127
cacgccgtaa acgatggata ctagctgttg gaggtatcga ccccttcagt agcgaagcta   60
acgcgttaag tatcccgcct gtggagtacg gtcgcaagac taaaacataa aggaattgac  120
ggggacccgc acaagcggtg gagcgtgttc tttaattcga tgataaacga agaaccttac  180
cagggcttga catcccttga attttgtcga aagacgagag tgctttattg agcaaggtga  240
caggtgttgc atggccgtcg tcagctcgtg tcgtgagatg tttggttaag tccatcaacg  300
agcgcaaccc ttgtgattag ttgtattttt ctaatcaaac tgccccggta acggggagga  360
aggaggggat gatgtcaggt cagtattacc cttacaccct gggctagaaa cgcgctacaa  420
tggccagtac aatgggcagc gaagtcgcga gatggagcaa atcgcatcaa agctggtccc  480
agttcggata gtaggctgaa actcgcctgc ttgaagtggg aatcgctagt aatcgcaaat  540
cagcatgttg cggtgaatac gttcccgggt ct                                 572
```

```
<210> SEQ ID NO 128
<211> LENGTH: 185
<212> TYPE: DNA
<213> ORGANISM: Unknown
<220> FEATURE:
<223> OTHER INFORMATION: 16S DNA Tag

<400> SEQUENCE: 128
gatggatact agctgttgga ggtatcgacc ccttcagtag cgaagctaac gcgttaagta   60
tcccgcctgt ggagtacggt cgcaagacta aaacataaag gaattgacgg ggacccgcac  120
```

```
aagcggtgga gcgtgttctt taattcgatg ataaacgaag aaccttacca gggcttgaca      180
tccct                                                                 185

<210> SEQ ID NO 129
<211> LENGTH: 594
<212> TYPE: DNA
<213> ORGANISM: Unknown
<220> FEATURE:
<223> OTHER INFORMATION: 16S DNA Tag

<400> SEQUENCE: 129
cacgccgtaa acggtgggaa ctaggtgttg gcgacattcc acgtcgtcgg tgccgcagct       60
aacgcattaa gttccccgcc tggggagtac ggccgcaagg ctaaaactca aggaattga      120 cggggggccg cacaagcagc ggagcatgtg gcttaattcg acgcaacgcg aagaaccta      180 ccaaggcttg acatacaccg gaaacggcca gagatggtcg ccccttgtg gtcggtgtac      240 aggtggtgca tggctgtcgt cagctcgtgt cgtgagatgt tgggttaagt cccgcaacga      300
gcgcaaccct tgttctgtgt tgccagcatg cccttcgggg tgatgggac tcacaggaga      360 ctgccggggt caactcggag gaaggtgggg acgacgtcaa gtcatcatgc ccttatgtc      420 ttgggctgca cacgtgctac aatggccggt acaaagagct gcgaaccgt gaggtggagc      480 gaatctcaaa aagccggtct cagttcggat tggggtctgc aactcgaccc catgaagtcg      540
gagttgctag taatcgcaga tcagcattgc tgcggtgaat acgttcccgg gcct            594

<210> SEQ ID NO 130
<211> LENGTH: 594
<212> TYPE: DNA
<213> ORGANISM: Unknown
<220> FEATURE:
<223> OTHER INFORMATION: 16S DNA Tag

<400> SEQUENCE: 130
cacgccgtaa acggtgggaa ctaggtgttg gcgacattcc acgtcgtcgg tgccgcagct       60
aacgcattaa gttccccgcc tggggagtac ggccgcaagg ctaaaactca aggaattga      120 cggggggccg cacaagcagc ggagcatgtg gcttaattcg acgcaacgcg aagaaccta      180 ccaaggcttg acatacaccg gaaacggcca gagatggtcg ccccttgtg gtcggtgtac      240 aggtggtgca tggctgtcgt cagctcgtgt cgtgagatgt tgggttaagt cccgcaacga      300
gcgcaaccct tgttctgtgt tgccagcatg cccttcgggg tgatgggac tcacaggaga      360 ctgccggggt caactcggag gaaggtgggg acgacgtcaa gtcatcatgc ccttatgtc      420 ttgggctgca cacgtgctac aatggcaggt acaaagagct gcgaagccgt gaggcggagc      480
gaatctcaaa aagcctgtct cagttcggat tggggtctgc aactcgaccc catgaagtcg      540
gagttgctag taatcgcaga tcagcattgc tgcggtgaat acgttcccgg gcct            594

<210> SEQ ID NO 131
<211> LENGTH: 250
<212> TYPE: DNA
<213> ORGANISM: Unknown
<220> FEATURE:
<223> OTHER INFORMATION: 16S DNA Tag

<400> SEQUENCE: 131
cacgccgtaa acgatggatg ctagctgtgg ggggtatcga ccccttccgt agcgaagcta       60
acgcgttaag catcccgcct gtggagtacg gccgcaaggc taaaacataa aggaattgac     120
```

```
ggggacccgc acaagtggag gagcgtgttc tttaattcga tgataaacga aaaaccttac    180
cagggtttga catcccaaga attttgtcga aagacgagag tgctttattg aacttggtga    240
cagctgttgc                                                          250

<210> SEQ ID NO 132
<211> LENGTH: 92
<212> TYPE: DNA
<213> ORGANISM: Unknown
<220> FEATURE:
<223> OTHER INFORMATION: 16S DNA Tag

<400> SEQUENCE: 132
ttccgtagcg aagctaacgc gttaagcatc ccgcctgtgg agtacggccg caaggctaaa    60
acataaagga attgacgggg acccgcacaa gt                                 92

<210> SEQ ID NO 133
<211> LENGTH: 1419
<212> TYPE: DNA
<213> ORGANISM: Unknown
<220> FEATURE:
<223> OTHER INFORMATION: 16S DNA Tag

<400> SEQUENCE: 133
atggctcaga ttgaacgctg gcggcaggcc taacacatgc aagtcgagcg gtagagagaa    60
gcttgcttct cttgagagcg gcggacgggt gagtaatgcc taggaatctg cctggtagtg    120
ggggataacg ttcggaaacg gacgctaata ccgcatacgt cctacgggag aaagcagggg    180
accttcgggc cttgcgctat cagatgagcc taggtcggat tagctagttg gtgaggtaat    240
ggctcaccaa ggcgacgatc cgtaactggt ctgagaggat gatcagtcac actggaactg    300
agacacggtc cagactccta cgggaggcag cagtggggaa tattggacaa tgggcgaaag    360
cctgatccag ccatgccgcg tgtgtgaaga aggtcttcgg attgtaaagc actttaagtt    420
gggaggaagg gcagttacct aatacgtgat tgttttgacg ttaccgacag aataagcacc    480
ggctaactct gtgccagcag ccgcggtaat acagagggtg caagcgttaa tcggaattac    540
tgggcgtaaa gcgcgcgtag gtggtttgtt aagttggatg tgaaatcccc gggctcaacc    600
tgggaactgc attcaaaact gactgactag agtgtggtag agggtggtgg aatttcctgt    660
gtagcggtga aatgcgtaga tataggaagg aacaccagtg gcgaaggcga ccacctggac    720
caacactgac actgaggtgc gaaagcgtgg ggagcaaaca ggattagata ccctggtagt    780
ccacgccgta aacgatgtca actagccgtt gggagccttg agctcttagt ggcgcagcta    840
acgcattaag ttgaccgcct ggggagtacg gccgcaaggt taaaactcaa atgaattgac    900
gggggcccgc acaagcggtg gagcatgtgg tttaattcga agcaacgcga gaaccttac    960 caggccttga catccaatga actttctaga gatagattgg tgccttcggg aacattgaga    1020
caggtgctgc atggctgtcg tcagctcgtg tcgtgagatg ttgggttaag tcccgtaacg    1080
agcgcaaccc ttgtccttag ttaccagcac gtaatggtgg gcactctaag gagactgccg    1140
gtgacaaacc ggaggaaggt ggggatgacg tcaagtcatc atggccctta cggcctgggc    1200
tacacacgtg ctacaatggt cggtacagag ggttgccaag ccgcgaggtg gagctaatcc    1260
cacaaaaccg atcgtagtcc ggatcgcagt ctgcaactcg actgcgtgaa gtcggaatcg    1320
ctagtaatcg cgaatcagaa tgtcgcggtg aatacgttcc cgggccttgt acacaccgcc    1380
cgtcacacca tgggagtggg ttgcaccaga agtagctag                          1419
```

<210> SEQ ID NO 134
<211> LENGTH: 1827
<212> TYPE: DNA
<213> ORGANISM: Unknown
<220> FEATURE:
<223> OTHER INFORMATION: 16S DNA Tag

<400> SEQUENCE: 134

| | | | | | |
|---|---|---|---|---|---|
| cggtaaggct | ccttcgggag | tacacgagcg | gcgaacgggt | gagtaacacg | tgagcaatct | 60 |
| gcccttcaca | tcgggataac | tccgggaaac | cgaagctaat | accgaatacg | accacttccg | 120 |
| gcatcggatg | gtggtggaaa | gttccggcgg | tgaaggatga | gctcgcggcc | tatcagcttg | 180 |
| ttggtggggt | aacggcccac | caaggcttcg | acgggtagcc | ggcctgagag | ggtgaccggc | 240 |
| cacactggga | ctgagacacg | gcccagactc | ctacgggagg | cagcagtggg | gaatattgga | 300 |
| caatgggcga | aagcctgatc | cagcaacgcc | gcgtgaggga | tgacggcctt | cgggttgtaa | 360 |
| acctctttca | gcagggacga | agcgcaagtg | acggtacctg | cagaagaagc | accggccaac | 420 |
| tacgtgccag | cagccgcggt | aatacgtagg | gtgcgagcgt | tgtccggaat | tattgggcgt | 480 |
| aaagggctcg | taggcggtct | gtcgcgtcgg | gagtgaaaac | tcagggctta | accctgagcc | 540 |
| tgcttccgat | acgggcagac | tagaggtatg | caggggagaa | cggaattcct | ggtgtagcgg | 600 |
| tgaaatgcgc | agatatcagg | aggaacaccg | gtggcgaagg | cggttctctg | gcattacct | 660 |
| gacgctgagg | agcgaaagtg | tggggagcga | acaggattag | ataccctggt | agtccacacc | 720 |
| gtaaacgttg | ggcgctaggt | gtgggactca | ttccacgagt | tccgtgccgc | agctaacgca | 780 |
| ttaagcgccc | cgcctgggga | gtacggccgc | aaggctaaaa | ctcaaaggaa | ttgacggggg | 840 |
| cccgcacaag | cggcggagca | tgcggattaa | ttcgatgcaa | cgcgaagaac | cttacctagg | 900 |
| tttgacatat | agggaaatct | gctagagata | gcaggtccgt | aagggctcta | tacaggtggt | 960 |
| gcatggctgt | cgtcagctcg | tgtcgtgaga | tgttgggtta | agtcccgcaa | cgagcgcaac | 1020 |
| cctcgtctta | tgttgccagc | acgtcatggt | ggggactcat | aagagactgc | cggggtcaac | 1080 |
| tcggaggaag | gtgggatga | cgtcaagtca | tcatgcccct | tatgcctagg | gcttcacgca | 1140 |
| tgctacaatg | gccggtacaa | agggctgcga | atcgcaaga | tggagcgaat | cccaaaaagc | 1200 |
| cggtctcagt | tcggattggg | gtctgcaact | cgaccccatg | aagtcggagt | cgctagtaat | 1260 |
| cgcagatcag | caacgctgcg | gtgaatacgt | tcccgggcct | tgtacacacc | gcccgtcacg | 1320 |
| tcacgaaagt | tggcaacacc | cgaagccggt | ggcccaaccc | ttgtgaggg | agccgtcgaa | 1380 |
| ggtggggcga | gcgattggga | cgaagtcgta | acaaggtagc | cgtaccggaa | ggtgcggctg | 1440 |
| gatcacctcc | tttctaagga | gcatcactgg | cagcctcgag | ctgtccaggc | ttccttgttt | 1500 |
| cgtggacaaa | cgttccacgg | caaggactgc | tcactagtgg | aacgtcgatt | atttggtctg | 1560 |
| cgaccggaca | acatctcgtc | agtacttccg | ccgtcctcgg | acggatcacg | gagtggaacc | 1620 |
| tcgagcgtcg | cgaacggaag | caaaccaggc | acactgttgg | gtcctgaggg | atcgagtcac | 1680 |
| tcgacctctc | cgggcctcca | tcccctcgaa | ctgccgacca | ctggtcggca | agcgaggatc | 1740 |
| cgatggcggc | accgcccgta | tcttgagaac | tacacagtgg | acgcgagcat | ctttgtagca | 1800 |
| agacaagcta | ctaaagggca | catggtg | | | | 1827 |

<210> SEQ ID NO 135
<211> LENGTH: 312
<212> TYPE: DNA
<213> ORGANISM: Unknown
<220> FEATURE:
<223> OTHER INFORMATION: 16S DNA Tag

<400> SEQUENCE: 135

```
atcgggataa ctccgggaaa ccgaagctaa taccgaatac gaccacttcc ggcatcggat      60
ggtggtggaa agttccggcg gtgaaggatg agctcgcggc ctatcagctt gttggtgggg     120
taacggccca ccaaggcttc gacgggtagc cggcctgaga gggtgaccgg ccacactggg    180
actgagacac ggcccagact cctacgggag gcagcagtgg ggaatattgg acaatgggcg    240
aaagcctgat ccagcaacgc cgcgtgaggg atgacggcct cgggttgta aacctctttc    300
agcagggacg aa                                                         312
```

<210> SEQ ID NO 136
<211> LENGTH: 252
<212> TYPE: DNA
<213> ORGANISM: Unknown
<220> FEATURE:
<223> OTHER INFORMATION: 16S DNA Tag

<400> SEQUENCE: 136

```
cacgccgtaa acgatggaag ctagccgttg gcaagtttac ttgtcggtgg cgcagctaac     60
gcattaagct tcccgcctgg ggagtacggt cgcaagatta aaactcaaag gaattgacgg    120
gggcccgcac aagcggtgga gcatgtggtt taattcgaag caacgcgcag aaccttacca    180
gcccttgaca tcccggtcgc ggtttccaga gatggagacc ttcagttcgg ctggaccggt    240
gacaggtgct gc                                                         252
```

<210> SEQ ID NO 137
<211> LENGTH: 587
<212> TYPE: DNA
<213> ORGANISM: Unknown
<220> FEATURE:
<223> OTHER INFORMATION: 16S DNA Tag

<400> SEQUENCE: 137

```
cacgccgtaa acgatggaag ctagccgttg gcaagtttac ttgtcggtgg cgcagctaac     60
gcattaagct tcccgcctgg ggagtacggt cgcaagatta aaactcaaag gaattgacgg    120
gggcccgcac aagcggtgga gcatgtggtt taattcgaag caacgcgcag aaccttacca    180
gcccttgaca tcccggtcgc ggtttccaga gatggagacc ttcagttcgg ctggaccggt    240
gacaggtgct gcatggctgt cgtcagctcg tgtcgtgaga tgttgggtta agtcccgcaa    300
cgagcgcaac cctcgccctt agttgccagc attcagttgg gcactctaag gggactgccg    360
gtgataagcc gagaggaagg tggggatgac gtcaagtcct catggccctt acgggctggg    420
ctacacacgt gctacaatgg tggtgacagt gggcagcgag accgcgaggt cgagctaatc    480
tccaaaagcc atctcagttc ggattgcact ctgcaactcg agtgcatgaa gttggaatcg    540
ctagtaatcg cggatcagca tgccgcggtg aatacgttcc cgggcct                  587
```

<210> SEQ ID NO 138
<211> LENGTH: 1406
<212> TYPE: DNA
<213> ORGANISM: Unknown
<220> FEATURE:
<223> OTHER INFORMATION: 16S DNA Tag

<400> SEQUENCE: 138

```
aggggagcgg cagacgggtg agtaacgcgt gggaatctac ccatctctac ggaacaactc     60
cgggaaactg gagctaatac cgtatacgtc cttttggaga aagatttatc ggagatggat    120
gagcccgcgt tggattagct agttggtggg gtaatggcct accaaggcga cgatccatag    180
```

```
ctggtctgag aggatgatca gccacactgg gactgagaca cggcccagac tcctacggga    240
ggcagcagtg gggaatattg gacaatgggc gcaagcctga tccagccatg ccgcgtgagt    300
gatgaaggcc ctagggttgt aaagctcttt caacggtgaa gataatgacg gtaaccgtag    360
aagaagcccc ggctaacttc gtgccagcag ccgcggtaat acgaagggggg ctagcgttgt    420 tcggaattac tgggcgtaaa gcgcacgtag gcggatactt aagtcagggg tgaaatcccg    480
gggctcaacc ccggaactgc ctttgatact gggtatctcg agtccggaag aggtgagtgg    540
aattccgagt gtagaggtga aattcgtaga tattcggagg aacaccagtg gcgaaggcgg    600
ctcactggtc cggtactgac gctgaggtgc gaaagcgtgg ggagcaaaca ggattagata    660
ccctggtagt ccacgccgta aacgatggaa gctagccgtt ggcaagttta cttgtcggtg    720
gcgcagctaa cgcattaagc ttcccgcctg gggagtacgg tcgcaagatt aaaactcaaa    780
ggaattgacg ggggcccgca caagcggtgg agcatgtggt ttaattcgaa gcaacgcgca    840
gaaccttacc agcccttgac atcccggtcg cggtttccag agatggagac cttcagttcg    900
gctggaccgg tgacaggtgc tgcatggctg tcgtcagctc gtgtcgtgag atgttgggtt    960
aagtcccgca acgagcgcaa ccctcgccct tagttgccag cattcagttg gcactctaa    1020 ggggactgcc ggtgataagc cgagaggaag gtggggatga cgtcaagtcc tcatggccct    1080
tacgggctgg gctacacacg tgctacaatg gtggtgacga tgggcagcga accgcgagg    1140 tcgagctaat ctccaaaagc catctcagtt cggattgcac tctgcaactc gagtgcatga    1200
agttggaatc gctagtaatc gcggatcagc atgccgcggt gaatacgttc ccgggccttg    1260
tacacaccgc ccgtcacacc atgggagttg gttttacccg aaggcgctgt gctaaccgca    1320
aggaggcagg cgaccacggt agggtcagcg actggggtga agtcgtaaca aggtagccgt    1380
aggggaacct gcggctggat cacctc                                         1406

<210> SEQ ID NO 139
<211> LENGTH: 279
<212> TYPE: DNA
<213> ORGANISM: Unknown
<220> FEATURE:
<223> OTHER INFORMATION: 16S DNA Tag

<400> SEQUENCE: 139
ccggtactga cgctgaggtg cgaaagcgtg gggagcaaac aggattagat accctggtag     60
tccacgccgt aaacgatgga agctagccgt tggcaagttt acttgtcggt ggcgcagcta    120
acgcattaag cttcccgcct ggggagtacg gtcgcaagat taaaactcaa aggaattgac    180
gggggcccgc acaagcggtg gagcatgtgg tttaattcga agcaacgcgc agaaccttac    240
cagcccttga catcccggtc gcggtttcca gagatggag                            279

<210> SEQ ID NO 140
<211> LENGTH: 634
<212> TYPE: DNA
<213> ORGANISM: Unknown
<220> FEATURE:
<223> OTHER INFORMATION: 16S DNA Tag

<400> SEQUENCE: 140
atggctcaga ttgaacgctg gcggcaggcc taacacatgc aagtcgagcg gtagagagaa     60
gcttgcttct cttgagagcg gcggacgggt gagtaatgcc taggaatctg cctggtagtg    120
ggggataacg ttcggaaacg gacgctaata ccgcatacgt cctacgggag aaagcagggg    180
```

```
accttcgggc cttgcgctat cagatgagcc taggtcggat tagctagttg gtgaggtaat    240
ggctcaccaa ggcgacgatc cgtaactggt ctgagaggat gatcagtcac actggaactg    300
agacacggtc cagactccta cgggaggcag cagtgggaa tattggacaa tgggcgaaag    360
cctgatccag ccatgccgcg tgtgtgaaga aggtcttcgg attgtaaagc actttaagtt    420
gggaggaagg gcagttacct aatacgtgat tgttttgacg ttaccgacag aataagcacc    480
ggctaactct gtgccagcag ccgcggtaat acagagggtg caagcgttaa tcggaattac    540
tgggcgtaaa gcgcgcgtag gtggtttgtt aagttggatg tgaaatcccc gggctcaacc    600
tgggaactgc attcaaaact gactgactag agtg                                634

<210> SEQ ID NO 141
<211> LENGTH: 586
<212> TYPE: DNA
<213> ORGANISM: Unknown
<220> FEATURE:
<223> OTHER INFORMATION: 16S DNA Tag

<400> SEQUENCE: 141
cacgccgtaa acgatgtcaa ctagccgttg ggagccttga gctcttagtg gcgcagctaa     60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
aggccttgac atccaatgaa ctttccagag atggattggt gccttcggga gcattgagac    240
aggtgctgca tggctgtcgt cagctcgtgt cgtgagatgt tgggttaagt cccgtaacga    300
gcgcaaccct tgtccttagt taccagcaca ttaaggtggg cactctaagg agactgccgg    360
tgacaaaccg gaggaaggtg gggatgacgt caagtcatca tggcccttac ggcctgggct    420
acacacgtgc tacaatggtc ggtacagagg gttgccaagc cgcgaggtgg agctaatccc    480
ataaaaccga tcgtagtccg gatcgcagtc tgcaactcga ctgcgtgaag tcggaatcgc    540
tagtaatcgc gaatcagaat gtcgcggtga atacgttccc gggcct                   586

<210> SEQ ID NO 142
<211> LENGTH: 117
<212> TYPE: DNA
<213> ORGANISM: Unknown
<220> FEATURE:
<223> OTHER INFORMATION: 16S DNA Tag

<400> SEQUENCE: 142
ggtgccttcg ggagcattga gacaggtgct gcatggctgt cgtcagctcg tgtcgtgaga     60
tgttgggtta agtcccgtaa cgagcgcaac ccttgtcctt agttaccagc acattaa      117

<210> SEQ ID NO 143
<211> LENGTH: 585
<212> TYPE: DNA
<213> ORGANISM: Unknown
<220> FEATURE:
<223> OTHER INFORMATION: 16S DNA Tag

<400> SEQUENCE: 143
cacgccgtaa acgatgtcaa ctagccgttg ggagccttga gctcttagtg gcgcagctaa     60
cgcattaagt tgaccgcctg gggagtacgg ccgcaaggtt aaaactcaaa tgaattgacg    120
ggggcccgca caagcggtgg agcatgtggt ttaattcgaa gcaacgcgaa gaaccttacc    180
aggccttgac atccaatgaa ctttccagag atggattggt gccttcggga gcattgagac    240
aggtgctgca tggctgtcgt cagctcgtgt cgtgagatgt tgggttaagt cccgtaacga    300
```

```
gcgcaaccct tgtccttagt taccagcacg tgatggtggg cactctaagg agactgccgg   360
tgacaaaccg gaggaaggtg gggatgacgt caagtcatca tggcccttac ggcctgggct   420
acacacgtgc tacaatggtc ggtacagagg gttgccaagc cgcgaggtgg agctaatccc   480
ataaaaccga tcgtagtccg gatcgcagtc tgcaactcga ctgcgtgaag tcggaatcgc   540
tagtaatcgc gaatcagaat gtcgcggtga atacgtcccg ggcct                   585
```

<210> SEQ ID NO 144
<211> LENGTH: 439
<212> TYPE: DNA
<213> ORGANISM: Unknown
<220> FEATURE:
<223> OTHER INFORMATION: 16S DNA Tag

<400> SEQUENCE: 144

```
cttagtggcg cagctaacgc attaagttga ccgcctgggg agtacggccg caaggttaaa   60
actcaaatga attgacgggg gcccgcacaa gcggtggagc atgtggttta attcgaagca   120
acgcgaagaa ccttaccagg ccttgacatc caatgaactt tccagagatg gattggtgcc   180
ttcgggagca ttgagacagg tgctgcatgg ctgtcgtcag ctcgtgtcgt gagatgttgg   240
gttaagtccc gtaacgagcg caaccccttgt ccttagttac cagcacgtga tggtgggcac   300
tctaaggaga ctgccggtga caaaccggag gaaggtgggg atgacgtcaa gtcatcatgg   360
cccttacggc ctgggctaca cacgtgctac aatggtcggt acagagggtt gccaagccgc   420
gaggtggagc taatcccat                                                 439
```

<210> SEQ ID NO 145
<211> LENGTH: 588
<212> TYPE: DNA
<213> ORGANISM: Unknown
<220> FEATURE:
<223> OTHER INFORMATION: 16S DNA Tag

<400> SEQUENCE: 145

```
cacgccctaa acgatgcgaa ctggatgttg gtctcaactc ggagatcagt gtcgaagcta   60
acgcgttaag ttcgccgcct ggggagtacg gtcgcaagac tgaaactcaa aggaattgac   120
gggggcccgc acaagcggtg gagtatgtgg tttaattcga tgcaacgcga agaaccttac   180
ctggccttga catgtccgga atcctgcaga gatgcggag tgccttcggg aatcggaaca   240
caggtgctgc atggctgtcg tcagctcgtg tcgtgagatg ttgggttaag tcccgcaacg   300
agcgcaaccc ttgtccttag ttgccagcac gtaatggtgg gaactctaag gagactgccg   360
gtgacaaacc ggaggaaggt ggggatgacg tcaagtcatc atggcccttta cggccagggc   420 tacacacgta ctacaatggt cggtacagag ggttgcaata ccgcgaggtg gagccaatcc   480
cagaaagccg atcccagtcc ggatcgaagt ctgcaactcg acttcgtgaa gtcggaatcg   540
ctagtaatcg cggatcagct atgccgcggt gaatacgttc ccgggcct                 588
```

<210> SEQ ID NO 146
<211> LENGTH: 337
<212> TYPE: DNA
<213> ORGANISM: Unknown
<220> FEATURE:
<223> OTHER INFORMATION: 16S DNA Tag

<400> SEQUENCE: 146

```
gggagtgcct tcgggaatcg gaacacaggt gctgcatggc tgtcgtcagc tcgtgtcgtg   60
```

```
agatgttggg ttaagtcccg caacgagcgc aacccttgtc cttagttgcc agcacgtaat    120
ggtgggaact ctaaggagac tgccggtgac aaaccggagg aaggtgggga tgacgtcaag    180
tcatcatggc ccttacggcc agggctacac acgtactaca atggtcggta cagagggttg    240
caataccgcg aggtggagcc aatcccagaa agccgatccc agtccggatc gaagtctgca    300
actcgacttc gtgaagtcgg aatcgctagt aatcgcg                             337
```

<210> SEQ ID NO 147
<211> LENGTH: 249
<212> TYPE: DNA
<213> ORGANISM: Unknown
<220> FEATURE:
<223> OTHER INFORMATION: 16S DNA Tag

<400> SEQUENCE: 147

```
cacgccgtaa acggtgggaa ctaggtgttg gcgacattcc acgtcgtcgg tgccgcagct     60
aacgcattaa gttccccgcc tggggagtac ggccgcaagg ctaaaactca aggaattga    120 cgggggcccg cacaagcagc ggagcatgtg gcttaattcg acgcaacgcg aagaacctta    180
ccaaggcttg acatacaccg gaaacatcca gagatgggtg ccccttgtg gtcggtgtac     240 aggtggtgc                                                            249
```

<210> SEQ ID NO 148
<211> LENGTH: 594
<212> TYPE: DNA
<213> ORGANISM: Unknown
<220> FEATURE:
<223> OTHER INFORMATION: 16S DNA Tag

<400> SEQUENCE: 148

```
cacgccgtaa acggtgggaa ctaggtgttg gcgacattcc acgtcgtcgg tgccgcagct     60
aacgcattaa gttccccgcc tggggagtac ggccgcaagg ctaaaactca aggaattga    120 cgggggcccg cacaagcagc ggagcatgtg gcttaattcg acgcaacgcg aagaacctta    180
ccaaggcttg acatacaccg gaaacatcca gagatgggtg ccccttgtg gtcggtgtac     240 aggtggtgca tggctgtcgt cagctcgtgt cgtgagatgt tgggttaagt cccgcaacga    300
gcgcaaccct tgtcccgtgt tgccagcatg cccttcgggg tgatggggac tcacgggaga    360 ccgccgggt caactcggag gaaggtgggg acgacgtcaa gtcatcatgc cccttatgtc     420
ttgggctgca cacgtgctac aatggccggt acaatgagct gcgataccgt gaggtggagc    480
gaatctcaaa aagccggtct cagttcggat tggggtctgc aactcgaccc catgaagtcg    540
gagttgctag taatcgcaga tcagcagtgc tgcggtgaat acgttcccgg gcct          594
```

<210> SEQ ID NO 149
<211> LENGTH: 248
<212> TYPE: DNA
<213> ORGANISM: Unknown
<220> FEATURE:
<223> OTHER INFORMATION: 16S DNA Tag

<400> SEQUENCE: 149

```
catgccgtaa acgttgggaa ctagatgtgg ggaccattcc acggtctccg tgtcgcagct     60
aacgcattaa gttccccgcc tggggagtac ggccgcaagg ctaaaactca aggaattga    120 cgggggcccg cacaagcggc ggagcatgcg gattaattcg atgcaacgcg aagaacctta    180
ccaaggcttg acatatagag gaaaagtgca gaaatgtact ccccgcaagg tctctataca    240
ggtggtgc                                                             248
```

<210> SEQ ID NO 150
<211> LENGTH: 586
<212> TYPE: DNA
<213> ORGANISM: Unknown
<220> FEATURE:
<223> OTHER INFORMATION: 16S DNA Tag

<400> SEQUENCE: 150

| | | | | | |
|---|---|---|---|---|---|
| catgccgtaa | acgttgggaa | ctagatgtgg | ggaccattcc | acggtctccg | tgtcgcagct | 60 |
| aacgcattaa | gttccccgcc | tggggagtac | ggccgcaagg | ctaaaactca | aggaattga | 120 |
| cgggggcccg | cacaagcggc | ggagcatgcg | gattaattcg | atgcaacgcg | aagaacctta | 180 |
| ccaaggcttg | acatatagag | gaaaagtgca | gaaatgtact | ccccgcaagg | tctctataca | 240 |
| ggtggtgcat | ggttgtcgtc | agctcgtgtc | gtgagatgtt | gggttaagtc | ccgcaacgag | 300 |
| cgcaaccctc | gtcctatgtt | gccagcacgt | aatggtggga | actcatggga | tactgccggg | 360 |
| gtcaactcgg | aggaaggtgg | ggatgacgtc | aaatcatcat | gccccttatg | tcttgggctt | 420 |
| cacgcatgct | acaatggccg | gtacaaaggg | ctgcaatacc | gtaaggtgga | gcgaatccca | 480 |
| aaaagccggt | ctcagttcgg | attgaggtct | gcaactcgac | ctcatgaagt | cggagtcgct | 540 |
| agtaatcgca | gatcagcaac | gctgcggtga | atacgttccc | gggcct | | 586 |

<210> SEQ ID NO 151
<211> LENGTH: 161
<212> TYPE: DNA
<213> ORGANISM: Unknown
<220> FEATURE:
<223> OTHER INFORMATION: 16S DNA Tag

<400> SEQUENCE: 151

| | | | | | |
|---|---|---|---|---|---|
| tctccgtgtc | gcagctaacg | cattaagttc | cccgcctggg | gagtacggcc | gcaaggctaa | 60 |
| aactcaaagg | aattgacggg | ggcccgcaca | agcggcggag | catgcggatt | aattcgatgc | 120 |
| aacgcgaaga | accttaccaa | ggcttgacat | atagaggaaa | a | | 161 |

<210> SEQ ID NO 152
<211> LENGTH: 250
<212> TYPE: DNA
<213> ORGANISM: Unknown
<220> FEATURE:
<223> OTHER INFORMATION: 16S DNA Tag

<400> SEQUENCE: 152

| | | | | | |
|---|---|---|---|---|---|
| cacgccctaa | acgatgcgaa | ctggatgttg | ggtgcaacta | ggcactcagt | atcgaagcta | 60 |
| acgcgttaag | ttcgccgcct | ggggagtacg | gtcgcaagac | tgaaactcaa | aggaattgac | 120 |
| gggggcccgc | acaagcggtg | gagtatgtgg | tttaattcga | tgcaacgcga | agaaccttac | 180 |
| ctggccttga | catccacgga | actttccaga | gatggattgg | tgccttcggg | aaccgtgaga | 240 |
| caggtgctgc | | | | | | 250 |

<210> SEQ ID NO 153
<211> LENGTH: 588
<212> TYPE: DNA
<213> ORGANISM: Unknown
<220> FEATURE:
<223> OTHER INFORMATION: 16S DNA Tag

<400> SEQUENCE: 153

| | | | | | |
|---|---|---|---|---|---|
| cacgccctaa | acgatgcgaa | ctggatgttg | ggtgcaacta | ggcactcagt | atcgaagcta | 60 |

```
acgcgttaag ttcgccgcct ggggagtacg gtcgcaagac tgaaactcaa aggaattgac    120
gggggcccgc acaagcggtg gagtatgtgg tttaattcga tgcaacgcga agaaccttac    180
ctggccttga catccacgga actttccaga gatggattgg tgccttcggg aaccgtgaga    240
caggtgctgc atggctgtcg tcagctcgtg tcgtgagatg ttgggttaag tcccgcaacg    300
agcgcaaccc ttgtccctag ttgccagcac gtaatggtgg gaactctagg gagaccgccg    360
gtgacaaacc ggaggaaggt ggggatgacg tcaagtcatc atggccctta cggcagggc    420 tacacacgta ctacaatgga aggacagag gctgcgatc ccgcgagggt gagccaatcc     480
cagaaacctt ttctcagtcc ggattggagt ctgcaactcg actccatgaa gtcggaatcg    540
ctagtaatcg cagatcagca ttgctgcggt gaatacgttc ccgggcct                 588
```

<210> SEQ ID NO 154
<211> LENGTH: 250
<212> TYPE: DNA
<213> ORGANISM: Unknown
<220> FEATURE:
<223> OTHER INFORMATION: 16S DNA Tag

<400> SEQUENCE: 154

```
cacgccctaa acgatgtcta ctagttgtcg ggtcttaatt gacttggtaa cgcagctaac    60
gcgtgaagta daccgcctgg ggagtacggt cgcaagatta aaactcaaag gaattgacgg   120
ggacccgcac aagcggtgga tgatgtggat taattcgatg caacgcgaaa aaccttacct   180
acccttgaca tgtcaggaac ctccgagaga tcggagggtg cccgaaaggg agcctgaaca   240
caggtgctgc                                                           250
```

<210> SEQ ID NO 155
<211> LENGTH: 580
<212> TYPE: DNA
<213> ORGANISM: Unknown
<220> FEATURE:
<223> OTHER INFORMATION: 16S DNA Tag

<400> SEQUENCE: 155

```
cacgccctaa acgatgtcta ctagttgtcg ggtcttaatt gacttggtaa cgcagctaac    60
gcgtgaagta daccgcctgg ggagtacggt cgcaagatta aaactcaaag gaattgacgg   120
ggacccgcac aagcggtgga tgatgtggat taattcgatg caacgcgaaa aaccttacct   180
acccttgaca tgtcaggaac ctccgagaga tcggagggtg cccgaaaggg agcctgaaca   240
caggtgctgc atggctgtcg tcagctcgtg tcgtgagatg ttgggttaag tcccgcaacg   300
agcgcaaccc ttgtcattag ttgctacgaa agggcactct aatgagactg ccggtgacaa   360
accggaggaa ggtgggggatg acgtcaagtc ctcatggccc ttatgggtag gcttcacac   420 gtcatacaat ggtacataca gagggccgcc aacccgcgag ggggagctaa tcccagaaag   480
tgtatcgtag tccggatcgc agtctgcaac tcgactgcgt gaagttggaa tcgctagtaa   540
tcgcggatca gcatgccgcg gtgaatacgt tcccgggtct                          580
```

<210> SEQ ID NO 156
<211> LENGTH: 520
<212> TYPE: DNA
<213> ORGANISM: Unknown
<220> FEATURE:
<223> OTHER INFORMATION: 16S DNA Tag

<400> SEQUENCE: 156

```
acgccctaaa cgatgtctac tagttgtcgg gtcttaattg acttggtaac gcagctaacg    60
```

```
cgtgaagtag accgcctggg gagtacggtc gcaagattaa aactcaaagg aattgacggg    120
gacccgcaca agcggtggat gatgtggatt aattcgatgc aacgcgaaaa accttaccta    180
cccttgacat gtcaggaacc tccgagagat cggagggtgc ccgaaaggga gcctgaacac    240
aggtgctgca tggctgtcgt cagctcgtgt cgtgagatgt tgggttaagt cccgcaacga    300
gcgcaaccct tgtcattagt tgctacgaaa gggcactcta atgagactgc cggtgacaaa    360
ccggaggaag gtgggatga cgtcaagtcc tcatggccct tatgggtagg gcttcacacg    420
tcatacaatg gtacatacag agggccgcca acccgcgagg gggagctaat cccagaaagt    480
gtatcgtagt ccggatcgca gtctgcaact cgactgcgtg                          520
```

```
<210> SEQ ID NO 157
<211> LENGTH: 248
<212> TYPE: DNA
<213> ORGANISM: Unknown
<220> FEATURE:
<223> OTHER INFORMATION: 16S DNA Tag

<400> SEQUENCE: 157
cacgccgtaa acgttgggaa ctaggtgtgg gccacattcc acgtggtctg tgccgcagct     60
aacgcattaa gttccccgcc tggggagtac ggccgcaagg ctaaaactca aaggaattga    120
cgggggcccg cacaagcggc ggagcatgtg gcttaattcg atgcaacgcg aagaacctta    180
cctgggtttg acatgcaggg aaatctcgta gagatacggg gtccgtaagg gccttgcaca    240
ggtggtgc                                                             248
```

```
<210> SEQ ID NO 158
<211> LENGTH: 586
<212> TYPE: DNA
<213> ORGANISM: Unknown
<220> FEATURE:
<223> OTHER INFORMATION: 16S DNA Tag

<400> SEQUENCE: 158
cacgccgtaa acgttgggaa ctaggtgtgg gccacattcc acgtggtctg tgccgcagct     60
aacgcattaa gttccccgcc tggggagtac ggccgcaagg ctaaaactca aaggaattga    120
cgggggcccg cacaagcggc ggagcatgtg gcttaattcg atgcaacgcg aagaacctta    180
cctgggtttg acatgcaggg aaatctcgta gagatacggg gtccgtaagg gccttgcaca    240
ggtggtgcat ggctgtcgtc agctcgtgtc gtgagatgtt gggttaagtc ccgcaacgag    300
cgcaaccctc gtcctatgtt gccagcgagt aatgtcgggg actcatagga gactgccggg    360
gtcaactcgg aggaaggtgg ggatgacgtc aagtcatcat gccccttata tccagggctg    420
cacacatgct acaatggccg gtacaaagag ctgcgatacc gcaaggtgga gcgaatctca    480
taaagccggt ctcagttcgg attggggtct gcaactcgac cccatgaagt cggagtcgct    540
agtaatcgca gatcagcaac gctgcggtga atacgttccc gggcct                  586
```

```
<210> SEQ ID NO 159
<211> LENGTH: 196
<212> TYPE: DNA
<213> ORGANISM: Unknown
<220> FEATURE:
<223> OTHER INFORMATION: 16S DNA Tag

<400> SEQUENCE: 159
tccccgcctg gggagtacgg ccgcaaggct aaaactcaaa ggaattgacg ggggcccgca     60
```

```
caagcggcgg agcatgtggc ttaattcgat gcaacgcgaa gaaccttacc tgggtttgac      120
atgcagggaa atctcgtaga gatacggggt ccgtaagggc cttgcacagg tggtgcatgg      180
ctgtcgtcag ctcgtg                                                      196

<210> SEQ ID NO 160
<211> LENGTH: 250
<212> TYPE: DNA
<213> ORGANISM: Unknown
<220> FEATURE:
<223> OTHER INFORMATION: 16S DNA Tag

<400> SEQUENCE: 160
cacgccctaa acgatgtcta ctagttgtcg ggtcttaatt gacttggtaa cgcagctaac      60
gcgtgaagta gaccgcctgg ggagtacggt cgcaagatta aaactcaaag gaattgacgg     120
ggacccgcac aagcggtgga tgatgtggat taattcgatg caacgcgaaa accttaccT     180 acccttgaca tgtcaggaac ctccgagaga ttggagggtg cccgaaaggg agcctgaaca     240
caggtgctgc                                                            250

<210> SEQ ID NO 161
<211> LENGTH: 580
<212> TYPE: DNA
<213> ORGANISM: Unknown
<220> FEATURE:
<223> OTHER INFORMATION: 16S DNA Tag

<400> SEQUENCE: 161
cacgccctaa acgatgtcta ctagttgtcg ggtcttaatt gacttggtaa cgcagctaac      60
gcgtgaagta gaccgcctgg ggagtacggt cgcaagatta aaactcaaag gaattgacgg     120
ggacccgcac aagcggtgga tgatgtggat taattcgatg caacgcgaaa accttaccT     180 acccttgaca tgtcaggaac ctccgagaga ttggagggtg cccgaaaggg agcctgaaca     240
caggtgctgc atggctgtcg tcagctcgtg tcgtgagatg ttgggttaag tcccgcaacg     300
agcgcaaccc ttgtcattag ttgctacgaa agggcactct aatgagactg ccggtgacaa     360
accggaggaa ggtggggatg acgtcaagtc ctcatggccc ttatgggtag gcttcacac     420 gtcatacaat ggtacataca gagggccgcc aacccgcgag ggggagctaa tcccagaaag     480
tgtatcgtag tccggatcgc agtctgcaac tcgactgcgt gaagttggaa tcgctagtaa     540
tcgcggatca gcatgccgcg gtgaatacgt tcccgggtct                           580

<210> SEQ ID NO 162
<211> LENGTH: 252
<212> TYPE: DNA
<213> ORGANISM: Unknown
<220> FEATURE:
<223> OTHER INFORMATION: 16S DNA Tag

<400> SEQUENCE: 162
cacgccgtaa acgatgagtg ctaagtgtta gagggtttcc gcccttagt gctgcagcta      60 acgcattaag cactccgcct ggggagtacg gtcgcaagac tgaaactcaa aggaattgac     120
gggggcccgc acaagcggtg gagcatgtgg tttaattcga agcaacgcga agaaccttac     180
caggtcttga catcctctga caactctaga gatagagcgt tccccttcgg gggacagagt     240
gacaggtggt gc                                                         252

<210> SEQ ID NO 163
<211> LENGTH: 587
```

```
<212> TYPE: DNA
<213> ORGANISM: Unknown
<220> FEATURE:
<223> OTHER INFORMATION: 16S DNA Tag

<400> SEQUENCE: 163
cacgccgtaa acgatgagtg ctaagtgtta gagggtttcc gcccttagt gctgcagcta        60 acgcattaag cactccgcct ggggagtacg gtcgcaagac tgaaactcaa aggaattgac      120
gggggcccgc acaagcggtg gagcatgtgg tttaattcga agcaacgcga agaaccttac      180
caggtcttga catcctctga caactctaga gatagagcgt tcccttcgg gggacagagt      240 gacaggtggt gcatggttgt cgtcagctcg tgtcgtgaga tgttgggtta agtcccgcaa      300
cgagcgcaac ccttgatctt agttgccagc atttagttgg gcactctaag gtgactgccg      360
gtgacaaacc ggaggaaggt ggggatgacg tcaaatcatc atgcccctta tgacctgggc      420
tacacacgtg ctacaatgga tggtacaaag ggctgcaaga ccgcgaggtc aagccaatcc      480
cataaaacca ttctcagttc ggattgtagg ctgcaactcg cctacatgaa gctggaatcg      540
ctagtaatcg cggatcagca tgccgcggtg aatacgttcc cgggcct                    587

<210> SEQ ID NO 164
<211> LENGTH: 586
<212> TYPE: DNA
<213> ORGANISM: Unknown
<220> FEATURE:
<223> OTHER INFORMATION: 16S DNA Tag

<400> SEQUENCE: 164
cacgccgtaa acgatgtcaa ctagccgttg ggagccttga gctcttagtg gcgcagctaa       60
cgcattaagt tgaccgcctg gggagtacgg ccgcaaggtt aaaactcaaa tgaattgacg      120
ggggcccgca caagcggtgg agcatgtggt ttaattcgaa gcaacgcgaa gaaccttacc      180
aggccttgac atccaatgaa ctttccagag atggattggt gccttcggga gcattgagac      240
aggtgctgca tggctgtcgt cagctcgtgt cgtgagatgt tgggttaagt cccgtaacga      300
gcgcaaccct tgtccttagt taccagcacg ttatggtggg cactctaagg agactgccgg      360
tgacaaaccg gaggaaggtg gggatgacgt caagtcatca tggcccttac ggcctgggct      420
acacacgtgc tacaatggtc ggtacagagg gttgccaagc cgcgaggtgg agctaatccc      480
ataaaaccga tcgtagtccg gatcgcagtc tgcaactcga ctgcgtgaag tcggaatcgc      540
tagtaatcgc gaatcagaat gtcgcggtga atacgttccc gggcct                    586
```